(12) United States Patent
Watkins et al.

(10) Patent No.: US 7,569,724 B2
(45) Date of Patent: Aug. 4, 2009

(54) CARBAMIC ACID COMPOUNDS COMPRISING AN AMIDE LINKAGE AS HDAC INHIBITORS

(75) Inventors: Clare J Watkins, Abingdon (GB); Maria Rosario Romero-Martin, Didcot (GB); Kathryn G Moore, Abingdon (GB); James Ritchie, Abingdon (GB); Paul W Finn, Abingdon (GB); Ivars Kalvinsh, Riga (LV); Einars Loza, Riga (LV); Igor Starchenkov, Riga (LV); Klara Dikovska, Riga (LV); Rasma M Bokaldere, Riga (LV); Vija Gailite, Riga (LV); Maxim Vorona, Riga (LV); Victor Andrianov, Riga (LV); Daina Lolya, Riga (LV); Valentina Semenikhina, Riga (LV); Andris Amolins, Riga (LV); C. John Harris, Sittingbourne (GB); James E. S. Duffy, Sittingbourne (GB)

(73) Assignee: Topotarget UK Limited, Oxford (GB)

( * ) Notice: Subject to any disclaimer, the term of this patent is extended or adjusted under 35 U.S.C. 154(b) by 974 days.

(21) Appl. No.: 10/381,791

(22) PCT Filed: Sep. 27, 2001

(86) PCT No.: PCT/GB01/04329

§ 371 (c)(1),
(2), (4) Date: Aug. 27, 2003

(87) PCT Pub. No.: WO02/26696

PCT Pub. Date: Apr. 4, 2002

(65) Prior Publication Data

US 2004/0092598 A1    May 13, 2004

Related U.S. Application Data

(60) Provisional application No. 60/297,785, filed on Jun. 14, 2001.

(30) Foreign Application Priority Data

Sep. 29, 2000  (GB) ................... 0023985.5

(51) Int. Cl.
C07C 239/00  (2006.01)
(52) U.S. Cl. ..................................... 564/155
(58) Field of Classification Search .................. 564/155
See application file for complete search history.

(56) References Cited

U.S. PATENT DOCUMENTS

| 5,369,108 A | 11/1994 | Breslow |
| 5,700,811 A | 12/1997 | Breslow |
| 5,804,601 A | 9/1998 | Kato |
| 5,834,249 A | 11/1998 | Furukawa |
| 6,225,311 B1 * | 5/2001 | Levin et al. ............... 514/227.5 |

FOREIGN PATENT DOCUMENTS

| EP | 0 301 861 A1 | 2/1989 |
| EP | 0 827 742 A1 | 3/1998 |
| JP | 10-114681 A2 | 5/1998 |
| JP | 10-182583 | 7/1998 |
| WO | WO 93/12075 | 6/1993 |
| WO | WO 95/31977 | 11/1995 |
| WO | 98/26773 A | 6/1998 |
| WO | WO 98/55449 | 12/1998 |
| WO | WO 00/21979 | 4/2000 |
| WO | 00/44709 A | 8/2000 |
| WO | 00/44713 A | 8/2000 |
| WO | WO 01/18171 | 3/2001 |
| WO | WO 01/38322 | 5/2001 |
| WO | WO 02/22577 | 3/2002 |

OTHER PUBLICATIONS

Jung et al; "Analogues of Trichostatin A and Trapoxin B as Histone Deacetylase Inhibitors"; Bioorganic & Medicinal Chemistry Letters, Oxford, GB, vol. 7, No. 13, Jul. 8, 1997, pp. 1655-1658, XP004136274.

Schmidt et al; "Inhibitors of Histone Deacetylase Suppress the Growth of MCF-7 Breast Cancer Cells"; Archiv DER Pharmazie, VCH Verlagsgesellschaft MBH, Weinheim, DE, vol. 332, No. 10, 1999, pp. 353-357, XP000985303.

Jung et al; "Amide Analogues of Trichostatin A as Inhibitors of Histone Deacetylase and Inducers of Terminal Cell Differentiation"; Journal of Medicinal Chemistry, American Chemical Society, Washington, US, vol. 42, NO. 22, Nov. 4, 1999, pp. 4669-4679, XP002144226.

(Continued)

*Primary Examiner*—Janet L. Andes
*Assistant Examiner*—Raymond Covington
(74) *Attorney, Agent, or Firm*—Nixon & Vanderhye P.C.

(57) ABSTRACT

This invention pertains to certain active carbamic acid compounds which inhibit HDAC activity and which have the formula (1) wherein: A is an aryl group; Q1 is an aryl leader group having a backbone of at least 2 carbon atoms; J is an amide linkage selected from: —NR1C(=O)— and —C(=O)NR1-; R1 is an amido substituent; and, Q2 is an acid leader group; and pharmaceutically acceptable salts, solvates, amides, esters, ethers, chemically protected forms, and prodrugs thereof. The present invention also pertains to pharmaceutical compositions comprising such compounds, and the use of such compounds and compositions, both in vitro and in vivo, to inhibit HDAC, and, e.g., to inhibit proliferative conditions, such as cancer and psoriasis.

93 Claims, No Drawings

OTHER PUBLICATIONS

Andrews et al., 2000, "Anti-malarial effect of histone deacetylation inhibitors and mammalian tumour cytodifferentiating agents" *Int. J. Parasitol.*, vol.30, No. 6, pp. 761-768.

Anghelova, Y. et al, 1973, "Kondensation, der Äthylester von Croton-, 3-Methylcroton- und Isopropylidenmalonsäure mit aromatischen Aldehyden" *Chem. Ber.*, vol. 106, p. 2643.

Backer, H.J., et al., 1940, "Condensation de la benzile avec les acides oxy-, thio, et sélénodiacetiques" *Recl. Trav. Chim. Pays-Bas*, vol. 59, p. 423.

Banerji, A., et al., 1984, "Substituent effects on carbon-13 NMR chemical shifts of side-chain carbons in 5-aryl-2E,4E-pentadienoic acid derivatives" *Indian J. Chem.*, vol. 23B, pp. 546-549.

Bellamy, F.D., et al., 1984, "Selective reduction of aromatic nitro compounds with stannous chloride in non-acidic and non-aqueous medium." *Tetrahedron Letters*, vol. 25, No. 8, p. 839.

Bernhard, D. et al., 1999, "Apoptosis induced by the histone deacetylase inhibitor sodium butyrate in human leukemic lymphoblasts," *FASEB J.*, vol. 13, No. 14, pp. 1991-2001.

Bernstein et al., 2000, "Genomewide studies of histone deacetylase function in yeast." *Proc. Natl. Acad. Sci. USA*, vol. 97, No. 25, pp. 13708-13713.

Bistrzycki A et al 1912, "Die Konstitution der Verbindungen aus o-Diaminen and □-Oxysäuren" *Chem. Ber.*, vol. 45, p. 3483.

Brehm, A., et al., 1998, "Retinoblastoma protein recruits histone deacetylase to repress transcription," *Nature*, 1998, vol. 391, pp. 597-601.

Carbonnier, J., et al., 1981, "Activité antitranspirante d'analogues de l'acide abscissique" *Physiol. Plant.*, 1981, vol. 51, p. 1.

Chang et al., 2000, "Activation of the BRLF1 promoter and lytic cycle of Epstein-Barr virus by histone acetylation." *Nucleic Acids Res.*, vol. 28, No. 20, pp. 3918-3925.

Chen, W.-S., et al., 1978," Ambivalent active-site-directed inactivators of liver alcohol dehydrogenase." *Biochemistry*, vol. 17, No. 23, p. 4916.

Copeland, R.A.B., et al., 1943, The Preparation and Reactions of 2-Benzimidazolecarboxylic Acid and 2-Benzimidazoleacetic Acid *J. Amer. Chem. Soc.*, vol. 65, p. 1072.

Dangond et al., 1998, "Differential display cloning of a novel human histone deacetylase (HDAC3) cDNA from PHA-activated immune cells." *Biochem. Biophys. Res. Commun.*, vol. 242, No. 3, pp. 648-652.

David, G., et al., 1998, "Histone deacetylase associated with mSin3A mediates repression by the acute promyelocytic leukaemia-associated PLZF protein." *Oncogene*, vol. 16(19), pp. 2549-2556.

Davie, J.R., 1998, "Covalent modifications of histones: expression from chromatin templates," *Curr. Opin. Genet. Dev.*, vol. 8, pp. 173-178.

Desai, D et al., 1999, "Chemopreventive efficacy of suberanilohydroxamic acid (SAHA), a cytodifferentiating agent, against tobacco-specific nitrosamine 4-(-methylnitros-amino)-1-(3-pyridyl)-1-butanone (NNK)-induced lung tumorigenesis in female A/J mice." *Proc. AACR*, vol. 40, abstract #2396.

Emiliani, S., et al., 1998, "Characterization of a human RPD3 ortholog, HDAC3," *Proc. Natl. Acad. Sci. USA*, vol. 95, p. 2795-2800.

Finnin et al., 1999, "Structures of a histone deacetylase homologue bound to the TSA and SAHA inhibitors." *Nature*, vol. 401, pp. 188-193.

Glick, R.D., et al., 1999, "Hybrid polar histone deacetylase inhibitor induces apoptosis and CD95/CD95 ligand expression in human neuroblastoma," *Cancer Research*, vol. 59, No. 17, pp. 4392-4399.

Grozinger et al., 1999, "Three proteins define a class of human histone deacetylases related to yeast Hda1p." *Proc. Natl. Acad. Sci. USA*, vol. 96, pp. 4868-4873.

Hoshikawa, Y., et al., 1994, "Trichostatin A induces morphological changes and gelsolin expression by inhibiting histone deacetylase in human carcinoma cell lines."*Exp. Cell. Res.*, vol. 214(1), pp. 189-197.

Jung et al., 1997, "Analogues of trichostatin A and trapoxin B as histone deacetylase inhibitors" *Bioorg. Med. Chem. Lett.*, vol. 7, No. 13, pp. 1655-1658.

Jung et al., 1999, "Amide analogues of trichostatin A as inhibitors of histone deacetylase and inducers of terminal cell differentiation." *J. Med. Chem.*, vol. 42, pp. 4669-4679.

Kao et al., 2000, "Isolation of a novel histone deacetylase reveals that class I and class II deactylases promote SMRT-mediated repression" *Genes Dev.*, vol. 14, p. 55-66.

Kijima et al., 1993, "Trapoxin, an antitumor cyclic tetrapeptide, is an irreversible inhibitor of mammalian histone deacetylase." *J. Biol. Chem.*, vol. 268, pp. 22429-22435.

Howe, L., et al., 1999, "Histone acetyltransferase complexes and their link to transcription" *Crit. Rev. Eukaryot. Gene Expr.*, vol. 9(3-4), pp. 231-243.

Iavarone et al., 1999, "E2F and histone deacetylase mediate transforming growth factor beta repression of cdc25A during keratinocyte cell cycle arrest." *Mol. Cell Biol.*, vol. 19, No. 1, pp. 916-922.

Kim, M.S., et al., 2001 "Histone deacetylase induce angiogenesis by negative regulation of tumour suppressor genes," *Nature Medicine*, vol. 7. No. 4 pp. 437-443.

Kimura et al., 1994, "Dual modes of action of platelet-derived growth factor and its inhibition by trichostatin-A for DNA synthesis in primary cultured smooth muscle cells of rat aorta". *Biol. Pharm. Bull.*, vol. 17, No. 3, pp. 399-402.

Kitamura, K., et al., 2000, Histone deacetylase inhibitor but not arsenic trioxide differentiates acute promyelocytic leukaemia cells with t(11;17) in combination with all-trans retinoic acid *Br. J. Haematol.*, vol. 108(4), pp. 696-702.

Kouzarides, T., 1999, "Histone acetylases and deacetylase in cell proliferation," *Curr. Opin. Genet. Dev.*, vol. 9, No. 1, pp. 40-48.

Kuusisto et al., 2001, "Ubiquitin-binding protein p62 expression is induced during apoptosis and proteasomal inhibition in neuronal cells."*Biochem. Biophys. Res. Commun.*, vol. 280, No. 1, pp. 223-228.

Kwon et al., 1998, "Depudecin induces morphological reversion of transformed fibroblasts via the inhibition of histone deacetylase" *Proc. Natl. Acad. Sci. USA*, vol. 95, pp. 3356-3361.

Laherty, C.D., et al., 1997, "Histone deacetylases associated with the mSin3 corepressor mediate mad transcriptional repression" *Cell*, vol. 89(3), pp. 349-356.

Lea et al 1995, "Discordant effects of butyrate analogues on erythroleukemia cell proliferation, differentiation and histone deacetylase" *Anticancer Res.*, vol. 15, pp. 879-883.

Lea et al., 1999, "Increased acetylation of histones induced by diallyl disulfide and structurally related molecules" *Int. J. Oncol.*, vol. 2, pp. 347-352.

Lin, R.J., et al., 1998, "Role of the histone deacetylase complex in acute promyelocytic leukaemia." *Nature*, vol. 391(6669), pp. 811-814.

Massa et al., 2001, "3-(4-aroyl-1H-pyrrol-2-yl)-N-hydroxy-2-propenamides, a new class of synthetic histone deacetylase inhibitors" *J. Med. Chem.*, vol. 44, No. 13, pp. 2069-2072.

McCaffrey et al., 1997, "Induction of gamma-globin by histone deacetylase inhibitors" *Blood*, vol. 90, No. 5, pp. 2075-2083.

Kim et al., 1999, "Oxamflatin is a novel antitumor compound that inhibits mammalian histone deacetylase" *Oncogene*, vol. 18(15), pp. 2461-2470.

Meilnicki, L.M., et al., 1999, "Epigenetic regulation of gelsolin expression in human breast camcer cells." *Exp. Cell. Res.*, vol. 249(1), pp. 161-176.

Ng, H.H. and Bird, A., 2000, "Histone deacetylase: silencers for hire." *Trends Biochem. Sci.*, vol. 25(3), pp. 121-126.

Niki et al., 1999, "A histone deacetylase inhibitor, trichostatin A, suppresses myofibroblastic differentiation of rat hepatic stellate cells in primary culture" *Hepatology*, vol. 29, No. 3, pp. 858-867.

Nokajima et al., 1998, "FR901228; a potent antitumor antibiotic, is a novel histone deacetylase inhibitor" *Exp. Cell Res.*, vol. 241, pp. 126-133.

Ohtani et al., 1996, "(2E)-5-[3-[(Phenylsulfonyl)amino] phenyl]-pent-2-en-4-yno-hydroxamic acid and its derivatives as novel and potent inhibitors of ras transformation," *J. Med. Chem.*, vol. 39, No. 15, pp. 2871-2873.

Onishi et al., 1996, "Antibacterial agents that inhibit lipid A biosynthesis" *Science*, vol. 274, pp. 939-940.

Pazin, M.J., et al., 1997, "What's up and down with histone deacetylation and transcription?," *Cell*, vol. 89, No. 3, pp. 325-328.

Richon et al, 1996, "Second generation hybrid polar compounds are potent inducers of transformed cell differentiation" *Proc. Natl. Acad. Sci. USA*, vol. 93, pp. 5705-5708.

Richon et al., 1998, "A class of hybrid poler inducers of transformed cell differentiation inhibits histone deacetylases," *Proc. Natl. Acad. Sci. USA*, vol. 95, pp. 3003-3007.

Saito et al., 1999, "A synthetic inhibitor of histone deacetylase, MS-27-275, with marked in vivo anitumor activity against human tumors" *Proc. Natl. Acad. Sci. USA*, vol. 96, pp. 4592-4597.

Saunders, N. et al, 1999 "Histone deacetylase inhibitors as potential anti-skin cancer agents," *Cancer Res.*, vol. 59, No. 2 pp. 399-404.

Sonoda, H. et al., 1996, Oxamflatin: a novel compound which reverses malignant phenotype to normal one via induction of JunD *Oncogene*, vol. 13, pp. 143-149.

Spencer, V.A. et al., 1999, "Role of covalent modifications of histones in regulating gene expression." *Gene*, vol. 240(1), pp. 1-12.

Suzuki et al., 1999, "Synthesis and histone deacetylase inhibitory activity of new benzamide derivatives," *J. Med. Chem.*, vol. 42, pp. 3001-3003.

Takahashi, I., et al, 1996, "Selective inhibition of IL-2 gene expression by trichostatin A, a potent inhibitor of mammalian histone deacetylase," *J. Antibiot.* (Tokyo), vol. 49, No. 5, pp. 453-457.

Taunton, J., et al., 1996, "A mammalian histone deacetylase related to the yeast transcriptional regulator Rpd3p," *Science*, vol. 272, pp. 408-411.

Tsuji et al., 1976, "A new antifungal antibiotic, trichostatin" *J. Antibiot.* (Tokyo), vol. 29, No. 1, pp. 1-6.

Ueda, H., et al., 1994 "FR901228, a novel antitumor bicyclic depsipeptide produced by *Chromabacterium violaceum* No. 968. III. Antitumor activities on experimental tumors in mice" .*J. Antibiot.* (Tokyo), vol. 47(3), pp. 315-323.

Van den Wyngaert et al., 2000, "Cloning and characterization of human histone deacetylase 8". *FEBS Lett.*, vol. 478, pp. 77-83.

Vig, B., et al., 1977, "Synthesis of analogues of 6-phenylpenta-trans-2, trans-4-dienoic acid amide." *Indian J. Chem.*, vol. 15B, pp. 1048-1049.

Vigushin et al., 2001, "Trichostatin A is a histone deacetylase inhibitor with potent antitumor activity against breast cancer in vivo" *Clin. Cancer Res.*, vol. 7, No. 4, pp. 971-976.

Villieras, J., et al., 1983, "Wittig-Horner reactions in heterogeneous media; $2^1$. A convenient synthesis of a,b-unsaturated esters and ketones using weak bases in water." *Synthesis*, pp. 300-303.

Warrell et al., 1998, "Therapeutic targeting of transcription in acute promyelocytic leukemia by used of an inhibitor of histone deacetylase." *J. Natl. Cancer Inst.*, vol. 90, pp. 1621-1625.

Wong, J. et al., 1998, "Distinct requirements for chromatin assembly in transcriptional repression by thyroid hormone receptor and histone deacetylase" *EMBO J.*, vol. 17(2), pp. 520-534.

Yang, W.M., et al., 1996, "Transcriptional repression of YY1 is mediated by interaction with a mammalian homolog of the yeast global regulator RPD3," *Proc. Natl. Acad. Sci. USA*, vol. 93, pp. 12845-12850.

Yang, W.M., et al., 1997, "Isolation and characterization of cDNAs corresponding to an additional member of the human histone deacetylase gene family," *J. Biol. Chem.*, vol. 272, pp. 28001-28007.

Yoshida et al., 1995, "Trichostatin A and trapoxin: novel chemical probes for the role of histone acetylation in chromatin structure and function" *Bioessays*, vol. 17, pp. 423-430.

Yoshida, M. et al 1999, " Trichostatin and leptomycin: inhibition of histone deacetylation ánd signal-dependent nuclear export" *Ann. N.Y. Acad. Sci.*, vol. 886, pp. 23-36.

Yoshida, M., et al 1988, "Reversible arrest of proliferation of rat 3Y1 fibroblasts in both G1 and G2 phases by trichostatin A," *Exp. Cell. Res.*, vol. 177, pp. 122-131.

Yoshida, M., et al., 1990, "Potent and specific inhibition of mammalian histone deacetylase both in vivo and in vitro by trichostatin A" *J. Biol. Chem.*, vol. 265(28), pp. 17174-17179.

Yoshida, M., et al., 1990, "Structural specificity for biological activity of trichostatin A, a specific inhibitor of mammalian cell cycle with potent differentiation-inducing activity in Friend leukemia cells". *J. Antibiot.* (Tokyo), vol. 43(9), pp. 1101-1106.

Onishi et al, *Science*, vol. 274, pp. 980-982 (Nov. 8, 1996).

Kato et al CA 91:107818d(1979) JP 54-36229.

Warrell et al., Journal of the National Cancer Institute, vol. 90, No. 21, Nov. 4, 1998 "Therapeutic Targeting of Transcription in Acute Promyelocytic Leukemia by Use of an Inhibitor of Histone Deacetylase".

* cited by examiner

CARBAMIC ACID COMPOUNDS COMPRISING AN AMIDE LINKAGE AS HDAC INHIBITORS

This application is the U.S. national phase of international application PCT/GB01/04329 filed 27 Sep. 2001, which designated the U.S., and claims benefit of U.S. Provisional application Ser. No. 60/297,785, filed 14 Jun. 2001.

RELATED APPLICATIONS

This application claims priority to United Kingdom Patent Application Number GB 0023985.5 filed 29 Sep. 2000; and U.S. Provisional Patent Application No. 60/297,785 filed 14 Jun. 2001; the contents of each of which are incorporated herein by reference in their entirety.

TECHNICAL FIELD

This invention pertains generally to the field of biologically active compounds, and more specifically to certain active carbamic acid compounds which inhibit HDAC (histone deacetylase) activity. The present invention also pertains to pharmaceutical compositions comprising such compounds, and the use of such compounds and compositions, both in vitro and in vivo, to inhibit HDAC, and, e.g., to inhibit proliferative conditions, such as cancer and psoriasis.

BACKGROUND

DNA in eukaryotic cells is tightly complexed with proteins (histones) to form chromatin. Histones are small, positively charged proteins which are rich in basic amino acids (positively charged at physiological pH), which contact the phosphate groups (negatively charged at physiological pH) of DNA. There are five main classes of histones, H1, H2A, H2B, H3, and H4. The amino acid sequences of histones H2A, H2B, H3, and H4 show remarkable conservation between species, whereas H1 varies somewhat, and in some cases is replaced by another histone, e.g., H5. Four pairs of each of H2A, H2B, H3, and H4 together form a disk-shaped octomeric protein core, around which DNA (about 140 base pairs) is wound to form a nucleosome. Individual nucleosomes are connected by short stretches of linker DNA associated with another histone molecule (e.g., H1, or in certain cases, H5) to form a structure resembling a beaded string, which is itself arranged in a helical stack, known as a solenoid.

The majority of histones are synthesised during the S phase of the cell cycle, and newly synthesised histones quickly enter the nucleus to become associated with DNA. Within minutes of its synthesis, new DNA becomes associated with histones in nucleosomal structures.

A small fraction of histones, more specifically, the amino side chains thereof, are enzymatically modified by post-translational addition of methyl, acetyl, or phosphate groups, neutralising the positive charge of the side chain, or converting it to a negative charge. For example, lysine and arginine groups may be methylated, lysine groups may be acetylated, and serine groups may be phosphorylated. For lysine, the —$(CH_2)_4$—$NH_2$ sidechain may be acetylated, for example by an acetyltransferase enzyme, to give the amide —$(CH_2)_4$—$NHC(=O)CH_3$. Methylation, acetylation, and phosphorylation of amino termini of histones which extend from the nucleosomal core affects chromatin structure and gene expression. (See, for example, Spencer and Davie, 1999).

Acetylation and deacetylation of histones is associated with transcriptional events leading to cell proliferation and/or differentiation. Regulation of the function of transcription factors is also mediated through acetylation. Recent reviews of histone deacetylation include Kouzarides, 1999 and Pazin et al., 1997.

The correlation between the acetylation status of histones and the transcription of genes has been known for over 30 years (see, for example, Howe et al., 1999). Certain enzymes, specifically acetylases (e.g., histone acetyltransferase, HAT) and deacetylases (e.g., histone deacetylase, HDAC), which regulate the acetylation state of histones have been identified in many organisms and have been implicated in the regulation of numerous genes, confirming the link between acetylation and transcription. See, for example, Davie, 1998. In general, histone acetylation correlates with transcriptional activation, whereas histone deacetylation is associated with gene repression.

A growing number of histone deacetylases (HDACs) have been identified (see, for example, Ng and Bird, 2000). The first deacetylase, HDAC1, was identified in 1996 (see, for example, Tauton et al., 1996). Subsequently, two other nuclear mammalian deacetylases has been found, HDAC2 and HDAC3 (see, for example, Yang et al., 1996, 1997, and Emiliani et al., 1998). See also, Grozinger et al., 1999; Kao et al., 2000; and Van den Wyngaert et al., 2000.

Eight human HDACs have been cloned so far:

HDAC1 (Genbank Accession No. NP_004955)

HDAC2 (Genbank Accession No. NP_001518)

HDAC3 (Genbank Accession No. O15739)

HDAC4 (Genbank Accession No. AAD29046)

HDAC5 (Genbank Accession No. NP_005465)

HDAC6 (Genbank Accession No. NP_006035)

HDAC7 (Genbank Accession No. AAF63491)

HDAC8 (Genbank Accession No. AAF73428)

These eight human HDACs fall in two distinct classes: HDACs 1,2,3 and 8 are in class I, and HDACs 4,5,6 and 7 are in class II.

There are a number of histone deacetylases in yeast, including the following:

RPD3 (Genbank Accession No. NP_014069)

HDA1 (Genbank Accession No. P53973)

HOS1 (Genbank Accession No. Q12214)

HOS2 (Genbank Accession No. P53096)

HOS3 (Genbank Accession No. Q02959)

There are also numerous plant deacetylases, for example, HD2, in *Zea mays* (Genbank Accession No. AF254073_1).

HDACs function as part of large multiprotein complexes, which are tethered to the promoter and repress transcription. Well characterised transcriptional repressors such as Mad (Laherty et al., 1997), pRb (Brehm et al., 1998), nuclear receptors (Wong et al., 1998) and YY1 (Yang et al., 1997) associate with HDAC complexes to exert their repressor function.

The study of inhibitors of histone deacetylases indicates that these enzymes play an important role in cell proliferation and differentiation. The inhibitor Trichostatin A (TSA) (Yoshida et al., 1990a) causes cell cycle arrest at both G1 and G2 phases (Yoshida and Beppu, 1988), reverts the transformed phenotype of different cell lines, and induces differentiation of Friend leukaemia cells and others (Yoshida et al., 1990b). TSA (and SAHA) have been reported to inhibit cell growth, induce terminal differentiation, and prevent the formation of tumours in mice (Finnin et al., 1999).

Trichostatin A (TSA)

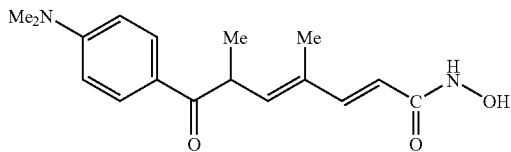

Suberoylanilide Hydroxamic Acid (SAHA)

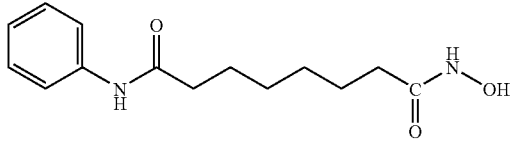

Cell cycle arrest by TSA correlates with an increased expression of gelsolin (Hoshikawa et al., 1994), an actin regulatory protein that is down regulated in malignant breast cancer (Mielnicki et al., 1999). Similar effects on cell cycle and differentiation have been observed with a number of deacetylase inhibitors (Kim et al., 1999).

Trichostatin A has also been reported to be useful in the treatment of fibrosis, e.g., liver fibrosis and liver cirrhosis. See, e.g., Geerts et al., 1998.

Recently, certain compounds that induce differentiation have been reported to inhibit histone deacetylases. Several experimental antitumour compounds, such as trichostatin A (TSA), trapoxin, suberoylanilide hydroxamic acid (SAHA), and phenylbutyrate have been reported to act, at least in part, by inhibiting histone deacetylase (see, e.g., Yoshida et al., 1990; Richon et al., 1998; Kijima et al., 1993). Additionally, diallyl sulfide and related molecules (see, e.g., Lea et al., 1999), oxamflatin (see, e.g., Kim et al., 1999), MS-27-275, a synthetic benzamide derivative (see, e.g., Saito et al., 1999; Suzuki et al., 1999; note that MS-27-275 was later re-named as MS-275), butyrate derivatives (see, e.g., Lea and Tulsyan, 1995), FR901228 (see, e.g., Nokajima et al., 1998), depudecin (see, e.g., Kwon et al., 1998), and m-carboxycinnamic acid bishydroxamide (see, e.g., Richon et al., 1998) have been reported to inhibit histone deacetylases. In vitro, some of these compounds are reported to inhibit the growth of fibroblast cells by causing cell cycle arrest in the G1 and G2 phases, and can lead to the terminal differentiation and loss of transforming potential of a variety of transformed cell lines (see, e.g., Richon et al, 1996; Kim et al., 1999; Yoshida et al., 1995; Yoshida & Beppu, 1988). In vivo, phenybutyrate is reported to be effective in the treatment of acute promyelocytic leukemia in conjunction with retinoic acid (see, e.g., Warrell et al., 1998). SAHA is reported to be effective in preventing the formation of mammary tumours in rats, and lung tumours in mice (see, e.g., Desai et al., 1999).

The clear involvement of HDACs in the control of cell proliferation and differentiation suggest that aberrant HDAC activity may play a role in cancer. The most direct demonstration that deacetylases contribute to cancer development comes from the analysis of different acute promyelocytic leukaemias (APL). In most APL patients, a translocation of chromosomes 15 and 17 (t(15;17)) results in the expression of a fusion protein containing the N-terminal portion of PML gene product linked to most of RARα (retinoic acid receptor). In some cases, a different translocation (t(11;17)) causes the fusion between the zinc finger protein PLZF and RARα. In the absence of ligand, the wild type RARα represses target genes by tethering HDAC repressor complexes to the promoter DNA. During normal hematopoiesis, retinoic acid (RA) binds RARα and displaces the repressor complex, allowing expression of genes implicated in myeloid differentiation. The RARα fusion proteins occurring in APL patients are no longer responsive to physiological levels of RA and they interfere with the expression of the RA-inducible genes that promote myeloid differentiation. This results in a clonal expansion of promyelocytic cells and development of leukaemia. In vitro experiments have shown that TSA is capable of restoring RA-responsiveness to the fusion RARα proteins and of allowing myeloid differentiation. These results establish a link between HDACs and oncogenesis and suggest that HDACs are potential targets for pharmaceutical intervention in APL patients. (See, for example, Kitamura et al., 2000; David et al., 1998; Lin et al., 1998).

Furthermore, different lines of evidence suggest that HDACs may be important therapeutic targets in other types of cancer. Cell lines derived from many different cancers (prostate, colorectal, breast, neuronal, hepatic) are induced to differentiate by HDAC inhibitors (Yoshida and Horinouchi, 1999). A number of HDAC inhibitors have been studied in animal models of cancer. They reduce tumour growth and prolong the lifespan of mice bearing different types of transplanted tumours, including melanoma, leukaemia, colon, lung and gastric carcinomas, etc. (Ueda et al., 1994; Kim et al., 1999).

Psoriasis is a common chronic disfiguring skin disease which is characterised by well-demarcated, red, hardened scaly plaques: these may be limited or widespread. The prevalence rate of psoriasis is approximately 2%, i.e., 12.5 million sufferers in the triad countries (US/Europe/Japan). While the disease is rarely fatal, it clearly has serious detrimental effects upon the quality of life of the patient: this is further compounded by the lack of effective therapies. Present treatments are either ineffective, cosmetically unacceptable, or possess undesired side effects. There is therefore a large unmet clinical need for effective and safe drugs for this condition.

Psoriasis is a disease of complex etiology. Whilst there is clearly a genetic component, with a number of gene loci being involved, there are also undefined environmental triggers. Whatever the ultimate cause of psoriasis, at the cellular level, it is characterised by local T-cell mediated inflammation, by keratinocyte hyperproliferation, and by localised angiogenesis. These are all processes in which histone deacetylases have been implicated (see, e.g., Saunders et al., 1999; Bernhard et al, 1999; Takahashi et al, 1996; Kim et al, 2001). Therefore HDAC inhibitors may be of use in therapy for psoriasis. Candidate drugs may be screened, for example, using proliferation assays with T-cells and/or keratinocytes.

Thus, one aim of the present invention is the provision of compounds which are potent inhibitors of histone deacetylases (HDACs). There is a pressing need for such compounds, particularly for use as antiproliferatives, for example, anticancer agents, agents for the treatment of psoriasis, etc.

Such molecules desirably have one or more of the following properties and/or effects:

(a) easily gain access to and act upon tumour cells;
(b) down-regulate HDAC activity;
(c) inhibit the formation of HDAC complexes;

(d) inhibit the interactions of HDAC complexes;
(e) inhibit tumour cell proliferation;
(e) promote tumour cell apoptosis;
(f) inhibit tumour growth; and,
(g) complement the activity of traditional chemotherapeutic agents.

A number of carbamic acid compounds have been described.

Amides

Hashimoto et al., 1989 describe hydroxamic acid compounds which are claimed to inhibit cell proliferation. Some of the compounds are carbamic acid compounds having a substituted phenyl-dione group linked to a carbamic acid group (—CONHOH) via an aryl-substituted alkylene group.

Ohtani et al., 1993 describe a number of hydroxamic acid compounds which are claimed to be inhibitors of ras transformation. A few of the compounds are carbamic acid compounds having a phenylacylamido group (—NHCOPh) linked to a carbamic acid group (—CONHOH) via a phenylene-meta-alkylene group having a carbon-carbon triple bond. See, for example, compounds I-29 (page 69), I-39 (page 87), and I-41 (page 90). Compound I-41, shown below, employs an aryl leader.

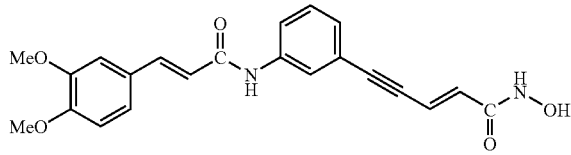

Onishi et al., 1996, describe several hydroxamic acid compounds which have a phenyl (or substituted phenyl) group linked via an oxazole group to a carbamic acid group. These compounds were reported to inhibit a deacetylase enzyme critical in the biosynthesis of lipid A (a component of the outer membrane of Gram-negative bacteria).

Parsons et al., 1998 describe a number of hydroxamic acid compounds which are claimed to selectively prevent the growth of a variety of human tumour cell lines.

Some of the compounds are carbamic acid compounds having an arylamide group linked to a carbamic acid group via a methylene or substituted methylene group (see, for example, pages 16 and 17).

Some of the compounds are carbamic acid compounds having a phenylamido group (—CONHPh) linked to a carbamic acid group (—CONHOH) via a long alkylene chain, —(CH$_2$)$_n$—, wherein n is from 4 to 7 (see, for example, pages 47, 48, and 58 therein).

Some of the compounds are carbamic acid compounds having an aryl group linked via a short chain to an amide group (—CONH—), which in turn is linked via a short chain (e.g., 3 atoms or less) to a carbamic acid group (—CONHOH). See, for example, page 16, 2nd formula; page 46, 4th formula; page 51, compound 7; and page 61, 2nd formula.

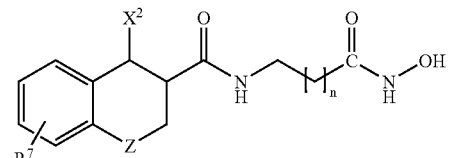

n = 0, 1, 2

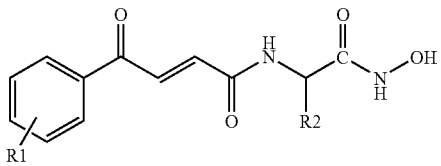

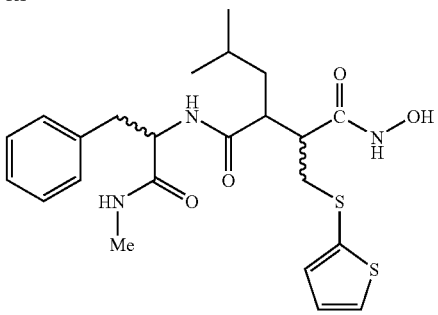

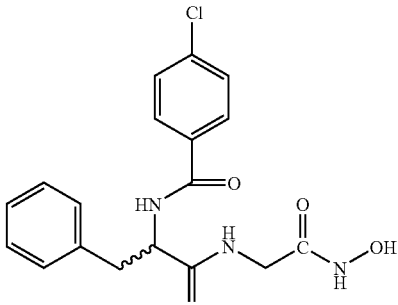

Richon et al., 1998 describe several hydroxamic acid compounds, including SAHA, which apparently inhibit HDAC activity, and induce terminal differentiation and/or apoptosis in various transformed cells (see, for example, Table 1 therein).

Suzuki et al., 1998 describe a number of hydroxamic acid compounds which are claimed to have antitumour activity. Some of the compounds are carbamic acid compounds having a substituted phenylamido group (—CONHPh) linked to a carbamic acid (—CONHOH) group via a phenylene-meta-ethenylene or phenylene-para-ethenylene group (see, for example, pages 8 and 9, compounds 31-50).

Breslow et al., 1994, 1995, 1997 describe a number of hydroxamic acid compounds which are claimed to selectively induce terminal differentiation of neoplastic cells.

Some of the compounds are carbamic acid compounds having a substituted phenylacylamido group (—NHCOPh) linked to a carbamic acid (—CONHOH) group via a long alkylene chain, —(CH$_2$)$_n$—, wherein n is from 4 to 8

Some of the compounds are carbamic acid compounds having a substituted phenylamido group (—CONHPh) or phenylacylamido group (—NHCOPh) linked to a carbamic acid (—CONHOH) group via a long alkylene chain, —(CH$_2$)$_n$—, wherein n is from 4 to 8 (see, for example, columns 7 and 13 of Breslow et al., 1997), or via a phenylene group (see, for example, columns 24, 30-31 and compounds 20-55 in Table 1 of Breslow et al., 1997).

One of the compounds is a carbamic acid compound having benzylamido group (—CONHCH$_2$Ph) linked to a carbamic acid group (—CONHOH) via a —(CH$_2$)$_6$— group (see, for example, compound 19 in Table 1, at column 37 of Breslow et al., 1997).

Jung et al., 1997, 1999, describe several aromatic hydroxamic acid compounds which apparently inhibit HDAC. Some of the compounds have a phenylamido group (PhCONH—). One compound, a peptide analog, is shown below (see, e.g., compound 6 in Jung et al., 1997; compound 4 in Jung et al., 1999).

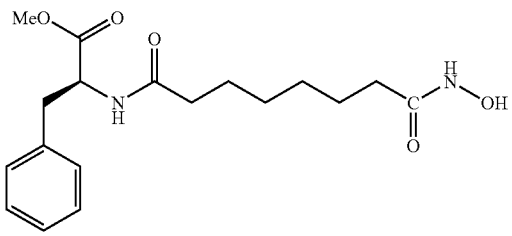

Kato et al., 1998, describe a number of aromatic hydroxamic acid compounds, comprising an aryl group linked via an alkylene group to a carbamic acid group, which are apparently active in the treatment of neurodegenerative conditions. One compound, 4-1 at columns 63-64, has a phenylamido group (PhCONH—) linked via a —(CH$_2$)$_5$— group to a carbamic acid group.

Glick et al., 1999, describe the apparent apoptotic and differentiating effects of m-carboxy-cinnamic acid bishydroxamide (CBHA) on various tumour cell lines.

Massa et al., 2001, describe various hydroxamic acid compounds which have a benzoyl (or substituted benzoyl) group linked via a pyrrolyl group and an C$_2$alkylene group (—CH=CH— or —CH$_2$CH$_2$—) to a carbamic acid group. The compounds apparently showed HDAC inhibitory activity in the micromolar range.

Sulfonamides

Oxamflatin, also known as (2E)-5-[3-[(phenylsulfonyl)amino]phenyl]-pent-2-en-4-ynohydroxamic acid, shown below, has been reported to have in vitro antiproliferative activity against various mouse and human tumour cell lines, and in vivo antitumour activity against B16 melanoma (see, e.g., Sonoda et al., 1996; Kim et al., 1999).

Oxamflatin

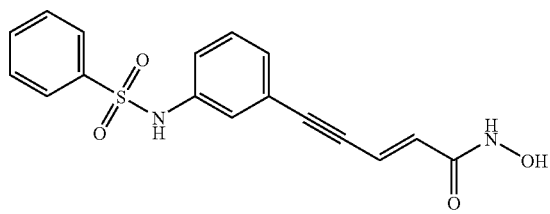

Ohtani et al., 1993, describe a number of hydroxamic acid compounds which are claimed to be inhibitors of ras transformation. Many of the compounds are hydroxmic acid compounds which have a sulfonamide group, and which employ an acid leader which is: a phenylene-ortho-alkylene (e.g., I-10); phenylene-meta-alkylene (e.g., I-24); phenylene-para-alkylene (e.g., I-12); or napthylen-1,2-diyl (e.g., I-20). However, in every case, the sulfonamide group is —SO$_2$NR—, as opposed to —NRSO$_2$—. Also, in every case, the terminal aryl group is linked directly to the —SO$_2$NR— sulfonamide group, without an intervening aryl leader. Ohtani et al., 1996, describe similar compounds.

Richon et al., 2001, describe various branched compounds which apparently inhibit histone deacetylase. See the table at pages 96-101 therein. Some of the compounds are carbamic acid compounds having a carbamic acid group (—CONHOH) linked to a branch point, from which two aryl groups are appended. A few linear carbamic acid compounds are also described, including a single —SO$_2$NH— sulfonamide carbamic acid with a —(CH$_2$)$_5$— acid leader (compound 671).

Delorme et al., 2001, describe various carbamic acid compounds, including compounds having, inter alia, a sulfonamide group. Of the 108 compounds in the table at pages 114-123 therein, 88 are carbamic acids (—CONHOH), and the remainder are terminal amides, —CONHR. Of the 88 carbamic acid compounds, 54 have a sulfonamide linkage.

Of the 54 sulfonamide carbamic acids, 51 are indicated to have a —SO$_2$NR— sulfonamide group, and 3 (compounds 98, 161, and 162) are indicated to have a —NRSO$_2$— sulfonamide group.

All of the 54 sulfonamide carbamic acids employ a phenylene-alkylene acid leader group (analogous to Q$^2$ herein). Of the 54 compounds, 52 employ a phenylene-para-alkylene group, and only 2 (compounds 41 and 26) employ a phenylene-meta-alkylene group (-Ph—CH$_2$— and -Ph—(CH$_2$)$_4$—, respectively). Compounds 41 and 26 both have a —SO$_2$NR— sulfonamide group, as opposed to a —NRSO$_2$— sulfonamide group; the former has a benzothiophenyl group, and the latter has a phenyl group.

All but one of the 54 sulfonamide carbamic acids have an aryl group linked directly to the sulfonamide; compound 100 has a benzyl group (Ph—CH$_2$—) linked a —SO$_2$NR— sulfonamide group linked to phenylene-para-ethylene.

SUMMARY OF THE INVENTION

One aspect of the invention pertains to active carbamic acid compounds, as described herein, which inhibit HDAC activity.

Another aspect of the invention pertains to active compounds, as described herein, which treat a proliferative condition, such as cancer, psoriasis, etc.

Another aspect of the invention pertains to active compounds, as described herein, which treat conditions which are known to be mediated by HDAC, or which are known to be treated by HDAC inhibitors (such as, e.g., trichostatin A).

Another aspect of the present invention pertains to a composition comprising a compound as described herein and a pharmaceutically acceptable carrier.

Another aspect of the present invention pertains to methods of inhibiting HDAC in a cell, comprising contacting said cell with an effective amount of an active compound, as described herein.

Another aspect of the present invention pertains to methods of inhibiting cell proliferation, comprising contacting a cell with an effective amount of an active compound, as described herein, whether in vitro or in vivo.

Another aspect of the present invention pertains to methods of treating a proliferative condition in a patient comprising administering to said patient a therapeutically-effective amount of an active compound, as described herein. In one preferred embodiment, the proliferative condition is cancer. In one preferred embodiment, the proliferative condition is psoriasis.

Another aspect of the present invention pertains to methods of treating a condition in a patient which is known to be mediated by HDAC, or which is known to be treated by HDAC inhibitors (such as, e.g., trichostatin A), comprising administering to said patient a therapeutically-effective amount of an active compound, as described herein.

Another aspect of the present invention pertains to an active compound, as described herein, for use in a method of treatment of the human or animal body.

Another aspect of the present invention pertains to use of an active compound, as described herein, for the manufacture of a medicament for use in the treatment of a proliferative condition. In one preferred embodiment, the proliferative condition is cancer. In one preferred embodiment, the proliferative condition is psoriasis.

Another aspect of the present invention pertains to use of an active compound for the manufacture of a medicament, for example, for the treatment of conditions which are known to be mediated by HDAC, or which are known to be treated by HDAC inhibitors (such as, e.g., trichostatin A), as discussed herein.

Another aspect of the present invention pertains to a kit comprising (a) the active compound, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

In one embodiment, the present invention pertains to carbamic acid compounds of the formula:

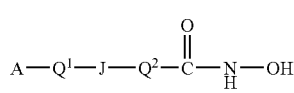

(1)

wherein:
A is an aryl group;
$Q^1$ is an aryl leader group having a backbone of at least two carbon atoms;
J is an amide linkage selected from:

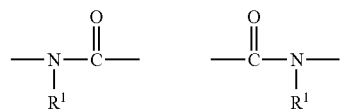

$R^1$ is an amido substituent; and,
$Q^2$ is an acid leader group;

and pharmaceutically acceptable salts, solvates, amides, esters, ethers, chemically protected forms, and prodrugs thereof.

In preferred embodiments, the carbamic acid group, —C(=O)NHOH, is unmodified (e.g., is not an ester).

In one preferred embodiment, J is —$NR^1CO$—, and the compounds have the following formula:

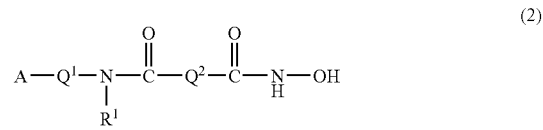

(2)

In one preferred embodiment, J is —$CONR^1$—, and the compounds have the following formula:

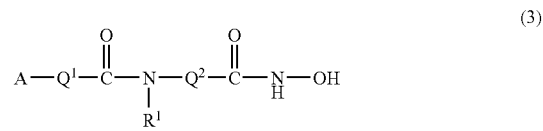

(3)

In one embodiment, where $Q^1$ is an aryl leader, the aryl group, A, is linked to $Q^1$ via a covalent single bond.

In one embodiment, where $Q^1$ is a cyclic aryl leader, the aryl group, A, may be fused to $Q^1$ and so the moiety A-$Q^1$- forms a fused polycyclic structure. For example, the moiety 2,3-dihydro-1H-indene-2-yl, derived from indan (2,3-dihydro-1H-indene), is considered to be a phenyl group (A) fused to a $C_5$cycloalkyl group ($Q^1$):

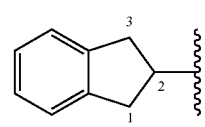

In such cases, the tridentate aryl leader, $Q^1$, may be denoted as:

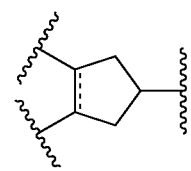

In a similar example, the moiety 9H-fluorene-9-yl, derived from fluorene, is considered to be two phenyl groups (either of which is A), fused to a $C_5$cycloalkyl group, which forms part of $Q^1$:

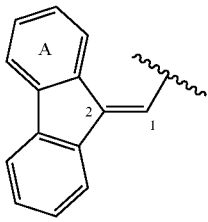

In such cases, the pentadentate aryl leader, $Q^1$, may be denoted as:

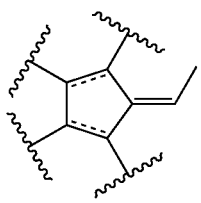

The Aryl Group, A

The aryl group, A, is a $C_{5-20}$aryl group, and is optionally substituted.

In one preferred embodiment, A is a $C_{5-20}$heteroaryl group, and is optionally substituted. In one preferred embodiment, A is a monocyclic $C_{5-20}$heteroaryl group, and is optionally substituted. In one preferred embodiment, A is a monocyclic $C_{5-6}$heteroaryl group, and is optionally substituted.

In one preferred embodiment, A is a $C_{5-20}$carboaryl group, and is optionally substituted. In one preferred embodiment, A is a monocyclic $C_{5-20}$carboaryl group, and is optionally substituted. In one preferred embodiment, A is a monocyclic $C_{5-6}$carboaryl group, and is optionally substituted. In one preferred embodiment, A is a phenyl group, and is optionally substituted.

In one preferred embodiment, A is a $C_{5-20}$aryl group derived from one of the following: benzene, pyridine, furan, indole, pyrrole, imidazole, naphthalene, quinoline, benzimidazole, benzothiofuran, fluorene, acridine, and carbazole.

In one preferred embodiment, Ar is a pyridyl group, or a substituted pyridyl group, for example, 2-pyridyl, 3-pyridyl, or 4-pyridyl:

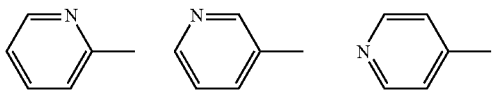

In one preferred embodiment, Ar is a furanyl group, or a substituted furanyl group, for example, furan-2-yl or furan-3-yl:

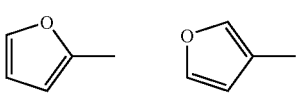

In one preferred embodiment, Ar is a thiophenyl group, or a substituted thiophenyl group, for example, thiophen-2-yl or thiophen-3-yl:

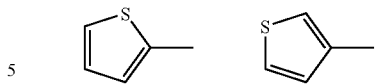

In one preferred embodiment, Ar is a pyrrolyl group, or a substituted pyrrolyl group, for example, pyrrol-2-yl or pyrrol-3-yl:

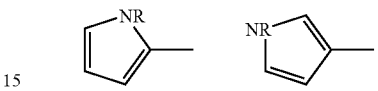

In one preferred embodiment, Ar is a naphthyl group, or a substituted naphthyl group, for example, naphth-1-yl or naphth-2-yl:

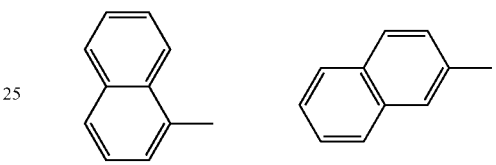

In one preferred embodiment, Ar is a benzimidazolyl group, or a substituted benzimidazolyl group, for example, benzimidazol-2-yl:

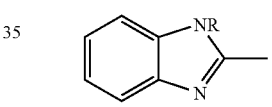

In one preferred embodiment, Ar is a indolyl group, or a substituted indolyl group, for example, indol-2-yl or indol-3-yl:

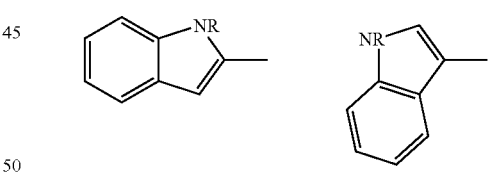

In one preferred embodiment, A is an optionally substituted phenyl group of the formula:

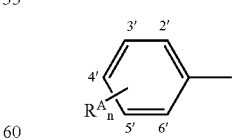

wherein n is an integer from 0 to 5, and each $R^4$ is independently a substituent as defined herein.

In one preferred embodiment, A is an optionally substituted phenyl group, J is —$NR^1CO$—, and the compounds have the following formula:

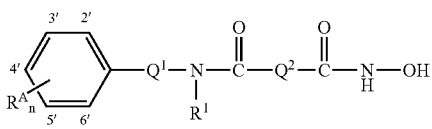
(4)

In one preferred embodiment, A is an optionally substituted phenyl group, J is —CONR¹—, and the compounds have the following formula:

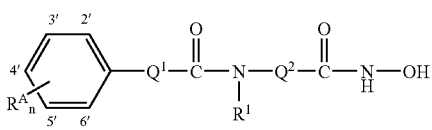
(5)

In one preferred embodiment, n is an integer from 0 to 5.
In one preferred embodiment, n is an integer from 0 to 4.
In one preferred embodiment, n is an integer from 0 to 3.
In one preferred embodiment, n is an integer from 0 to 2.
In one preferred embodiment, n is 0 or 1.
In one preferred embodiment, n is an integer from 1 to 5.
In one preferred embodiment, n is an integer from 1 to 4.
In one preferred embodiment, n is an integer from 1 to 3.
In one preferred embodiment, n is 1 or 2.
In one preferred embodiment, n is 5.
In one preferred embodiment, n is 4.
In one preferred embodiment, n is 3.
In one preferred embodiment, n is 2.
In one preferred embodiment, n is 1.
In one preferred embodiment, n is 0.

If the phenyl group has less than the full complement of ring substituents, $R^A$, they may be arranged in any combination. For example, if n is 1, $R^A$ may be in the 2'-, 3'-, 4'-, 5'-, or 6'-position. Similarly, if n is 2, the two $R^A$ groups may be in, for example, the 2',3'-, 2',4'-, 2',5'-, 2',6'-, 3',4'-, or 3',5'-positions. If n is 3, the three $R^A$ groups may be in, for example, the 2',3',4'-, 2',3',5'-, 2',3',6'-, or 3',4',5'-positions.

In one preferred embodiment, n is 1, and the $R^A$ group is in the 4'-position.

In one preferred embodiment, n is 2, and one $R^A$ group is in the 4'-position, and the other $R^A$ group is in the 2'-position.

In one preferred embodiment, n is 2, and one $R^A$ group is in the 4'-position, and the other $R^A$ group is in the 3'-position.

Each aryl substituent, $R^A$, is a substituent as defined herein.

Examples of preferred aryl substituents, $R^A$, include, but are not limited to, the following: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido (unsubstituted, i.e., —CONH₂), acetamido, acetyl, nitro, sulfonamido (unsubstituted, i.e., —SO₂NH₂), and phenyl.

In one preferred embodiment, A is a substituted phenyl group selected from:
  para-(fluoro)phenyl; ortho-(fluoro)phenyl; meta-(fluoro)phenyl;
  para-(chloro)phenyl; ortho-(chloro)phenyl; meta-(chloro)phenyl;
  para-(bromo)phenyl; ortho-(bromo)phenyl; meta-(bromo)phenyl;
  para-(iodo)phenyl; ortho-(iodo)phenyl; meta-(iodo)phenyl;
  para-(methyl)phenyl; ortho-(methyl)phenyl; meta-(methyl)phenyl;
  para-(ethyl)phenyl; ortho-(ethyl)phenyl; meta-(ethyl)phenyl;
  para-(isopropyl)phenyl; ortho-(isopropyl)phenyl; meta-(isopropyl)phenyl;
  para-(t-butyl)phenyl; ortho-(t-butyl)phenyl; meta-(t-butyl)phenyl;
  para-(cyano)phenyl; ortho-(cyano)phenyl; meta-(cyano)phenyl;
  para-(trifluoromethyl)phenyl; ortho-(trifluoromethyl)phenyl; meta-(trifluoromethyl)phenyl;
  para-(hydroxy)phenyl; ortho-(hydroxy)phenyl; meta-(hydroxy)phenyl;
  para-(methoxy)phenyl; ortho-(methoxy)phenyl; meta-(methoxy)phenyl;
  para-(ethoxy)phenyl; ortho-(ethoxy)phenyl; meta-(ethoxy)phenyl;
  para-(isopropoxy)phenyl; ortho-(isopropoxy)phenyl; meta-(isopropoxy)phenyl;
  para-(trifluoromethoxy)phenyl; ortho-(trifluoromethoxy)phenyl; meta-(trifluoromethoxy)phenyl;
  para-(phenoxy)phenyl; ortho-(phenoxy)phenyl; meta-(phenoxy)phenyl;
  para-(methylthio)phenyl; ortho-(methylthio)phenyl; meta-(methylthio)phenyl;
  para-(trifluoromethylthio)phenyl; ortho-(trifluoromethylthio)phenyl; meta-(trifluoromethylthio)phenyl;
  para-(hydroxymethyl)phenyl; ortho-(hydroxymethyl)phenyl; meta-(hydroxymethyl)phenyl;
  para-(amino)phenyl; ortho-(amino)phenyl; meta-(amino)phenyl;
  para-(dimethylamino)phenyl; ortho-(dimethylamino)phenyl; meta-(dimethylamino)phenyl;
  para-(diethylamino)phenyl; ortho-(diethylamino)phenyl; meta-(diethylamino)phenyl;
  para-(morpholino)phenyl; ortho-(morpholino)phenyl; meta-(morpholino)phenyl;
  para-(amido)phenyl; ortho-(amido)phenyl; meta-(amido)phenyl;
  para-(acetamido)phenyl; ortho-(acetamido)phenyl; meta-(acetamido)phenyl;
  para-(acetyl)phenyl; ortho-(acetyl)phenyl; meta-(acetyl)phenyl;
  para-(nitro)phenyl; ortho-(nitro)phenyl; meta-(nitro)phenyl;
  para-(sulfonamido)phenyl; ortho-(sulfonamido)phenyl; meta-(sulfonamido)phenyl; and,
  para-(phenyl)phenyl; ortho-(phenyl)phenyl; meta-(phenyl)phenyl.

In one preferred embodiment, A is a substituted phenyl group selected from:
  para-(fluoro)phenyl;
  para-(chloro)phenyl;
  para-(bromo)phenyl;
  para-(iodo)phenyl;
  para-(methyl)phenyl;
  para-(ethyl)phenyl;
  para-(isopropyl)phenyl;
  para-(t-butyl)phenyl;
  para-(cyano)phenyl;
  para-(trifluoromethyl)phenyl;
  para-(hydroxy)phenyl;
  para-(methoxy)phenyl;
  para-(ethoxy)phenyl;

para-(isopropoxy)phenyl;
para-(trifluoromethoxy)phenyl;
para-(phenoxy)phenyl;
para-(methylthio)phenyl;
para-(trifluoromethylthio)phenyl;
para-(hydroxymethyl)phenyl;
para-(amino)phenyl;
para-(dimethylamino)phenyl;
para-(diethylamino)phenyl;
para-(morpholino)phenyl;
para-(amido)phenyl;
para-(acetamido)phenyl;
para-(acetyl)phenyl;
para-(nitro)phenyl;
para-(sulfonamido)phenyl; and,
para-(phenyl)phenyl.

In one preferred embodiment, A is a substituted phenyl group selected from:
ortho,para-di(methoxy)phenyl;
ortho,para-di(halo)phenyl;
ortho,para-di(fluoro)phenyl;
ortho-(methoxy),para-(methyl)phenyl;
ortho-(methoxy),para-(trifluoromethyl)phenyl;
ortho-(trifluoromethyl),para-(halo)phenyl;
ortho,meta-di(trifluoromethyl)phenyl;
ortho-(halo),meta-(trifluoromethyl)phenyl;
meta,para-di(halo)phenyl;
meta, para-di(hydroxy)phenyl;
meta,para-di(methyl)phenyl;
meta,para-di(methoxy)phenyl;
meta-(halo),para-(nitro)phenyl;
3',5'-di(trifluoromethyl)phenyl;
3'-(trifluoromethyl),5'-(methoxy)phenyl;
3'-(trifluoromethyl),5'-(halo)phenyl;
2'-(halo),5'-(methyl)phenyl;
2',6'-di(methyl)phenyl;
2',6'-di(halo)phenyl;
2',6'-di(isopropyl)phenyl;
2',4',6'-tri(halo)phenyl;
3',4',5'-tri(halo)phenyl;
3',4',5'-tri(methoxy)phenyl;
2',5'-di(halo)-4'-(hydroxy)phenyl; and
3'-(trifluoromethyl),5',6'-di(halo)phenyl.

In one embodiment, n is 2 or larger, and two substituents, $R^4$, together form a bidentate substituent. In one embodiment, the bidentate substituent is attached to adjacent phenyl ring carbon atoms. In one embodiment, the bidentdate substituent is —O—$CH_2$—O . In one embodiment, A is, for example, one of:

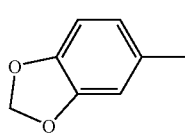
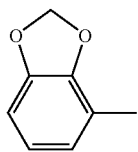

The Aryl Leader Group, $Q^1$: Backbone Length

The aryl leader group, $Q^1$, has a backbone of at least 2 carbon atoms; that is, the shortest chain of atoms linking the aryl group, A, and the linker group, J, has 2 or more atoms, more specifically, 2 or more carbon atoms. In this way, groups such as methylene (—$CH_2$—) and substituted methylene (—$CR_2$— and —CHR—) are excluded.

If there are two or more paths linking the aryl group, A, and the amide group, J, then the shortest path is relevant. For example, in the embodiments shown below, where the moiety A-$Q^1$- is derived from indan (2,3-dihydro-1H-indene), A is considered to be a phenyl group fused to $Q^1$, a $C_5$cycloalkyl group:

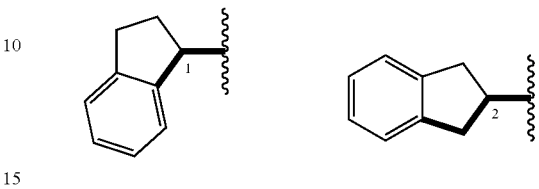

In each case, there are two paths to the aryl group. In the first case, one path has 1 carbon atom, and the other path has 3 carbon atoms, and so the relevant backbone length is 1. In the second case, both paths have 2 carbon atoms, and so the relevant backbone length is 2.

In one embodiment, there is only a single path (i.e., a single chain) linking the aryl group, A, and the amide group, J.

If the group A-$Q^1$- has two or more aryl groups, the aryl group furthest from the amide group, J, as measured by counting chain atoms, is identified as A; the relevant backbone is then the shortest chain of atoms linking that aryl group and the amide group, J. For example, where the group A-$Q^1$- is as shown below, the phenyl group marked "1" is identified as the A, $Q^1$ is —$CH_2$CH(Ph)- (i.e., substituted ethylene), and the backbone length is 2.

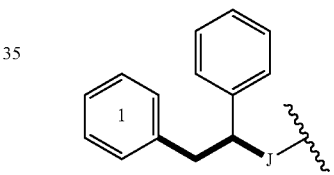

If the amide group is —$NR^1$CO— (as opposed to —$CONR^1$—), and substituent, $R^1$, discussed below, is or comprises an aryl group (or two or more aryl groups), then the aryl group furthest from the amide group nitrogen atom, as measured by counting chain atoms, is identified as A. For example, where the group A-$Q^1$-$NR^1$CO— is as shown below, the phenyl group marked "1" is identified as the A, $Q^1$ is —$CH_2$—, and the backbone length is 1.

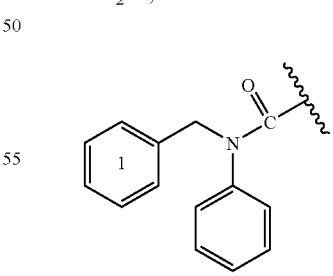

In one preferred embodiment, the aryl leader group, $Q^1$, has a backbone of at least 3 carbon atoms.

In one preferred embodiment, the aryl leader group, $Q^1$, has a backbone of at least 4 carbon atoms.

In one preferred embodiment, the aryl leader group, $Q^1$, has a backbone of at least 5 carbon atoms.

In one embodiment, the aryl leader group, $Q^1$, has a backbone of:
from 2 to 7 carbon atoms;
from 2 to 6 carbon atoms; or,
from 2 to 5 carbon atoms.

In one embodiment, the aryl leader group, $Q^1$, has a backbone of:
from 3 to 7 carbon atoms;
from 3 to 6 carbon atoms; or,
from 3 to 5 carbon atoms.

In one embodiment, the aryl leader group, $Q^1$, has a backbone of:
from 4 to 7 carbon atoms;
from 4 to 6 carbon atoms; or,
from 4 to 5 carbon atoms.

In one embodiment, the aryl leader group, $Q^1$, has a backbone of 2 carbon atoms.

In one embodiment, the aryl leader group, $Q^1$, has a backbone of 3 carbon atoms.

In one embodiment, the aryl leader group, $Q^1$, has a backbone of 4 carbon atoms.

In one embodiment, the aryl leader group, $Q^1$, has a backbone of 5 carbon atoms.

The Aryl Leader Group, $Q^1$: Alkylene

The aryl leader group, $Q^1$, is an alkylene group, and has a backbone of at least 2 carbon atoms.

In one preferred embodiment, the aryl leader group, $Q^1$, has a backbone of at least 2 carbon atoms, and is a $C_{2-7}$alkylene group.

In one preferred embodiment, the aryl leader group, $Q^1$, has a backbone of at least 3 carbon atoms, and is a $C_{3-7}$alkylene group.

In one preferred embodiment, $Q^1$ has a backbone of at least 2 carbon atoms, and is a saturated $C_{2-7}$alkylene group.

In one preferred embodiment, $Q^1$ has a backbone of at least 3 carbon atoms, and is a saturated $C_{3-7}$alkylene group.

In one preferred embodiment, $Q^1$ has a backbone of at least 2 carbon atoms, and is a partially unsaturated $C_{2-7}$alkylene group.

In one preferred embodiment, $Q^1$ has a backbone of at least 3 carbon atoms, and is a partially unsaturated $C_{3-7}$alkylene group.

In one preferred embodiment, $Q^1$ has a backbone of at least 2 carbon atoms, and is an aliphatic $C_{2-7}$alkylene group.

In one preferred embodiment, $Q^1$ has a backbone of at least 3 carbon atoms, and is an aliphatic $C_{3-7}$alkylene group.

In one preferred embodiment, $Q^1$ has a backbone of at least 2 carbon atoms, and is a linear $C_{2-7}$alkylene group.

In one preferred embodiment, $Q^1$ has a backbone of at least 3 carbon atoms, and is a linear $C_{3-7}$alkylene group.

In one preferred embodiment, $Q^1$ has a backbone of at least 2 carbon atoms, and is a branched $C_{2-7}$alkylene group.

In one preferred embodiment, $Q^1$ has a backbone of at least 3 carbon atoms, and is a branched $C_{3-7}$alkylene group.

In one preferred embodiment, $Q^1$ has a backbone of at least 2 carbon atoms, and is an alicyclic $C_{2-7}$alkylene group.

In one preferred embodiment, $Q^1$ has a backbone of at least 3 carbon atoms, and is an alicyclic $C_{3-7}$alkylene group.

In one preferred embodiment, $Q^1$ has a backbone of at least 2 carbon atoms, and is a saturated aliphatic $C_{2-7}$alkylene group.

In one preferred embodiment, $Q^1$ has a backbone of at least 3 carbon atoms, and is a saturated aliphatic $C_{3-7}$alkylene group.

In one preferred embodiment, $Q^1$ has a backbone of at least 2 carbon atoms, and is a saturated linear $C_{2-7}$alkylene group.

In one preferred embodiment, $Q^1$ has a backbone of at least 3 carbon atoms, and is a saturated linear $C_{3-7}$alkylene group.

In one preferred embodiment, $Q^1$ has a backbone of at least 2 carbon atoms, and is a saturated branched $C_{2-7}$alkylene group.

In one preferred embodiment, $Q^1$ has a backbone of at least 3 carbon atoms, and is a saturated branched $C_{3-7}$alkylene group.

In one preferred embodiment, $Q^1$ has a backbone of at least 2 carbon atoms, and is a saturated alicyclic $C_{2-7}$alkylene group.

In one preferred embodiment, $Q^1$ has a backbone of at least 3 carbon atoms, and is a saturated alicyclic $C_{3-7}$alkylene group.

In one preferred embodiment, $Q^1$ has a backbone of at least 2 carbon atoms, and is a partially unsaturated aliphatic $C_{2-7}$alkylene group.

In one preferred embodiment, $Q^1$ has a backbone of at least 3 carbon atoms, and is a partially unsaturated aliphatic $C_{3-7}$alkylene group.

In one preferred embodiment, $Q^1$ has a backbone of at least 2 carbon atoms, and is a partially unsaturated linear $C_{2-7}$alkylene group.

In one preferred embodiment, $Q^1$ has a backbone of at least 3 carbon atoms, and is a partially unsaturated linear $C_{3-7}$alkylene group.

In one preferred embodiment, $Q^1$ has a backbone of at least 2 carbon atoms, and is a partially unsaturated branched $C_{2-7}$alkylene group.

In one preferred embodiment, $Q^1$ has a backbone of at least 3 carbon atoms, and is a partially unsaturated branched $C_{3-7}$alkylene group.

In one preferred embodiment, $Q^1$ has a backbone of at least 2 carbon atoms, and is a partially unsaturated alicyclic $C_{2-7}$alkylene group.

In one preferred embodiment, $Q^1$ has a backbone of at least 3 carbon atoms, and is a partially unsaturated alicyclic $C_{3-7}$alkylene group.

In one preferred embodiment, where $Q^1$ is a partially unsaturated alkylene group, it is not saturated at the carbon atom adjacent to J. For example, in such an embodiment, -$Q^1$-J- as —CH=CH—CH$_2$-J- is excluded, but -$Q^1$-J- as —CH$_2$—CH=CH-J- is included. Compounds of this embodiment have surprising and unexpected activity, as compared to the analogous excluded compounds.

Note that, as discussed below in the context of isomers, where unsaturation permits isomers, e.g., cis- and trans-, E- and Z-, etc., and combinations thereof, a reference to one isomer is to be considered a reference to all such isomers, unless otherwise specified.

The Aryl Leader Group, $Q^1$: Substituents

In one embodiment, $Q^1$ is unsubstituted.

In one embodiment, $Q^1$ is optionally substituted.

In one embodiment, $Q^1$ is substituted.

Examples of substituents on $Q^1$ include, but are not limited to, those described under the heading "Substituents" below.

In one preferred embodiment, substituents on $Q^1$, if present, are independently selected from: halo, hydroxy, ether (e.g., $C_{1-7}$alkoxy), $C_{5-20}$aryl, acyl, amido, and oxo.

In one preferred embodiment, substituents on $Q^1$, if present, are independently selected from —F, —Cl, —Br, —I, —OH, —OMe, —OEt, —OPr, -Ph, and =O.

In one preferred embodiment, substituents on $Q^1$, if present, are —OH or -Ph.

In one preferred embodiment, substituents on $Q^1$, if present, are -Ph.

For example, in one embodiment, $Q^1$ is unsubstituted ethylene, and is —CH$_2$—CH$_2$—; in one embodiment, $Q^1$ is oxo (═O) subsituted ethylene, and is —C(═O)—CH$_2$—; in one embodiment, $Q^1$ is hydroxy (—OH) subsituted ethylene, and is —CH(OH)—CH$_2$—; in one embodiment, $Q^1$ is phenyl (-Ph) substituted ethylene, and is —CH$_2$CH(Ph)-.

In one embodiment, if $Q^1$ is substituted, it is not substituted at the carbon atom adjacent to J. For example, in such an embodiment, -$Q^1$-J- as —CH═CH(Me)-J- is excluded, but -$Q^1$-J- as —CH(Me)═CH-J- is included. Compounds of this embodiment have surprising and unexpected activity, as compared to the analogous excluded compounds.

The Aryl Leader Group, $Q^1$: Certain Embodiments

Note that, for embodiments excluding, e.g., certain backbone lengths, etc., it is to be understood that the corresponding species listed below are similarly excluded from the respective embodiments discussed below.

In one preferred embodiment, $Q^1$ is selected from the following:
—(CH$_2$)$_n$— where n is an integer from 2 to 7;
—CH(CH$_3$)CH$_2$— and —CH$_2$CH(CH$_3$)—;
—CH(CH$_3$)CH$_2$CH$_2$—, —CH$_2$CH(CH$_3$)CH$_2$—, and —CH$_2$CH$_2$CH(CH$_3$)—;
—CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, and —CH$_2$CH$_2$CH$_2$CH(CH$_3$)—;
—CH(CH$_3$)CH$_2$CH$_2$CH$_2$CH$_2$—, —CH$_2$CH(CH$_3$)CH$_2$CH$_2$CH$_2$—, —CH$_2$CH$_2$CH(CH$_3$)CH$_2$CH$_2$—, —CH$_2$CH$_2$CH$_2$CH(CH$_3$)CH$_2$—, and —CH$_2$CH$_2$CH$_2$CH$_2$CH(CH$_3$)—;
—CH(CH$_2$CH$_3$)CH$_2$— and —CH$_2$CH(CH$_2$CH$_3$)—;
—CH(CH$_2$CH$_3$)CH$_2$CH$_2$—, —CH$_2$CH(CH$_2$CH$_3$)CH$_2$—, and —CH$_2$CH$_2$CH(CH$_2$CH$_3$)—;
—CH(CH$_2$CH$_3$)CH$_2$CH$_2$CH$_2$—, —CH$_2$CH(CH$_2$CH$_3$)CH$_2$CH$_2$—, —CH$_2$CH$_2$CH(CH$_2$CH$_3$)CH$_2$—, and —CH$_2$CH$_2$CH$_2$CH(CH$_2$CH$_3$)—;
—CH(CH$_2$CH$_3$)CH$_2$CH$_2$CH$_2$CH$_2$—, —CH$_2$CH(CH$_2$CH$_3$)CH$_2$CH$_2$CH$_2$—, —CH$_2$CH$_2$CH(CH$_2$CH$_3$)CH$_2$CH$_2$—, —CH$_2$CH$_2$CH$_2$CH(CH$_2$CH$_3$)CH$_2$—, and —CH$_2$CH$_2$CH$_2$CH$_2$CH(CH$_2$CH$_3$)—;
—CH═CH—;
—CH═CHCH$_2$— and —CH$_2$CH═CH—;
—CH═CHCH$_2$CH$_2$—, —CH$_2$CH═CHCH$_2$—, and —CH$_2$CH$_2$CH═CH—;
—CH═CHCH$_2$CH$_2$CH$_2$—, —CH$_2$CH═CHCH$_2$CH$_2$—, —CH$_2$CH$_2$CH═CHCH$_2$—, and —CH$_2$CH$_2$CH$_2$CH═CH—;
—CH═CHCH$_2$CH$_2$CH$_2$CH$_2$—, —CH$_2$CH═CHCH$_2$CH$_2$CH$_2$—, —CH$_2$CH$_2$CH═CHCH$_2$CH$_2$—, —CH$_2$CH$_2$CH$_2$CH═CHCH$_2$—, and —CH$_2$CH$_2$CH$_2$CH$_2$CH═CH—;
—C(CH$_3$)═CH— and —CH═C(CH$_3$)—;
—C(CH$_3$)═CHCH$_2$—, —CH═C(CH$_3$)CH$_2$—, and —CH═CHCH(CH$_3$)—;
—CH(CH$_3$)CH═CH—, —CH$_2$C(CH$_3$)═CH—, and —CH$_2$CH═C(CH$_3$)—;
—CH═CHCH═CH—;
—CH═CHCH═CHCH$_2$—, —CH═CHCH$_2$CH═CH—, and —CH$_2$CH═CHCH═CH—;
—CH═CHCH═CHCH$_2$CH$_2$—, —CH═CHCH$_2$CH═CHCH$_2$—, —CH═CHCH$_2$CH$_2$CH═CH—, —CH$_2$CH═CHCH═CHCH$_2$—, and —CH$_2$CH$_2$CH═CHCH═CH—;
—C(CH$_3$)═CHCH═CH—, —CH═C(CH$_3$)CH═CH—, —CH═CHC(CH$_3$)═CH—, and —CH═CHCH═C(CH$_3$)—;
—C≡C—;
—C≡CCH$_2$—, —CH$_2$C≡C—; —C≡CCH(CH$_3$)—, and —CH(CH$_3$)C≡C—;
—C≡CCH$_2$CH$_2$—, —CH$_2$C≡CCH$_2$—, and —CH$_2$CH$_2$C≡C—;
—C≡—CCH(CH$_3$)CH$_2$— and —C≡CCH$_2$CH(CH$_3$)—;
—CH(CH$_3$)C≡CCH$_2$— and —CH$_2$C≡CCH(CH$_3$)—;
—CH(CH$_3$)CH$_2$C≡C— and —CH$_2$CH(CH$_3$)C≡C—;
—C≡CCH═CH—, —CH═CHC≡C—, and —C≡CC≡C—;
—C≡CCH$_2$CH$_2$CH$_2$— and —CH$_2$CH$_2$CH$_2$C≡C—;
—C≡CCH$_2$CH$_2$CH$_2$CH$_2$— and —CH$_2$CH$_2$CH$_2$CH$_2$C≡C—;
—C≡CCH═CHCH═CH—, —CH═CHC≡CCH═CH—, and —CH═CHCH═CHC≡C—;
—C(CH$_3$)═CHC≡C—, —CH═C(CH$_3$)C≡C—, —C≡CC(CH$_3$)═CH—, and —C≡CCH═C(CH$_3$)—;
cyclopentylene and cyclopentenylene; and,
cyclohexylene, cyclohexenylene, and cyclohexadienylene.
In one preferred embodiment, $Q^1$ is selected from:
—(CH$_2$)$_2$—, —(CH$_2$)$_3$—, —(CH$_2$)$_4$—, —(CH$_2$)$_5$—, and —(CH$_2$)$_6$—;
—CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, and —CH$_2$CH$_2$CH$_2$CH(CH$_3$)—;
—CH═CH—;
—CH═CH—CH═CH—;
—CH═CHCH$_2$CH$_2$— and —CH$_2$CH$_2$CH═CH—;
—CH═CHCH$_2$CH$_2$CH$_2$— and —CH$_2$CH$_2$CH$_2$CH═CH—;
—C(CH$_3$)═CHCH═CH—, —CH═C(CH$_3$)CH═CH—, —CH═CHC(CH$_3$)═CH—, and —CH═CHCH═C(CH$_3$)—;

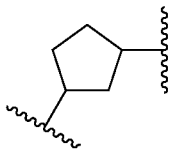

(cyclopent-1,3-ylene)

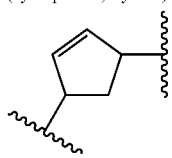

(4-cyclopenten-1,3-ylene)

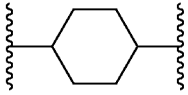

(cyclohex-1,4-ylene)

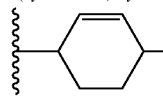

(2-cyclohexen-1,4-ylene)

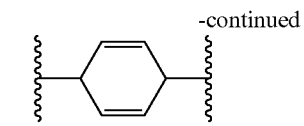

(2,5-cyclohexadien-1,4-ylene)

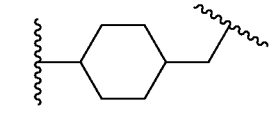

(cyclohex-1,4-ylene-methylene)

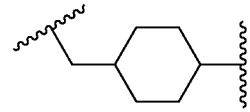

(methylene-cyclohex-1,4-ylene)

In one preferred embodiment, $Q^1$ is selected from:
—(CH$_2$)$_2$—, —(CH$_2$)$_3$—, —(CH$_2$)$_4$—, —(CH$_2$)$_5$—;
—CH=CH—;
—CH=CH—CH=CH—;
—C(CH$_3$)=CHCH=CH—, —CH=C(CH$_3$)CH=CH—, —CH=CHC(CH$_3$)=CH—, and —CH=CHCH=C(CH$_3$)—;
—CH=CHCH$_2$CH$_2$CH$_2$— and —CH$_2$CH$_2$CH$_2$CH=CH—; and,

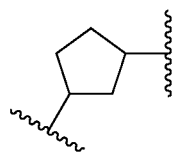

(cyclopent-1,3-ylene)

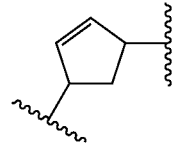

(4-cyclopenten-1,3-ylene)

In one preferred embodiment, $Q^1$ is selected from:
—CH$_2$CH$_2$—, —CH=CH—, —CH=CH—CH=CH—, —C(CH$_3$)=CH—CH=CH—, —CH=CH—C(CH$_3$)=CH—, —CH=CH—CH=C(CH$_3$)—, or —C≡C—CH=CH—.

In one preferred embodiment, $Q^1$ is selected from:
—CH$_2$CH$_2$—, —CH=CH—, —CH=CH—CH=CH—, and —C(CH$_3$)=CH—CH=CH—.

In one preferred embodiment, $Q^1$ is selected from:

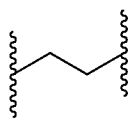 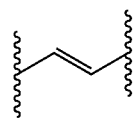

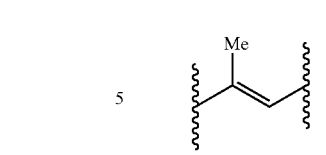

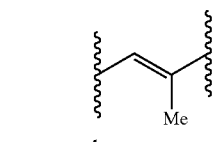

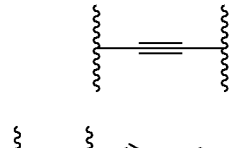

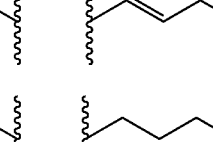

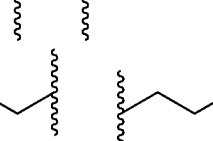

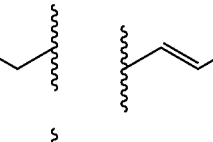

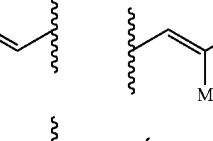

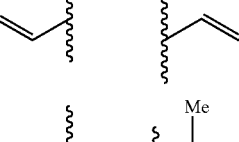

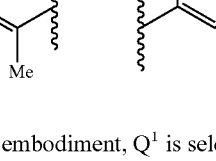

In one preferred embodiment, $Q^1$ is selected from:

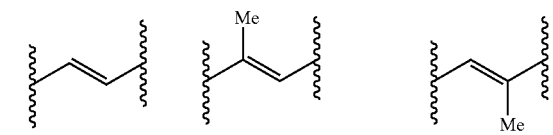

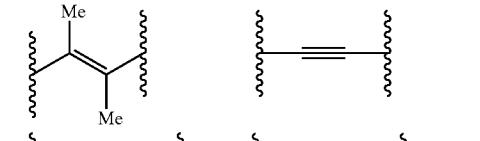

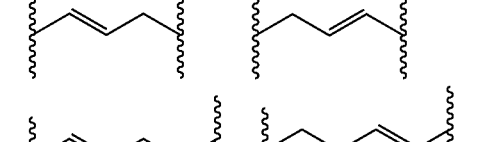

-continued

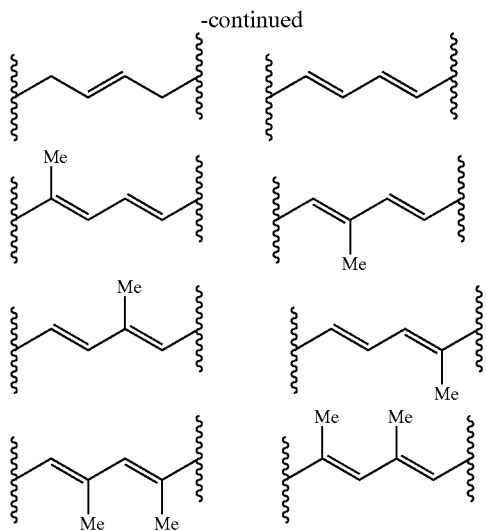

In one preferred embodiment, $Q^1$ is selected from:

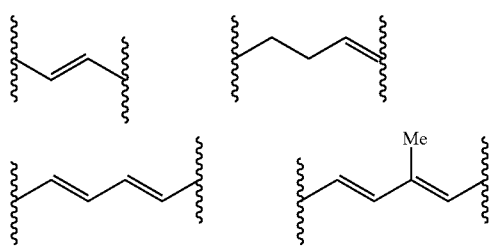

In one preferred embodiment, $Q^1$ is selected from:

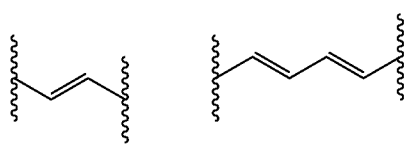

The Amido Substituent, $R^1$

The amido substituent, $R^1$, is hydrogen, $C_{1-7}$alkyl (including, e.g., $C_{5-20}$aryl-$C_{1-7}$alkyl), $C_{3-20}$heterocyclyl, or $C_{5-20}$aryl.

Note that $R^1$ is a monodentate species. It is not intended that $R^1$ be additionally linked to A, $Q^1$, and/or $Q^2$, thereby forming a cyclic group.

In one preferred embodiment, $R^1$ is hydrogen, $C_{1-7}$alkyl, or $C_{5-20}$aryl.

In one preferred embodiment, $R^1$ is hydrogen or $C_{1-7}$alkyl.

In one preferred embodiment, $R^1$ is hydrogen, saturated $C_{1-7}$alkyl, or $C_{5-20}$aryl.

In one preferred embodiment, $R^1$ is hydrogen or saturated $C_{1-7}$alkyl.

In one preferred embodiment, $R^1$ is hydrogen, saturated aliphatic $C_{1-7}$alkyl, or $C_{5-20}$aryl.

In one preferred embodiment, $R^1$ is hydrogen or saturated aliphatic $C_{1-7}$alkyl.

In one preferred embodiment, $R^1$ is —H, -Me, -Et, -nPr, -iPr, -nBu, —sBu, -tBu, -Ph, or —Bn.

In one preferred embodiment, $R^1$ is —H, -Me, -Et, -nPr, -iPr, -nBu, —sBu, or -tBu.

In one preferred embodiment, $R^1$ is —H, -Me, -Et, -Ph, or —Bn.

In one preferred embodiment, $R^1$ is —H, -Me, or -Et.

In one preferred embodiment, $R^1$ is —H.

The Acid Leader Group, $Q^2$

The acid leader group, $Q^2$, is $C_{1-10}$alkylene; $C_{5-20}$arylene; $C_{5-20}$arylene-$C_{1-10}$alkylene; or $C_{1-10}$alkylene-$C_{5-20}$arylene; and is optionally substituted.

In one preferred embodiment, $Q^2$ is $C_{1-7}$alkylene; $C_{5-20}$arylene; $C_{5-20}$arylene-$C_{1-7}$alkylene; or $C_{1-7}$alkylene-$C_{5-20}$arylene; and is optionally substituted.

In one embodiment, $Q^2$ is unsubstituted.
In one embodiment, $Q^2$ is optionally substituted.
In one embodiment, $Q^2$ is substituted.

The Acid Leader Group, $Q^2$: Backbone Length

Tthe acid leader group, $Q^2$, has a backbone of at least 3 carbon atoms; that is, the shortest chain of atoms linking the group, J, and the carbamic acid group (—C(=O)NHOH) has 3 or more atoms, more specifically, 3 or more carbon atoms. In this way, groups such as methylene (—CH$_2$—), substituted methylene (—CR$_2$— and —CHR—), ethylene (—CH$_2$CH$_2$—), and substituted ethylene (e.g., —CHRCH$_2$—) are excluded.

In one embodiment, the acid leader group, $Q^2$, has a backbone of at least 4 carbon atoms.

In one embodiment, the acid leader group, $Q^2$, has a backbone of at least 5 carbon atoms.

In one embodiment, the acid leader group, $Q^2$, has a backbone of:
    from 3 to 10 carbon atoms;
    from 3 to 9 carbon atoms;
    from 3 to 8 carbon atoms;
    from 3 to 7 carbon atoms;
    from 3 to 6 carbon atoms; or,
    from 3 to 5 carbon atoms.

In one embodiment, the acid leader group, $Q^2$, has a backbone of:
    from 4 to 10 carbon atoms;
    from 4 to 9 carbon atoms;
    from 4 to 8 carbon atoms;
    from 4 to 7 carbon atoms;
    from 4 to 6 carbon atoms; or,
    from 4 to 5 carbon atoms.

In one embodiment, the acid leader group, $Q^2$, has a backbone of:
    from 5 to 10 carbon atoms;
    from 5 to 9 carbon atoms;
    from 5 to 8 carbon atoms;
    from 5 to 7 carbon atoms; or,
    from 5 to 6 carbon atoms.

In one embodiment, the acid leader group, $Q^2$, has a backbone of:
    3 carbon atoms;
    4 carbon atoms;
    5 carbon atoms;
    6 carbon atoms;
    7 carbon atoms;
    8 carbon atoms;
    9 carbon atoms; or,
    10 carbon atoms.

The Acid Leader Group, $Q^2$: Alkylene

In one preferred embodiment, the acid leader group, $Q^2$, is $C_{1-10}$alkylene and is optionally substituted.

In one preferred embodiment, the acid leader group, $Q^2$, is $C_{1-7}$alkylene and is optionally substituted.

In one preferred embodiment, $Q^2$ is a $C_{1-10}$alkylene group.

In one preferred embodiment, $Q^2$ is a $C_{1-7}$alkylene group.

In one preferred embodiment, $Q^2$ is a saturated $C_{1-10}$alkylene group.

In one preferred embodiment, $Q^2$ is a saturated $C_{1-7}$alkylene group.

In one preferred embodiment, $Q^2$ is a partially unsaturated $C_{1-10}$alkylene group.

In one preferred embodiment, $Q^2$ is a partially unsaturated $C_{1-7}$alkylene group.

In one preferred embodiment, $Q^2$ is an aliphatic $C_{1-10}$alkylene group.

In one preferred embodiment, $Q^2$ is an aliphatic $C_{1-7}$alkylene group.

In one preferred embodiment, $Q^2$ is a linear $C_{1-10}$alkylene group.

In one preferred embodiment, $Q^2$ is a linear $C_{1-7}$alkylene group.

In one preferred embodiment, $Q^2$ is a branched $C_{1-10}$alkylene group.

In one preferred embodiment, $Q^2$ is a branched $C_{1-7}$alkylene group.

In one preferred embodiment, $Q^2$ is an alicyclic $C_{1-10}$alkylene group.

In one preferred embodiment, $Q^2$ is an alicyclic $C_{1-7}$alkylene group.

In one preferred embodiment, $Q^2$ is a saturated aliphatic $C_{1-10}$alkylene group.

In one preferred embodiment, $Q^2$ is a saturated aliphatic $C_{1-7}$alkylene group.

In one preferred embodiment, $Q^2$ is a saturated linear $C_{1-10}$alkylene group.

In one preferred embodiment, $Q^2$ is a saturated linear $C_{1-7}$alkylene group.

In one preferred embodiment, $Q^2$ is a saturated branched $C_{1-10}$alkylene group.

In one preferred embodiment, $Q^2$ is a saturated branched $C_{1-7}$alkylene group.

In one preferred embodiment, $Q^2$ is a saturated alicyclic $C_{1-10}$alkylene group.

In one preferred embodiment, $Q^2$ is a saturated alicyclic $C_{1-7}$alkylene group.

In one preferred embodiment, $Q^2$ is a partially unsaturated aliphatic $C_{1-10}$alkylene group.

In one preferred embodiment, $Q^2$ is a partially unsaturated aliphatic $C_{1-7}$alkylene group.

In one preferred embodiment, $Q^2$ is a partially unsaturated linear $C_{1-10}$alkylene group.

In one preferred embodiment, $Q^2$ is a partially unsaturated linear $C_{1-7}$alkylene group.

In one preferred embodiment, $Q^2$ is a partially unsaturated branched $C_{1-10}$alkylene group.

In one preferred embodiment, $Q^2$ is a partially unsaturated branched $C_{1-7}$alkylene group.

In one preferred embodiment, $Q^2$ is a partially unsaturated alicyclic $C_{1-10}$alkylene group.

In one preferred embodiment, $Q^2$ is a partially unsaturated alicyclic $C_{1-7}$alkylene group.

For the avoidance of doubt, for each of the above embodiments, $Q^2$ may additionally have a backbone length as described in the preceding section.

For example, in one preferred embodiment, $Q^2$ is a saturated aliphatic $C_{1-10}$alkylene group, with a backbone length of 3 to 7 carbon atoms.

The Aryl Leader Group, $Q^2$: Alkylene: Certain Embodiments

Note that, for embodiments excluding, e.g., certain backbone lengths, etc., it is to be understood that the corresponding species listed below are similarly excluded from the respective embodiments discussed below.

In one preferred embodiment, $Q^2$ is selected from:

—$(CH_2)_n$— where n is an integer from 1 to 7;

—$CH(CH_3)$—;

—$CH(CH_3)CH_2$— and —$CH_2CH(CH_3)$—;

—$CH(CH_3)CH_2CH_2$—, —$CH_2CH(CH_3)CH_2$—, and —$CH_2CH_2CH(CH_3)$—;

—$CH(CH_3)CH_2CH_2CH_2$—, —$CH_2CH(CH_3)CH_2CH_2$—, —$CH_2CH_2CH(CH_3)CH_2$—, and —$CH_2CH_2CH_2CH(CH_3)$—;

—$CH(CH_3)CH_2CH_2CH_2CH_2$—, —$CH_2CH(CH_3)CH_2CH_2CH_2$—, —$CH_2CH_2CH(CH_3)CH_2CH_2$—, —$CH_2CH_2CH_2CH(CH_3)CH_2$—, and —$CH_2CH_2CH_2CH_2CH(CH_3)$—;

—$CH(CH_2CH_3)$—;

—$CH(CH_2CH_3)CH_2$— and —$CH_2CH(CH_2CH_3)$—;

—$CH(CH_2CH_3)CH_2CH_2$—, —$CH_2CH(CH_2CH_3)CH_2$—, and —$CH_2CH_2CH(CH_2CH_3)$—;

—$CH(CH_2CH_3)CH_2CH_2CH_2$—, —$CH_2CH(CH_2CH_3)CH_2CH_2$—, —$CH_2CH_2CH(CH_2CH_3)CH_2$—, and —$CH_2CH_2CH_2CH(CH_2CH_3)$—;

—$CH(CH_2CH_3)CH_2CH_2CH_2CH_2$—, —$CH_2CH(CH_2CH_3)CH_2CH_2CH_2$—, —$CH_2CH_2CH(CH_2CH_3)CH_2CH_2$—, —$CH_2CH_2CH_2CH(CH_2CH_3)CH_2$—, and —$CH_2CH_2CH_2CH_2CH(CH_2CH_3)$—;

—CH=CH—;

—CH=CHCH$_2$— and —CH$_2$CH=CH—;

—CH=CHCH$_2$CH$_2$—, —CH$_2$CH=CHCH$_2$—, and —CH$_2$CH$_2$CH=CH—;

—CH=CHCH$_2$CH$_2$CH$_2$—, —CH$_2$CH=CHCH$_2$CH$_2$—, —CH$_2$CH$_2$CH=CHCH$_2$—, and —CH$_2$CH$_2$CH$_2$CH=CH—;

—CH=CHCH$_2$CH$_2$CH$_2$CH$_2$—, —CH$_2$CH=CHCH$_2$CH$_2$CH$_2$—, —CH$_2$CH$_2$CH=CHCH$_2$CH$_2$—, —CH$_2$CH$_2$CH$_2$CH=CHCH$_2$—, and —CH$_2$CH$_2$CH$_2$CH$_2$CH=CH—;

—C(CH$_3$)=CH— and —CH=C(CH$_3$)—;

—C(CH$_3$)=CHCH$_2$—, —CH=C(CH$_3$)CH$_2$—, and —CH=CHCH(CH$_3$)—;

—CH(CH$_3$)CH=CH—, —CH$_2$C(CH$_3$)=CH—, and —CH$_2$CH=C(CH$_3$)—;

—CH=CHCH=CH—;

—CH=CHCH=CHCH$_2$—, —CH$_2$CH=CHCH=CH—, and —CH=CHCH$_2$CH=CH—;

—CH=CHCH=CHCH$_2$CH$_2$—, —CH=CHCH$_2$CH=CHCH$_2$—, —CH=CHCH$_2$CH$_2$CH=CH—, —CH$_2$CH=CHCH=CHCH$_2$—, —CH$_2$CH=CHCH$_2$CH=CH—, and —CH$_2$CH$_2$CH=CHCH=CH—;

—C(CH$_3$)=CHCH=CH—, —CH=C(CH$_3$)CH=CH—, —CH=CHC(CH$_3$)=CH—, and —CH=CHCH=C(CH$_3$)—;

—C≡C—;

—C≡CCH$_2$—, —CH$_2$C≡C—; —C≡CCH(CH$_3$)—, and —CH(CH$_3$)C≡C—;

—C≡CCH$_2$CH$_2$—, —CH$_2$C≡CCH$_2$—, and —CH$_2$CH$_2$C≡C—;

—C≡CCH(CH$_3$)CH$_2$— and —C≡CCH$_2$CH(CH$_3$)—;

—CH(CH$_3$)C≡CCH$_2$— and —CH$_2$C≡CCH(CH$_3$)—;

—CH(CH$_3$)CH$_2$C≡C— and —CH$_2$CH(CH$_3$)C≡C—;

—C≡CCH=CH—, —CH=CHC≡C—, and —C≡CC≡C—;
—C≡CCH₂CH₂CH₂— and —CH₂CH₂CH₂C≡C—;
—C≡CCH₂CH₂CH₂CH₂— and —CH₂CH₂CH₂CH₂C≡C—;
—C≡CCH=CHCH=CH—, —CH=CHC≡CCH=CH—, and —CH=CHCH=CHC≡C—;
—C(CH₃)=CHC≡C—, —CH=C(CH₃)C≡C—, —C≡CC(CH₃)=CH—, and —C≡CCH=C(CH₃)—;
cyclopentylene and cyclopentenylene; and,
cyclohexylene, cyclohexenylene, and cyclohexadienylene.

In one preferred embodiment, Q² is selected from:
—CH₂—, —(CH₂)₂—, —(CH₂)₃—, —(CH₂)₄—, —(CH₂)₅—, and —(CH₂)₆—;
—CH(CH₃)CH₂CH₂CH₂CH₂—, —CH₂CH(CH₃)CH₂CH₂CH₂—, —CH₂CH₂CH₂CH(CH₃)CH₂—, and —CH₂CH₂CH₂CH₂CH(CH₃)—;
—CH=CHCH₂CH₂CH₂— and —CH₂CH₂CH₂CH=CH—;
—CH=CHCH₂CH₂CH₂CH₂— and —CH₂CH₂CH₂CH₂CH=CH—;

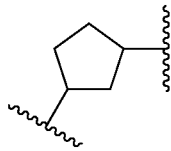
(cyclopent-1,3-ylene)

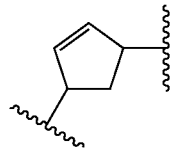
(4-cyclopenten-1,3-ylene)

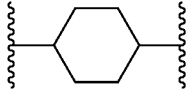
(cyclohex-1,4-ylene)

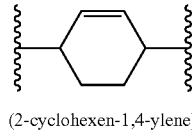
(2-cyclohexen-1,4-ylene)

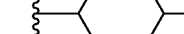
(2,5-cyclohexadien-1,4-ylene)

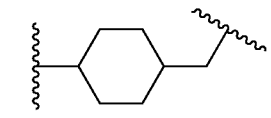
(cyclohex-1,4-ylene-methylene)

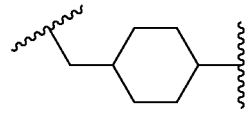
(methylene-cyclohex-1,4-ylene)

In one preferred embodiment, Q² is selected from:
—CH₂—, —(CH₂)₂—, —(CH₂)₃—, —(CH₂)₄—, —(CH₂)₅—, and —(CH₂)₆—;

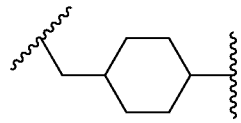

—CH(CH₃)CH₂CH₂CH₂CH₂— and —CH₂CH₂CH₂CH₂CH(CH₃)—;
—CH₂CH₂CH₂CH=CH—; and,
—CH₂CH₂CH₂CH₂CH=CH—.

In one preferred embodiment, Q² is selected from —(CH₂)ₙ— wherein n is an integer from:
1 to 10; 1 to 8; 1 to 7; 1 to 6;
2 to 10; 2 to 8; 2 to 7; 2 to 6;
3 to 10; 3 to 8; 3 to 7; 3 to 6;
4 to 10; 4 to 8; 4 to 7; 4 to 6;
5 to 10; 5 to 8; 5 to 7; or, 5 to 6.

In one preferred embodiment, Q² is selected from:
—(CH₂)₃—, —(CH₂)₄—, —(CH₂)₅—, —(CH₂)₆— and —(CH₂)₇—.

In one preferred embodiment, Q² is selected from:
—(CH₂)₄—, —(CH₂)₅—, —(CH₂)₆— and —(CH₂)₇—.

In one preferred embodiment, Q² is selected from:
—(CH₂)₄—, —(CH₂)₅—, and —(CH₂)₆—.

In one preferred embodiment, Q² is selected from:
—(CH₂)₅—, and —(CH₂)₆—.

In one preferred embodiment, the compound has the following formula:

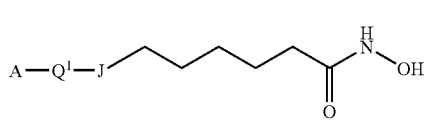
(6)

In one preferred embodiment, the compound has the following formula:

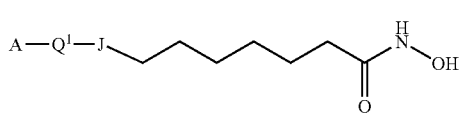
(7)

The Acid Leader Group, Q²: Arylene

In one preferred embodiment, the acid leader group, Q², is $C_{5-20}$arylene, and is optionally substituted.

In one preferred embodiment, Q² is $C_{5-20}$arylene. In one preferred embodiment, Q² is $C_{5-6}$arylene. In one preferred embodiment, Q² is phenylene.

The Acid Leader Group, Q²: Alkylene-Arylene and Arylene-Alkylene

In one preferred embodiment, the acid leader group, Q², is $C_{5-20}$arylene-$C_{1-7}$alkylene or $C_{1-7}$alkylene-$C_{5-20}$arylene, and is optionally substituted.

In one preferred embodiment, Q² is $C_{5-6}$arylene-$C_{1-7}$alkylene or $C_{1-7}$alkylene-$C_{5-6}$arylene, and is optionally substituted.

In one preferred embodiment, $Q^2$ is $C_{1-7}$alkylene-$C_{5-20}$arylene. In one preferred embodiment, $Q^2$ is $C_{1-7}$alkylene-$C_{5-6}$arylene.

In one preferred embodiment, $Q^2$ is $C_{5-20}$arylene-$C_{1-7}$alkylene. In one preferred embodiment, $Q^2$ is $C_{5-6}$arylene-$C_{1-7}$alkylene.

In one preferred embodiment, $Q^2$ is $C_{5-20}$arylene-$C_{1-7}$alkylene, wherein said $C_{1-7}$alkylene moiety does not comprise a carbon-carbon triple bond.

In one preferred embodiment, $Q^2$ is $C_{5-6}$arylene-$C_{1-7}$alkylene, wherein said $C_{1-7}$alkylene moiety does not comprise a carbon-carbon triple bond.

In one preferred embodiment, $Q^2$ is phenylene-$C_{1-7}$alkylene, wherein said $C_{1-7}$alkylene moiety does not comprise a carbon-carbon triple bond.

In one preferred embodiment, $Q^2$ is $C_{1-7}$alkylene-$C_{5-20}$arylene, wherein said $C_{1-7}$alkylene moiety does not comprise a carbon-carbon triple bond.

In one preferred embodiment, $Q^2$ is $C_{1-7}$alkylene-$C_{5-6}$arylene, wherein said $C_{1-7}$alkylene moiety does not comprise a carbon-carbon triple bond.

In one preferred embodiment, $Q^2$ is $C_{1-7}$alkylene-phenylene, wherein said $C_{1-7}$alkylene moiety does not comprise a carbon-carbon triple bond.

In one preferred embodiment, $Q^2$ is $C_{5-20}$arylene-$C_{1-7}$alkylene, wherein $Q^2$ has a backbone of less than 7 carbon atoms, preferably less than 6 carbon atoms.

In one preferred embodiment, $Q^2$ is $C_{5-6}$arylene-$C_{1-7}$alkylene, wherein $Q^2$ has a backbone of less than 7 carbon atoms, preferably less than 6 carbon atoms.

In one preferred embodiment, $Q^2$ is phenylene-$C_{1-7}$alkylene, wherein $Q^2$ has a backbone of less than 7 carbon atoms, preferably less than 6 carbon atoms.

In one preferred embodiment, $Q^2$ is $C_{1-7}$alkylene-$C_{5-20}$arylene, wherein $Q^2$ has a backbone of less than 7 carbon atoms, preferably less than 6 carbon atoms.

In one preferred embodiment, $Q^2$ is $C_{1-7}$alkylene-$C_{5-6}$arylene, wherein $Q^2$ has a backbone of less than 7 carbon atoms, preferably less than 6 carbon atoms.

In one preferred embodiment, $Q^2$ is $C_{1-7}$alkylene-phenylene, wherein $Q^2$ has a backbone of less than 7 carbon atoms, preferably less than 6 carbon atoms.

In one preferred embodiment, $Q^2$ is $C_{5-20}$arylene-$C_{1-7}$alkylene, wherein said $C_{1-7}$alkylene moiety is saturated.

In one preferred embodiment, $Q^2$ is $C_{5-6}$arylene-$C_{1-7}$alkylene, wherein said $C_{1-7}$alkylene moiety is saturated.

In one preferred embodiment, $Q^2$ is phenylene-$C_{1-7}$alkylene, wherein said $C_{1-7}$alkylene moiety is saturated.

In one preferred embodiment, $Q^2$ is $C_{1-7}$alkylene-$C_{5-20}$arylene, wherein said $C_{1-7}$alkylene moiety is saturated.

In one preferred embodiment, $Q^2$ is $C_{1-7}$alkylene-$C_{5-6}$arylene, wherein said $C_{1-7}$alkylene moiety is saturated.

In one preferred embodiment, $Q^2$ is $C_{1-7}$alkylene-phenylene, wherein said $C_{1-7}$alkylene moiety is saturated.

In one preferred embodiment, $Q^2$ is $C_{1-7}$alkylene-phenylene. In one preferred embodiment, $Q^2$ is methylene-phenylene, ethylene-phenylene, propylene-phenylene, and ethenylene-phenylene (also known as vinylene-phenylene).

In one preferred embodiment, $Q^2$ is phenylene-$C_{1-7}$alkylene. In one preferred embodiment, $Q^2$ is phenylene-methylene, phenylene-ethylene, phenylene-propylene, or phenylene-ethenylene (also known as phenylene-vinylene).

In the above alkylene-phenylene and phenylene-alkylene groups, the phenylene linkage may be ortho, meta, or para, and the phenylene group is optionally substituted with from 1 to 4 aryl substituents, $R^B$:

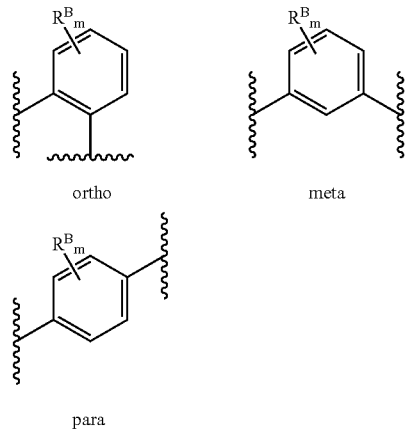

ortho  meta para

In one preferred embodiment, the phenylene linkage is meta or para. In one preferred embodiment, the phenylene linkage is para. In one preferred embodiment, the phenylene linkage is meta.

In one preferred embodiment, m is an integer from 0 to 4.
In one preferred embodiment, m is an integer from 0 to 3.
In one preferred embodiment, m is an integer from 0 to 2.
In one preferred embodiment, m is 0 or 1.
In one preferred embodiment, m is an integer from 1 to 4.
In one preferred embodiment, m is an integer from 1 to 3.
In one preferred embodiment, m is 1 or 2.
In one preferred embodiment, m is 4.
In one preferred embodiment, m is 3.
In one preferred embodiment, m is 2.
In one preferred embodiment, m is 1.
In one preferred embodiment, m is 0.

Each aryl substituent, $R^B$, is a substituent as defined herein.

Examples of preferred aryl substituents, $R^B$, include, but are not limited to, the following: fluoro, chloro, methyl, ethyl, isopropyl, t-butyl, trifluoromethyl, hydroxy, methoxy, ethoxy, isopropoxy, methylthio, amino, dimethylamino, diethylamino, morpholino, acetamido, nitro, and phenyl.

In one preferred embodiment, the phenylene linkage is meta, and $Q^2$ has the following formula, wherein $R^{Q2}$ is $C_{1-7}$alkylene and is optionally substitued (referred to herein as "phenylene-meta-$C_{1-7}$alkylene"):

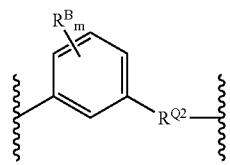

In one preferred embodiment, $R^{Q2}$ is a saturated $C_{1-7}$alkylene group.

In one preferred embodiment, $R^{Q2}$ is a partially unsaturated $C_{1-7}$alkylene group.

In one preferred embodiment, $R^{Q2}$ is an aliphatic $C_{1-7}$alkylene group.

In one preferred embodiment, $R^{Q2}$ is a linear $C_{1-7}$alkylene group.

In one preferred embodiment, $R^{Q2}$ is a branched $C_{1-7}$alkylene group.

In one preferred embodiment, $R^{Q2}$ is an alicyclic $C_{1-7}$alkylene group.

In one preferred embodiment, $R^{Q2}$ is a saturated aliphatic $C_{1-7}$alkylene group.

In one preferred embodiment, $R^{Q2}$ is a saturated linear $C_{1-7}$alkylene group.

In one preferred embodiment, $R^{Q2}$ is a saturated branched $C_{1-7}$alkylene group.

In one preferred embodiment, $R^{Q2}$ is a saturated alicyclic $C_{1-7}$alkylene group.

In one preferred embodiment, $R^{Q2}$ is a partially unsaturated aliphatic $C_{1-7}$alkylene group.

In one preferred embodiment, $R^{Q2}$ is a partially unsaturated linear $C_{1-7}$alkylene group.

In one preferred embodiment, $R^{Q2}$ is a partially unsaturated branched $C_{1-7}$alkylene group.

In one preferred embodiment, $R^{Q2}$ is a partially unsaturated alicyclic $C_{1-7}$alkylene group.

In one preferred embodiment, $R^{Q2}$ is selected from:
—(CH$_2$)$_n$— where n is an integer from 1 to 7;
—CH(CH$_3$)—;
—CH(CH$_3$)CH$_2$— and —CH$_2$CH(CH$_3$)—;
—CH(CH$_3$)CH$_2$CH$_2$—, —CH$_2$CH(CH$_3$)CH$_2$—, and —CH$_2$CH$_2$CH(CH$_3$)—;
—CH(CH$_3$)CH$_2$CH$_2$CH$_2$—, —CH$_2$CH(CH$_3$)CH$_2$CH$_2$—, —CH$_2$CH$_2$CH(CH$_3$)CH$_2$—, and —CH$_2$CH$_2$CH$_2$CH(CH$_3$)—;
—CH(CH$_3$)CH$_2$CH$_2$CH$_2$CH$_2$—, —CH$_2$CH(CH$_3$)CH$_2$CH$_2$CH$_2$—, —CH$_2$CH$_2$CH(CH$_3$)CH$_2$CH$_2$—, —CH$_2$CH$_2$CH$_2$CH(CH$_3$)CH$_2$—, and —CH$_2$CH$_2$CH$_2$CH$_2$CH(CH$_3$)—;
—CH(CH$_2$CH$_3$)—;
—CH(CH$_2$CH$_3$)CH$_2$— and —CH$_2$CH(CH$_2$CH$_3$)—;
—CH(CH$_2$CH$_3$)CH$_2$CH$_2$—, —CH$_2$CH(CH$_2$CH$_3$)CH$_2$—, and —CH$_2$CH$_2$CH(CH$_2$CH$_3$)—;
—CH(CH$_2$CH$_3$)CH$_2$CH$_2$CH$_2$—, —CH$_2$CH(CH$_2$CH$_3$)CH$_2$CH$_2$—, —CH$_2$CH$_2$CH(CH$_2$CH$_3$)CH$_2$—, and —CH$_2$CH$_2$CH$_2$CH(CH$_2$CH$_3$)—;
—CH(CH$_2$CH$_3$)CH$_2$CH$_2$CH$_2$CH$_2$—, —CH$_2$CH(CH$_2$CH$_3$)CH$_2$CH$_2$CH$_2$—, —CH$_2$CH$_2$CH(CH$_2$CH$_3$)CH$_2$CH$_2$—, —CH$_2$CH$_2$CH$_2$CH(CH$_2$CH$_3$)CH$_2$—, and —CH$_2$CH$_2$CH$_2$CH$_2$CH(CH$_2$CH$_3$)—;
—CH=CH—;
—CH=CHCH$_2$— and —CH$_2$CH=CH—;
—CH=CHCH$_2$CH$_2$—, —CH$_2$CH=CHCH$_2$—, and —CH$_2$CH$_2$CH=CH—;
—CH=CHCH$_2$CH$_2$CH$_2$—, —CH$_2$CH=CHCH$_2$CH$_2$—,
—CH$_2$CH$_2$CH=CHCH$_2$—, and
—CH$_2$CH$_2$CH$_2$CH=CH—;
—CH=CHCH$_2$CH$_2$CH$_2$CH$_2$—,
—CH$_2$CH=CHCH$_2$CH$_2$CH$_2$—,
—CH$_2$CH$_2$CH=CHCH$_2$CH$_2$—,
—CH$_2$CH$_2$CH$_2$CH=CHCH$_2$—, and
—CH$_2$CH$_2$CH$_2$CH$_2$CH=CH—;
—C(CH$_3$)=CH— and —CH=C(CH$_3$)—;
—C(CH$_3$)=CHCH$_2$—, —CH=C(CH$_3$)CH$_2$—, and —CH=CHCH(CH$_3$)—;
—CH(CH$_3$)CH=CH—, —CH$_2$C(CH$_3$)=CH—, and —CH$_2$CH=C(CH$_3$)—;
—CH=CHCH=CH—;
—CH=CHCH=CHCH$_2$—,
—CH$_2$CH=CHCH=CH—, and
—CH=CHCH$_2$CH=CH—;
—CH=CHCH=CHCH$_2$CH$_2$—,
—CH=CHCH$_2$CH=CHCH$_2$—,
—CH=CHCH$_2$CH$_2$CH=CH—,
—CH$_2$CH=CHCH=CHCH$_2$—,
—CH$_2$CH=CHCH$_2$CH=CH—, and
—CH$_2$CH$_2$CH=CHCH=CH—;

—C(CH$_3$)=CHCH=CH—, —CH=C(CH$_3$)CH=CH—, —CH=CHC(CH$_3$)=CH—, and —CH=CHCH=C(CH$_3$)—;

cyclopentylene and cyclopentenylene; and, cyclohexylene, cyclohexenylene, and cyclohexadienylene.

In one preferred embodiment, $R^{Q2}$ is selected from:
—CH$_2$—, —(CH$_2$)$_2$—, —(CH$_2$)$_3$—, —(CH$_2$)$_4$—, —(CH$_2$)$_5$—, and —(CH$_2$)$_6$—;
—CH=CH—, —CH=CH—CH=CH—;

In one preferred embodiment, $R^{Q2}$ is cis or trans —CH=CH—.

In one preferred embodiment, $R^{Q2}$ is cis —CH=CH—.

In one preferred embodiment, $R^{Q2}$ is trans —CH=CH—.

In one preferred embodiment, $R^{Q2}$ is —CH=CH—, and $Q^2$ is (referred to herein as "phenylene-meta-trans-ethylene"):

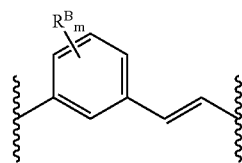

In one preferred embodiment, m is 0, and $Q^2$ is (referred to herein as "unsubstituted phenylene-meta-trans-ethylene"):

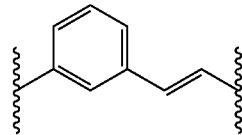

In one preferred embodiment, $Q^2$ is selected from:

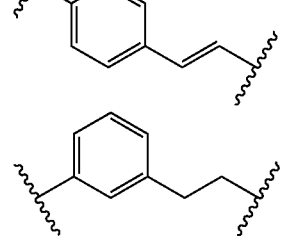

Certain Embodiments

As discussed above, in all embodiments:

(a) the aryl leader, $Q^1$, is $C_{1-7}$alkylene with backbone of at least 2 carbon atoms, and is optionally substituted; and, (b) the acid leader, $Q^2$, is $C_{1-10}$alkylene; $C_{5-20}$arylene; $C_{5-20}$arylene-$C_{1-10}$alkylene; or $C_{1-10}$alkylene-$C_{5-20}$arylene; and is optionally substituted.

Certain preferred embodiments are described below.

(1-A) In one embodiment, the aryl leader, $Q^1$, is a partially unsaturated aliphatic $C_{1-7}$alkylene group with a backbone of at least 2 carbon atoms.

(1-B) In one embodiment, the aryl leader, $Q^1$, is a partially unsaturated aliphatic $C_{1-7}$alkylene group with a backbone of at least 2 carbon atoms, and in $Q^1$, the carbon atom adjacent to J is not saturated.

(1-C) In one embodiment, the aryl leader, $Q^1$, is a partially unsaturated aliphatic $C_{1-7}$alkylene group with a backbone of at least 3 carbon atoms.

(1-D) In one embodiment, the aryl leader, $Q^1$, is a partially unsaturated aliphatic $C_{1-7}$alkylene group with a backbone of at least 3 carbon atoms, and in $Q^1$, the carbon atom adjacent to J is not saturated.

(1-E) In one embodiment, the aryl leader, $Q^1$, is an unsubstituted partially unsaturated aliphatic $C_{1-7}$alkylene group with a backbone of at least 2 carbon atoms.

(1-F) In one embodiment, the aryl leader, $Q^1$, is an unsubstituted partially unsaturated aliphatic $C_{1-7}$alkylene group with a backbone of at least 2 carbon atoms and $Q^1$ is not saturated at the carbon atom adjacent to J.

(1-G) In one embodiment, the aryl leader, $Q^1$, is an unsubstituted partially unsaturated aliphatic $C_{1-7}$alkylene group with a backbone of at least 3 carbon atoms.

(1-H) In one embodiment, the aryl leader, $Q^1$, is an unsubstituted partially unsaturated aliphatic $C_{1-7}$alkylene group with a backbone of at least 3 carbon atoms and $Q^1$ is not saturated at the carbon atom adjacent to J.

(2-A) In one embodiment, the acid leader, $Q^2$ has a backbone of at least 4 carbon atoms.

(2-B) In one embodiment, the acid leader, $Q^2$ is a $C_{1-10}$alkylene group with backbone of at least 4 carbon atoms.

(2-C) In one embodiment, the acid leader, $Q^2$ is an aliphatic $C_{1-10}$alkylene group with backbone of at least 4 carbon atoms.

(2-D) In one embodiment, the acid leader, $Q^2$ is a linear $C_{1-10}$alkylene group with backbone of at least 4 carbon atoms.

(2-E) In one embodiment, the acid leader, $Q^2$ is a linear saturated $C_{1-10}$alkylene group with backbone of at least 4 carbon atoms.

(2-F) In one embodiment, the acid leader, $Q^2$ is a $C_{5-20}$arylene-$C_{1-7}$alkylene group, wherein:
(i) said $C_{1-7}$alkylene moiety does not comprise a carbon-carbon triple bond; or,
(ii) $Q^2$ has a backbone of less than 7 carbon atoms; or,
(iii) both (i) and (ii); or,
(iv) $Q^2$ is unsubstituted phenylene-meta-trans-ethylene.

Additional preferred embodiments are those which are combinations of one of (1-A) through (1-H) with one of (2-B) through (2-F). Each one of these combinations is explicitly included herein, as if it were individually recited.

For example, in one embodiment:
(1-C) the aryl leader, $Q^1$, is a partially unsaturated aliphatic $C_{1-7}$alkylene group a backbone of at least 3 carbon atoms; and,
(2-E) In one embodiment, the acid leader, $Q^2$ is a linear saturated $C_{1-10}$alkylene group with backbone of at least 4 carbon atoms.

In one embodiment, $Q^1$ and $Q^2$ are as defined in any one of the embodiments above, and A is optionally substituted phenyl.

Examples of Specific Embodiments

Examples of compounds with no $Q^1$ group (i.e., where $Q^1$ is a covalent bond) are shown below, for comparison purposes.

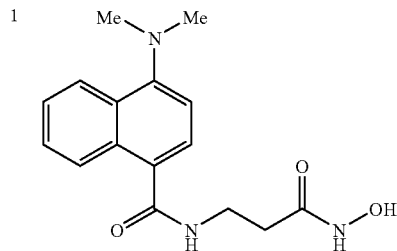

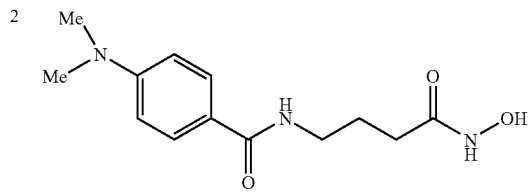

-continued
| | | |
|---|---|---|
| 3 | 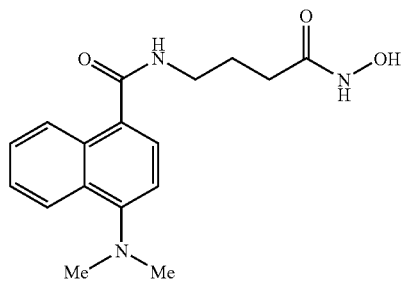 | PX082533 |
| 4 | 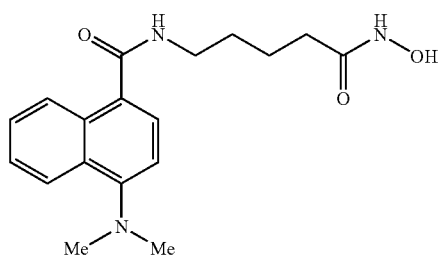 | PX082534 |
| 5 | 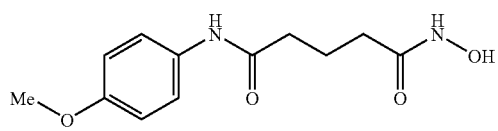 | PX082546 |
| 6 | 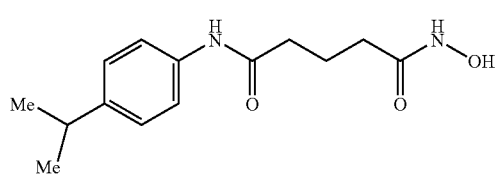 | PX082548 |
| 7 | 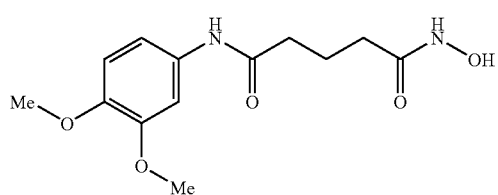 | PX082549 |
| 8 | 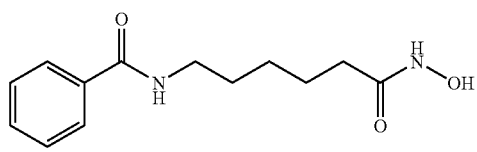 | PX083449 |
| 9 | 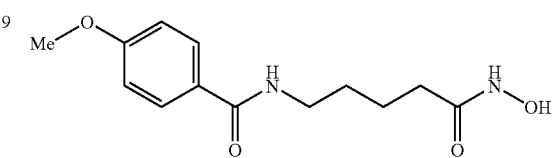 | PX089048 |
| 10 | 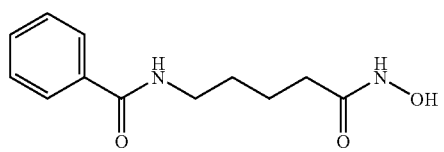 | PX089049 |

-continued
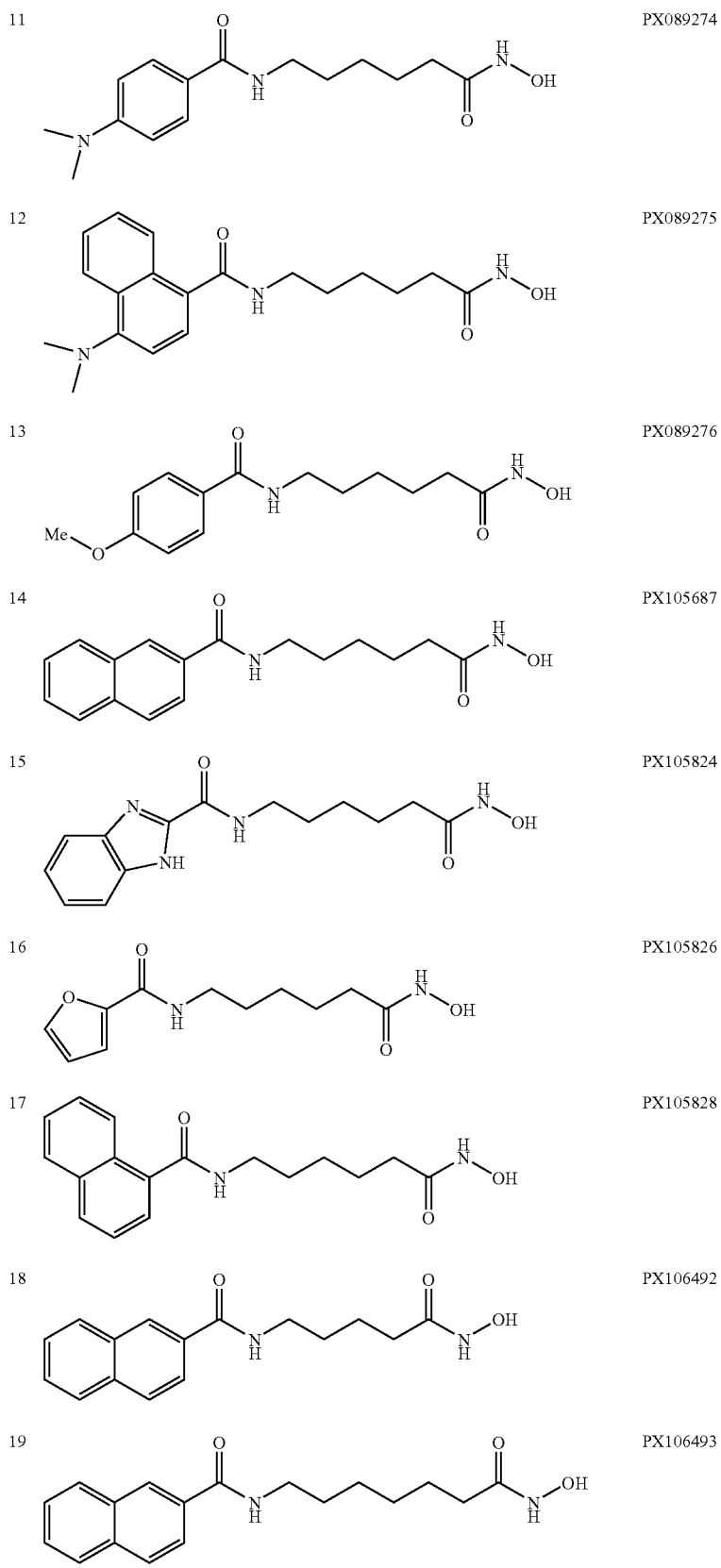
| 11 | PX089274 |
| 12 | PX089275 |
| 13 | PX089276 |
| 14 | PX105687 |
| 15 | PX105824 |
| 16 | PX105826 |
| 17 | PX105828 |
| 18 | PX106492 |
| 19 | PX106493 |

-continued

| | | |
|---|---|---|
| 20 | 4-iodo-benzamide-(CH2)4-C(O)NHOH | PX106494 |
| 21 | 4-nitro-benzamide-(CH2)4-C(O)NHOH | PX106495 |
| 22 | 4-tert-butyl-benzamide-(CH2)4-C(O)NHOH | PX106496 |
| 23 | 4-cyano-benzamide-(CH2)4-C(O)NHOH | PX106497 |
| 24 | naphthalene-2-carboxamide-(CH2)5-C(O)NHOH | PX106515 |
| 25 | 4-amino-furazan-3-carboxamide-(CH2)4-C(O)NHOH | PX106519 |
| 26 | 3,4-dimethoxy-benzamide-(CH2)4-C(O)NHOH | PX116213 |
| 27 | 4-bromo-benzamide-(CH2)4-C(O)NHOH | PX116215 |
| 28 | naphthalen-1-yl-NHC(O)-(CH2)5-C(O)NHOH | PX116218 |

-continued
| | | |
|---|---|---|
| 29 | 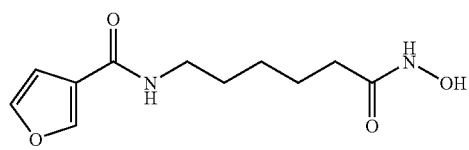 | PX116219 |
| 30 | 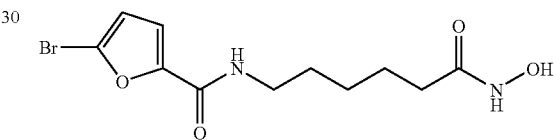 | PX116221 |
| 31 | 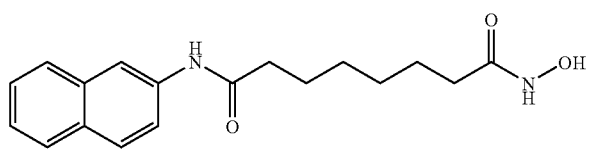 | PX116223 |
| 32 | 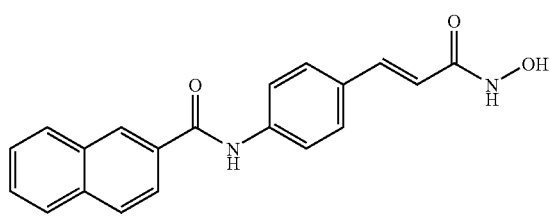 | PX116246 |
| 33 | 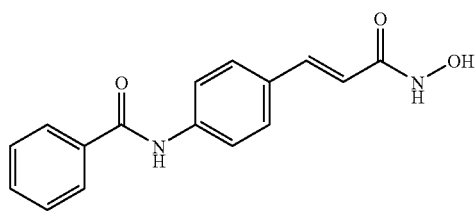 | PX117231 |
| 34 | 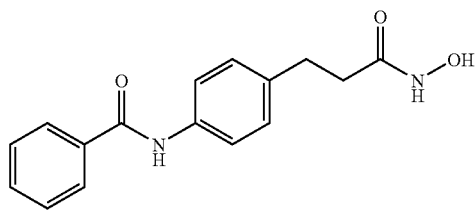 | PX117232 |
| 35 | 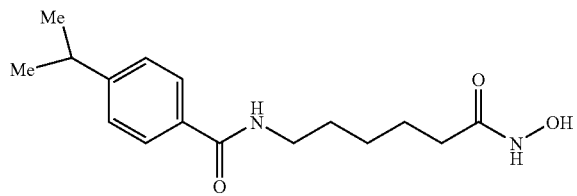 | PX117421 |
| 36 | 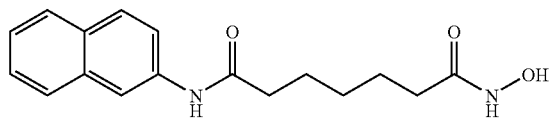 | PX117461 |

-continued
| | | |
|---|---|---|
| 37 | 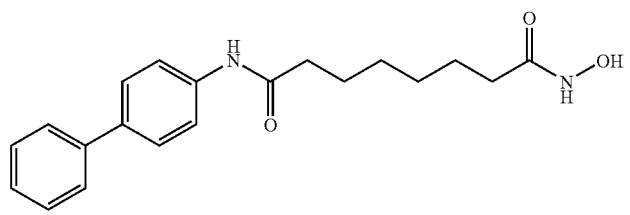 | PX117720 |
| 38 | 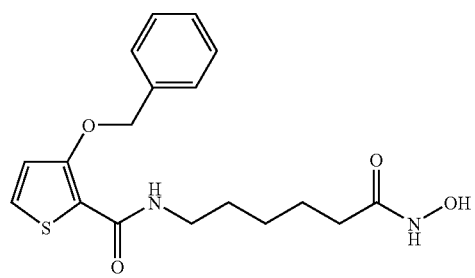 | PX117723 |
| 39 | 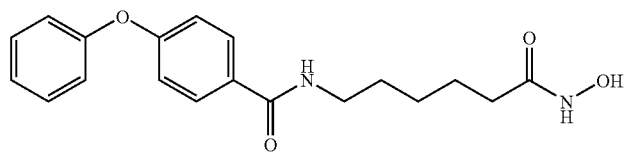 | PX117726 |
Examples of compounds where $Q^1$ has a backbone length 1 are shown below, for comparison purposes.
| | | |
|---|---|---|
| 40 | 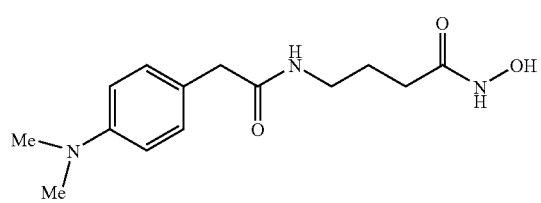 | PX082532 |
| 41 | 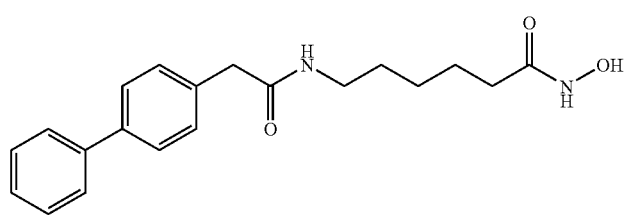 | PX106488 |
| 42 | 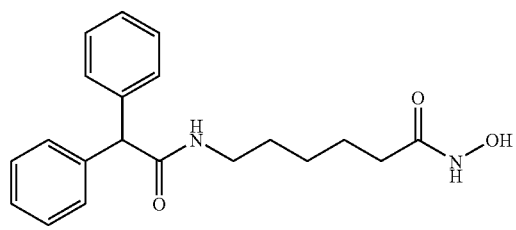 | PX106489 |

-continued
| | | |
|---|---|---|
| 43 | 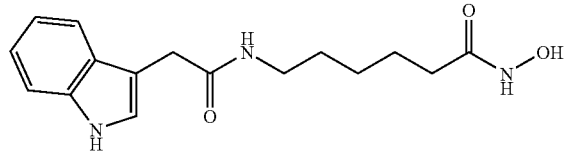 | PX116214 |
| 44 | 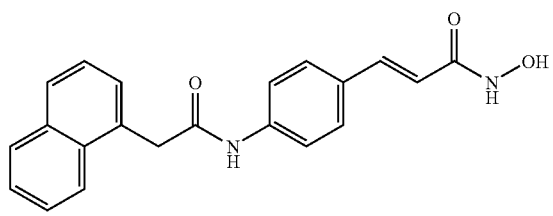 | PX116244 |
| 45 | 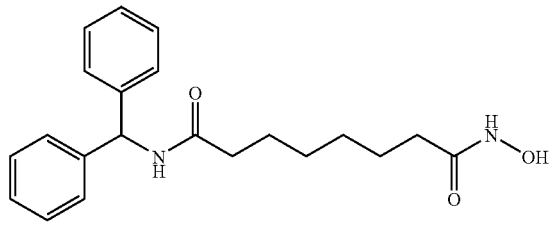 | PX117417 |
| 46 | 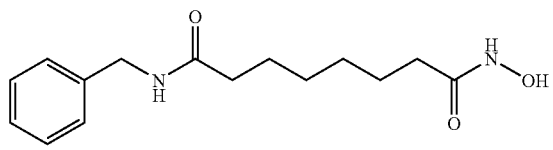 | PX117418 |
| 47 | 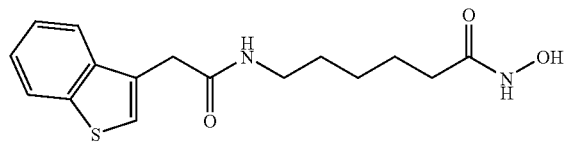 | PX117442 |
| 48 | 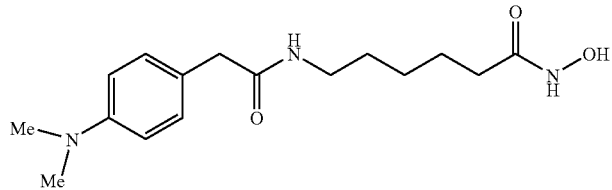 | PX117458 |
| 49 | 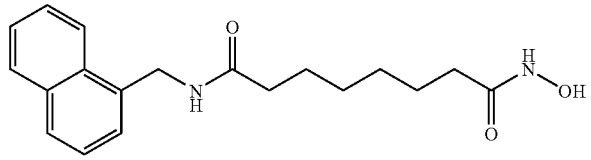 | PX117459 |

-continued
| 50 | 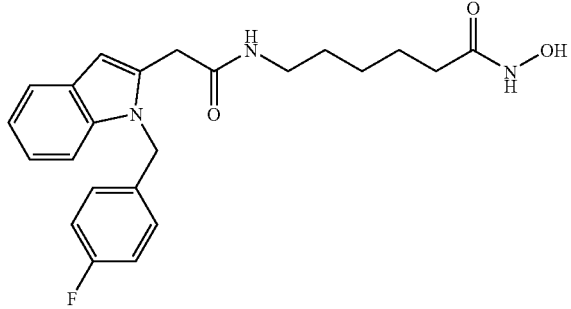 | PX117721 |
| 51 | 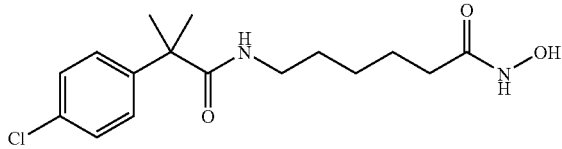 | PX117722 |
| 52 | 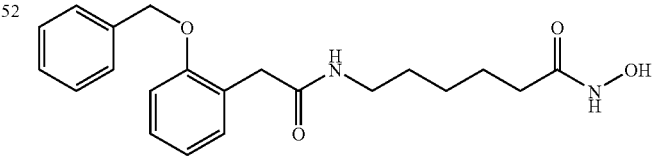 | PX117728 |
Some individual embodiments of the present invention, where $Q^1$ has a backbone length of at least 2, include the following compounds.
| 53 | 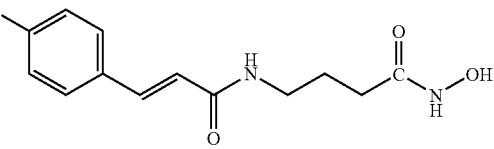 | PX083447 |
| 54 | 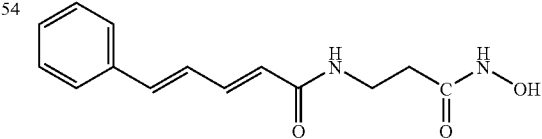 | PX083448 |
| 55 | 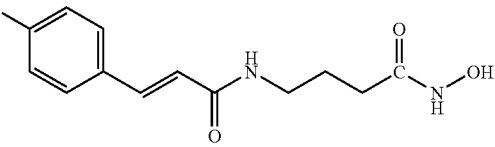 | PX083803 |
| 56 | 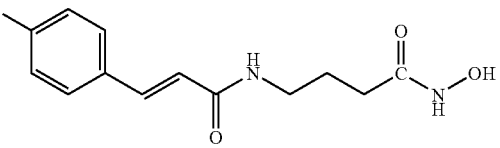 | PX083804 |

| | | |
|---|---|---|
| 57 | 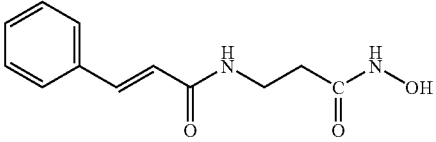 | PX083806 |
| 58 | 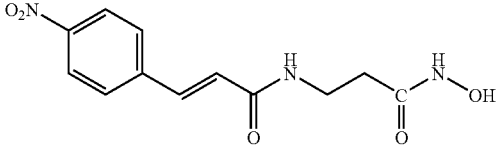 | PX083807 |
| 59 | 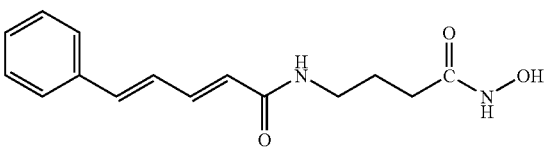 | PX083808 |
| 60 | 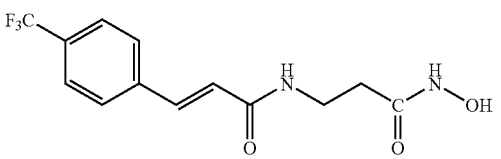 | PX089283 |
| 61 | 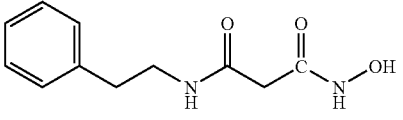 | PX099268 |
| 62 | 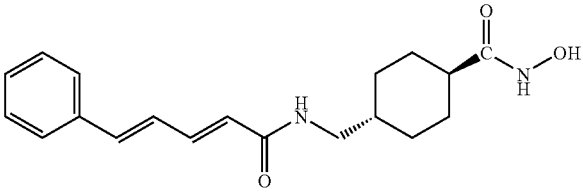 | PX105552 |
| 63 | 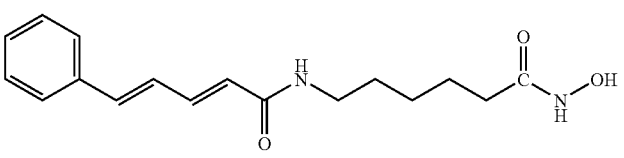 | PX105553 |
| 64 | 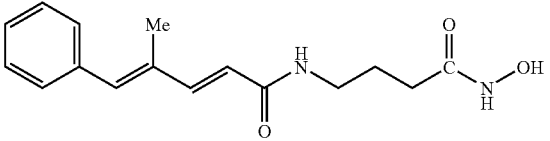 | PX105554 |
| 65 | 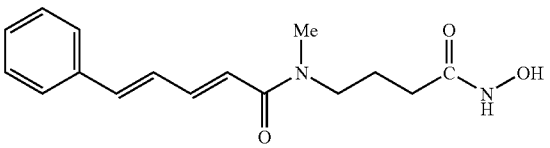 | PX105668 |
| 66 | 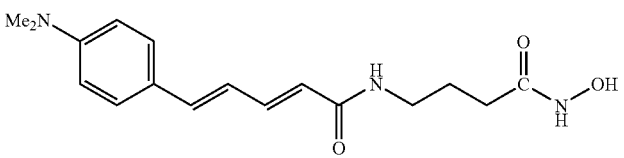 | PX105669 |

-continued
| | | |
|---|---|---|
| 67 | 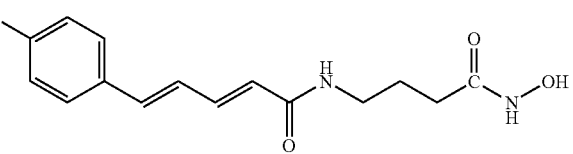 | PX105670 |
| 68 | 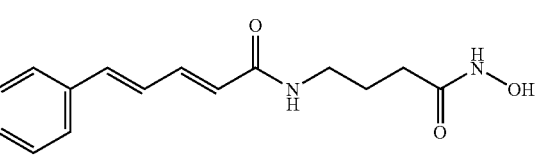 | PX105816 |
| 69 | 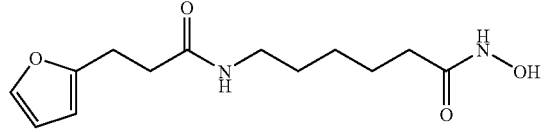 | PX105827 |
| 70 | 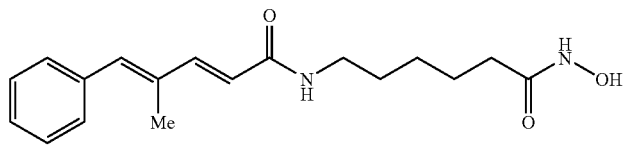 | PX105829 |
| 71 | 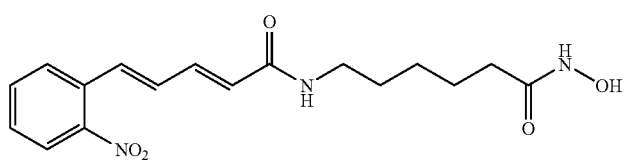 | PX105830 |
| 72 | 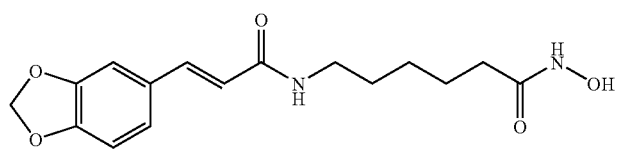 | PX105831 |
| 73 | 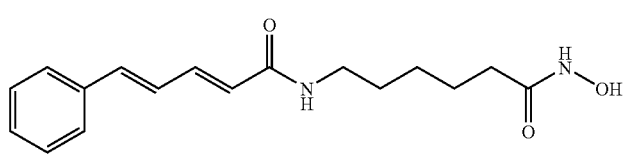 | PX105832 |
| 74 | 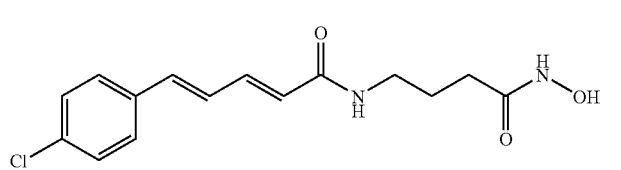 | PX105845 |

| | | |
|---|---|---|
| 75 | 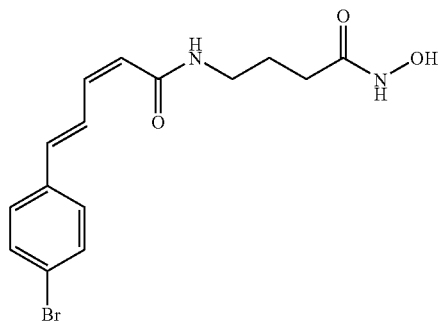 | PX105846 |
| 76 | 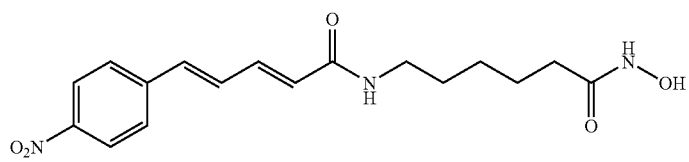 | PX105847 |
| 77 | 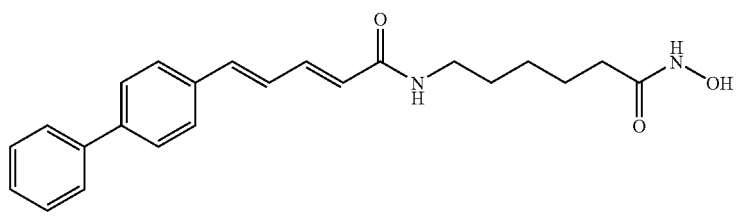 | PX105848 |
| 78 | 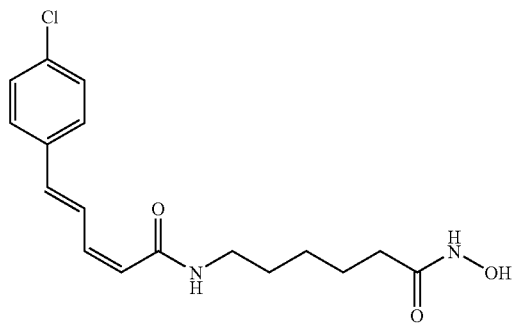 | PX105849 |
| 79 | 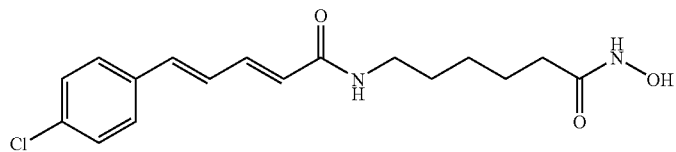 | PX105850 |
| 80 | 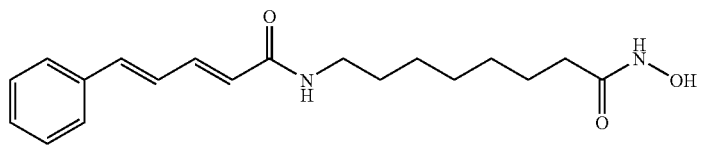 | PX105851 |
| 81 | 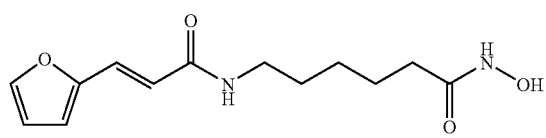 | PX106491 |

-continued
| | | |
|---|---|---|
| 82 | 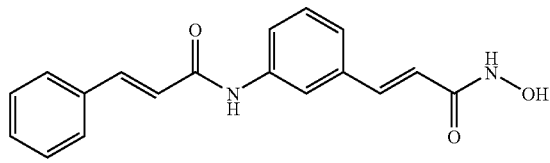 | PX106513 |
| 83 | 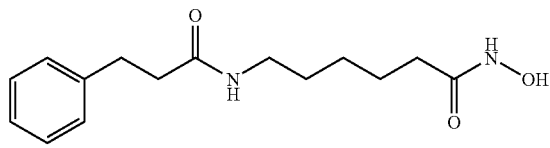 | PX106516 |
| 84 | 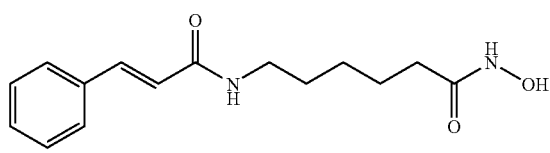 | PX106517 |
| 85 | 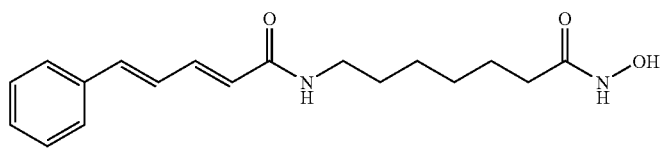 | PX106518 |
| 86 | 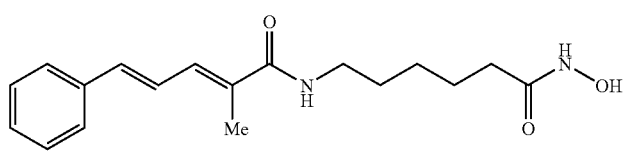 | PX106520 |
| 87 | 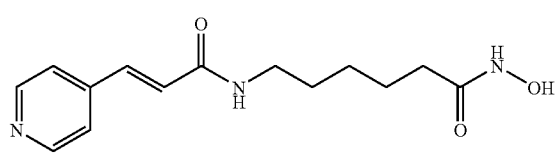 | PX106521 |
| 88 | 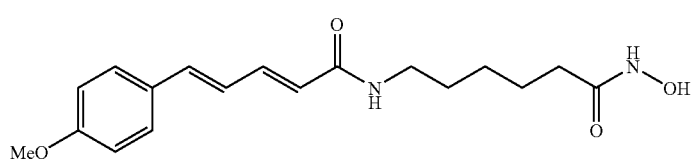 | PX106524 |
| 89 | 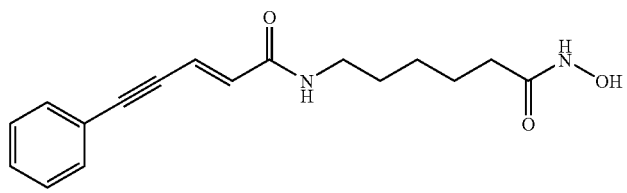 | PX106525 |
| 90 | 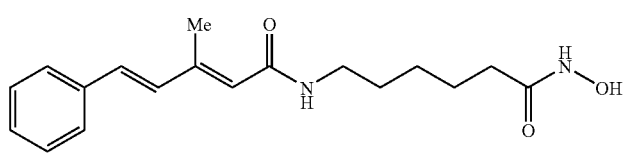 | PX106526 |

| | | |
|---|---|---|
| 91 | 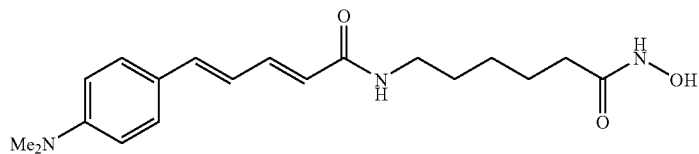 | PX106527 |
| 92 | 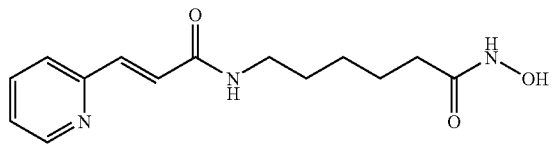 | PX106528 |
| 93 | 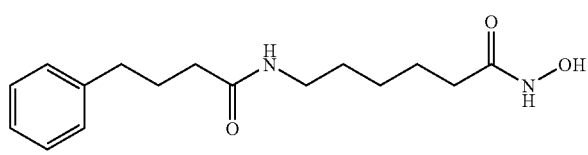 | PX116210 |
| 94 | 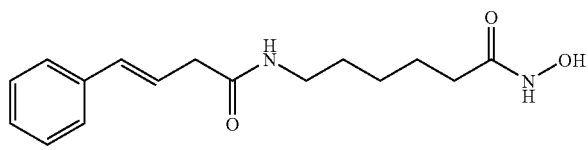 | PX116211 |
| 95 | 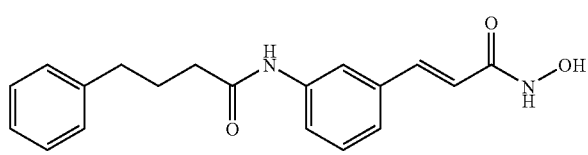 | PX116212 |
| 96 | 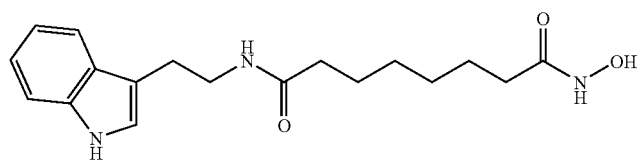 | PX116216 |
| 97 | 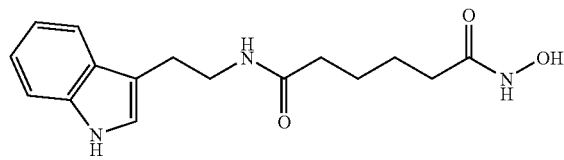 | PX116217 |
| 98 | 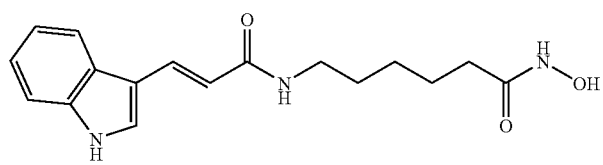 | PX116220 |
| 99 | 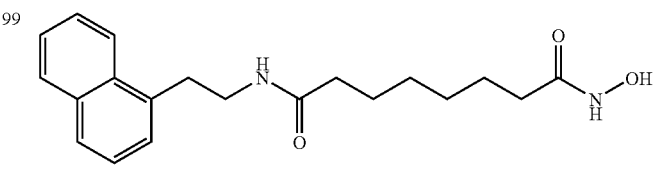 | PX116224 |

-continued

| # | Structure | Code |
|---|---|---|
| 100 | 2-hydroxy-2-phenylethyl-NH-C(O)-(CH2)5-C(O)-NHOH | PX116226 |
| 101 | furan-2-yl-CH=CH-CH=CH-C(O)-NH-(CH2)4-C(O)-NHOH | PX116230 |
| 102 | pyridin-3-yl-CH=CH-C(O)-NH-(CH2)5-C(O)-NHOH | PX116231 |
| 103 | naphthalen-2-yl-CH=CH-C(O)-NH-(CH2)5-C(O)-NHOH | PX116232 |
| 104 | Ph-CH=CH-CH=CH-C(O)-N(Me)-(CH2)4-C(O)-NHOH | PX116234 |
| 105 | 5-(4-chlorophenoxy)furan-2-yl-CH=CH-C(O)-NH-(CH2)5-C(O)-NHOH | PX116235 |
| 106 | 1H-benzimidazol-2-yl-CH2CH2-NH-C(O)-(CH2)6-C(O)-NHOH | PX116241 |
| 107 | 5-(3,5-bis(trifluoromethyl)phenyl)furan-2-yl-CH=CH-C(O)-NH-(CH2)4-C(O)-NHOH | PX117224 |
| 108 | naphthalen-1-yl-CH=CH-CH=CH-C(O)-NH-(CH2)4-C(O)-NHOH | PX117237 |

-continued
| | | |
|---|---|---|
| 109 | 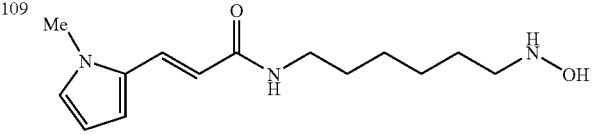 | PX117239 |
| 110 | 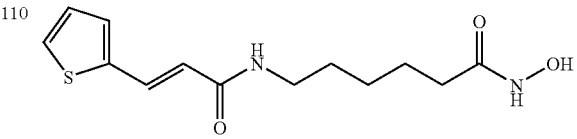 | PX117247 |
| 111 | 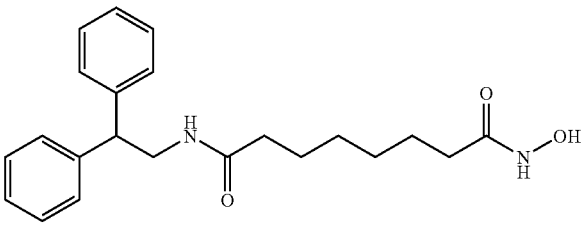 | PX117249 |
| 112 | 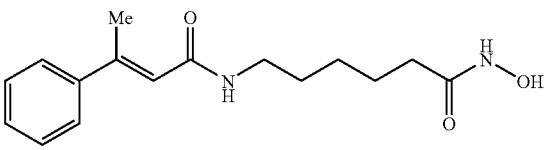 | PX117254 |
| 113 | 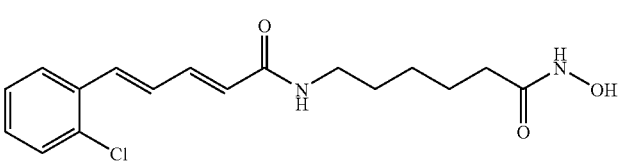 | PX117255 |
| 114 | 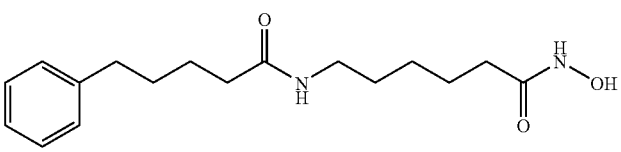 | PX117261 |
| 115 | 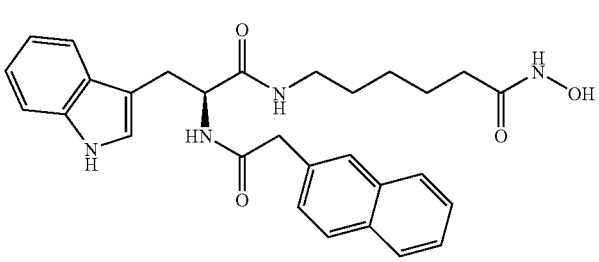 | PX117406 |
| 116 | 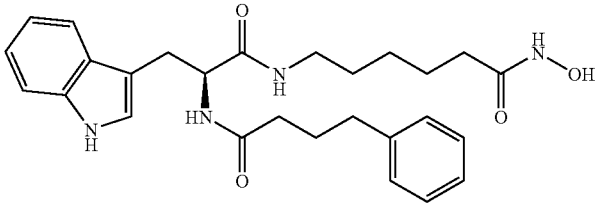 | PX117407 |

-continued
| | | |
|---|---|---|
| 117 | 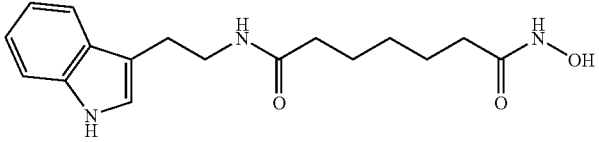 | PX117408 |
| 118 | 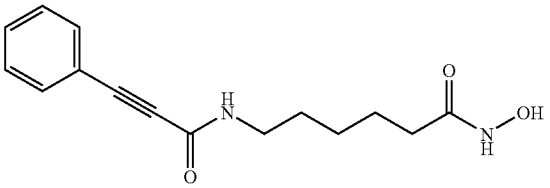 | PX117415 |
| 119 | 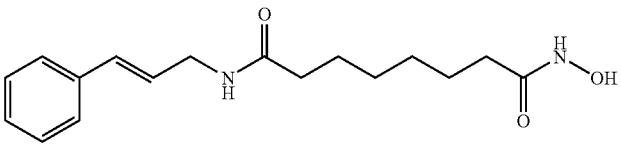 | PX117416 |
| 120 | 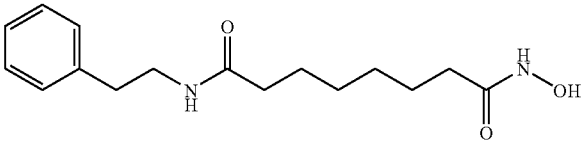 | PX117419 |
| 121 | 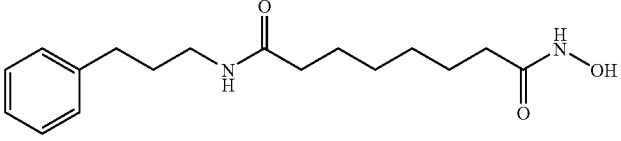 | PX117420 |
| 122 | 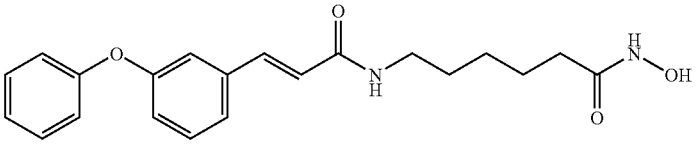 | PX117430 |
| 123 | 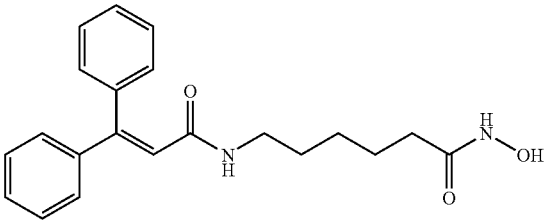 | PX117436 |
| 124 | 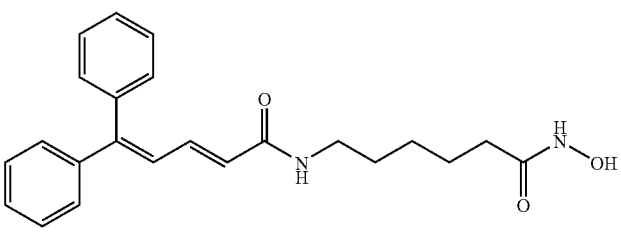 | PX117437 |
| 125 | 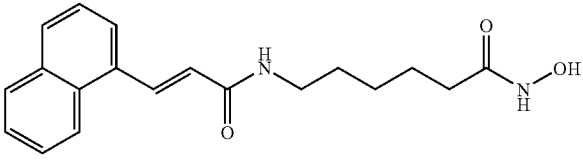 | PX117441 |

| | | |
|---|---|---|
| 126 | 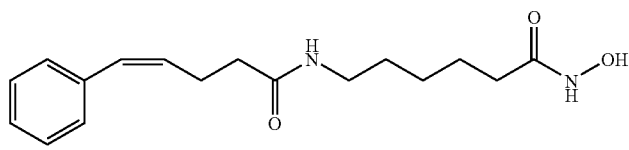 | PX117444 |
| 127 | 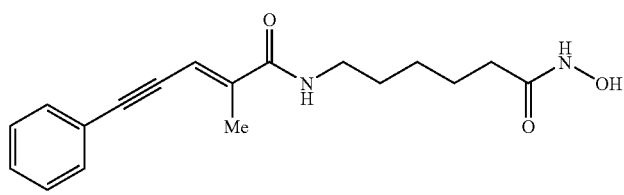 | PX117451 |
| 128 | 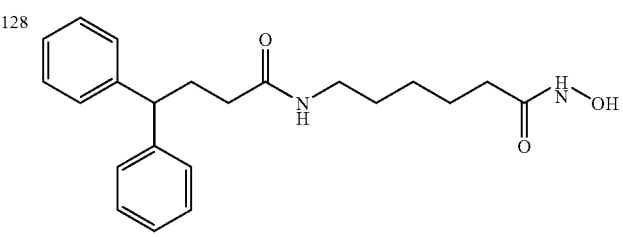 | PX117454 |
| 129 | 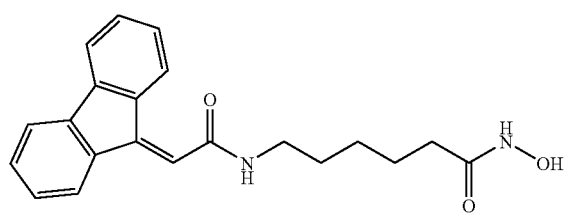 | PX117456 |
| 130 | 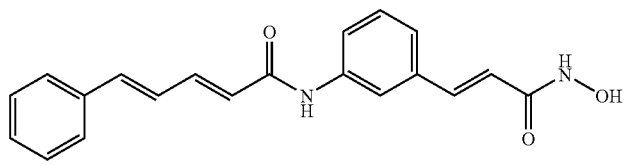 | PX117706 |
| 131 | 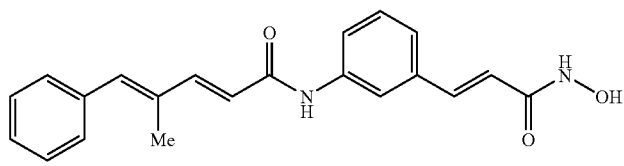 | PX117707 |
| 132 | 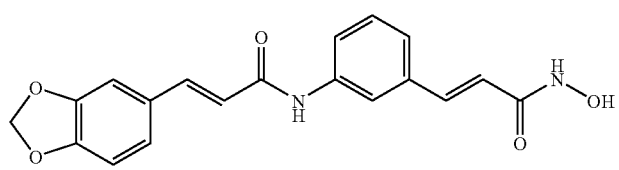 | PX117711 |
| 133 | 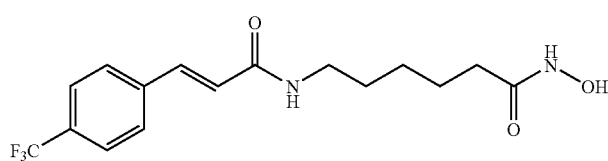 | PX117717 |

-continued
| | | |
|---|---|---|
| 134 | 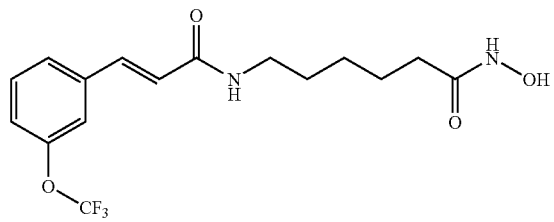 | PX117718 |
| 135 | 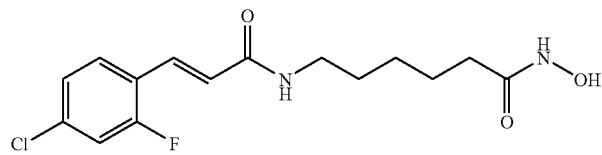 | PX117719 |
| 136 | 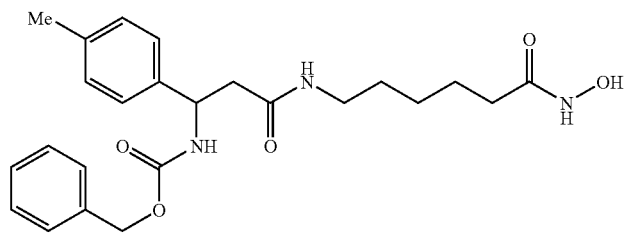 | PX117729 |
| 137 | 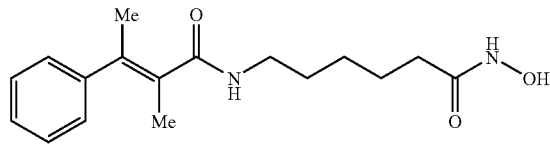 | PX117737 |
| 138 | 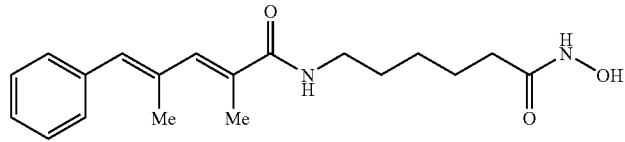 | PX117738 |
| 139 | 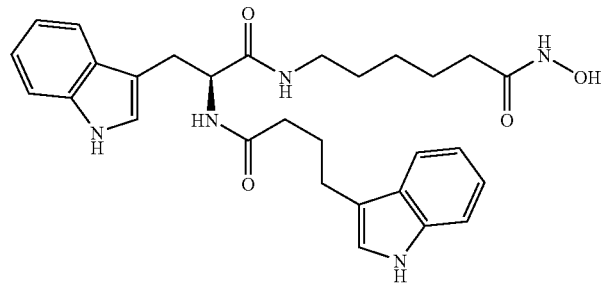 | PX117767 |
| 140 | 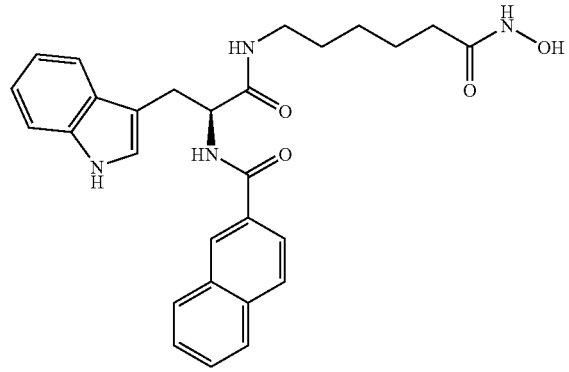 | PX117783 |

-continued
141 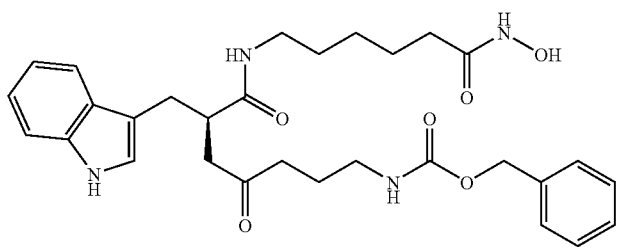 PX117785
142 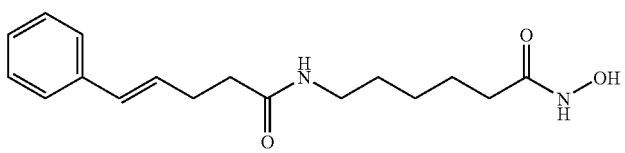 PX117797
143 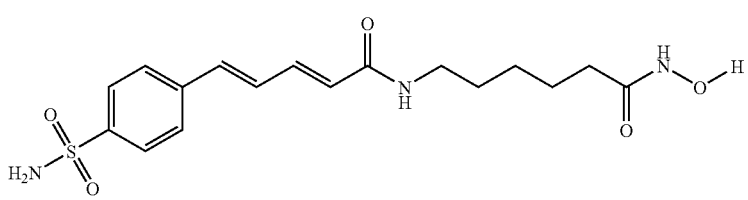
144 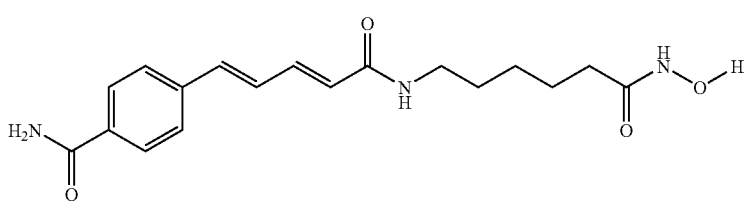
145 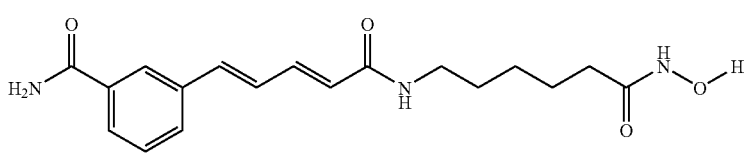
146 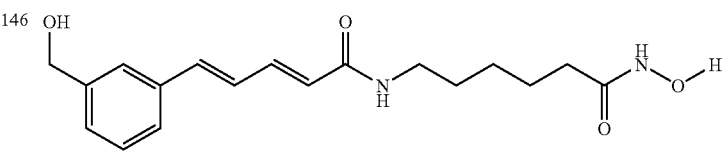
147 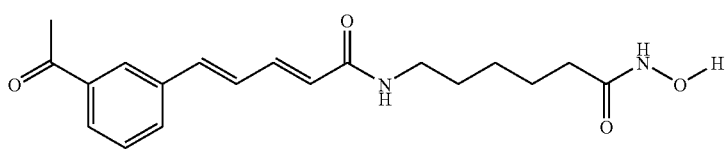
148 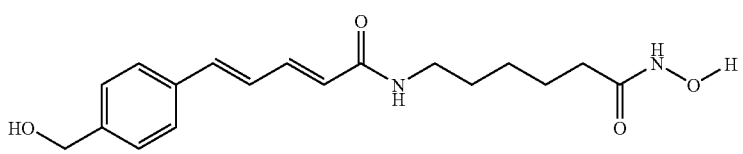

-continued
| | |
|---|---|
| 149 | 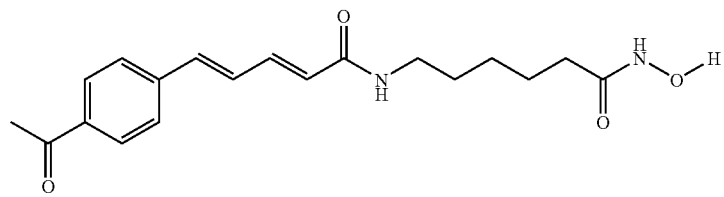 |
| 150 | 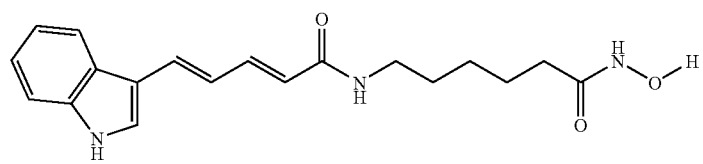 |
| 151 | 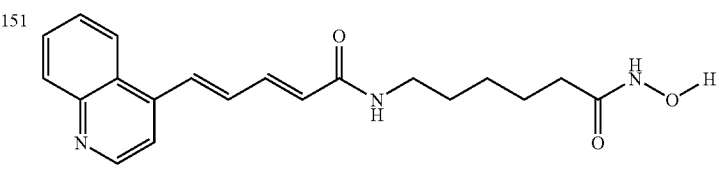 |
| 152 | 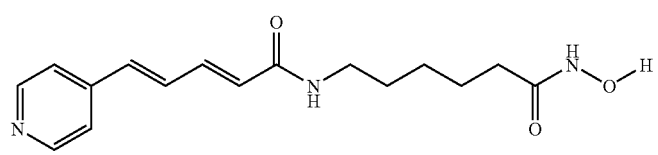 |
| 153 | 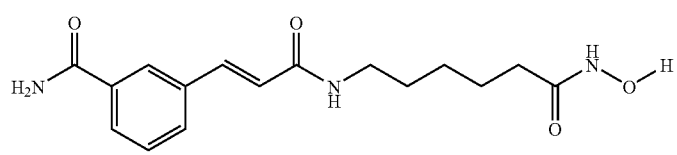 |
| 154 | 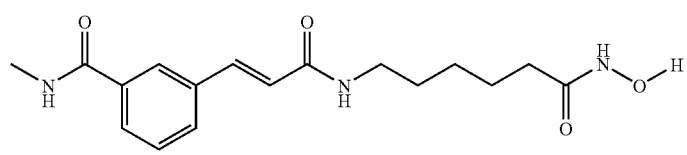 |
| 155 | 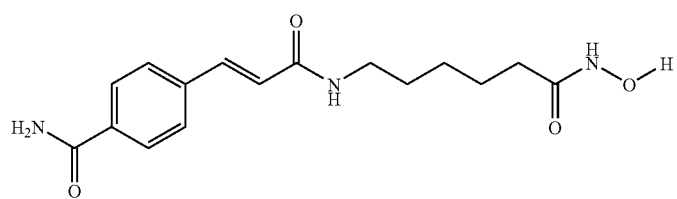 |
| 156 | 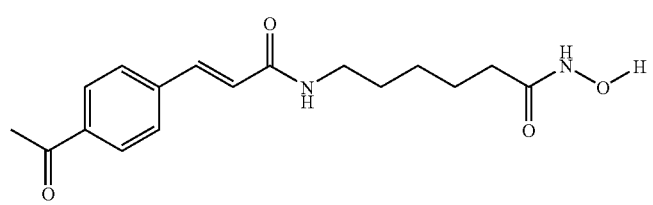 |

| | |
|---|---|
| 157 | 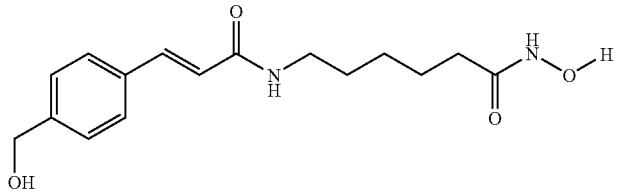 |
| 158 | 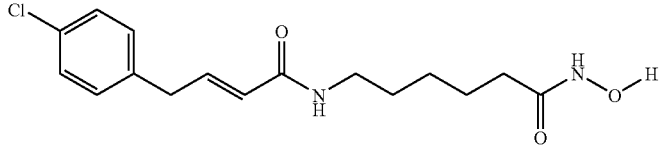 |
| 159 | 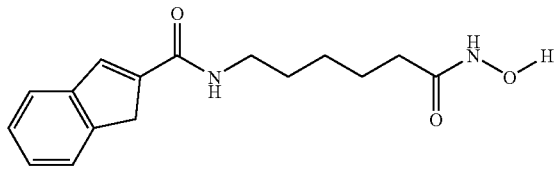 |
| 160 | 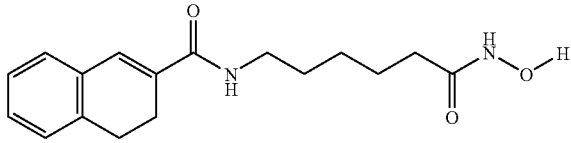 |
| 161 | 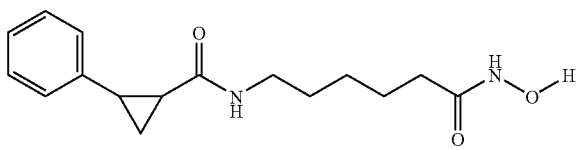 |

Chemical Terms

The term "carbo," "carbyl," "hydrocarbo," and "hydrocarbyl," as used herein, pertain to compounds and/or groups which have only carbon and hydrogen atoms.

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, and sulfur, and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "ring," as used herein, pertains to a closed ring of from 3 to 10 covalently linked atoms, more preferably 3 to 8 covalently linked atoms.

The term "aromatic ring," as used herein, pertains to a closed ring of from 3 to 10 covalently linked atoms, more preferably 5 to 8 covalently linked atoms, which ring is aromatic.

The term "heterocyclic ring," as used herein, pertains to a closed ring of from 3 to 10 covalently linked atoms, more preferably 3 to 8 covalently linked atoms, wherein at least one of the ring atoms is a multivalent ring heteroatom, for example, nitrogen, phosphorus, silicon, oxygen, and sulfur, though more commonly nitrogen, oxygen, and sulfur.

The term "alicyclic," as used herein, pertains to compounds and/or groups which have one ring, or two or more rings (e.g., spiro, fused, bridged), wherein said ring(s) are not aromatic.

The term "aromatic," as used herein, pertains to compounds and/or groups which have one ring, or two or more rings (e.g., fused), wherein at least one of said ring(s) is aromatic.

The term "heterocyclic," as used herein, pertains to cyclic compounds and/or groups which have one heterocyclic ring, or two or more heterocyclic rings (e.g., spiro, fused, bridged), wherein said ring(s) may be alicyclic or aromatic.

The term "heteroaromatic," as used herein, pertains to cyclic compounds and/or groups which have one heterocyclic ring, or two or more heterocyclic rings (e.g., fused), wherein said ring(s) is aromatic.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

In one preferred embodiment, the substituent(s), often referred to herein as R, are independently selected from: halo; hydroxy; ether (e.g., $C_{1-7}$alkoxy); formyl; acyl (e.g., $C_{1-7}$alkylacyl, $C_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

In one preferred embodiment, the substituent(s), often referred to herein as R, are independently selected from:
—F, —Cl, —Br, and —I;
—OH;
—OMe, —OEt, —O(tBu), and —OCH$_2$Ph;
—SH;
—SMe, —SEt, —S(tBu), and —SCH$_2$Ph;
—C(=O)H;
—C(=O)Me, —C(=O)Et, —C(=O)(tBu), and —C(=O)Ph;
—C(=O)OH;
—C(=O)OMe, —C(=O)OEt, and —C(=O)O(tBu);
—C(=O)NH$_2$, —C(=O)NHMe, —C(=O)NMe$_2$, and —C(=O)NHEt;
—NHC(=O)Me, —NHC(=O)Et, —NHC(=O)Ph, succinimidyl, and maleimidyl;
—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;
—CN;
—NO$_2$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$;
—CH$_2$OH, —CH$_2$CH$_2$OH, and —CH(OH)CH$_2$OH;
—CH$_2$NH$_2$, —CH$_2$CH$_2$NH$_2$, and —CH$_2$CH$_2$NMe$_2$; and,
optionally substituted phenyl.

In one preferred embodiment, the substituent(s), often referred to herein as R, are independently selected from: —F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, and -Ph.

In one preferred embodiment, the substituent(s), often referred to herein as R, are independently selected from: hydroxy; ether (e.g., $C_{1-7}$alkoxy); ester; amido; amino; and, $C_{1-7}$alkyl (including, e.g., $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl).

In one preferred embodiment, the substituent(s), often referred to herein as R, are independently selected from:
—OH;
—OMe, —OEt, —O(tBu), and —OCH$_2$Ph;
—C(=O)OMe, —C(=O)OEt, and —C(=O)O(tBu);
—C(=O)NH$_2$, —C(=O)NHMe, —C(=O)NMe$_2$, and —C(=O)NHEt;
—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$CH$_2$OH, and —CH(OH)CH$_2$OH; and,
—CH$_2$NH$_2$, —CH$_2$CH$_2$NH$_2$, and —CH$_2$CH$_2$NMe$_2$.

The substituents are described in more detail below.

$C_{1-7}$alkyl: The term "$C_{1-7}$alkyl," as used herein, pertains to a monovalent moiety obtained by removing a hydrogen atom from a $C_{1-7}$hydrocarbon compound having from 1 to 7 carbon atoms, which may be aliphatic or alicyclic, or a combination thereof, and which may be saturated, partially unsaturated, or fully unsaturated.

Examples of (unsubstituted) saturated linear $C_{1-7}$alkyl groups include, but are not limited to, methyl, ethyl, n-propyl, n-butyl, and n-pentyl (amyl).

Examples of (unsubstituted) saturated branched $C_{1-7}$alkyl groups include, but are not limited to, iso-propyl, iso-butyl, sec-butyl, tert-butyl, and neo-pentyl.

Examples of saturated alicyclic (also carbocyclic) $C_{1-7}$alkyl groups (also referred to as "$C_{3-7}$cycloalkyl" groups) include, but are not limited to, unsubstituted groups such as cyclopropyl, cyclobutyl, cyclopentyl, cyclohexyl, and norbornane, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of (unsubstituted) unsaturated $C_{1-7}$alkyl groups which have one or more carbon-carbon double bonds (also referred to as "$C_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of (unsubstituted) unsaturated $C_{1-7}$alkyl groups which have one or more carbon-carbon triple bonds (also referred to as "$C_{2-7}$alkynyl" groups) include, but are not limited to, ethynyl (ethinyl) and 2-propynyl (propargyl).

Examples of unsaturated alicyclic (also carbocyclic) $C_{1-7}$alkyl groups which have one or more carbon-carbon double bonds (also referred to as "$C_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

Additional examples of substituted $C_{3-7}$cycloalkyl groups include, but are not limited to, those with one or more other rings fused thereto, for example, those derived from: indene ($C_9$), indan (2,3-dihydro-1H-indene) ($C_9$), tetraline (1,2,3,4-tetrahydronaphthalene ($C_{10}$), adamantane ($C_{10}$), decalin (decahydronaphthalene) ($C_{12}$), fluorene ($C_{13}$), phenalene ($C_{13}$). For example, 2H-inden-2-yl is a $C_5$cycloalkyl group with a substituent (phenyl) fused thereto.

$C_{3-20}$heterocyclyl: The term "$C_{3-20}$heterocyclyl," as used herein, pertains to a monovalent moiety obtained by removing a hydrogen atom from a ring atom of a $C_{3-20}$heterocyclic compound, said compound having one ring, or two or more rings (e.g., spiro, fused, bridged), and having from 3 to 20 ring atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$heteroclyl, $C_{5-7}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranose, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

$C_{5-20}$aryl: The term "$C_{5-20}$aryl," as used herein, pertains to a monovalent moiety obtained by removing a hydrogen atom from an aromatic ring atom of a $C_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms. In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{5-7}$aryl, $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene (C16).

Examples of aryl groups which comprise fused rings, at least one of which is an aromatic ring, include, but are not limited to, groups derived from indene ($C_9$), isoindene ($C_9$), and fluorene (C13).

Alternatively, the ring atoms may include one or more heteroatoms, including but not limited to oxygen, nitrogen, and sulfur, as in "heteroaryl groups." In this case, the group may conveniently be referred to as a "$C_{5-20}$heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), purine ($N_4$) (e.g., adenine, guanine), benzimidazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$heterocyclic groups (with 2 fused rings) derived from benzodioxan ($O_2$), quinoline ($N_1$), isoquinoline ($N_1$), benzoxazine ($N_1O_1$), benzodiazine ($N_2$), pyridopyridine ($N_2$), quinoxaline ($N_2$), quinazoline ($N_2$);

$C_{13}$heterocyclic groups (with 3 fused rings) derived from carbazole ($N_1$), dibenzofuran ($O_1$), dibenzothiophene ($S_1$); and, $C_{14}$heterocyclic groups (with 3 fused rings) derived from acridine ($N_1$), xanthene ($O_1$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)= (also denoted —N$^+$(→O$^-$)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms. Monocyclic examples of such groups include, but are not limited to, those derived from:

$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:
$C_9$: indenedione;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone ($C_9$) (e.g., guanine).

Still more examples of cyclic groups which bear one or more oxo (=O) groups on ring carbon atoms include, but are not limited to, those derived from:
cyclic anhydrides (—C(=O)—O—C(=O)— in a ring), including but not limited to maleic anhydride ($C_5$), succinic anhydride ($C_5$), and glutaric anhydride ($C_6$);
cyclic carbonates (—O—C(=O)—O— in a ring), such as ethylene carbonate ($C_5$) and 1,2-propylene carbonate ($C_5$);
imides (—C(=O)—NR—C(=O)— in a ring), including but not limited to, succinimide ($C_5$), maleimide ($C_5$), phthalimide, and glutarimide ($C_6$);
lactones (cyclic esters, —O—C(=O)— in a ring), including, but not limited to, β-propiolactone, γ-butyrolactone, δ-valerolactone (2-piperidone), and ε-caprolactone;
lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);
cyclic carbamates (—O—C(=O)—NR— in a ring), such as 2-oxazolidone ($C_5$);
cyclic ureas (—NR—C(=O)—NR— in a ring), such as 2-imidazolidone ($C_5$) and pyrimidine-2,4-dione (e.g., thymine, uracil) ($C_6$).

The above $C_{1-7}$alkyl, $C_{3-20}$heterocyclyl, and $C_{5-20}$aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$hetercyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam, δ-valerolactam, and ε-caprolactam.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of imino groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Acylhalide (haloformyl, halocarbonyl): —C(=O)X, wherein X is —F, —Cl, —Br, or —I, preferably —Cl, —Br, or —I.

Carboxy (carboxylic acid): —COOH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)NH(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, a $C_{1-7}$alkyl group, a $C_{3-20}$heterocyclyl group, or a $C_{5-20}$aryl group, preferably a $C_{1-7}$alkyl group, and R$^2$ is an acyl substituent, for example, a $C_{1-7}$alkyl group, a $C_{3-20}$heterocyclyl group, or a $C_{5-20}$aryl group, preferably a $C_{1-7}$alkyl group. Examples of acylamido groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, for example, succinimidyl, maleimidyl, and phthalimidyl:

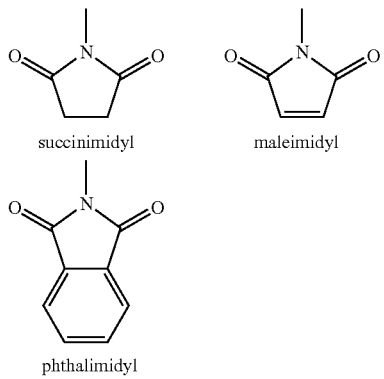

succinimidyl    maleimidyl phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)NH(CH$_3$)$_2$, and —C(=S)NHCH$_2$CH$_3$.

Tetrazolyl: a five membered aromatic ring having four nitrogen atoms and one carbon atom,

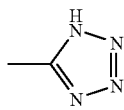

Amino: —NR$^1$R$^2$, wherein R$^1$ and R$^2$ are independently amino substituents, for example, hydrogen, a C$_{1-7}$alkyl group (also referred to as C$_{1-7}$alkylamino or di-C$_{1-7}$alkylamino), a C$_{3-20}$heterocyclyl group, or a C$_{5-20}$aryl group, preferably H or a C$_{1-7}$alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridino, azetidino, piperidino, piperazino, morpholino, and thiomorpholino.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.

Thioether (sulfide): —SR, wherein R is a thioether substituent, for example, a C$_{1-7}$alkyl group (also referred to as a C$_{1-7}$alkylthio group), a C$_{3-20}$heterocyclyl group, or a C$_{5-20}$aryl group, preferably a C$_{1-7}$alkyl group. Examples of C$_{1-7}$alkylthio groups include, but are not limited to, —SCH$_3$ and —SCH$_2$CH$_3$.

Sulfonic acid (sulfo): —S(=O)$_2$OH.

Sulfonate (sulfonic acid ester): —S(=O)$_2$OR, wherein R is a sulfonate substituent, for example, a C$_{1-7}$alkyl group, a C$_{3-20}$heterocyclyl group, or a C$_{5-20}$aryl group, preferably a C$_{1-7}$alkyl group. Examples of sulfonate groups include, but are not limited to, —S(=O)$_2$OCH$_3$ and —S(=O)$_2$OCH$_2$CH$_3$.

Sulfone (sulfonyl): —S(=O)$_2$R, wherein R is a sulfone substituent, for example, a C$_{1-7}$alkyl group, a C$_{3-20}$heterocyclyl group, or a C$_{5-20}$aryl group, preferably a C$_{1-7}$alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Sulfonyloxy: —OS(=O)$_2$R, wherein R is a sulfonyloxy substituent, for example, a C$_{1-7}$alkyl group, a C$_{3-20}$heterocyclyl group, or a C$_{5-20}$aryl group, preferably a C$_{1-7}$alkyl group. Examples of sulfonyloxy groups include, but are not limited to, —OS(=O)$_2$CH$_3$ and —OS(=O)$_2$CH$_2$CH$_3$.

Sulfinyloxy: —OS(=O)R, wherein R is a sulfinyloxy substituent, for example, a C$_{1-7}$alkyl group, a C$_{3-20}$heterocyclyl group, or a C$_{5-20}$aryl group, preferably a C$_{1-7}$alkyl group. Examples of sulfinyloxy groups include, but are not limited to, —OS(=O)CH$_3$ and —OS(=O)CH$_2$CH$_3$.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$alkyl group, a C$_{3-20}$heterocyclyl group, or a C$_{5-20}$aryl group, preferably a C$_{1-7}$alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido: —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

As mentioned above, a C$_{1-7}$alkyl group may be substituted with, for example, hydroxy (also referred to as a C$_{1-7}$hydroxyalkyl group), C$_{1-7}$alkoxy (also referred to as a C$_{1-7}$alkoxyalkyl group), amino (also referred to as a C$_{1-7}$aminoalkyl group), halo (also referred to as a C$_{1-7}$haloalkyl group), carboxy (also referred to as a C$_{1-7}$carboxyalkyl group), and C$_{5-20}$aryl (also referred to as a C$_{5-20}$aryl-C$_{1-7}$alkyl group).

Similarly, a C$_{5-20}$aryl group may be substituted with, for example, hydroxy (also referred to as a C$_{5-20}$hydroxyaryl group), halo (also referred to as a C$_{5-20}$haloaryl group), amino (also referred to as a C$_{5-20}$aminoaryl group, e.g., as in aniline), C$_{1-7}$alkyl (also referred to as a C$_{1-7}$alkyl-C$_{5-20}$aryl group, e.g., as in toluene), and C$_{1-7}$alkoxy (also referred to as a C$_{1-7}$alkoxy-C$_{5-20}$aryl group, e.g., as in anisole).

These and other specific examples of such substituted groups are also discussed below.

C$_{1-7}$haloalkyl group: The term "C$_{1-7}$haloalkyl group," as used herein, pertains to a C$_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a $C_{1-7}$perhaloalkyl group."
Examples of $C_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

$C_{1-7}$hydroxyalkyl: The term "$C_{1-7}$hydroxyalkyl group," as used herein, pertains to a $C_{1-7}$alkyl group in which at least one hydrogen atom has been replaced with a hydroxy group. Examples of $C_{1-7}$hydroxyalkyl groups include, but are not limited to, —CH$_2$OH, —CH$_2$CH$_2$OH, and —CH(OH)CH$_2$OH.

$C_{1-7}$carboxyalkyl: The term "$C_{1-7}$carboxyalkyl group," as used herein, pertains to a $C_{1-7}$alkyl group in which at least one hydrogen atom has been replaced with a carboxy group. Examples of $C_{1-7}$carboxyalkyl groups include, but are not limited to, —CH$_2$COOH and —CH$_2$CH$_2$COOH.

$C_{1-7}$aminoalkyl: The term "$C_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —CH$_2$NH$_2$, —CH$_2$CH$_2$NH$_2$, and —CH$_2$CH$_2$N(CH$_3$)$_2$.

$C_{1-7}$alkyl-$C_{5-20}$aryl: The term "$C_{1-7}$alkyl-$C_{5-20}$aryl," as used herein, describes certain $C_{5-20}$aryl groups which have been substituted with a $C_{1-7}$alkyl group. Examples of such groups include, but are not limited to, tolyl (as in toluene), xylyl (as in xylene), mesityl (as in mesitylene), styryl (as in styrene), and cumenyl (as in cumene).

$C_{5-20}$aryl-$C_{1-7}$alkyl: The term "$C_{5-20}$aryl-$C_{1-7}$alkyl," as used herein, describers certain $C_{1-7}$alkyl groups which have been substituted with a $C_{5-20}$aryl group. Examples of such groups include, but are not limited to, benzyl (phenylmethyl), tolylmethyl, phenylethyl, and triphenylmethyl (trityl).

$C_{5-20}$haloaryl: The term "$C_{5-20}$haloaryl," as used herein, describes certain $C_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Bidentate Substituents

Some substituents are bidentate, that is, have two points for covalent attachment. For example, a bidentate group may be covalently bound to two different atoms on two different groups, thereby acting as a linker therebetween. Alternatively, a bidentate group may be covalently bound to two different atoms on the same group, thereby forming, together with the two atoms to which it is attached (and any intervening atoms, if present) a cyclic or ring structure. In this way, the bidentate substituent may give rise to a heterocyclic group/compound and/or an aromatic group/compound. Typically, the ring has from 3 to 8 ring atoms, which ring atoms are carbon or divalent heteroatoms (e.g., boron, silicon, nitrogen, phosphorus, oxygen, and sulfur, typically nitrogen, oxygen, and sulfur), and wherein the bonds between said ring atoms are single or double bonds, as permitted by the valencies of the ring atoms. Typically, the bidentate group is covalently bound to vicinal atoms, that is, adjacent atoms, in the parent group.

$C_{1-7}$alkylene: The term "$C_{1-7}$alkylene," as used herein, pertains to a bidentate moiety obtained by removing two hydrogen atoms, either both from the same carbon atom, or one from each of two different carbon atoms, of a $C_{1-7}$hydrocarbon compound having from 1 to 7 carbon atoms, which may be aliphatic or alicyclic, or a combination thereof, and which may be saturated, partially unsaturated, or fully unsaturated.

Examples of linear saturated $C_{1-7}$alkylene groups include, but are not limited to, —(CH$_2$)$_n$— where n is an integer from 1 to 7, for example, —CH$_2$— (methylene), —CH$_2$CH$_2$— (ethylene), —CH$_2$CH$_2$CH$_2$— (propylene), and —CH$_2$CH$_2$CH$_2$CH$_2$— (butylene).

Examples of branched saturated $C_{1-7}$alkylene groups include, but are not limited to, —CH(CH$_3$)—, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated $C_{1-7}$alkylene groups include, but are not limited to, —CH=CH— (vinylene), —CH=CH—CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—CH$_2$—, —CH=CH—CH$_2$—CH=CH—, and —CH=CH—CH$_2$—CH$_2$—CH=CH—.

Examples of branched partially unsaturated $C_{1-7}$alkylene groups include, but are not limited to, —C(CH$_3$)=CH—, —C(CH$_3$)=CH—CH$_2$—, and —CH=CH—CH(CH$_3$)—.

Examples of alicyclic saturated $C_{1-7}$alkylene groups include, but are not limited to, cyclopentylene (e.g., cyclopent-1,3-ylene), and cyclohexylene (e.g., cyclohex-1,4-ylene).

Examples of alicyclic partially unsaturated $C_{1-7}$alkylene groups include, but are not limited to, cyclopentenylene (e.g., 4-cyclopenten-1,3-ylene), cyclohexenylene (e.g., 2-cyclohexen-1,4-ylene, 3-cyclohexen-1,2-ylene, 2,5-cyclohexadien-1,4-ylene).

$C_{5-20}$arylene: The term "$C_{5-20}$arylene," as used herein, pertains to a bidentate moiety obtained by removing two hydrogen atoms, one from each of two different ring atoms of a $C_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboarylene groups," in which case the group may conveniently be referred to as a "$C_{5-20}$carboarylene" group.

Alternatively, the ring atoms may include one or more heteroatoms, including but not limited to oxygen, nitrogen, and sulfur, as in "heteroarylene groups." In this case, the group may conveniently be referred to as a "$C_{5-20}$heteroarylene" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$arylene groups which do not have ring heteroatoms (i.e., $C_{5-20}$carboarylene groups) include, but are not limited to, those derived from benzene (i.e., phenyl) ($C_6$), naphthalene ($C_{10}$), anthracene ($C_{14}$), phenanthrene ($C_{14}$), and pyrene ($C_{16}$).

Examples of $C_{5-20}$heteroarylene groups include, but are not limited to, $C_5$heteroarylene groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$heteroarylene groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

$C_{5-20}$Arylene-$C_{1-7}$alkylene: The term "$C_{5-20}$arylene-$C_{1-7}$alkylene," as used herein, pertains to a bidentate moiety comprising a $C_{5-20}$arylene moiety, -Arylene-, linked to a $C_{1-7}$alkylene moiety, -Alkylene-, that is, -Arylene-Alkylene-.

Examples of $C_{5-20}$arylene-$C_{1-7}$alkylene groups include, but are not limited to, phenylene-methylene, phenylene-ethylene, phenylene-propylene, and phenylene-ethenylene (also known as phenylene-vinylene).

$C_{5-20}$Alkylene-$C_{1-7}$arylene: The term "$C_{5-20}$alkylene-$C_{1-7}$arylene," as used herein, pertains to a bidentate moiety comprising a $C_{5-20}$alkylene moiety, -Alkylene-, linked to a $C_{1-7}$arylene moiety, -Arylene-, that is, -Alkylene-Arylene-.

Examples of $C_{5-20}$alkylene-$C_{1-7}$arylene groups include, but are not limited to, methylene-phenylene, ethylene-phenylene, propylene-phenylene, and ethenylene-phenylene (also known as vinylene-phenylene).

Included in the above are the well known ionic, salt, solvate (e.g., hydrate), and protected forms of these substituents. For example, a reference to carboxylic acid (—COOH) also includes carboxylate (—COO$^-$). Similarly, a reference to an amino group includes a salt, for example, a hydrochloride salt, of the amino group. A reference to a hydroxyl group also includes conventional protected forms of a hydroxyl group. Similarly, a reference to an amino group also includes conventional protected forms of an amino group.

Acronyms

For convenience, many chemical moieties are represented herein using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented herein using well known abbreviations, including but not limited to, methanol (MeOH), ethanol (EtOH), iso-propanol (i-PrOH), methyl ethyl ketone (MEK), acetic acid (AcOH), dichloromethane (methylene chloride, DCM), trifluoroacetic acid (TFA), dimethylformamide (DMF), and tetrahydrofuran (THF).

Isomers, Salts, Hydrates, Protected Forms, and Prodrugs

A certain compound may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

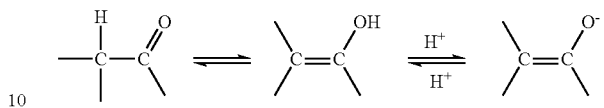

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein in a known manner.

Unless otherwise specified, a reference to a particular compound also includes ionic, salt, solvate (e.g., hydrate), protected forms, and prodrugs thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na+ and K+, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, ethylenediamine, ethanolamine, diethanolamine, piperazine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, anions from the following organic acids: acetic, propionic, succinic, gycolic, stearic, lactic, malic, tartaric, citric, ascorbic, maleic, hydroxymaleic, phenylacetic, glutamic, benzoic, salicylic, sulfanilic, 2-acetyoxybenzoic, fumaric, toluenesulfonic, methanesulfonic, ethanesulfonic, ethane disulfonic, oxalic, isethionic, and valeric.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1991), and *Protective Groups in Organic Synthesis* (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O°).

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised, yields the desired active compound. Typically, the prodrug is inactive, or less active than the active compound, but may provide advantageous handling, administration, or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Synthesis

Several methods for the chemical synthesis of compounds of the present invention are described herein. These methods may be modified and/or adapted in known ways in order to facilitate the synthesis of additional compounds within the scope of the present invention.

The compounds of the present invention may be prepared, for example, by the methods described herein, or by adapting these or other well known methods in well known ways.

In one method, a suitable resin with pendant hydroxy groups is reacted with a suitable carboxylic acid having a protected amino group, to form a pendant group which is linked to the solid support via an ester group, and which has a terminal protected amino group. The terminal protected amino group is then reacted with a suitable aryl carboxoylic acid, to give a terminal aryl amide. The resulting compound is then cleaved from the resin using hydroxylamine to give the desired carbamic acid.

One example of this approach is illustrated below, wherein the resin is ArgoGelJ-OH resin, and the reaction conditions are as follows: (i) DIC, DMAP, DCM, room temperature, 4 hours; (ii) DCM/TFA/TES (70:25:5, v/v), room temperature, 30 min.; (iii) aryl carboxoylic acid, HOBT, TBTU, DIPEA, NMP, room temperature, 16 hours; (iv) 50% NH$_2$OH, dioxane, room temperature, 48 hours.

Scheme 1

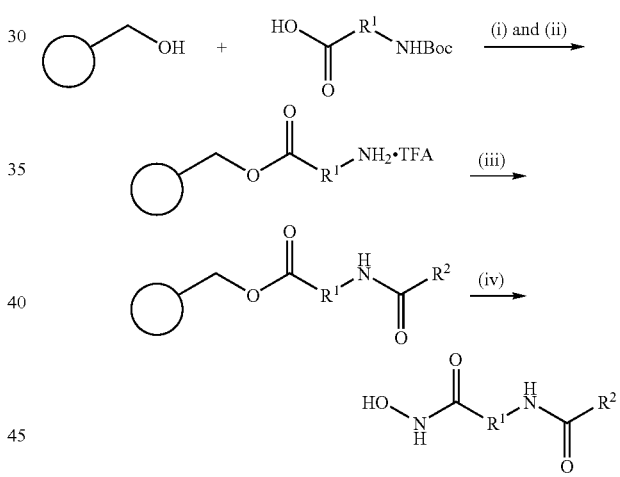

In another method, a aryl-alkyl-carboxylic acid is reacted with a suitable amine having a terminal protected carboxylic acid (e.g, as an ester), to form a product having, on the one hand, an aryl amide, and on the other hand, a protected carboxylic acid. The protected carboxylic acid is then deprotected, and the product reacted with hydroxylamine, to give the desired carbamic acid.

One example of this approach is illustrated below, wherein the reaction conditions are as follows: (i) 1,1'-carbonyl-diimidazole, TEA, THF, room temperature, 6 hours; (ii) NH$_2$OH, room temperature, 4 hours.

Scheme 2

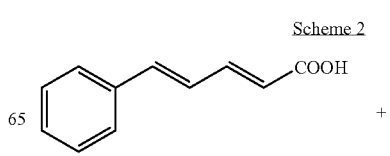

+

89

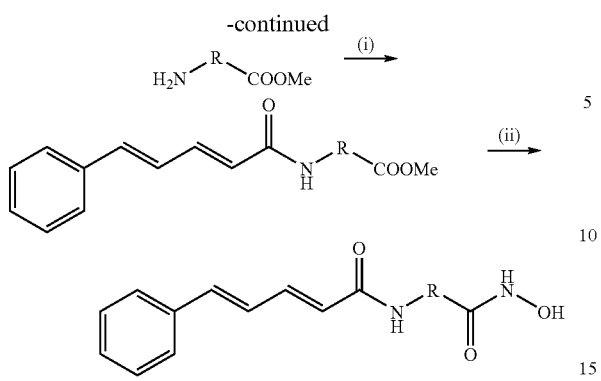

In another method, a m-aminophenylacrylic acid methyl ester is reacted with a phenylacryloylchloride, and the product is reacted with hydroxylamine and sodium hydroxide in methanol, to give the desired carbamic acid.

One example of this approach is illustrated below, wherein the reaction conditions are as follows: (i) NaHCO$_3$, H$_2$O, THF, room temperature, 1 hour; (ii) NaOH/MeOH—H$_2$O, NH$_2$OH, room temperature, 1.5 hours.

Scheme 3

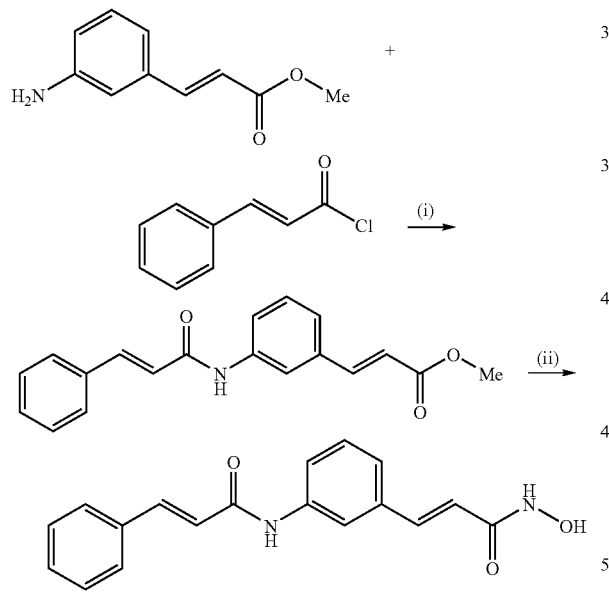

Additional methods for the synthesis of compounds of the present invention are illustrated below and are exemplified in the examples below.

Scheme 4

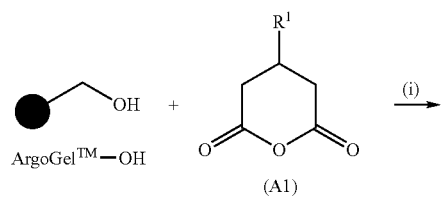

90

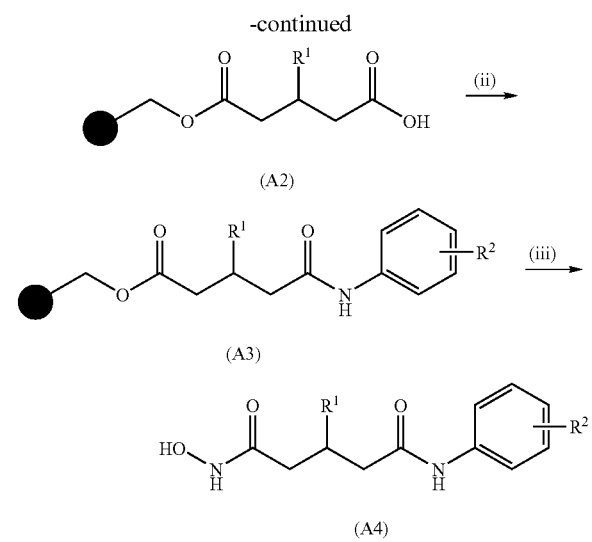

Conditions:
(i) DCM/pyridine (1:1, v/v), DMAP, RT, 16 h;
(ii) NH$_2$R$^2$, HOBT, TBTU, DIPEA, NMP, RT, 16 h;
(iii) 50% NH$_2$OH (aq), dioxane, RT, 48 h.

Scheme 5

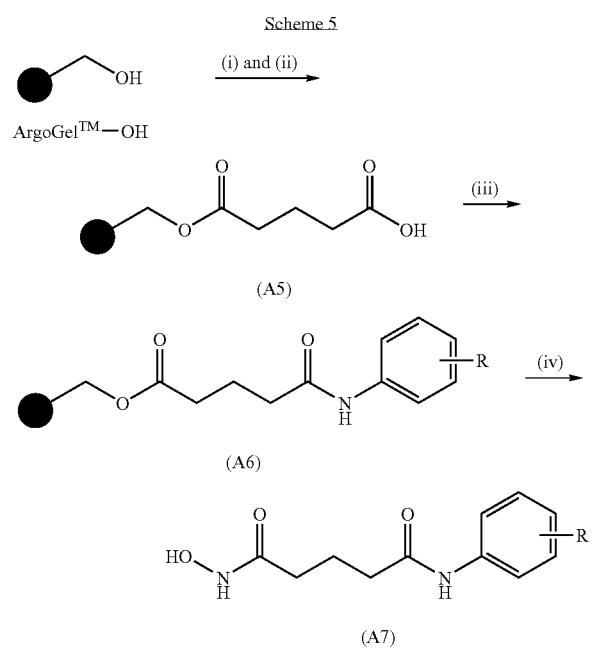

Conditions:
(i) (A9), DIC, DMAP, DCM, RT, 4 h;
(ii) DCM/TFA/TES (70:25:5, v/v), RT 30 min.,
(iii) NH$_2$R, HOBT, TBTU, DIPEA, NMP, RT, 16 h;
(iv) 50% NH2OH (aq), dioxane, RT, 48 h.

Scheme 6

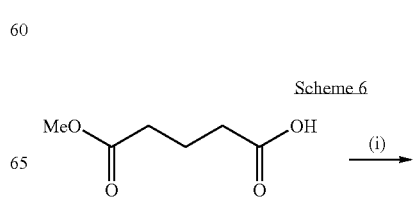

-continued (A8)

(ii) →

(A9)

Conditions:
(i) N,N-dimethylformamide di-tert-butylacetal, toluene, 115° C., 1 h,
(ii) 1M LiOH (aq), dioxane, 0° C. - RT.

Scheme 7

ArgoGel™—OH + HO−C(=O)−R−NHBoc → (i) and (ii)

(C1)

(iii) →

(C2)

(iv) →

(C3)

Conditions:
(i) DIC, DMAP, DCM, RT, 4 h;
(ii) DCM/TFA/TES (70;25:5, v/v), RT, 30 min.,
(iii) 4-dimethylaminonaphthalene-1-carboxylic acid, HOBT, TBTU, DIPEA, NMP, RT, 16 h;
(iv) 50% NH$_2$OH, dioxane, RT, 48 h.

Scheme 8

ArgoGel™—OH + HO−C(=O)−R$^1$−NHBoc → (i) and (ii)

(D1)

(iii) →

-continued (D2)

(iv) →

(D3)

Conditions:
(i) DIC, DMAP, DCM, 4 h;
(ii) DCM/TFA/TES (70;25:5, v/v), RT, 30 min.,
(iii) carboxylic acid, HOBT, TBTU, DIPEA, NMP, RT, 16 h;
(iv) 50% NH$_2$OH, dioxane, RT, 48 h.

Scheme 9

ArgoGel™—OH + HO−C(=O)−R$^1$−NHBoc → (i) and (ii)

(E1)

(iii) →

(E2)

(iv) →

(E3)

Conditions:
(i) DIC, DMAP, DCM, RT, 4 h;
(ii) DCM/TFA/TES (70;25:5, v/v), RT, 30 min.,
(iii) carboxylic acid, HOBT, TBTU, DIPEA, NMP, RT, 16 h;
(iv) 50% NH$_2$OH, dioxane, RT, 48 h.

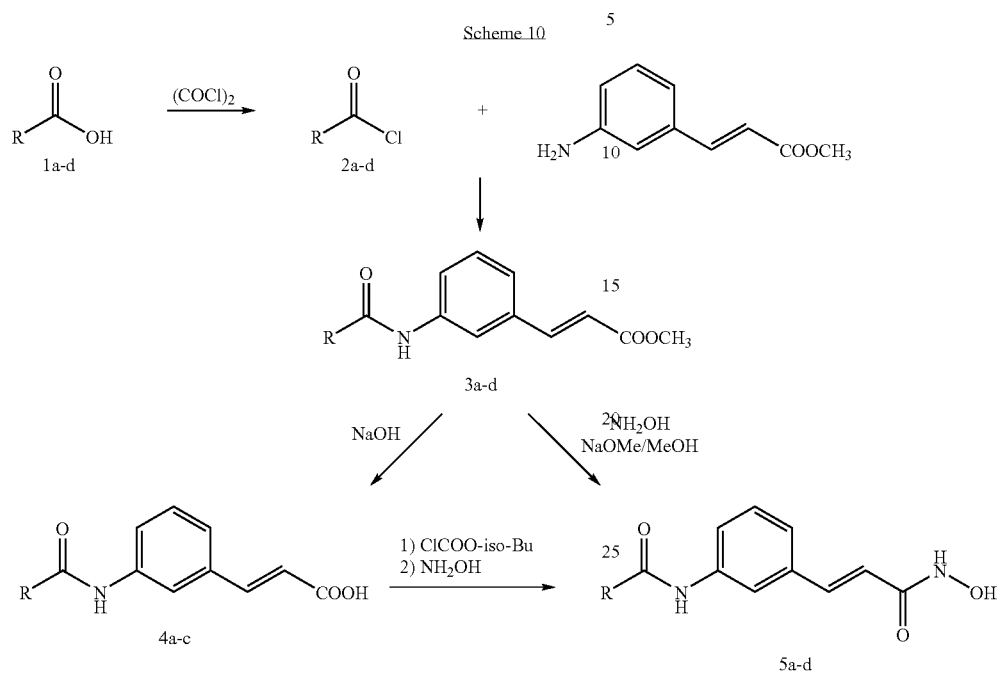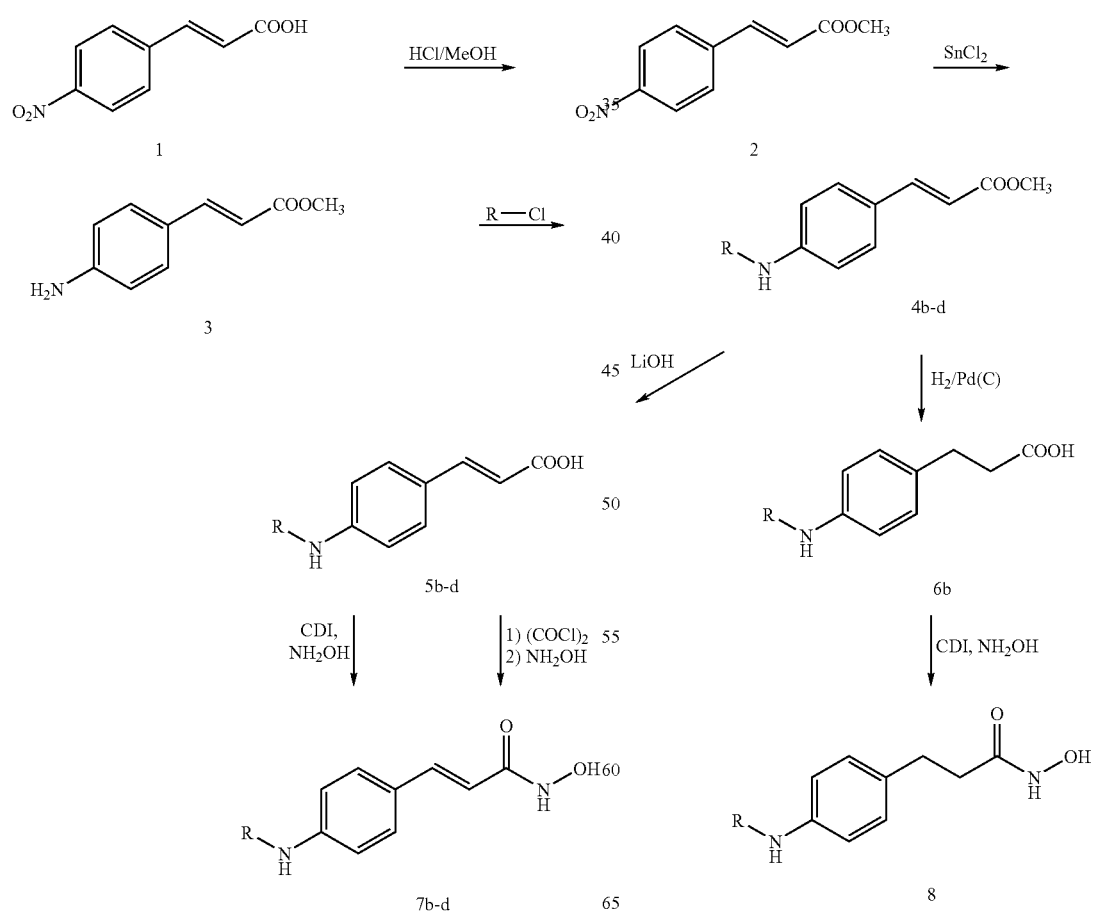

Scheme 12
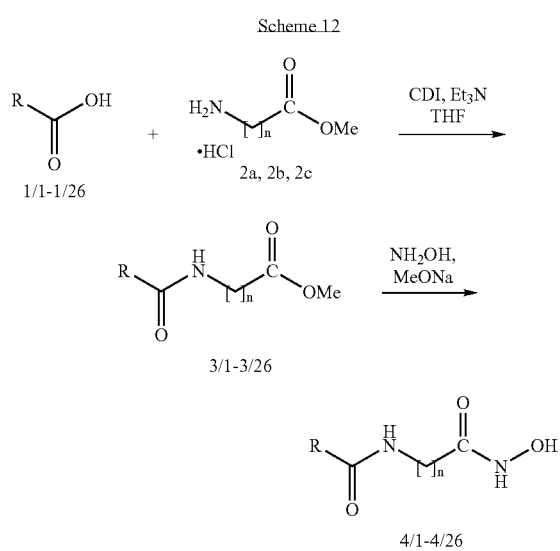
Scheme 13
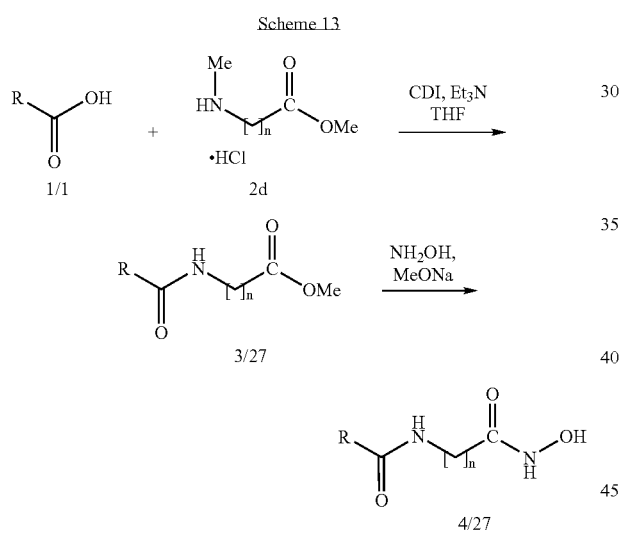
Scheme 14
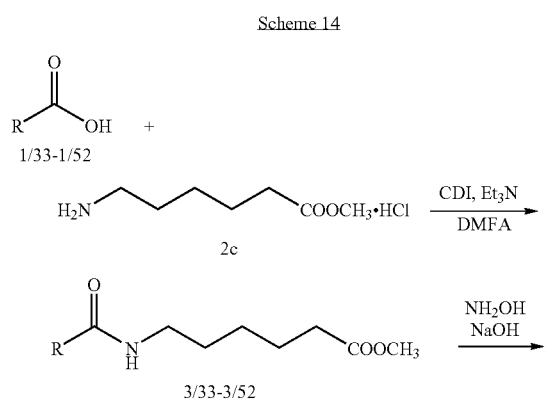
Scheme 15
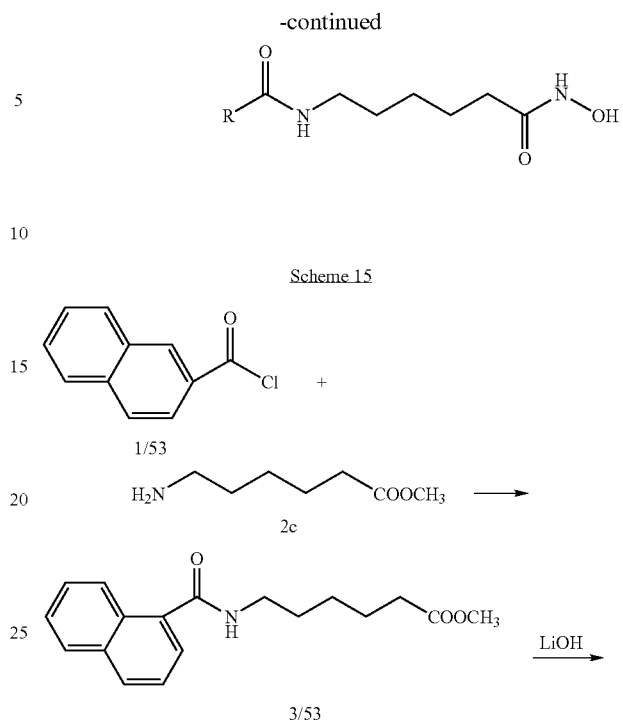
PX105687
Scheme 16
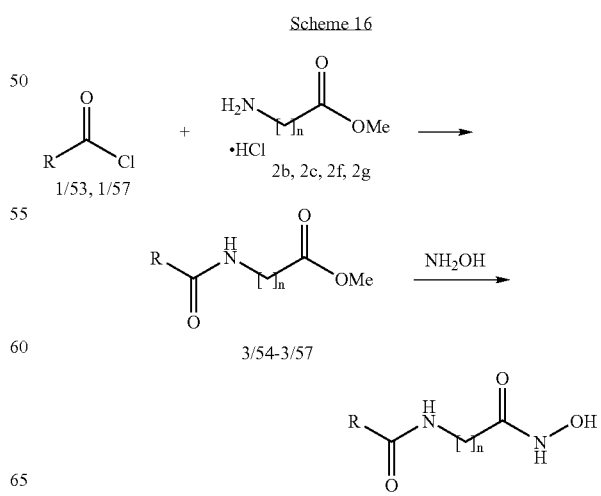

Scheme 17
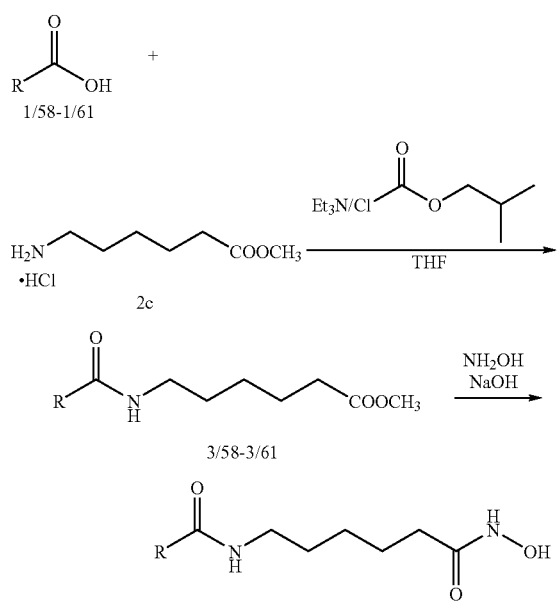
Scheme 18
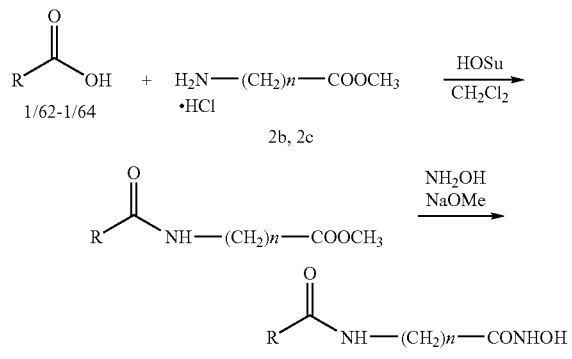
Scheme 19
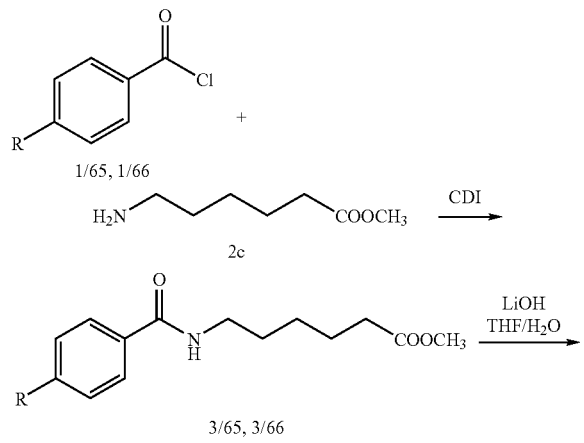
-continued
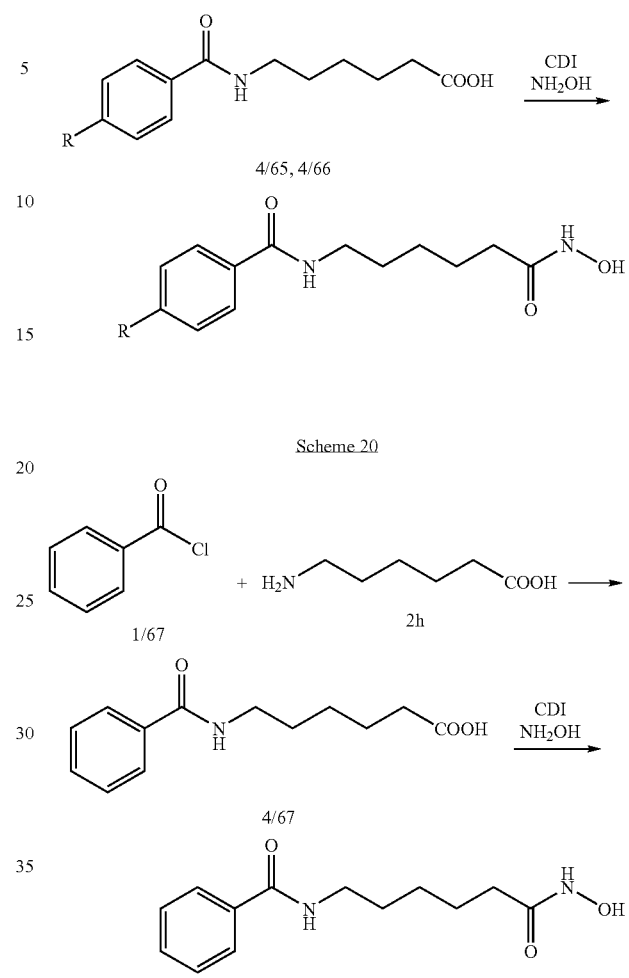
Scheme 20
Scheme 21
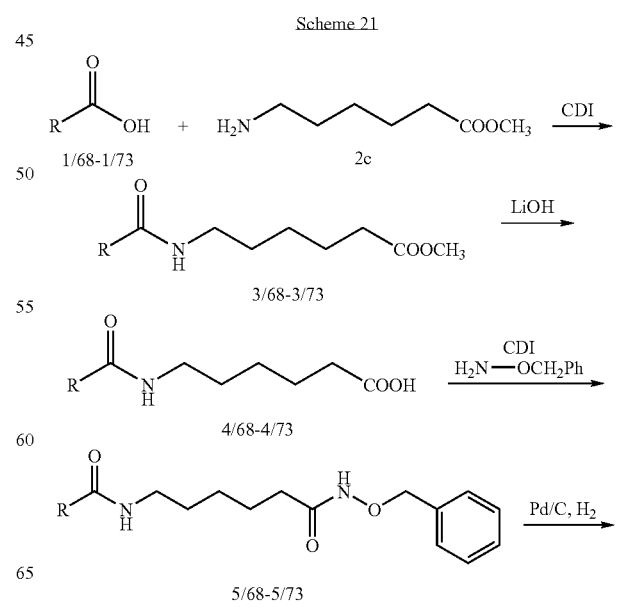

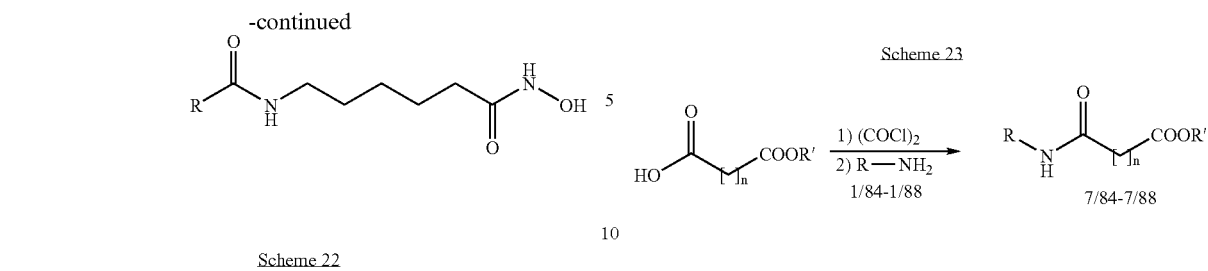
Scheme 22
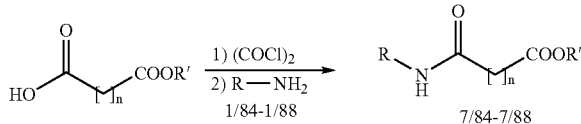
Scheme 23
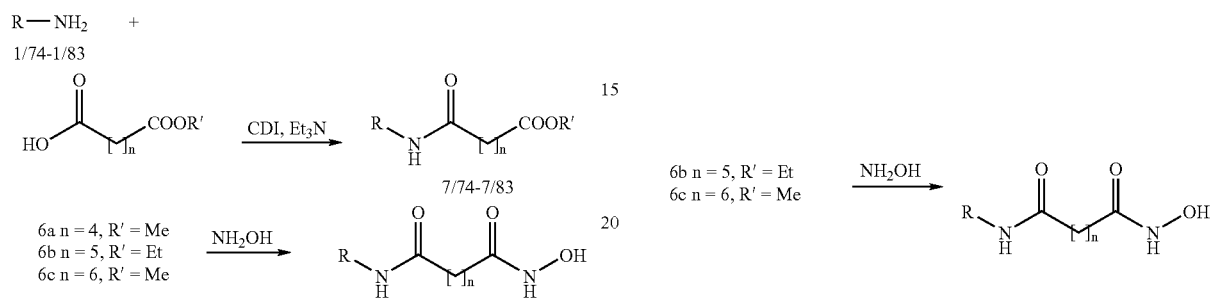
Scheme 24
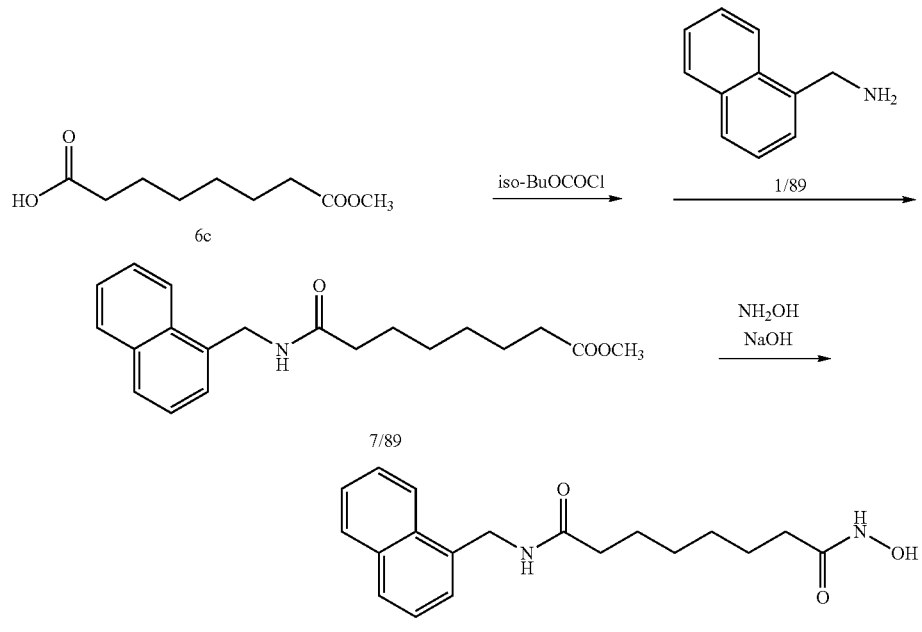
Scheme 25
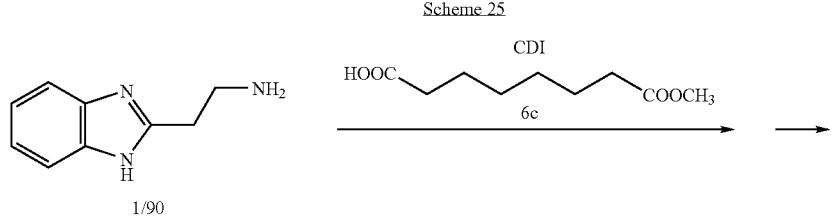

-continued
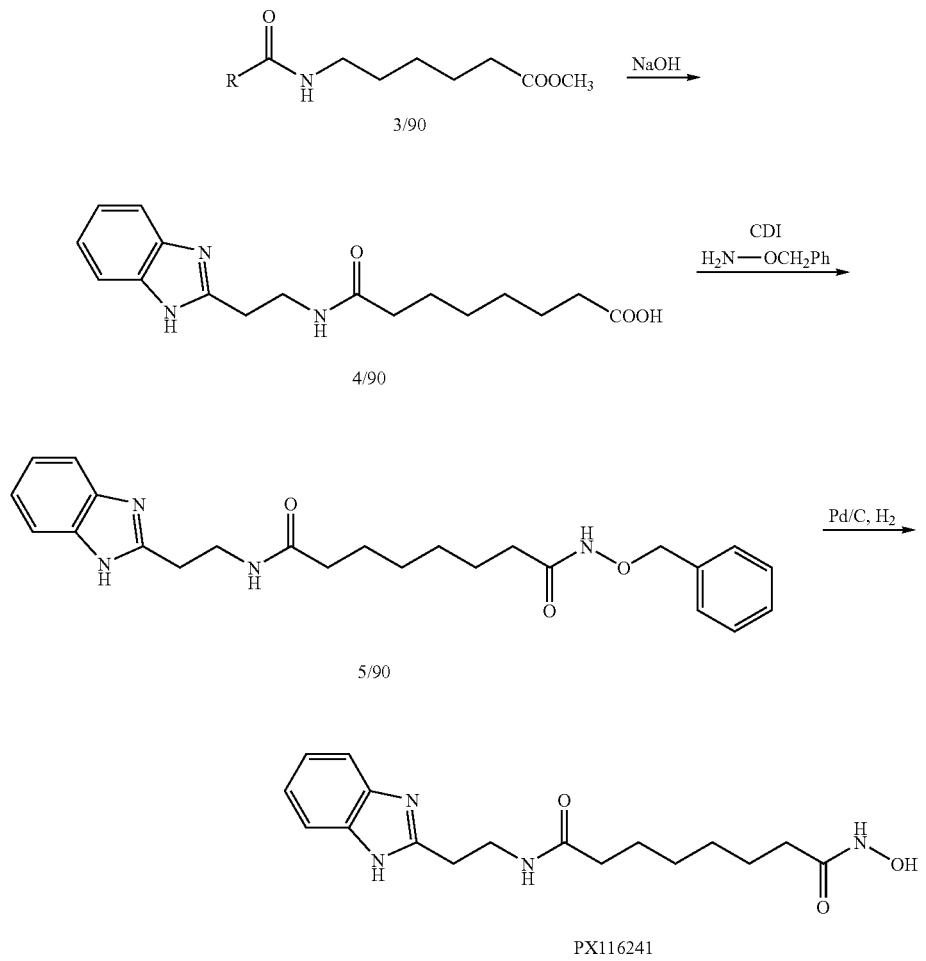
Scheme X
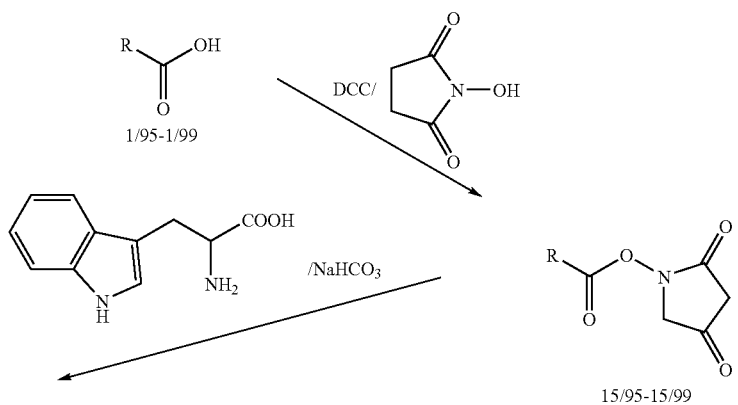

-continued

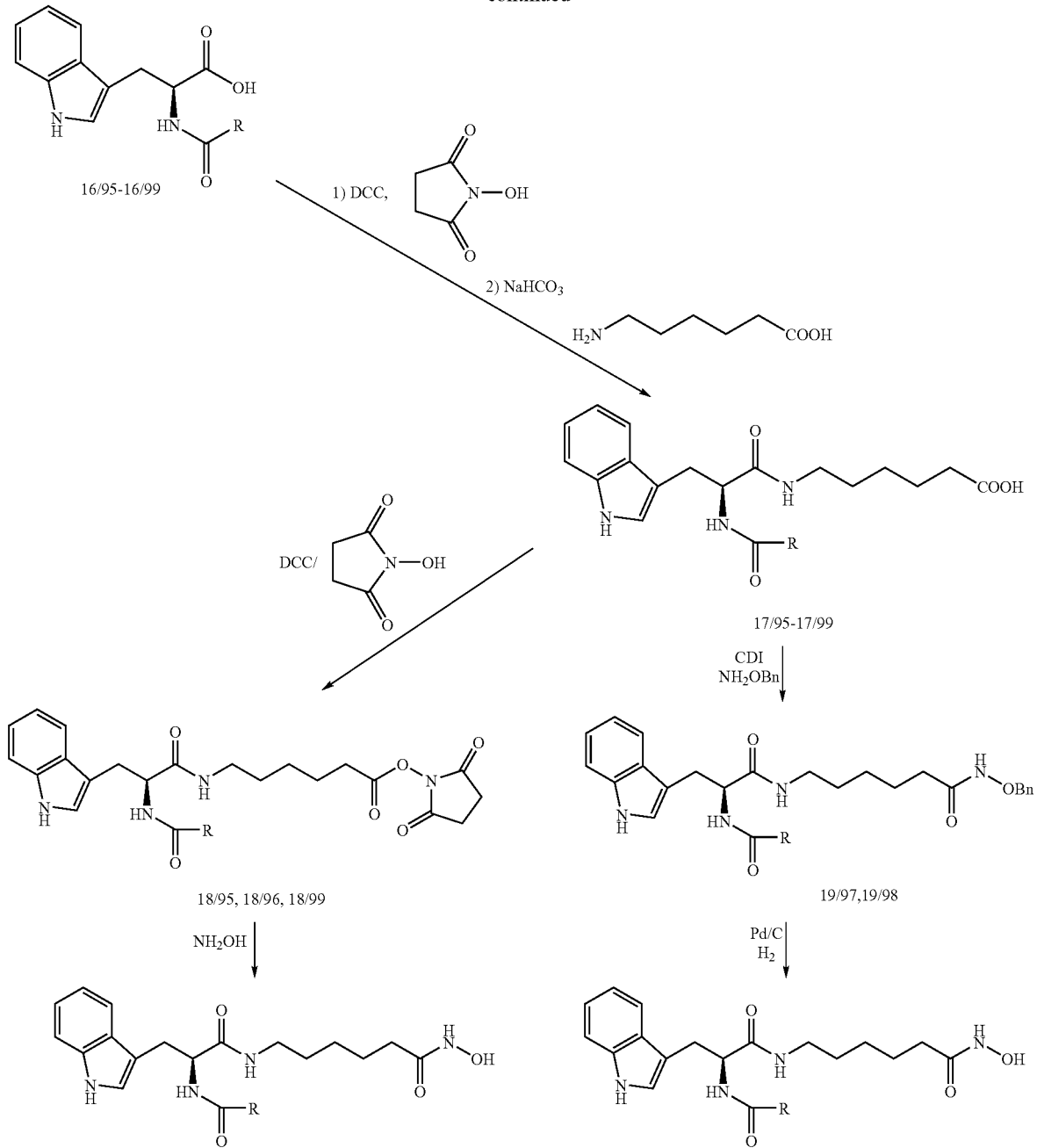

Uses

The present invention provides active compounds which are capable of inhibiting HDAC (for example, inhibiting HDAC activity, inhibiting formation of HDAC complexes, inhibiting activity of HDAC complexes), as well as methods of inhibiting HDAC activity, comprising contacting a cell with an effective amount of an active compound, whether in vitro or in vivo.

The term "active," as used herein, pertains to compounds which are capable of inhibiting HDAC activity, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound is active, that is, capable of inhibiting HDAC activity. For example, assays which may conveniently be used to assess the inhibition offered by a particular compound are described in the examples below.

For example, a sample of cells (e.g., from a tumour) may be grown in vitro and a candidate compound brought into contact with the cells, and the effect of the compound on those cells observed. As examples of "effect," the morphological status of the cells may be determined (e.g., alive or dead), or the expression levels of genes regulated by HDAC. Where the candidate compound is found to exert an influence on the cells, this may be used as a prognostic or diagnostic marker of the efficacy of the compound in methods of treating a patient carrying cells of the same type (e.g., the tumour or a tumour of the same cellular type).

In one aspect, the present invention provides antiproliferative agents. The term "antiproliferative agent" as used herein, pertains to a compound which treats a proliferative condition (i.e., a compound which is useful in the treatment of a proliferative condition).

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

Antiproliferative compounds of the present invention have application in the treatment of cancer, and so the present invention further provides anticancer agents. The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

The compounds of the present invention may also be used in the treatment of conditions which are known to be mediated by HDAC, or which are known to be treated by HDAC inhibitors (such as, e.g., trichostatin A). Examples of such conditions include, but are not limited to, the following:

Cancer (see, e.g., Vigushin et al., 2001).

Psoriasis (see, e.g., Iavarone et al., 1999).

Fibroproliferative disorders (e.g., liver fibrosis) (see, e.g., Niki et al., 1999; Corneil et al., 1998).

Smooth muscle proliferative disorder (e.g., atherosclerosis, restenosis) (see, e.g., Kimura et al., 1994).

Neurodegenerative diseases (e.g., Alzheimer's, Parkinson's, Huntington's chorea, amyotropic lateral sclerosis, spino-cerebellar degeneration) (see, e.g., Kuusisto et al., 2001).

Inflammatory disease (e.g., osteoarthritis, rheumatoid arthritis) (see, e.g., Dangond et al., 1998; Takahashi et al., 1996).

Diseases involving angiogenesis (e.g., cancer, rheumatoid arthritis, psoriasis, diabetic retinopathy) (see, e.g., Kim et al., 2001).

Haematopoietic disorders (e.g., anaemia, sickle cell anaemia, thalassaeimia) (see, e.g., McCaffrey et al., 1997).

Fungal infection (see, e.g., Bernstein et al., 2000; Tsuji et al., 1976).

Parasitic infection (e.g., malaria, trypanosomiasis, helminthiasis, protozoal infections (see, e.g., Andrews et al., 2000).

Bacterial infection (see, e.g., Onishi et al., 1996).

Viral infection (see, e.g., Chang et al., 2000).

Conditions treatable by immune modulation (e.g., multiple sclerosis, autoimmune diabetes, lupus, atopic dermatitis, allergies, asthma, allergic rhinitis, inflammatory bowel disease; and for improving grafting of transplants) (see, e.g., Dangond et al., 1998; Takahashi et al., 1996).

The invention further provides active compounds for use in a method of treatment of the human or animal body. Such a method may comprise administering to such a subject a therapeutically-effective amount of an active compound, preferably in the form of a pharmaceutical composition.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

The invention further provides the use of an active compound for the manufacture of a medicament, for example, for the treatment of a proliferative condition, as discussed above.

The invention further provides the use of an active compound for the manufacture of a medicament, for example, for the treatment of conditions which are known to be mediated by HDAC, or which are known to be treated by HDAC inhibitors (such as, e.g., trichostatin A), as discussed above.

The invention further provides a method for inhibiting HDAC in a cell comprising said cell with an effective amount of an active compound.

The invention further provides a method of treatment of the human or animal body, the method comprising administering to a subject in need of treatment a therapeutically-effective amount of an active compound, preferably in the form of a pharmaceutical composition.

Active compounds may also be used, as described above, in combination therapies, that is, in conjunction with other agents, for example, cytotoxic agents.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other antiproliferative agents, etc.

The compounds of the present invention may also be used in methods of improving protein production by cultured cells (see, e.g., Furukawa et al., 1998).

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject

The subject may be a prokaryote (e.g., bacteria) or a eukaryote (e.g., protoctista, fungi, plants, animals).

The subject may be a protoctista, an alga, or a protozoan.

The subject may be a plant, an angiosperm, a dicotyledon, a monocotyledon, a gymnosperm, a conifer, a ginkgo, a cycad, a fern, a horsetail, a clubmoss, a liverwort, or a moss.

The subject may be an animal.

The subject may be a chordate, an invertebrate, an echinoderm (e.g., starfish, sea urchins, brittlestars), an arthropod, an annelid (segmented worms) (e.g., earthworms, lugworms, leeches), a mollusk (cephalopods (e.g., squids, octopi), pelecypods (e.g., oysters, mussels, clams), gastropods (e.g., snails, slugs)), a nematode (round worms), a platyhelminthes (flatworms) (e.g., planarians, flukes, tapeworms), a cnidaria (e.g., jelly fish, sea anemones, corals), or a porifera (e.g., sponges).

The subject may be an arthropod, an insect (e.g., beetles, butterflies, moths), a chilopoda (centipedes), a diplopoda (millipedes), a crustacean (e.g., shrimps, crabs, lobsters), or an arachnid (e.g., spiders, scorpions, mites).

The subject may be a chordate, a vertebrate, a mammal, a bird, a reptile (e.g., snakes, lizards, crocodiles), an amphibian (e.g., frogs, toads), a bony fish (e.g., salmon, plaice, eel, lungfish), a cartilaginous fish (e.g., sharks, rays), or a jawless fish (e.g., lampreys, hagfish).

The subject may be a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a spore, a seed, an egg, a larva, a pupa, or a foetus.

In one preferred embodiment, the subject is a human.

Formulations

While it is possible for the active ingredient to be administered alone, it is preferable to present it as a pharmaceutical composition (e.g., formulation) comprising at least one active ingredient, as defined above, together with one or more pharmaceutically acceptable carriers, excipients, buffers, adjuvants, stabilisers, or other materials well known to those skilled in the art and optionally other therapeutic agents.

Thus, the present invention further provides pharmaceutical compositions, as defined above, and methods of making a pharmaceutical composition comprising admixing at least one active ingredient, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations may be in the form of liquids, solutions, suspensions, emulsions, tablets, losenges, granules, powders, capsules, cachets, pills, ampoules, suppositories, pessaries, ointments, gels, pastes, creams, sprays, foams, lotions, oils, boluses, electuaries, or aerosols.

Formulations suitable for oral administration (e.g., by ingestion) may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, paste, gel, spray, aerosol, or oil. Alternatively, a formulation may comprise a patch or a dressing such as a bandage or adhesive plaster impregnated with active ingredients and optionally one or more excipients or diluents.

Formulations suitable for topical administration in the mouth include losenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active ingredient.

Formulations suitable for topical administration via the skin include ointments, creams, and emulsions. When formulated in an ointment, the active ingredient may optionally be employed with either a paraffinic or a water-miscible ointment base. Alternatively, the active ingredients may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active ingredient in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freese-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect.

Administration in vivo can be effected in one dose, continuously or intermittently throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 0.1 to about 250 mg per kilogram body weight of the subject per day. Where the active ingredient is a salt, an ester, prodrug, or the like, the amount administered is calculated on the basis the parent compound and so the actual weight to be used is increased proportionately.

Kits

One aspect of the invention pertains to a kit comprising (a) the active ingredient, preferably provided in a suitable container and/or with suitable packaging; and (b) instructions for use, for example, written instructions on how to administer the active compound.

The written instructions may also include a list of indications for which the active ingredient is a suitable treatment.

EXAMPLES

The following are examples are provided solely to illustrate the present invention and are not intended to limit the scope of the invention, as described herein.

General $^1$H NMR spectra were recorded at ambient temperature with WH-90/DS or Mercury 200 (Varian) spectrometers. The HPLC measurements were performed on a Gilson Model 302 system equipped with a spectrophotometer. Elemental analyses were obtained with a Carlo Erba EA 1108 instrument. Melting points were measured on a "Boëtius" or "Fisher" micro melting point apparatus and are uncorrected. Silicagel, 0.035-0.070 mm, (Acros) was employed for column chromatography. All the solvents were purified before use by routine techniques. To isolate reaction products, the solvents were removed by evaporation using a vacuum rotary evaporator, the water bath temperature not exceeding 40° C.

Various reagents were purchased from Sigma-Aldrich (The Old Brickyard, New Road, Gillingham, Dorset, UK), Acros Organics (Janssens Pharmaceuticalaan 3A, 2440 Geel, Belgium), Lancaster Synthesis Ltd. (Eastgate, White Lund, Morecambe, Lancashire, LA3 3DY, UK), and Maybridge pic (Trevillett, Tingagel, Cornwall, PL34 0HW, UK).

Example 1

4-(3-(4-Dimethylamino-phenyl)-acryoylamino)-N-hydroxy-butyramide (PX083447)

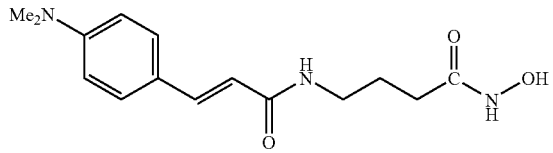

ArgoGelJ-OH resin (500 mg, 0.245 mmol) was placed in a reaction vessel and was swollen by the addition of dichloromethane (2.5 ml). A solution of N-tert-butoxycarbonyl-aminobutyric acid (249 mg, 1.225 mmol), N,N'-diisopropylcarbodiimide (DIC) (192 μl, 1.225 mmol) and 4-(dimethylamino)pyridine (DMAP) (3 mg, 0.0245 mmol) in dichloromethane (2.5 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1714 (urethane) and 1736 (ester).

The resin (500 mg, 0.245 mmol) obtained from the first step was treated with a mixture of dichloromethane/trifluoroacetic acid/triethylsilane (70:25:5, v/v) (5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1733 (ester).

The resin (500 mg, 0.245 mmol) obtained from the second step was placed in a reaction vessel and was swollen by the addition of 1-methylpyrrolidine (2 ml). A solution of 4-dimethylaminocinnamic acid (187 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure. The crude product obtained was purified by preparative hplc using a 150×21.2 mm 5 μm Hypersil7 Elite C$_{18}$ column eluting with a gradient of 5% ACN/95% H$_2$O+0.2% TFA to 95% ACN/5% H$_2$O+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the desired product as a yellow oil (7.8 mg, 12%), t$_R$ 1.35 (254 nm, 1.5 mlmin$^{-1}$, 10% ACN/90% H$_2$O+0.2% TFA), m/z [ES] 314 [M+Na]$^+$.

Example 2

5-Phenyl-penta-2,4-dienoic acid (2-hydroxycarbonyl-ethyl)amide (PX083448)

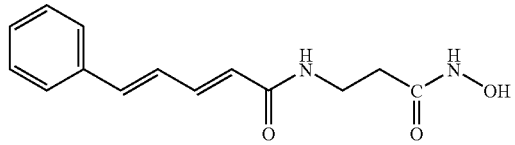

ArgoGelJ-OH resin (500 mg, 0.245 mmol) was placed in a reaction vessel and was swollen by the addition of dichloromethane (2.5 ml). A solution of N-tert-butoxycarbonyl-β-alanine (232 mg, 1.225 mmol), N,N'-diisopropylcarbodiimide (DIC) (192 μl, 1.225 mmol) and 4-(dimethylamino)pyridine (DMAP) (3 mg, 0.0245 mmol) in dichloromethane (2.5 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1714 (urethane) and 1736 (ester).

The resin (500 mg, 0.245 mmol) obtained from the first step was treated with a mixture of dichloromethane/trifluoroacetic acid/triethylsilane (70:25:5, v/v) (5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1738 (ester).

The resin (500 mg, 0.245 mmol) obtained from the second step was placed in a reaction vessel and was swollen by the addition of 1-methylpyrrolidine (2 ml). A solution of 5-phenylpenta-2,4-dienoic acid (171 mg, 0.98 mmol) (see Villieras J., Rambaud M., 1983, *Synthesis*, pp. 300-303; and Vig B., Kanwar R., Singh V., 1977, *Indian J. Chem. Soc.*, Vol. 15B, pp. 1048-1049), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure. The crude product obtained was purified by preparative hplc using a 150×21.2 mm 5 μm Hypersil7 Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the desired compound as a yellow oil (7.8 mg, 12%), $t_R$ 1.35 (254 nm, 1.5 mlmin$^{-1}$, 30% ACN/70% $H_2O$+0.2% TFA), m/z [ES] 261 [M+H]$^+$.

Example 3

N-Hydroxy-4-(3-4-(nitro-phenyl)-acryoylamino)-butyramide (PX083803)

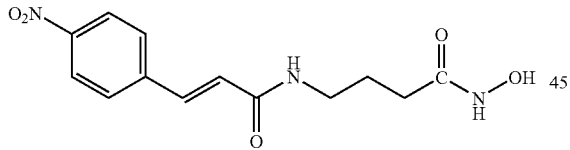

ArgoGelJ-OH resin (500 mg, 0.245 mmol) was placed in a reaction vessel and was swollen by the addition of dichloromethane (2.5 ml). A solution of N-tert-butoxycarbonyl-aminobutyric acid (249 mg, 1.225 mmol), N,N'-diisopropyl-carbodiimide (DIC) (192 μl, 1.225 mmol) and 4-(dimethylamino)pyridine (DMAP) (3 mg, 0.0245 mmol) in dichloromethane (2.5 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1714 (urethane) and 1736 (ester).

The resin (500 mg, 0.245 mmol) obtained from the first step was treated with a mixture of dichloromethane/trifluoroacetic acid/triethylsilane (70:25:5, v/v) (5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1733 (ester)).

The resin (500 mg, 0.245 mmol) obtained from the second step was placed in a reaction vessel and was swollen by the addition of 1-methylpyrrolidine (2 ml). A solution of 4-nitro-cinnamic acid (189 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure.

The crude product obtained was purified by preparative hplc using a 150×21.2 mm 5 μm Hypersil7 Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the desired compound as a yellow oil (24.1 mg, 34%), $t_R$ 4.55 (254 nm, 1.5 mlmin$^{-1}$, 25% ACN/75% $H_2O$+0.2% TFA), m/z [ES] 294 [M+H]$^+$.

Example 4

N-Hydroxy-4-(3-4-(trifluoromethyl-phenyl)-acryoylamino)-butyramide (PX083804)

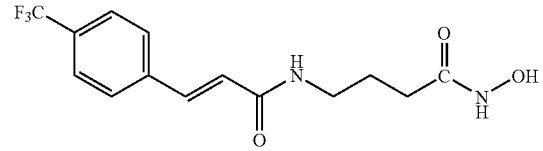

ArgoGelJ-OH resin (500 mg, 0.245 mmol) was placed in a reaction vessel and was swollen by the addition of dichloromethane (2.5 ml). A solution of N-tert-butoxycarbonyl-aminobutyric acid (249 mg, 1.225 mmol), N,N'-diisopropyl-carbodiimide (DIC) (192 μl, 1.225 mmol) and 4-(dimethylamino)pyridine (DMAP) (3 mg, 0.0245 mmol) in dichloromethane (2.5 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1714 (urethane) and 1736 (ester)).

The resin (500 mg, 0.245 mmol) obtained from the first step was treated with a mixture of dichloromethane/trifluoroacetic acid/triethylsilane (70:25:5, v/v) (5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1733 (ester)).

The resin (500 mg, 0.245 mmol) obtained from the second step was placed in a reaction vessel and was swollen by the addition of 1-methylpyrrolidine (2 ml). A solution of 4-trifluoromethylcinnamic acid (212 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure.

The crude product obtained was purified by preparative hplc using a 150×21.2 mm 5 μm Hypersil7 Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the desired product as a yellow oil (20.8 mg, 27%), $t_R$ 4.4 (254 nm, 1.5 mlmin$^{-1}$, 30% ACN/70% $H_2O$+0.2% TFA), m/z [ES] 317 [M+H]$^+$.

Example 5

N-(2-Hydroxycarbamoyl-ethyl)-3-phenyl)-acryamide (PX083806)

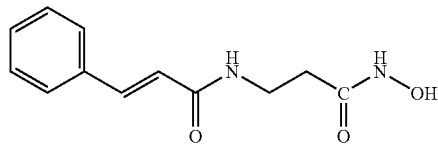

ArgoGelJ-OH resin (500 mg, 0.245 mmol) was placed in a reaction vessel and was swollen by the addition of dichloromethane (2.5 ml). A solution of N-tert-butoxycarbonyl-β-alanine (232 mg, 1.225 mmol), N,N'-diisopropylcarbodiimide (DIC) (192 μl, 1.225 mmol) and 4-(dimethylamino)pyridine (DMAP) (3 mg, 0.0245 mmol) in dichloromethane (2.5 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1714 (urethane) and 1736 (ester)).

The resin (500 mg, 0.245 mmol) obtained from the first step was treated with a mixture of dichloromethane/trifluoroacetic acid/triethylsilane (70:25:5, v/v) (5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1738 (ester)).

The resin (500 mg, 0.245 mmol) obtained from the second step was placed in a reaction vessel and was swollen by the addition of 1-methylpyrrolidine (2 ml). A solution of trans-cinnamic acid (145 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure.

The crude product obtained was purified by preparative hplc using a 150×21.2 mm 5 μm Hypersil7 Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the desired product as a white solid (20.9 mg, 36%), $t_R$ 3.79 (254 nm, 1.5 mlmin$^{-1}$, 25% ACN/75% $H_2O$+0.2% TFA), m/z [ES] 235 [M+H]$^+$.

Example 6

N-(2-Hydroxycarbamoyl-ethyl)-3-(4-nitro-phenyl)-acryamide (PX083807)

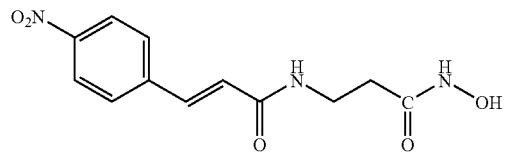

ArgoGelJ-OH resin (500 mg, 0.245 mmol) was placed in a reaction vessel and was swollen by the addition of dichloromethane (2.5 ml). A solution of N-tert-butoxycarbonyl-β-alanine (232 mg, 1.225 mmol), N,N'-diisopropylcarbodiimide (DIC) (192 μl, 1.225 mmol) and 4-(dimethylamino)pyridine (DMAP) (3 mg, 0.0245 mmol) in dichloromethane (2.5 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1714 (urethane) and 1736 (ester)).

The resin (500 mg, 0.245 mmol) obtained from the first step was treated with a mixture of dichloromethane/trifluoroacetic acid/triethylsilane (70:25:5, v/v) (5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1738 (ester)).

The resin (500 mg, 0.245 mmol) obtained from the second step was placed in a reaction vessel and was swollen by the addition of 1-methylpyrrolidine (2 ml). A solution of 4-nitrocinnamic acid (189 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure.

The crude product obtained was purified by preparative hplc using a 150×21.2 mm 5 μm Hypersil7 Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the desired product as a white solid (9.4 mg, 14%), $t_R$ 3.76 (254 nm, 3.0 mlmin$^{-1}$, 5% ACN/95% $H_2O$+0.2% TFA to 95% ACN/5% $H_2O$+0.2% TFA over 3.5 min then 2.5 min at 95% ACN/5% $H_2O$+0.2% TFA), m/z [ES] 392 [M+TFA]$^-$.

Example 7

5-Phenyl-penta-2,4-dienoic acid (2-hydroxycarbamoyl-propyl)amide (PX083808)

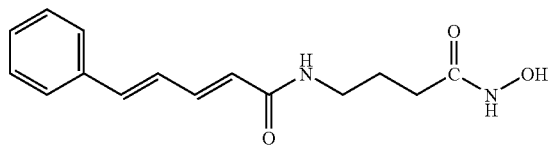

ArgoGelJ-OH resin (500 mg, 0.245 mmol) was placed in a reaction vessel and was swollen by the addition of dichloromethane (2.5 ml). A solution of N-tert-butoxycarbonyl-aminobutyric acid (249 mg, 1.225 mmol), N,N'-diisopropylcarbodiimide (DIC) (192 μl, 1.225 mmol) and 4-(dimethylamino)pyridine (DMAP) (3 mg, 0.0245 mmol) in dichloromethane (2.5 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1714 (urethane) and 1736 (ester)).

The resin (500 mg, 0.245 mmol) obtained from the first step was treated with a mixture of dichloromethane/trifluoroacetic acid/triethylsilane (70:25:5, v/v) (5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1733 (ester).

The resin (500 mg, 0.245 mmol) obtained from the second step was placed in a reaction vessel and was swollen by the addition of 1-methylpyrrolidine (2 ml). A solution of 5-phenylpenta-2,4-dienoic acid (171 mg, 0.98 mmol) (see Villieras J., Rambaud M., 1983, *Synthesis*, pp. 300-303; and Vig B., Kanwar R., Singh V., 1977, *Indian J. Chem. Soc.*, Vol. 15B, pp. 1048-1049), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure.

The crude product obtained was purified by preparative hplc using a 150×21.2 mm 5 μm Hypersil7 Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the desired product as a yellow oil (6.4 mg, 10%), $t_R$ 3.99 (254 nm, 3.0 mlmin$^{-1}$, 5% ACN/95% $H_2O$+0.2% TFA to 95% ACN/5% $H_2O$+0.2% TFA over 3.5 min then 2.5 min at 95% ACN/5% $H_2O$+0.2% TFA), m/z [ES] 275 [M+H]$^+$.

Example 8

N-(2-Hydroxycarbamoyl-ethyl)-3-(4-trifluoromethyl-phenyl)-acryamide (PX089283)

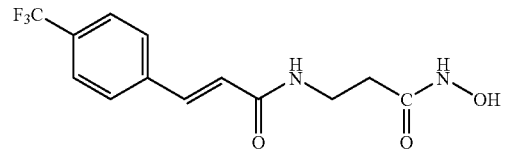

ArgoGelJ-OH resin (500 mg, 0.245 mmol) was placed in a reaction vessel and was swollen by the addition of dichloromethane (2.5 ml). A solution of N-tert-butoxycarbonyl-β-alanine (232 mg, 1.225 mmol), N,N'-diisopropylcarbodiimide (DIC) (192 μl, 1.225 mmol) and 4-(dimethylamino)

pyridine (DMAP) (3 mg, 0.0245 mmol) in dichloromethane (2.5 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1714 (urethane) and 1736 (ester)).

The resin (500 mg, 0.245 mmol) obtained from the first step was treated with a mixture of dichloromethane/trifluoroacetic acid/triethylsilane (70:25:5, v/v) (5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1738 (ester)).

The resin (500 mg, 0.245 mmol) obtained from the second step was placed in a reaction vessel and was swollen by the addition of 1-methylpyrrolidine (2 ml). A solution of 4-trifluoromethylcinnamic acid (145 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure.

The crude product obtained was purified by preparative hplc using a 150×21.2 mm 5 µm Hypersil7 Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the desired product as a white solid (10.6 mg, 14%), $t_R$ 4.15 (254 nm, 3.0 mlmin$^{-1}$, 5% ACN/95% $H_2O$+0.2% TFA to 95% ACN/5% $H_2O$+0.2% TFA over 3.5 min then 2.5 min at 95% ACN/5% $H_2O$+0.2% TFA), m/z [ES] 415 [M+H]$^+$.

Example 9

5-Phenyl-penta-2,4-dienoic acid (2-hydroxycarbamoyl-propyl)amide (PX083808)

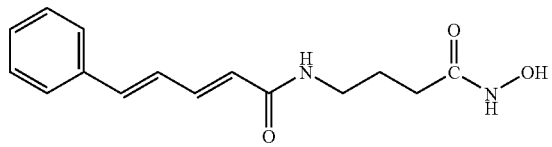

1,1'-Carbonyldiimidazole (0.81 g, 5 mmol) was added to a solution of 5-phenylpenta-2,4-dienoic acid (0.87 g, 5 mmol) in dry tetrahydrofuran (10 ml) and the obtained mixture was stirred for one hour at ambient temperature. Triethylamine (0.76 g 7.5 mmol) and methyl 4-aminobutyrate hydrochloride (0.84 g, 0.55 mmol) were added and the resultant mixture was stirred for six hours at ambient temperature. The residue was filtered off, washed with water and dried.

The intermediate product, 4-((2E)(4E)-5-phenylpenta-2,4-dienoylamino)butyric acid methyl ester, (0.93 g, 68%) was obtained as a white solid, m.p. 153-155° C. $^1$H NMR (DMSO-$d_6$, HMDSO), δ: 1.47-1.89 (2H, m, $CH_2$); 2.34 (2H, t, J=7.5 Hz, $CH_2$); 3.16 (2H, q, J=6.5 Hz, $CH_2$); 3.58 (3H, s, $CH_3$); 6.12 (1H, d, J=14.8 Hz, CH); 6.83-7.65 (8H, m, $C_6H_5$, CH=CH—CH); 8.07 (1H, unresolv. t, NH).

A solution of sodium methylate (18 mmol) in methanol (7 ml) was added to a solution of hydroxylamine hydrochloride (0.83 g, 12 mmol) in methanol (10 ml). A mixture was stirred for 10 min. and the precipitate was filtered off. 4-((2E)(4E)-5-Phenylpenta-2,4-dienoylamino)butyric acid methyl ester (0.82 g, 3 mmol) was added to the filtrate and the mixture was heated until a complete dissolving. The resultant mixture was stirred for 4 hours at ambient temperature and the solvent was removed under reduced pressure. The product was dissolved in water (15 ml) and the solution was acidified with 3% HCl. The precipitate was filtered and crystallised from ethanol.

The desired product (0.58 g, 70%) was obtained as a white solid, m.p. 178-179° C. $^1$H NMR (DMSO-$d_6$, HMDSO), δ: 1.55-1.81 (2H, m, $CH_2$); 1.98 (2H, t, J=7.2 Hz, $CH_2$); 3.13 (2H, q, J=6.2 Hz, $CH_2$); 6.11 (1H, d, J=14.4 Hz, CH); 6.81-7.77 (8H, m, $C_6H_5$, CH=CH—CH); 8.15 (1H, unresolv. t, NH); 8.73 (1H, s, NH), 10.40 (1H, s, OH).

HPLC analysis on Symmetry C18: impurities 1.0% (column size 3.9×150 mm; mobile phase acetonitrile–0.1M phosphate buffer (pH 2.5), 30:70; detector UV 230 nm; sample concentration 1 mg/ml). Anal. Calcd for $C_{15}H_{18}N_2O_3$, %: C, 65.68; H, 6.61; N, 10.21. Found, %: C, 65.63; H, 6.60; N, 10.17.

Example 10

4-[((2E)(4E)-5-Phenylpenta-2,4-dienoylamino)methyl] cyclohexanecarboxylic acid hydroxyamide (PX105552)

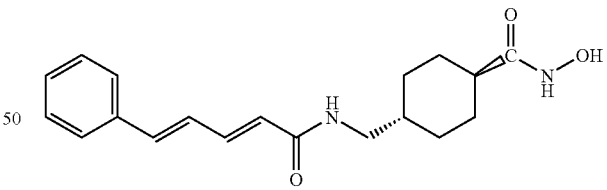

The intermediate product, 4-[((2E)(4E)-5-phenylpenta-2,4-dienoylamino)methyl] cyclohexanecarboxylic acid methyl ester, was prepared in a manner analogous to the intermediate compound in the previous example, using 4-(aminomethyl) cyclohexanecarboxylic acid methyl ester hydrochloride.

The intermediate product was obtained as a white solid (95%), m.p. 124-125° C. $^1$H NMR (DMSO-$d_6$, HMDSO), δ: 0.63-2.36 (10H, m, $C_6H_{10}$); 3.01 (2H, t, J=6.0 Hz, $CH_2N$); 3.56 (3H, s, $CH_3$); 6.16 (1H, d, J=14.8 Hz, CH); 6.83-7.18 (2H, m, CH=CH); 7.20-7.76 (6H, m, $C_6H_5$, CH); 8.03 (1H, unresolv. t, NH).

The desired product was prepared in a manner analagous to the desired product in the previous example.

The desired product was obtained as a white solid (34%), m.p. 210-212° C. $^1$H NMR (DMSO-$d_6$, HMDSO), δ: 0.63-2.09 (10H, m, $C_6H_{10}$); 3.01 (2H, t, J=6.5 Hz, $CH_2N$); 6.16 (1H, d, J=14.8 Hz, CH); 6.92-7.16 (2H, m, CH=CH); 7.23-7.69 (6H, m, $C_6H_5$, CH); 8.03 (1H, t, J=6.1 Hz, $CH_2NH$); 8.61 (1H, s, NH), 10.32 (1H, s, OH).

HPLC analysis on Symmetry C18: impurities 2.2% (column size 3.9×150 mm; mobile phase acetonitrile–0.1M phosphate buffer (pH 2.5), 35:65; detector UV 254 nm; sample concentration 0.8 mg/ml). Anal. Calcd for $C_{19}H_{24}N_2O_3$× 0.2$H_2O$, %: C, 68.73; H, 7.41; N, 8.44. Found, %: C, 68.48; H, 7.32; N, 8.28.

Example 11

4-(2E)(4E)-5-Phenyl-penta-2,4-dienoic acid (5-hydroxycarbamoyl-pentyl)-amide (PX105553)

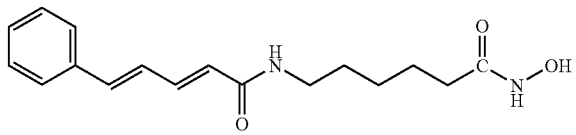

The intermediate product, 6-((2E)(4E)-5-phenylpenta-2,4-dienoylamino)hexanoic acid methyl ester, was prepared in a manner analogous to the intermediate product in the previous example, using 6-(amino)hexanoic acid methyl ester hydrochloride.

The product 3 was obtained as a white solid (60%), m.p. 125-127° C. $^1$H NMR (DMSO-$d_6$, HMDSO), δ: 1.05-1.72 (6H, m, $CH_2$); 2.29 (2H, t, J=7.3 Hz, $CH_2$); 3.12 (2H, q, J=6.0 Hz, $CH_2N$); 3.58 (3H, s, $CH_3$); 6.12 (1H, d, J=14.8 Hz, CH); 6.91-7.16 (2H, m, CH—CH); 7.23-7.66 (6H, m, $C_6H_5$, CH); 8.05 (1H, t, J=5.8 Hz, NH).

The desired product was prepared in a manner analogous to the desired product in the previous example.

The desired product was obtained as a white solid (78%), m.p. 160-161° C. $^1$H NMR (DMSO-$d_6$, HMDSO), δ: 1.05-1.69 (6H, m, $CH_2$); 1.81-2.07 (2H, m, $CH_2$); 3.12 (2H, q, J=5.8 Hz, $CH_2N$); 6.14 (1H, d, J=14.8 Hz, CH); 6.89-7.14 (2H, m, CH—CH); 7.23-7.65 (6H, m, $C_6H_5$, CH); 8.05 (1H, t, J=6.0 Hz, NH); 8.63 (1H, s, NH), 10.34 (1H, s, OH).

HPLC analysis on Symmetry C18: impurities 1.0% (column size 3.9×150 mm; mobile phase acetonitrile–0.1M phosphate buffer (pH 2.5), 30:70; detector UV 230 nm; sample concentration 1 mg/ml). Anal. Calcd for $C_{17}H_{22}N_2O_3$, %: C, 65.68; H, 6.61; N, 10.21. Found, %: C, 65.63; H, 6.60; N, 10.17.

Example 12

(PX099268)

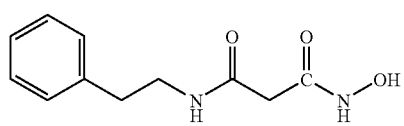

This compound was prepared in a manner analagous to that used in Examples 9-11.

Example 13

(PX105668)

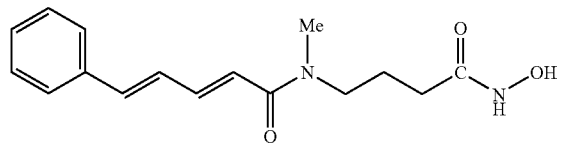

This compound was prepared in a manner analagous to that used in Examples 9-11.

Example 14

(PX105669)

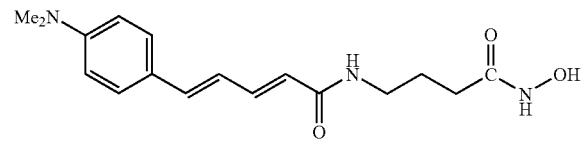

This compound was prepared in a manner analagous to that used in Examples 9-11.

Example 15

(PX105670)

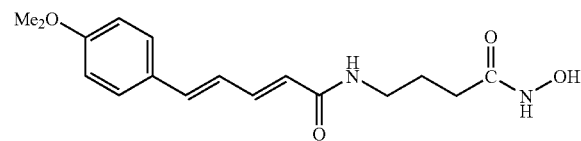

This compound was prepared in a manner analagous to that used in Examples 9-11.

Example 16

(PX105554)

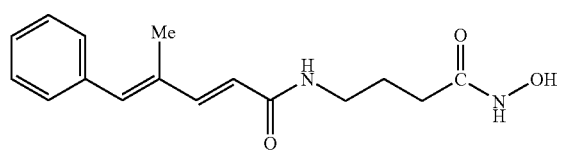

This compound was prepared in a manner analagous to that used in Examples 9-11.

Example 17 m-Aminophenyl acrylic acid methyl ester (7)

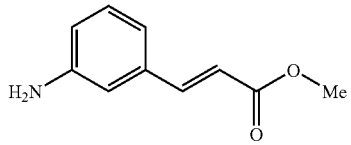

The title compound was prepared from m-nitrocinnamic acid (Acros) as described in Bellamy et al., 1984.

Example 18

3-[3-(3-Phenylacryloylamino)-phenyl]-acrylic acid methyl ester (8)

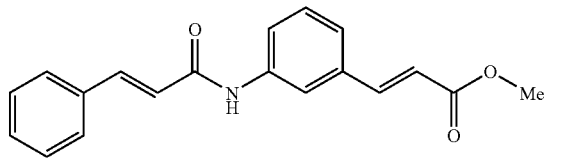

A solution of phenylacryloylchloride (0.47 g, 2.85 mmol) (Acros) in tetrahydrofuran (10.0 ml) was added to a mixture of m-aminophenylacrylic acid methyl ester (7) (0.44 g, 2.50 mmol) in tetrahydrofuran (15.0 ml) and NaHCO$_3$ (0.37 g, 4.50 mmol) in water (8.0 ml), and the resultant solution was stirred at room temperature for one hour. The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographed on silica gel with petroleum ether-ethyl acetate (2:1, v/v) as eluent. The obtained product was washed with diethyl ether to give the title compound (0.54 g, 70%). $^1$H NMR (DMSO-d$_6$, HMDSO), δ: 3.72 (3H, s); 6.52 (1H, d, J=16.0 Hz); 6.83 (1H, d, J=16.0 Hz); 7.29-7.85 (10H, m); 7.98 (1H, br s); 10.32 (1H, br s).

Example 19

N-Hydroxy-3-[3-(3-phenylacryloylamino)-phenyl]-acrylamide (PX106513)

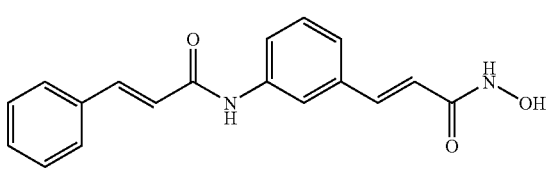

To a suspension of hydroxylamine hydrochloride (0.14 g, 2.01 mmol) (Acros) in methanol (2.0 ml) a solution of NaOH (0.16 g, 4.00 mmol) in H$_2$O (0.2 ml) was added and the resultant mixture was stirred at ambient temperature for 5 min. To the reaction mixture a 3-[3-(3-phenylacryloylamino)-phenyl]-acrylic acid methyl ester (8) (0.15 g, 0.49 mmol) solution in methanol (2.0 ml) was added and stirred at ambient temperature for 1.5 hour. The reaction mixture was partitioned between ethyl acetate and 2N HCl. The organic layer was washed successively with water and saturated NaCl, and the solvent was removed. The residue was crystallized from ethyl acetate-methanol giving pure title compound (0.040 g, 26%), m.p. 178° C. $^1$H NMR (DMSO-d$_6$, HMDSO), δ: 6.45 (d, 1H, J=16.0 Hz); 6.85 (d, 1H, J=16.0 Hz); 7.14-7.76 (m, 10 H); 8.00 (br s, 1H); 9.03 (br s, 1H); 10.32 (br s, 1H); 10.83 (br s, 1H). HPLC analysis on Zorbax SB-C$_{18}$ column: impurities 4.5% (column size 4.6×150 mm; mobile phase acetonitrile–0.1% H$_3$PO$_4$, gradient from 30 to 100%; sample concentration 0.25 mg/ml; flow rate 1.5 ml/min; detector: UV 270 nm). Anal. Calcd for C$_{18}$H$_{16}$N$_2$O$_3$×0.25 H$_2$O, %: C, 69.11; H, 5.32; N, 8.95. Found, %: C, 69.09; H, 5.06; N, 8.81.

Example 20

Methyl 6-aminohexanoate hydrochloride (10)

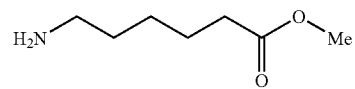

The title compound was prepared from 6-aminocaproic acid (Acros) as described in Chen et al., 1978 and Backer et al., 1940.

Example 21

6-Aminoheptanoate hydrochloride (11)

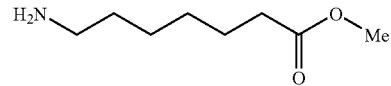

The title compound was prepared from 2-azacyclooctanone (Acros) as described in Chen et al., 1978 and Backer et al., 1940.

Example 22

6-aminooctanoate hydrochloride (12)

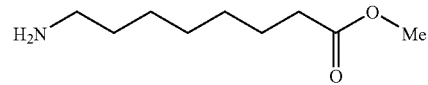

The title compound was prepared from 2-azacyclononanone (Acros) as described in Chen et al., 1978 and Backer et al., 1940.

Example 23

(2E,4E)-5-(2-nitrophenyl)penta-2,4-dienoic acid (9a)

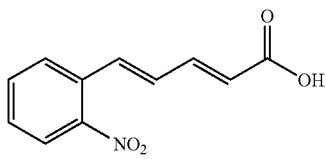

The title compound was synthesized by the procedures described in the literature (Villieras et al., 1983; Vig et al., 1977; Banerji et al., 1984), from o-nitrocinnamaldehyde (Acros).

Example 24

(2E,4E)-6-[5-(2-Nitrophenyl)penta-2,4-dienoylamino]hexanoic acid methyl ester (13a)

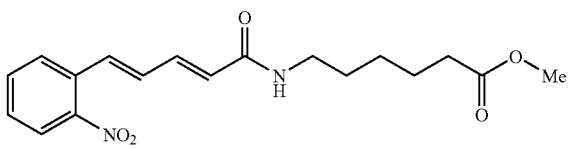

To a solution of (2E,4E)-5-(2-nitrophenyl)penta-2,4-dienoic acid (9a) (0.44 g, 2.0 mmol) in dry tetrahydrofuran (10 ml) 1,1'-carbonyldiimidazole (0.36 g, 2.2 mmol) (Sigma-Aldrich) was added and the mixture was stirred for 1 hour at ambient temperature. To the reaction mixture triethylamine (0.30 g 3.0 mmol) and methyl 6-aminohexanoate hydrochloride (10) (0.40 g, 2.2 mmol) successively were added and the resultant suspension was stirred for 6 hour at ambient temperature. The solvent was evaporated, to the obtained residue water (15 ml) was added and the precipitate was filtered off. The precipitate was washed with an additional amount of water and dried to give the title compound (0.62 g, 89%) as a yellow solid, m.p. 115-117° C. $^1$H NMR (DMSO-$d_6$, HMDSO), δ: 1.10-1.79 (6H, m, $CH_2$); 2.29 (2H, J=7.0 Hz, $CH_2$); 3.17 (2H, q, J=5.6 Hz, $CH_2N$);3.60 (3H, s); 6.24 (1H, d, J=14.8 Hz, CH); 7.04-8.10 (8H, m, CH—CH=CH, $C_6H_4$, NH).

Example 25

(2E,4E)-5-(2-Nitrophenyl)penta-2,4-dienoic acid (5-hydroxycarbamoyl-pentyl)amide (PX105830)

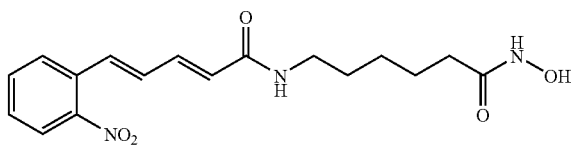

A solution of sodium methylate (6.0 mmol) in methanol (5 ml) was added to a solution of hydroxylamine hydrochloride (0.28 g, 4.0 mmol) (Acros) in methanol (8 ml). The mixture was stirred for 10 min. and the precipitate was filtered off. (2E,4E)-6-[5-(2-Nitrophenyl)penta-2,4-dienoylamino]hexanoic acid methyl ester (13a) (0.35 g, 1 mmol) was added to the filtrate and the obtained mixture was heated to the complete dissolving. The resultant mixture was stirred for 4 hours at ambient temperature and the solvent was removed under reduced pressure. The product was dissolved in water (10 ml) and the solution was acidified with 3% HCl. The precipitate was filtered and crystallized from acetonitrile to give the title compound (0.23 g, 66%) as a yellow solid. M.p. 131-133° C. $^1$H NMR (DMSO-$d_6$, HMDSO), δ: 1.06-1.73 (6H, m, $CH_2$); 1.87-2.09 (2H, m, $CH_2$); 3.15 (2H, q, J=5.6 Hz, $CH_2N$); 6.26 (1H, d, J=14.8 Hz, CH); 7.00-8.06 (8H, m, CH—CH=CH, $C_6H_4$, NH); 8.06 (1H, t, J=5.9 Hz, NH); 10.33 (1H, s, OH). HPLC analysis on Symmetry $C_{18}$ column: impurities <1.0% (column size 3.9×150 mm; mobile phase acetonitrile–0.1M phosphate buffer (pH 2.5), 35:65; detector UV 220 nm; sample concentration 0.15 mg/ml). Anal. Calcd for $C_{17}H_{21}N_3O_5$, %: 58.78; H, 6.09; N, 12.10. Found, %: C, 58.26; H, 6.08; N, 11.87.

Example 26

(2E,4E)-4-methyl-5-phenyl-2,4-pentadienoic acid (9b)

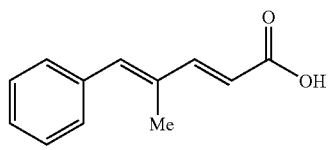

The title compound was synthesized by the procedures described in the literature (Villieras et al., 1983; Vig et al., 1977; Banerji et al., 1984), from α-methyl-trans-cinnamaldehyde (Sigma-Aldrich).

Example 27

(2E,4E)-6-(4-Methyl-5-phenylpenta-2,4-dienoylamino)-hexanoic acid methyl ester (13b)

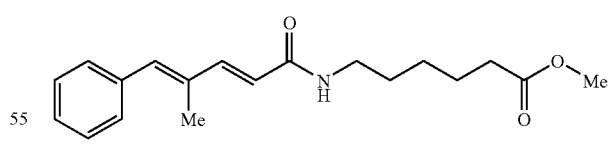

The title compound was obtained from (2E,4E)-4-methyl-5-phenyl-2,4-pentadienoic acid (9b) and methyl 6-aminohexanoate hydrochloride (10), in the same manner as described above in Example 24. Yield 49%, m.p. 53-55° C. $^1$H NMR (DMSO-$d_6$, HMDSO), δ: 1.01-1.69 (6H, m, $CH_2$);1.98 (3H, s, $CH_3$); 2.29 (2H, t, J=7.5 Hz, $CH_2$); 2.92-3.22 (2H, m, $CH_2N$);3.58 (3H, s, $CH_3$); 6.12 (1H, d, J=14.8 Hz, CH); 6.85 (1H, s, CH); 7.07-7.49 (6H, m, CH, $C_6H_5$); 7.98 (1H, unresolv. t, NH).

Example 28

(2E,4E)-4-Methyl-5-phenylpenta-2,4-dienoic acid (5-hydroxycarbamoylpentyl)amide (PX105829)

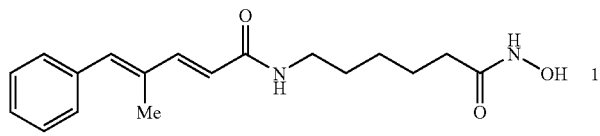

The title compound was obtained from (2E,4E)-6-(4-methyl-5-phenylpenta-2,4-dienoylamino)-hexanoic acid methyl ester (13b) in the same manner as described above in Example 25. Yield 74%, m.p. 129-131° C. $^1$H NMR (DMSO-$d_6$, HMDSO), δ: 1.05-1.69 (6H, m, $CH_2$); 1.82-2.06 (2H, m, $CH_2$); 1.98 (3H, s, $CH_3$); 3.12 (2H, q, J=5.7 Hz, $CH_2$N); 6.12 (1H, d, J=14.9 Hz, CH); 6.83 (1H, s, CH); 7.21 (1H, d, J=14.9 Hz, CH); 7.34 (5H, s, $C_6H_5$); 7.94 (1H, t, J=5.8 Hz, NH); 8.61 (1H, s, NH), 10.29 (1H, s, OH). HPLC analysis on Symmetry $C_{18}$ column: impurities 1.8% (column size 3.9×150 mm; mobile phase acetonitrile–0.1M phosphate buffer (pH 2.5), 35:65; detector UV 220 nm; sample concentration 0.5 mg/ml). Anal. Calcd for $C_{18}H_{24}N_2O_3 \times H_2O$, %: C, 64.65; H, 7.84; N, 8.38. Found, %: C, 64.65; H, 7.82; N, 8.28.

Example 29

(2E,4E)-5-(4-nitrophenyl)-2,4-pentadienoic acid (9c)

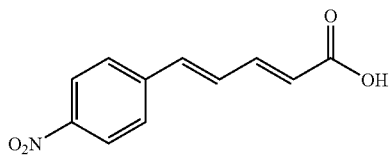

The title compound was synthesized by the procedures described in the literature (Villieras et al., 1983; Vig et al., 1977; Banerji et al., 1984), from 4-nitrocinnamaldehyde (Lancaster).

Example 30

(2E,4E)-6-[5-(4-Nitrophenyl)penta-2,4-dienoylamino]hexanoic acid methyl ester (13c)

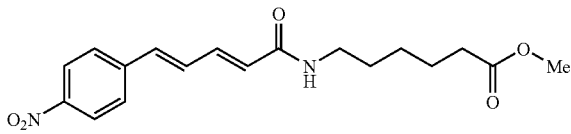

The title compound was obtained from (2E,4E)-5-(4-nitrophenyl)-2,4-pentadienoic acid (9c) and methyl 6-aminohexanoate hydrochloride (10), in the same manner as described above in Example 24. Yield 82%, m.p. 178-180° C. $^1$H NMR (DMSO-$d_6$, HMDSO), δ: 0.99-1.69 (6H, m, $CH_2$); 2.19 (2H, t, J=6.8 Hz, $CH_2$); 2.89-3.23 (2H, m, $CH_2$N); 3.61 (3H, s, $CH_3$O); 6.27 (1H, d, J=15.0 Hz, CH); 6.89-7.54 (3H, m, CH—CH=CH); 7.85 (2H, d, J=8.4 Hz, $C_6H_2$); 8.21 (2H, d, J=8.4 Hz, $C_6H_2$); 8.23 (1H, t, NH, overlapped with $C_6H_2$).

Example 31

(2E,4E)-5-(4-Nitrophenyl)penta-2,4-dienoic acid (5-hydroxycarbamoyl-pentyl)-amide (PX105847)

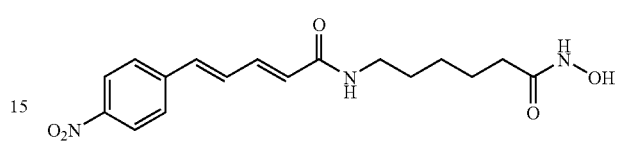

The title compound was obtained from (2E,4E)-6-[5-(4-nitrophenyl)penta-2,4-dienoylamino]hexanoic acid methyl ester (13c) in the same manner as described above in Example 25. Yield 44%, m.p. 111-113° C. $^1$H NMR (DMSO-$d_6$, HMDSO), δ: 0.99-1.69 (6H, m, $CH_2$); 1.76-2.29 (2H, m, $CH_2$); 2.91-3.29 (2H, m, $CH_2$N); 6.24 (1H, d, J=15.0 Hz, CH); 6.84-7.42 (4H, m, CH—CH=CH, NH); 7.80 (2H, d, J=8.4 Hz, $C_6H_2$); 8.20 (2H, d, J=8.4 Hz, $C_6H_2$); 8.13 (1H, t, NH, overlapped with $C_6H_2$); 10.34 (1H, s, OH). HPLC analysis on Symmetry $C_{18}$ column: impurities 1.0% (column size 3.9×150 mm; mobile phase acetonitrile–0.1M phosphate buffer (pH 2.5), 30:70; detector UV 220 nm; sample concentration 0.15 mg/ml). Anal. Calcd for $C_{17}H_{21}N_3O_5$, %: C, 58.78; H, 6.09; N, 12.10. Found, %: C, 58.38; H, 6.16; N, 12.15.

Example 32

(E)-6-(3-Benzo[1,3]dioxol-5-yl-acryloylamino)hexanoic acid methyl ester (13d)

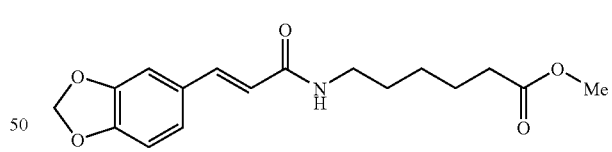

The title compound was obtained from (E)-3-(1,3-benzodioxol-5-yl)-2-propenoic acid (9d) (Acros) and methyl 6-aminohexanoate hydrochloride (10), in the same manner as described above in Example 24. Yield 70%, m.p. 73-75° C. $^1$H NMR (DMSO-$d_6$, HMDSO), δ: 0.95-1.70 (6H, m, $CH_2$); 1.96 (2H, t, J=7.5 Hz, $CH_2$); 3.14 (2H, q, J=5.7 Hz, $CH_2$N); 3.60 (3H, s, $CH_3$O); 6.05 (2H, s, $CH_2$); 6.45 (1H, d, J=15.0 Hz, CH); 6.72-7.18 (3H, s, $C_6H_3$); 7.34 (1H, d, J=15.0 Hz, CH); 7.94 (1H, unresolv. t, NH); 8.65 (1H, s, NH), 10.32 (1H, s, OH).

Example 33

(E)-3-Benzo[1,3]dioxol-5-yl-N-(5-hydroxycarbamoylpentyl)acrylamide (PX105831)

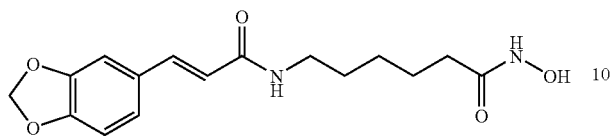

The title compound was obtained from (E)-6-(3-benzo[1,3]dioxol-5-yl-acryloylamino)hexanoic acid methyl ester (13d), in the same manner as described above in Example 25. Yield 67%, m.p. 191-193° C. $^1$H NMR (DMSO-$d_6$, HMDSO), δ: 1.00-1.72 (6H, m, CH$_2$); 1.81-2.05 (2H, unresolv. t, CH$_2$); 3.14 (2H, q, J=5.7 Hz, CH$_2$N); 6.05 (2H, s, CH$_2$); 6.45 (1H, d, J=15.0 Hz, CH); 6.72-7.18 (3H, s, C$_6$H$_3$); 7.34 (1H, d, J=15.0 Hz, CH); 7.94 (1H, unresolv. t, NH); 8.65 (1H, s, NH), 10.32 (1H, s, OH). HPLC analysis on Symmetry C$_{18}$ column: impurities 1.0% (column size 3.9×150 mm; mobile phase acetonitrile–0.1M phosphate buffer (pH 2.5), 35:65; detector UV 220 nm; sample concentration 0.25 mg/ml). Anal. Calcd for C$_{16}$H$_{20}$N$_2$O$_5$, %: C, 59.99; H, 6.29; N, 8.74. Found, %: C, 59.87; H, 6.29; N, 8.60.

Example 34

(2E,4E)-5-[1,1'-biphenyl]-4-yl-2,4-pentadienoic acid (9e)

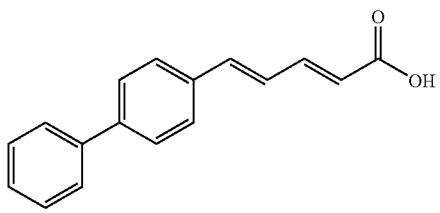

The title compound was synthesized by the procedures described in the literature (Villieras et al., 1983; Vig et al., 1977; Banerji et al., 1984), from 4-biphenylcarboxaldehyde (Acros).

Example 35

(2E,4E)-6-(5-Biphenyl-4-yl-penta-2,4-dienoylamino)-hexanoic acid methyl ester (13e)

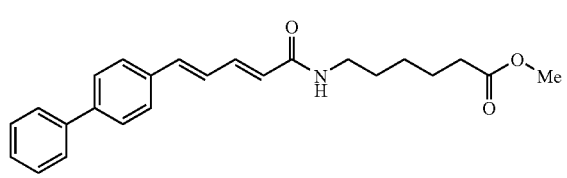

The title compound was obtained from (2E,4E)-5-[1,1'-biphenyl]-4-yl-2,4-pentadienoic acid (9e) and methyl 6-aminohexanoate hydrochloride (10), in the same manner as described above in Example 24. Yield 81%, m.p. 168-170° C. $^1$H NMR (DMSO-$d_6$, HMDSO), δ: 0.93-1.76 (6H, m, CH$_2$); 2.11-2.42 (2H, m, CH$_2$); 2.91-3.36 (2H, m, CH$_2$N); 3.56 (3H, s, CH$_3$O); 6.20 (1H, d, J=15.0 Hz, CH); 6.87-7.25 (2H, m, CH—CH); 7.24-7.91 (10H, m, C$_6$H$_5$—C$_6$H$_4$, CH); 8.05 (1H, unresolv. t, NH).

Example 36

(2E,4E)-5-Biphenyl-4-yl-penta-2,4-dienoic acid (5-hydroxycarbamoyl-pentyl)-amide (PX105848)

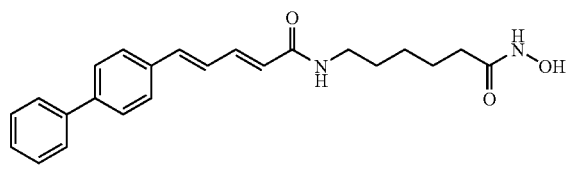

The title compound was obtained from (2E,4E)-6-(5-biphenyl-4-yl-penta-2,4-dienoylamino)-hexanoic acid methyl ester (9e) in the same manner as described above in Example 25. Yield 91%, m.p. 222-224° C. $^1$H NMR (DMSO-$d_6$, HMDSO), δ:0.96-1.72 (6H, m, CH$_2$); 1.78-2.09 (2H, m, CH$_2$); 2.94-3.34 (2H, m, CH$_2$N); 6.18 (1H, d, J=14.8 Hz, CH); 6.82-7.21 (2H, m, CH—CH); 7.21-7.87 (10H, m, C$_6$H$_5$—C$_6$H$_4$, CH); 8.05 (1H, unresolv. t, NH); 8.67 (1H, s, NH), 10.36 (1H, s, OH). HPLC analysis on Symmetry C$_{18}$ column: impurities 3.0% (column size 3.9×150 mm; mobile phase acetonitrile–0.1M phosphate buffer (pH 2.5), 50:50; detector UV 254 nm; sample concentration 0.07 mg/ml). Anal. Calcd for C$_{23}$H$_{26}$N$_2$O$_3$×0.5H$_2$O, %: C, 71.30; H, 7.02; N, 7.23. Found, %: C, 71.08; H, 6.73; N, 6.94.

Example 37

(2Z,4E)-5-(4-chlorophenyl)-2,4-pentadienoic acid (9f)

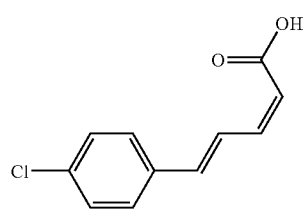

The title compound was synthesized from 4-chlorobenzaldehyde (Acros) as described in Carbonnier et al., 1981.

Example 38

(2Z,4E)-6-[5-(4-Chloro-phenyl)-penta-2,4-dienoy-lamino]-hexanoic acid methyl ester (13f)

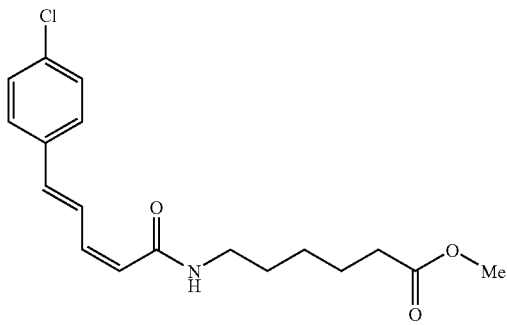

The title compound was obtained from (2Z,4E)-5-(4-chlorophenyl)-2,4-pentadienoic acid (9f) and methyl 6-aminohexanoate hydrochloride (10), in the same manner as described above in Example 24. Yield 62%, m.p. 83-85° C. $^1$H NMR (DMSO-$d_6$, HMDSO), δ: 1.05-1.74 (6H, m, $CH_2$); 2.29 (2H, t, J=7.5 Hz, $CH_2$); 3.12 (2H, q, J=6.0 Hz, $CH_2N$); 3.58 (3H, s, $CH_3O$); 5.78 (1H, d, J=11.2 Hz, CH); 6.58 (1H, t, J=11.2 Hz, CH); 6.74 (1H, d, J=15.8 Hz, CH); 7.27-7.60 (4H, m, $C_6H_4$); 8.07 (1H, unresolv. t, NH); 8.29 (1H, dd, J=11.2 Hz, and 15.8 Hz, CH).

Example 39

(2Z,4E)-5-(4-Chlorophenyl)penta-2,4-dienoic acid (5-hydroxycarbamoylpentyl)-amide (PX105849)

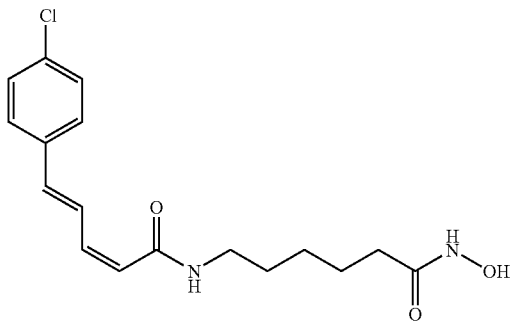

The title compound was obtained from (2Z,4E)-6-[5-(4-chloro-phenyl)-penta-2,4-dienoylamino]-hexanoic acid methyl ester (13f) in the same manner as described above in Example 25. Yield 56%, m.p. 158-160° C. $^1$H NMR (DMSO-$d_6$, HMDSO), δ: 0.92-1.69 (6H, m, $CH_2$); 1.74-2.09 (2H, m, $CH_2$); 2.82-3.36 (2H, m, $CH_2N$); 5.78 (1H, d, J=11.0 Hz, CH); 6.56 (1H, t, J=11.0 Hz, CH); 6.76 (1H, d, J=15.8 Hz, CH); 7.12-7.63 (4H, m, $C_6H_4$); 8.07 (1H, unresolv. t, NH); 8.26 (1H, dd, J=11.0 Hz, and 15.8 Hz, CH); 8.63 (1H, s, NH), 10.29 (1H, s, OH). HPLC analysis on Symmetry $C_{18}$ column: impurities 3.0% (column size 3.9×150 mm; mobile phase acetonitrile—0.1M phosphate buffer (pH 2.5), 40:60; detector UV 230 nm; sample concentration 0.33 mg/ml). Anal. Calcd for $C_{17}H_{21}ClN_2O_3$, %: C, 60.62; H, 6.28; N, 8.32. Found, %: C, 60.33; H, 6.26; N, 8.03.

Example 40

(2E,4E)-5-(4-chlorophenyl)-2,4-pentadienoic acid (9g)

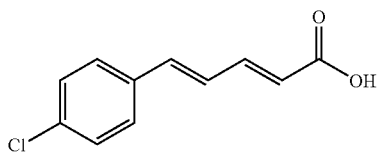

The title compound was synthesized from 4-chlorobenzaldehyde (Acros) by the procedures described in the literature (Villieras et al., 1983; Vig et al., 1977; Banerji et al., 1984).

Example 41

(2E,4E)-6-[5-(4-Chlorophenyl)penta-2,4-dienoy-lamino]hexanoic acid methyl ester (13g)

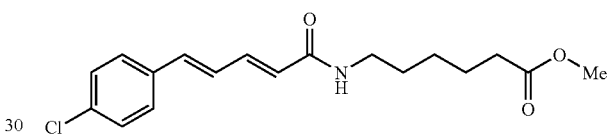

The title compound was obtained from (2E,4E)-5-(4-chlorophenyl)-2,4-pentadienoic acid (9g) and methyl 6-aminohexanoate hydrochloride (10), in the same manner as described above in Example 24. Yield 64%, m.p. 148-150° C. $^1$H NMR (DMSO-$d_6$, HMDSO), δ: 1.01-1.70 (6H, m, $CH_2$); 2.27 (2H, t, J=7.5 Hz, $CH_2$); 3.14 (2H, q, J=6.0 Hz, $CH_2N$); 3.57 (3H, s, $CH_3O$); 6.12 (1H, d, J=14.8 Hz, CH); 6.78-7.27 (3H, m, CH=CH—CH); 7.41 (2H, d, J=8.0 Hz, $C_6H_2$); 7.58 (2H, d, J=8.0 Hz, $C_6H_2$); 8.05 (1H, unresolv. t, NH).

Example 42

(2E,4E)-5-(4-Chlorophenyl)penta-2,4-dienoic acid (5-hydroxycarbamoylpentyl)-amide (PX105850)

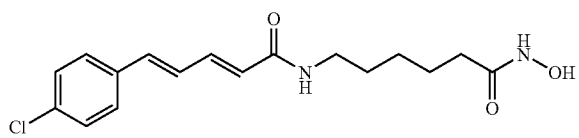

The title compound was obtained from (2E,4E)-6-[5-(4-chlorophenyl)penta-2,4-dienoylamino]hexanoic acid methyl ester (13g) in the same manner as described above in Example 25. Yield 90%, m.p. 164-168° C. $^1$H NMR (DMSO-$d_6$, HMDSO), δ: 0.98-1.67 (6H, m, $CH_2$); 1.94 (2H, t, J=7.0 Hz, $CH_2$); 2.94-3.50 (2H, m, $CH_2N$); 6.16 (1H, d, J=14.8 Hz, CH); 6.83-7.22 (3H, m, CH=CH—CH); 7.36 (2H, d, J=8.0 Hz, $C_6H_2$); 7.58 (2H, d, J=8.0 Hz, $C_6H_2$); 8.05 (1H, unresolv. t, NH); 8.63 (1H, s, NH), 10.29 (1H, s, OH). HPLC analysis on Symmetry $C_{18}$ column: impurities <1.0% (column size 3.9×150 mm; mobile phase acetonitrile–0.1M phosphate buffer (pH 2.5), 30:70; detector UV 230 nm; sample concentration 1.0 mg/ml). Anal. Calcd for $C_{17}H_{21}ClN_2O_3$, %: C, 60.62; H, 6.28; N, 8.32. Found, %: C, 60.20; H, 6.25; N, 8.00.

Example 43

(2E,4E)-5-phenyl-2,4-pentadienoic acid (9h)

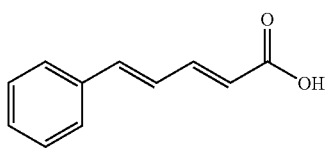

The title compound was synthesized by the procedures described in the literature (Villieras et al., 1983; Vig et al., 1977; Banerji et al., 1984), from cinnamaldehyde (Acros)

Example 44

(2E,4E)-8-(5-Phenylpenta-2,4-dienoylamino)octanoic acid methyl ester (13h)

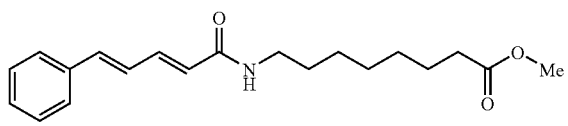

The title compound was obtained from (2E,4E)-5-phenyl-2,4-pentadienoic acid (9h) and methyl 6-aminooctanoate hydrochloride (12), in the same manner as described above in Example 24. Yield 43%, m.p. 98-100° C. $^1$H NMR (DMSO-$d_6$, HMDSO), δ:1.05-1.65 (10H, m, $CH_2$); 2.27 (2H, t, J=7.0 Hz, $CH_2$); 3.14 (2H, q, J=5.4 Hz, $CH_2N$); 3.59 (3H, s, $CH_3O$); 6.16 (1H, d, J=15.0 Hz, CH); 6.90-7.19 (2H, m, CH=CH); 7.24-7.70 (6H, m, $C_6H_5$, CH); 8.04 (1H, unresolv. t, NH).

Example 45

(2E,4E)-5-Phenylpenta-2,4-dienoic acid (5-hydroxycarbamoylheptyl)amide (PX105851)

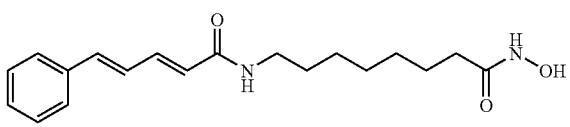

The title compound was obtained from (2E,4E)-8-(5-phenylpenta-2,4-dienoylamino)octanoic acid methyl ester (13h) in the same manner as described above in Example 25. Yield 60%, m.p. 160-162° C. $^1$H NMR (DMSO-$d_6$, HMDSO), δ: 1.07-1.67 (10H, m, $CH_2$); 1.94 (2H, t, J=7.0 Hz, $CH_2$); 3.14 (2H, q, J=5.4 Hz, $CH_2N$); 6.14 (1H, d, J=14.8 Hz, CH); 6.92-7.16 (2H, m, CH=CH); 7.23-7.67 (6H, m, $C_6H_5$, CH); 8.03 (1H, unresolv. t, NH); 8.63 (1H, s, NH), 10.32 (1H, s, OH). HPLC analysis on Zorbax SB-$C_{18}$ column: impurities 3.0% (column size 4.6×150 mm; mobile phase gradient 10 min. 50-100% acetonitrile–0.1% $H_3PO_4$; detector UV 270 nm; sample concentration 0.3 mg/ml). Anal. Calcd for $C_{19}H_{26}N_2O_3$, %: C, 69.06; H, 7.93; N, 8.48. Found, %: C, 68.81; H, 7.97; N, 8.36.

Example 46

(2E,4E)-7-(5-Phenylpenta-2,4-dienoylamino)heptanoic acid methyl ester (13i)

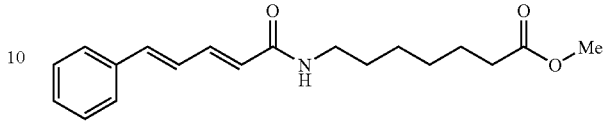

The title compound was obtained from (2E,4E)-5-phenyl-2,4-pentadienoic acid (9h) and methyl 6-aminoheptanoate hydrochloride (11), in the same manner as described above in Example 24. Yield 46%, m.p. 104-106° C. $^1$H NMR (DMSO-$d_6$, HMDSO), δ: 0.76-1.70 (8H, m, $CH_2$); 2.29 (2H, t, J=7.0 Hz, $CH_2$); 3.16 (2H, q, J=5.4 Hz, $CH_2N$); 3.57 (3H, s, $CH_3O$); 6.16 (1H, d, J=15.1 Hz, CH); 6.70-7.23 (2H, m, CH—CH); 7.23-7.67 (6H, m, $C_6H_5$, CH); 8.04 (1H, unresolv. t, NH).

Example 47

(2E,4E)-5-Phenylpenta-2,4-dienoic acid (5-hydroxycarbamoylhexyl)amide (PX106518)

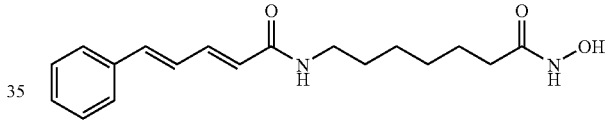

The title compound was obtained from (2E,4E)-7-(5-phenylpenta-2,4-dienoylamino)heptanoic acid methyl ester (13i) in the same manner as described above in Example 25. Yield 45%, m.p. 147-149° C. $^1$H NMR (DMSO-$d_6$, HMDSO), δ: 0.72-1.72 (8H, m, $CH_2$); 1.94 (2H, t, J=7.5 Hz, $CH_2$); 3.14 (2H, q, J=6.0 Hz, $CH_2N$); 6.14 (1H, d, J=15.0 Hz, CH); 6.72-7.21 (2H, m, CH—CH); 7.21-7.65 (6H, m, $C_6H_5$, CH); 8.01 (1H, unresolv. t, NH); 8.65 (1H, s, NH), 10.32 (1H, s, OH). HPLC analysis on Zorbax SB-$C_{18}$ column: impurities 1.5% (column size 4.6×150 mm; mobile phase gradient 10 min. 30-100% acetonitrile–0.1% $H_3PO_4$; detector UV 270 nm; sample concentration 0.25 mg/ml). Anal. Calcd for $C_{18}H_{24}N_2O_3$, %: C, 68.33; H, 7.65; N, 8.85. Found, %: C, 68.36; H, 7.74; N, 8.74.

Example 48

2E,4E)-2-methyl-5-phenyl-2,4-pentadienoic acid (9j)

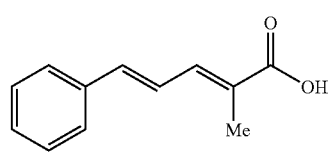

The title compound was synthesized from cinnamaldehyde (Acros) by the procedures described in the literature (Villieras et al., 1983; Vig et al., 1977; Banerji et al., 1984).

Example 49

(2E,4E)-6-(2-Methyl-5-phenylpenta-2,4-dienoylamino)hexanoic acid methyl ester (13j)

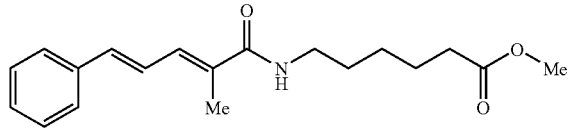

The title compound was obtained from (2E,4E)-2-methyl-5-phenyl-2,4-pentadienoic acid (9j) and methyl 6-aminohexanoate hydrochloride (10), in the same manner as described above in Example 24. Yield 94%, m.p. 68-70° C. $^1$H NMR (DMSO-$d_6$, HMDSO), δ: 1.02-1.77 (6H, m, $CH_2$); 2.29 (3H, s, $CH_3$); 1.98 (2H, t, J=7.0 Hz, $CH_2$); 3.12 (2H, q, J=5.8 Hz, $CH_2N$); 3.58 (3H, s, $CH_3O$); 6.67-7.11 (3H, m, CH=CH—CH); 7.14-7.47 (3H, m, $C_6H_3$); 7.49-7.69 (2H, m, $C_6H_2$); 7.78 (1H, t, J=5.5 Hz, NH).

Example 50

(2E,4E)-2-Methyl-5-phenylpenta-2,4-dienoic acid (5-hydroxycarbamoylpentyl)-amide (PX106520)

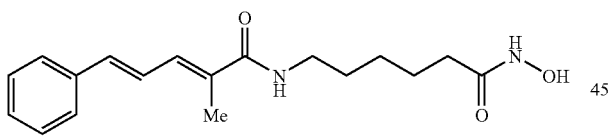

The title compound was prepared from (2E,4E)-6-(2-methyl-5-phenylpenta-2,4-dienoylamino)hexanoic acid methyl ester (13j) in the same manner as described above in Example 25. Yield 48%, m.p. 158-160° C. $^1$H NMR (DMSO-$d_6$, HMDSO), δ: 1.03-1.76 (6H, m, $CH_2$); 1.82-2.06 (2H, m, $CH_2$); 1.98 (3H, s, $CH_3$); 3.13 (2H, q, J=5.8 Hz, $CH_2N$); 6.67-7.09 (3H, m, CH=CH—CH); 7.09-7.41 (3H, m, $C_6H_3$); 7.41-7.63 (2H, m, $C_6H_2$); 7.76 (1H, t, J=5.5 Hz, NH); 8.56 (1H, s, NH), 10.27 (1H, s, OH). HPLC analysis on Symmetry $C_{18}$ column: impurities <1.0% (column size 3.9×150 mm; mobile phase acetonitrile–0.1M phosphate buffer (pH 2.5), 35:65; detector UV 230 nm; sample concentration 0.25 mg/ml). Anal. Calcd for $C_{18}H_{24}N_2O_3$, %: C, 68.33; H, 7.65; N, 8.85. Found, %: C, 68.32; H, 7.63; N, 8.87.

Example 51

(2E,4E)-5-(4-methoxyphenyl)-2,4-pentadienoic acid (9k)

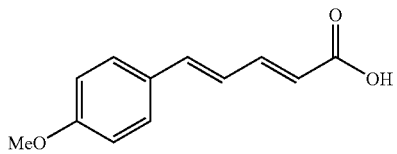

The title compound was synthesized by the procedures described in the literature (Villieras et al., 1983; Vig et al., 1977; Banerji et al., 1984), from 4-methoxycinnamaldehyde (Lancaster).

Example 52

(2E,4E)-6-[5-(4-Methoxyphenyl)penta-2,4-dienoylamino]hexanoic acid methyl ester (13k)

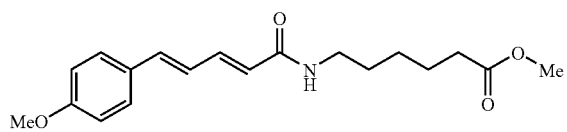

The title compound was obtained from (2E,4E)-5-(4-methoxyphenyl)-2,4-pentadienoic acid (9k) and methyl 6-aminohexanoate hydrochloride (10), in the same manner as described above in Example 24. Yield 87%, m.p. 129-131° C. $^1$H NMR (DMSO-$d_6$, HMDSO), δ: 1.11-1.79 (6H, m, $CH_2$); 2.27 (2H, t, J=7.0 Hz, $CH_2$); 3.13 (2H, q, J=5.8 Hz, $CH_2N$); 3.57 (3H, s, $CH_3O$); 3.75 (3H, s, $CH_3O$); 6.05 (1H, d, J=15.0 Hz, CH); 6.78-7.39 (3H, m, CH=CH—CH); 6.97 (2H, d, J=8.4 Hz, $C_6H_2$); 7.54 (2H, d, J=8.4 Hz, $C_6H_2$); 7.96 (1H, unresolv. t, NH).

Example 53

(2E,4E)-(4-Methoxyphenyl)penta-2,4-dienoic acid (5-hydroxycarbamoylpentyl)-amide (PX106524)

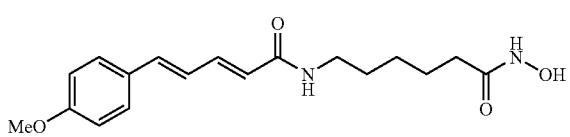

The title compound was obtained from (2E,4E)-6-[5-(4-methoxyphenyl)penta-2,4-dienoylamino]hexanoic acid methyl ester (13k) in the same manner as described above in Example 25. Yield 73%, m.p. 152-154° C. $^1$H NMR (DMSO-$d_6$, HMDSO), δ: 1.01-1.69 (6H, m, $CH_2$); 1.82-2.06 (2H, m, $CH_2$); 3.13 (2H, q, J=5.8 Hz, $CH_2N$); 3.76 (3H, s, $CH_3$); 6.05 (1H, d, J=15.0 Hz, CH); 6.76-7.36 (3H, m, CH=CH—CH); 6.94 (2H, d, J=8.4 Hz, $C_6H_2$); 7.52 (2H, d, J=8.4 Hz, $C_6H_2$); 7.98 (1H, unresolv. t, NH); 8.65 (1H, s, NH), 10.32 (1H, s, OH). HPLC analysis on Symmetry $C_{18}$ column: impurities <1.0% (column size 3.9×150 mm; mobile phase acetonitrile—0.1M phosphate buffer (pH 2.5), 35:65; detector UV 230 nm; sample concentration 0.33 mg/ml). Anal. Calcd for $C_{18}H_{24}N_2O_4$, %: C, 65.04; H, 7.28; N, 8.43. Found, %: C, 64.90; H, 7.28; N, 8.37.

Example 54

(E)-5-phenyl-2-penten-4-ynoic acid (9l)

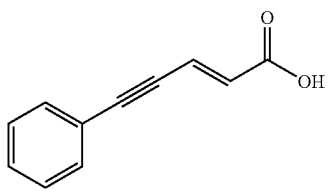

The title compound was synthesized by the procedures described in the literature (Villieras et al., 1983; Vig et al., 1977; Banerji et al., 1984), from phenylpropargyl aldehyde (Sigma-Aldrich).

Example 55

(E)-6-(5-Phenyl-pent-2-en-4-ynoylamino)-hexanoic acid methyl ester (13l)

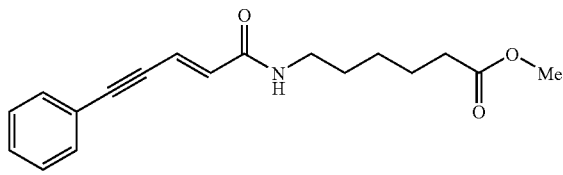

The title compound was obtained from (E)-5-phenyl-2-penten-4-ynoic acid (9l) and methyl 6-aminohexanoate hydrochloride (10), in the same manner as described above in Example 24. Yield 53%, m.p. 87-89° C. $^1$H NMR (DMSO-d$_6$, HMDSO), δ: 1.05-1.70 (6H, m, CH$_2$); 2.29 (2H, t, J=7.0 Hz, CH$_2$); 3.13 (2H, q, J=5.8 Hz, CH$_2$N); 3.55 (3H, s, CH$_3$O); 6.48 (1H, d, J=15.8 Hz, CH); 6.75 (1H, d, J=15.8 Hz, CH); 7.44 (5H, s, C$_6$H$_5$); 8.17 (1H, unresolv. t, NH).

Example 56

(E)-5-Phenylpent-2-en-4-ynoic acid (5-hydroxycarbamoylpentyl)amide (PX106525)

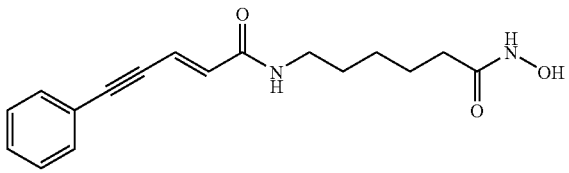

The title compound was obtained from (E)-6-(5-phenyl-pent-2-en-4-ynoylamino)-hexanoic acid methyl ester (13l) in the same manner as described above in Example 25. Yield 81%, m.p. 146-148° C. $^1$H NMR (DMSO-d$_6$, HMDSO), δ: 1.03-1.72 (6H, m, CH$_2$); 1.94 (2H, t, J=7.5 Hz, CH$_2$); 3.13 (2H, q, J=5.8 Hz, CH$_2$N); 6.47 (1H, d, J=15.8 Hz, CH); 6.76 (1H, d, J=15.8 Hz, CH); 7.45 (5H, s, C$_6$H$_5$); 8.16 (1H, unresolv. t, NH); 8.65 (1H, s, NH), 10.27 (1H, s, OH). HPLC analysis on Zorbax SB-C$_{18}$ column: impurities 1.5% (column size 4.6×150 mm; mobile phase gradient 10 min. 30-100% acetonitrile–0.1% H$_2$PO$_4$; detector UV 270 nm; sample concentration 1.0 mg/ml). Anal. Calcd for $C_{17}H_{20}N_2O_3$, %: C, 67.98; H, 6.71; N, 9.33. Found, %: C, 67.83; H, 6.71; N, 9.16.

Example 57

(2E,4E)-3-Methyl-5-phenyl-2,4-pentadienoic acid (9m)

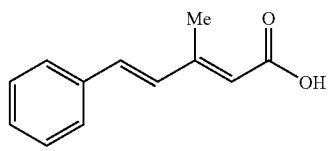

The title compound was prepared from benzaldehyde (Acros) and ethyl crotonate (Acros) as described by Anghelova et al., 1973.

Example 58

(2E,4E)-6-(3-Methyl-5-phenyl-penta-2,4-dienoylamino)-hexanoic acid methyl ester (13m)

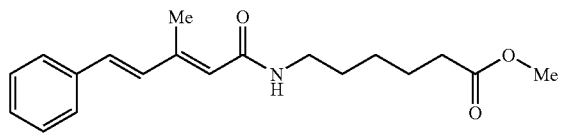

The title compound was obtained from (2E,4E)-3-methyl-5-phenyl-2,4-pentadienoic acid (9m) and methyl 6-aminohexanoate hydrochloride (10), in the same manner as described above in Example 24. Yield 90%, m.p. 83-85° C. $^1$H NMR (DMSO-d$_6$, HMDSO), δ: 1.01-1.78 (6H, m, CH$_2$); 2.28 (2H, t, J=7.0 Hz, CH$_2$); 2.29 (3H, s, CH$_3$); 3.09 (2H, q, J=6.0 Hz, CH$_2$N); 3.55 (3H, s, CH$_3$O); 5.94 (1H, s, CH); 6.88 (2H, s, CH=CH); 7.21-7.67 (5H, m, C$_6$H$_5$); 7.96 (1H, unresolv. t, NH).

Example 59

(2E,4E)-3-Methyl-5-phenylpenta-2,4-dienoic acid (5-hydroxycarbamoylpentyl)-amide (PX106526)

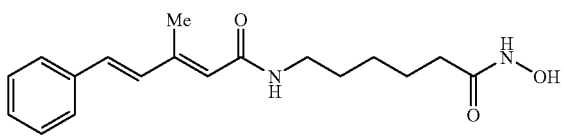

The title compound was prepared from (2E,4E)-6-(3-methyl-5-phenyl-penta-2,4-dienoylamino)-hexanoic acid methyl ester (13m) in the same manner as described above in Example 25. Yield 60%, m.p. 147-149° C. $^1$H NMR (DMSO-$d_6$, HMDSO), δ: 1.01-1.74 (6H, m, $CH_2$); 1.94 (2H, t, J=6.0 Hz, $CH_2$); 2.29 (3H, s, $CH_3$); 3.09 (2H, q, J=6.0 Hz, $CH_2N$); 5.94 (1H, s, CH); 6.89 (2H, s, CH=CH); 7.14-7.69 (5H, m, $C_6H_5$); 7.96 (1H, unresolv. t, NH); 8.67 (1H, s, NH), 10.29 (1H, s, OH). HPLC analysis on Symmetry $C_{18}$ column: impurities 1.0% (column size 3.9×150 mm; mobile phase acetonitrile–0.1M phosphate buffer (pH 2.5), 45:55; detector UV 270 nm; sample concentration 0.22 mg/ml). Anal. Calcd for $C_{18}H_{24}N_2O_3$, %: C, 68.33; H, 7.65; N, 8.85. Found, %: C, 68.32; H, 7.58; N, 8.89.

Example 60

(2E,4E)-5-[4-(dimethylamino)phenyl]-2,4-pentadienoic acid (9n)

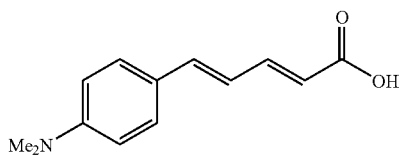

The title compound was synthesized by the procedures described in the literature (Villieras et al., 1983; Vig et al., 1977; Banerji et al., 1984), from 4-dimethylaminocinnamaldehyde (Acros).

Example 61

(2E,4E)-6-[5-(4-Dimethylaminophenyl)penta-2,4-dienoylamino]hexanoic acid methyl ester (13n)

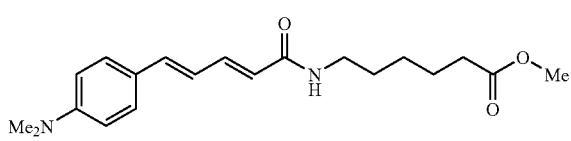

The title compound was obtained from (2E,4E)-5-[4-(dimethylamino)phenyl]-2,4-pentadienoic acid (9n) and methyl 6-aminohexanoate hydrochloride (10), in the same manner as described above in Example 24. Yield 88%, m.p. 118-120° C. $^1$H NMR (DMSO-$d_6$, HMDSO), δ: 0.97-1.64 (6H, m, $CH_2$); 2.28 (2H, t, J=7.0 Hz, $CH_2$); 2.94 (6H, s, $CH_3$); 3.13 (2H, q, J=6.0 Hz, $CH_2N$); 3.57 (3H, s, $CH_3O$); 5.98 (1H, d, J=15.0 Hz, CH); 6.63-7.26 (3H, m, CH=CH—CH); 6.74 (2H, d, J=8.8 Hz, $C_6H_2$); 7.43 (2H, d, J=8.8 Hz, $C_6H_2$); 7.89 (1H, unresolv. t, NH).

Example 62

(2E,4E)-5-(4-Dimethylamino-phenyl)-penta-2,4-dienoic acid (5-hydroxycarbamoyl-pentyl)-amide (PX106527)

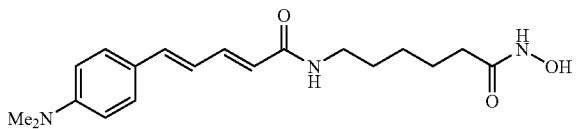

The title compound was obtained from (2E,4E)-6-[5-(4-dimethylaminophenyl)penta-2,4-dienoylamino]-hexanoic acid methyl ester (13n) in the same manner as described above in Example 25. Yield 64%, m.p. 172-174° C. $^1$H NMR (DMSO-$d_6$, HMDSO), δ: 0.94-1.61 (6H, m, $CH_2$); 1.83-2.07 (2H, m, $CH_2$); 2.94 (6H, s, $CH_3$); 3.12 (2H, q, J=6.0 Hz, $CH_2N$); 5.96 (1H, d, J=15.0 Hz, CH); 6.61-7.25 (3H, m, CH=CH—CH); 6.72 (2H, d, J=8.8 Hz, $C_6H_2$); 7.41 (2H, d, J=8.8 Hz, $C_6H_2$); 7.87 (1H, unresolv. t, NH); 8.61 (1H, s, NH), 10.29 (1H, s, OH). HPLC analysis on Symmetry $C_{18}$ column: impurities 2.6% (column size 3.9×150 mm; mobile phase acetonitrile–0.1M phosphate buffer (pH 2.5), 25:75; detector UV 270 nm; sample concentration 0.12 mg/ml). Anal. Calcd for $C_{19}H_{27}N_3O_3$, %: C, 66.06; H, 7.88; N, 12.16. Found, %: C, 65.78; H, 7.94; N, 12.06.

Example 63

Methyl 6-[(3-phenylpropanoyl)amino]hexanoate (13o)

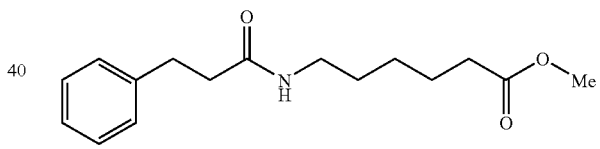

The title compound was obtained from 3-phenylpropanoic acid (9o) (Sigma-Aldrich (Dorset, UK)) and methyl 6-aminohexanoate hydrochloride (10), in the same manner as described above in Example 24. Yield 76%, m.p. 34-35° C. $^1$H NMR (CDCl$_3$, HMDSO), δ: 0.99-1.77 (6H, m, $CH_2$); 2.27 (2H, t, J=7.2 Hz, $CH_2$); 2.44 (2H, t, J=7.5 Hz, $CH_2$); 2.95 (2H, t, J=7.5 Hz, $CH_2$); 3.18 (2H, q, J=6.0 Hz, $CH_2N$); 3.64 (3H, s, $CH_3$); 5.47 (1H, br s, NH); 7.22 (5H, s, $C_6H_5$).

Example 64

6-(3-Phenylpropionylamino)hexanoic acid hydroxyamide (PX106516)

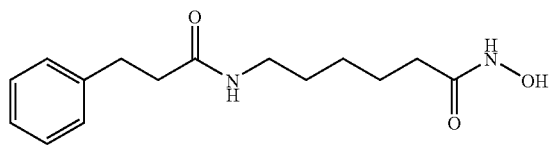

The title compound was obtained from methyl 6-[(3-phenylpropanoyl)amino]hexanoate (13o) in the same manner as described above in Example 25. Yield 95%, m.p. 107° C. ¹H NMR (DMSO-d₆, HMDSO), δ: 1.08-1.64 (6H, m); 1.91 (2H, t, J=6.6 Hz); 2.33 (2H, m); 2.66-3.12 (4H, m); 7.08-7.36 (5H, m); 7.73 (2H, unresolv. t); 8.61 (1H, br s); 10.29 (1H, br s). HPLC analysis on Symmetry $C_{18}$ column: impurities 1% (column size 3.9×150 mm; mobile phase acetonitrile–0.1M phosphate buffer (pH 2.5), 25:75; detector UV 220 nm; sample concentration 0.33 mg/ml; flow rate 1.0 ml/min). Anal. Calcd for $C_{15}H_{22}N_2O_3$, %: C, 64.73; H, 7.97; N, 10.06. Found, %: C, 64.85; H, 8.07; N, 9.94.

Example 65

Methyl 6-{[(E)-3-phenyl-2-propenoyl]amino}hexanoate (13p)

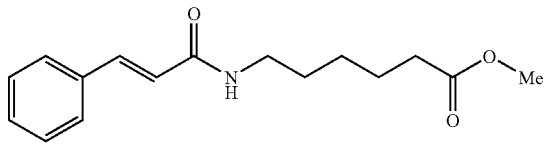

The title compound was obtained from (E)-3-phenyl-2-propenoic acid (9p) (Sigma-Aldrich (Dorset, UK)) and methyl 6-aminohexanoate hydrochloride (10), in the same manner as described above in Example 24, as a white solid, yield 42%. ¹H NMR (CDCl₃, HMDSO), δ: 1.11-1.86 (6H, m, CH₂); 2.32 (2H, t, J=6.5 Hz, CH₂); 3.38 (2H, q, J=5.8 Hz, CH₂N); 3.65 (3H, s, CH₃); 5.68 (1H, br s, NH); 6.37 (2H, d, J=15.6 Hz, CH); 7.13-7.61 (5H, m, C₆H₅); 7.59 (2H, d, J=15.6 Hz).

Example 66

N-(5-Hydroxycarbamoylpentyl)-3-phenylacrylamide (PX106517)

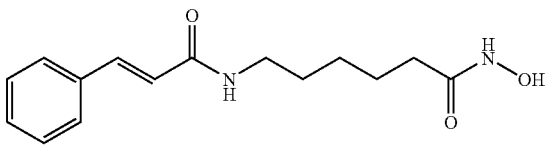

The title compound was obtained from methyl 6-{[(E)-3-phenyl-2-propenoyl]amino}hexanoate (13p) in the same manner as described above in Example 25. Yield 60%, m.p. 154-155° C. ¹H NMR (DMSO-d₆, HMDSO), δ: 1.05-1.74 (6H, m); 1.94 (2H, t, J=6.4 Hz); 3.16 (2H, m); 6.61 (1H, d, J=15.9 Hz); 7.16-7.66 (6H, m); 8.06 (1H, t, J=5.3 Hz, NH); 8.63 (1H, s); 10.32 (1H, s). HPLC analysis on Zorbax SB-$C_{18}$ column: impurities 4% (column size 4.6×150 mm; mobile phase acetonitrile–0.1% H3PO4, gradient from 30:70 to 100:0; detector UV 270 nm; sample concentration 0.2 mg/ml; flow rate 1.0 ml/min). Anal. Calcd for $C_{15}H_{22}N_2O_3$, %: C, 65.20; H, 7.30; N, 10.14. Found, %: C, 64.93; H, 7.33; N, 10.21.

Example 67

(E)-3-(4-pyridinyl)-2-propenoic acid (9q)

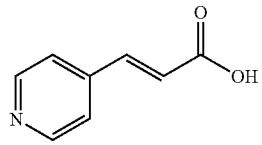

The title compound was synthesized by the procedures described in the literature (Villieras et al., 1983; Vig et al., 1977; Banerji et al., 1984), from 4-pyridinecarboxaldehyde (Acros).

Example 68

(E)-6-(3-Pyridin-4-yl-acryloylamino)hexanoic acid methyl ester (13q)

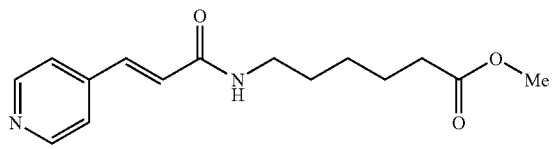

The title compound was obtained from (E)-3-(4-pyridinyl)-2-propenoic acid (9q) and methyl 6-aminohexanoate hydrochloride (10) in the same manner as described above in Example 24. The product was purified on silica gel, mobile phase—acetonitrile–water, 10:1, yield 34%, m.p. 92-94° C. ¹H NMR (DMSO-d₆, HMDSO), δ: 1.09-1.76 (6H, m, CH₂); 2.28 (2H, t, J=7.5 Hz, CH₂); 3.16 (2H, q, J=6.0 Hz, CH₂N); 3.57 (3H, s, CH₃O); 6.81 (1H, d, J=16.0 Hz, CH); 7.41 (1H, d, J=16.0 Hz, CH); 7.52 (2H, d, J=6.0 Hz, C₅H₂N); 8.23 (1H, unresolv. t, NH); 8.61(2H, d, J=6.0 Hz, C₅H₂N).

Example 69

(E)-N-(5-Hydroxycarbamoylpentyl)-3-pyridin-4-yl-acrylamide oxalate (PX106521)

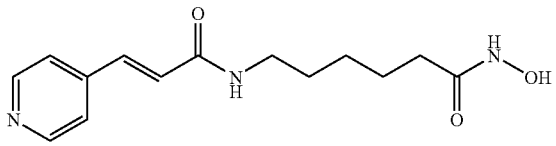

The title compound was obtained from (E)-6-(3-pyridin-4-yl-acryloylamino)hexanoic acid methyl ester (13q), in the same manner as described above in Example 25, and dissolved in ethanol. To the solution a solution of oxalic acid (2 equivalents) (Sigma-Aldrich) was added. The precipitate was filtered and crystallized from methanol. Yield 50%, m.p. 168-170° C. ¹H NMR (DMSO-d₆, HMDSO), δ: 1.09-1.69 (6H, m, CH₂); 1.94 (2H, t, J=7.5 Hz, CH₂); 3.16 (2H, q, J=6.0 Hz, CH₂N); 6.81 (1H, d, J=16.0 Hz, CH); 7.38 (1H, d, J=16.0 Hz, CH); 7.51 (2H, d, J=6.0 Hz, C₅H₂N); 8.19 (1H, unresolv. t, NH); 8.57 (2H, d, J=6.0 Hz, C$_5$H$_2$N); 10.21 (1H, s, OH). HPLC analysis on Symmetry C$_{18}$ column: impurities 2.7% (column size 3.9×150 mm; mobile phase acetonitrile–0.1M phosphate buffer (pH 2.5), 6.5:93.5; detector UV 270 nm; sample concentration 0.5 mg/ml). Anal. Calcd for C$_{14}$H$_{19}$N$_3$O$_3$×(COOH)$_2$×0.25H$_2$O, %: C, 51.68; H, 5.83; N, 11.30. Found, %: C, 51.44; H, 5.62; N, 11.23.

Example 70

(E)-3-(2-pyridinyl)-2-propenoic acid (9r)

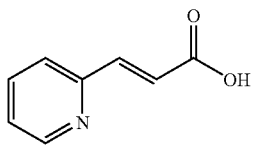

The title compound was synthesized by the procedures described in the literature (Villieras et al., 1983; Vig et al., 1977; Banerji et al., 1984), from 2-pyridinecarboxaldehyde (Acros).

Example 71

(E)-6-(3-Pyridin-2-yl-acryloylamino)hexanoic acid methyl ester (13r)

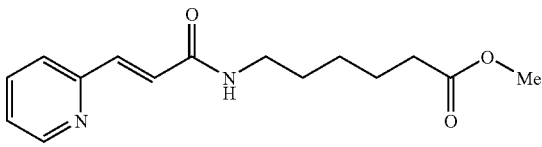

The title compound was obtained from (E)-3-(2-pyridinyl)-2-propenoic acid (9r) and methyl 6-aminohexanoate hydrochloride (10) in the same manner as described above in Example 24, as an oil, yield 45%. $^1$H NMR (DMSO-d$_6$, HMDSO), δ:1.02-1.72 (6H, m, CH$_2$); 2.28 (2H, t, J=7.0 Hz, CH$_2$); 3.16 (2H, q, J=6.0 Hz, CH$_2$N); 3.56 (3H, s, CH$_3$O); 6.89 (1H, d, J=15.2 Hz, CH); 7.21-7.42 (1H, m, C$_5$HN); 7.38 (1H, d, J=15.2 Hz, CH); 7.49 (1H, dt, J=1.9 Hz and J=7.5 Hz, C$_5$HN); 7.76-7.99 (1H, m, C$_5$HN); 8.23 (1H, t,J=5.6 Hz, NH); 8.50-8.74 (1H, m, C$_5$HN).

Example 72

(E)-N-(5-Hydroxycarbamoylpentyl)-3-pyridin-2-yl-acrylamide oxalate (PX106528)

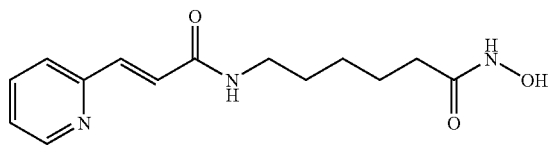

The title compound was obtained from (E)-6-(3-pyridin-2-yl-acryloylamino)hexanoic acid methyl ester (13r), in the same manner as described above in Example 25 and Example 70. Yield 46%, m.p. 126-128° C. $^1$H NMR (DMSO-d$_6$, HMDSO), δ: 1.15-1.65 (6H, m, CH$_2$); 1.94 (2H, t, J=7.2 Hz, CH$_2$); 3.16 (2H, q, J=6.0 Hz, CH$_2$N); 7.08 (1H, d, J=15.4 Hz, CH);7.32 (1H, dd, J=4.8 Hz and J=6.8 Hz, C$_5$HN); 7.42 (1H, d, J=15.4 Hz, CH); 7.56 (1H, d, J=7.8 Hz, C$_5$HN); 7.83 (1H, dt, J=1.8 Hz and J=7.8 Hz, C$_5$HN); 8.28 (1H, t, J=5.5 Hz, NH); 8.60 (1H, d, J=4.8 Hz, C$_5$HN); 10.35 (1H, s, OH). HPLC analysis on Symmetry C$_{18}$ column: impurities 1.8% (column size 3.9×150 mm; mobile phase acetonitrile–0.1M phosphate buffer (pH 2.5), 8:92; detector UV 254 nm; sample concentration 0.5 mg/ml). Anal. Calcd for C$_{14}$H$_{19}$N$_3$O$_3$×(COOH)$_2$×0.5H$_2$O, %: C, 51.06; H, 5.89; N, 11.16. Found, %: C, 50.95; H, 5.76; N, 11.34.

Example 73

6-{[(E)-3-(2-Furyl)-2-propenoyl]amino}hexanoate (2)

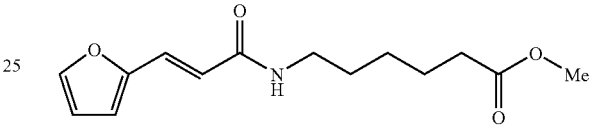

To a solution of 3-furyl-2-acrylic acid (0.389 g, 2.81 mmol) (Acros) in dimethylformamide (3 ml) at ice bath temperature carbonyldiimidazole (0.490 g, 3.02 mmol) was added. The mixture was stirred for 30 min, then successively triethylamine (1.0 ml, 7.17 mmol) and a solution of methyl 6-aminocaproate hydrochloride (0.500 g, 2.75 mmol) in dimethylformamide (3 ml) were added. The reaction mixture was stirred for 0.5 h at ice bath temperature, then the cooling bath was removed and the stirring was continued for 20 h at room temperature. The reaction mixture was diluted with brine (50 ml) and extracted with ethyl acetate (3×25 ml). The organic phase was washed successively with brine, 5% NaHCO$_3$, brine, saturated KH$_2$PO$_4$, brine, and dried (Na$_2$SO$_4$). The solvent was evaporated and the residue (0.526 g) was chromatographed on silica gel (20 g) with hexane-ethyl acetate (1.5:8.5) as eluent affording pure title compound (0.423 g, 57%). $^1$H-NMR (CDCl$_3$, HMDSO), δ: 1.22-1.79 (m, 6H); 2.24 (t, J=7.0 Hz, 2H); 3.17-3.44 (m, 2H); 5.51 (br s, 1H); 6.19 (d, J=16.0 Hz, 1H); 6.44 (dd, J=3.6 and 1.8 Hz, 1H); 6.53 (d, J=3.6 Hz, 1H); 7.37 (d, J=16.0 Hz, 1H); 7.43 (d, J=1.8 Hz, 1H).

Example 74

3-Furan-2-yl-N-(5-hydroxycarbamoyl-pentyl)-acrylamide (PX106491)

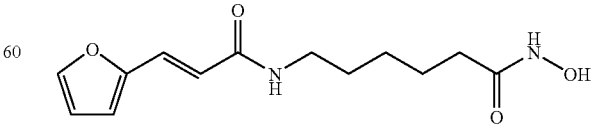

To a solution of 6-{[(E)-3-(2-furyl)-2-propenoyl]amino} hexanoate (0.200 g, 0.75 mmol) in methanol (2 ml) a solution of hydroxylamine hydrochloride (0.210 g, 3.02 mmol) in methanol (3 ml) and NaOH (242 mg, 6.04 mmol) in H$_2$O (1 ml) were added. The mixture was stirred for 30 min at room temperature and acidified with 1N HCl to pH 3 of the reaction medium. The mixture was extracted with ethyl acetate (3×25 ml), the organic phase was washed with brine and dried (Na$_2$SO$_4$). The solvent was evaporated and the residue (0.172 g) was crystallized from acetonitrile (5 ml) to give the title compound (0.117 g, 58%). M.p. 151-152.5° C. $^1$H-NMR (DMSO-d$_6$, HMDSO), δ: 1.15-1.62 (m, 6H); 1.94 (t, J=7.2 Hz, 2H); 3.14-3.22 (m, 2H); 6.40 (d, J=15.5 Hz, 1H); 6.57 (dd, J=1.6 and 3.2 Hz, 1H); 6.74 (d, J=3.2 Hz, 1H); 7.21 (d, J=15.5 Hz, 1H); 7.75 (s, 1H); 8.11 (t, J=5.6 Hz, 1H); 8.67 (d, J=1.6 Hz, 1H); 10.34 (s, 1H). HPLC analysis on Zorbax SB-C$_{18}$ column: impurities 1% (column size 4.6×150 mm; mobile phase acetonitrile +0.1% H$_3$PO$_4$, gradient from 25 to 100%; detector UV 270 nm; sample concentration 1.0 mg/ml; flow rate 1.5 ml/min). Anal. Calcd for C$_{13}$H$_{18}$N$_2$O$_4$, %: C, 58.64; H, 6.81; N, 10.52. Found, %: C, 58.64; H, 6.

Example 75

Mono-tert-butylglutarate (A9)

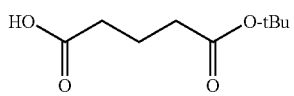

A solution of mono-methylglutarate (2.11 g, 13.7 mmol) in toluene (20 ml) was heated to 115° C. N,N-Dimethylformamide di-tert-butylacetate (14.58 ml, 54.8 mmol) was added to the solution over twenty minutes. The solution was heated at 115° C. for a further thirty minutes and then allowed to cool to ambient temperature. The solution was washed with saturated aqueous sodium hydrogen carbonate (2×20 ml), aqueous saturated sodium chloride (2×20 ml) and water (20 ml). The organic phase was dried (MgSO$_4$), filtered an the solvent was removed under reduced pressure to afford mono-tert-butyl-mono-methylglutarate (A8) as a yellow liquid (2.57 g, 93%), R$_F$ 0.55 (Ethyl acetate—hexane (1:2), I$_2$).

A 1M aqueous solution of lithium hydroxide (12.72 ml, 12.72 mmol) was added to a solution of diester (A8) (2.57 g, 12.72 mmol) in dioxane (20 ml) at 0° C. The solution was allowed to warm to ambient temperature and stirred for sixteen hours. The solution was concentrated under reduced pressure and aqueous saturated sodium hydrogen carbonate (20 ml) was added. The resultant solution was extracted with ethyl acetate (2×10 ml). The combined organic extracts were washed with aqueous saturated sodium hydrogen carbonate (10 ml). The aqueous extracts were combined and acidified to pH 4 with 10% aqueous citric acid. The acidified solution was extracted with ethyl acetate (5×20 ml). The combined organic extracts were dried (MgSO$_4$), filtered and the solvent was removed under reduced pressure to afford mono-tert-butylglutarate acid (A9) as a clear liquid (1.80 g, 75%), R$_F$ 0.6 (Ethyl acetate, KMnO$_4$).

Example 76

Pentanedioic acid hydroxyamide (4-methoxy-phenyl)-amide (PX082546)

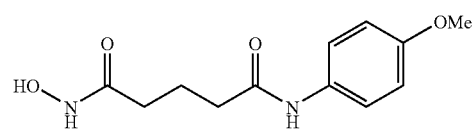

ArgoGel™-OH resin (250 mg, 0.1125 mmol) was placed in a reaction vessel and was swollen by the addition of dichloromethane (1 ml). A solution of mono-tert-butylglutaric acid (A9) (106 mg, 0.5625 mmol), N,N'-diisopropylcarbodiimide (DIC) (88 μl, 0.5625 mmol) and 4-(dimethylamino)pyridine (DMAP) (7 mg, 0.056 mmol) in dichloromethane (1.5 ml) was added and the resultant suspension was agitated at ambient temperature for four hours. The resin was filtered and was washed with 1-methylpyrrolidine (5 ml) and alternately with methanol (4×5 ml) and dichloromethane (4×5 ml). The resin was dried and a sample was analysed by IR spectroscopy (IR (resin/cm$^{-1}$) 1731 (ester) and 1738 (ester).

The resin (250 mg, 0.1125 mmol) obtained from the first step was treated with a mixture of dichloromethane/trifluoroacetic acid/triethylsilane (70:25:5, v/v) (2.5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR (resin/cm$^{-1}$) 1731 (ester).

The resin (250 mg, 0.1125 mmol) obtained from the second step was placed in a reaction vessel and was swollen by the addition of 1-methylpyrrolidine (1 ml). A solution of p-anisidine (62 mg, 0.5 mmol), 1-hydroxybenzotriazole (HOBT) (34 mg, 0.25 mmol), 2-(1H-benzotriazole-1-yl)-1,1,3,3-teramethyluronium tetrafluoroborate (TBTU) (161 mg, 0.5 mmol), N,N-diisopropylethylamine (DIPEA) (0.20 ml, 1.125 mmol) in 1-methylpyrrolidine (1.5 ml) was added and the resultant suspension was agitated at ambient temperature for seventy-two hours. The resin was filtered and was washed with 1-methylpyrrolidine (5 ml) and alternately with methanol (4×5 ml) and dichloromethane (4×5 ml).

The resin (250 mg, 0.1125 mmol) obtained from the third step was placed in a reaction vessel and was swollen by the addition of tetrahydrofuran (2 ml). A 50% wt solution of hydroxylamine in water (0.21 ml, 3.125 mmol) was added and the resultant suspension was agitated at ambient temperature for forty-eight hours. The resin was filtered and washed with a mixture of dioxane and water (1:1, v/v) (5 ml). The filtrates were combined and the solvent was removed under reduced pressure. The crude product obtained was purified by preparative hplc using a 150×21.2 mm 5 μm Hypersil® Elite C$_{18}$ column eluting with 25% ACN/75% H$_2$O+0.2% TFA. The flow rate was 20 mlmin$^{-1}$ and the detector was set at 254 nm. The fractions that contained the desired product were concentrated under reduced pressure and the resultant residue was lyophilised from a mixture of dioxane and water to afford the title compound as a light brown oil (7.5 mg, 26%), $t_R$ 1.86 (254 nm, 1.5 mlmin$^{-1}$, 25% ACN/70% H$_2$O+0.2% TFA.

Example 77

Pentanedioic acid hydroxyamide (4-isopropyl-phenyl)-amide (PX082548)

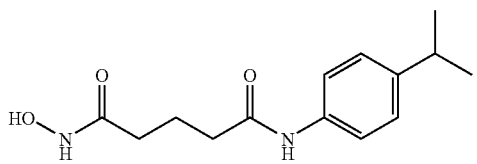

ArgoGel™-OH resin (250 mg, 0.1125 mmol) was placed in a reaction vessel and was swollen by the addition of dichloromethane (1 ml). A solution of mono-tert-butylglutaric acid (A9) (106 mg, 0.5625 mmol), N,N'-diisopropylcarbodiimide (DIC) (88 μl, 0.5625 mmol) and 4-(dimethylamino)pyridine (DMAP) (7 mg, 0.056 mmol) in dichloromethane (1.5 ml) was added and the resultant suspension was agitated at ambient temperature for four hours. The resin was filtered and was washed with 1-methylpyrrolidine (5 ml) and alternately with methanol (4×5 ml) and dichloromethane (4×5 ml). The resin was dried and a sample was analysed by IR spectroscopy (IR (resin/cm$^{-1}$) 1731 (ester) and 1738 (ester).

The resin (250 mg, 0.1125 mmol) obtained from the first step was treated with a mixture of dichloromethane/trifluoroacetic acid/triethylsilane (70:25:5, v/v) (2.5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR (resin/cm$^{-1}$) 1731 (ester).

The resin (250 mg, 0.1125 mmol) obtained from the second step was placed in a reaction vessel and was swollen by the addition of 1-methylpyrrolidine (1 ml). A solution of 4-isopropylaniline (68 μl mg, 0.5 mmol), 1-hydroxybenzotriazole (HOBT) (34 mg, 0.25 mmol), 2-(1H-benzotriazole-1-yl)-1,1,3,3-teramethyluronium tetrafluoroborate (TBTU) (161 mg, 0.5 mmol), N,N-diisopropylethylamine (DIPEA) (0.20 ml, 1.125 mmol) in 1-methylpyrrolidine (1.5 ml) was added and the resultant suspension was agitated at ambient temperature for seventy-two hours. The resin was filtered and was washed with 1-methylpyrrolidine (5 ml) and alternately with methanol (4×5 ml) and dichloromethane (4×5 ml).

The resin (250 mg, 0.1125 mmol) obtained from the third step was placed in a reaction vessel and was swollen by the addition of tetrahydrofuran (2 ml). A 50% wt solution of hydroxylamine in water (0.21 ml, 3.125 mmol) was added and the resultant suspension was agitated at ambient temperature for forty-eight hours. The resin was filtered and washed with a mixture of dioxane and water (1:1, v/v) (5 ml). The filtrates were combined and the solvent was removed under reduced pressure. The crude product obtained was purified by preparative hplc using a 150×21.2 mm 5 μm Hypersil® Elite C$_{18}$ column eluting with 30% ACN/70% H$_2$O+0.2% TFA. The flow rate was 20 mlmin$^{-1}$ and the detector was set at 254 nm. The fractions that contained the desired product were concentrated under reduced pressure and the resultant residue was lyophilised from a mixture of dioxane and water to afford the title compound as a light brown oil (4.1 mg, 14%), $t_R$ 4.74 (254 nm, 1.5 mlmin$^{-1}$, 30% ACN/70% H$_2$O+0.2% TFA, m/z [ES] 265 [M+H]$^+$.

Example 78

Pentanedioic acid (3,4-dimethoxy-phenyl)-amide hydroxyamide (PX082549)

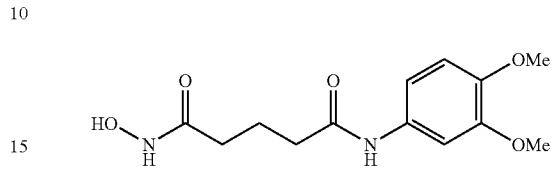

ArgoGel™-OH resin (250 mg, 0.1125 mmol) was placed in a reaction vessel and was swollen by the addition of dichloromethane (1 ml). A solution of mono-tert-butylglutaric acid (A9) (106 mg, 0.5625 mmol), N,N'-diisopropylcarbodiimide (DIC) (88 μl, 0.5625 mmol) and 4-(dimethylamino)pyridine (DMAP) (7 mg, 0.056 mmol) in dichloromethane (1.5 ml) was added and the resultant suspension was agitated at ambient temperature for four hours. The resin was filtered and was washed with 1-methylpyrrolidine (5 ml) and alternately with methanol (4×5 ml) and dichloromethane (4×5 ml). The resin was dried and a sample was analysed by IR spectroscopy (IR (resin/cm$^{-1}$) 1731 (ester) and 1738 (ester).

The resin (250 mg, 0.1125 mmol) obtained from the first step was treated with a mixture of dichloromethane/trifluoroacetic acid/triethylsilane (70:25:5, v/v) (2.5 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR (resin/cm$^{-1}$) 1731 (ester).

The resin (250 mg, 0.1125 mmol) obtained from the second step was placed in a reaction vessel and was swollen by the addition of 1-methylpyrrolidine (1 ml). A solution of 4-aminioveratrole (77 mg, 0.5 mmol), 1-hydroxybenzotriazole (HOBT) (34 mg, 0.25 mmol), 2-(1H-benzotriazole-1-yl)-1,1,3,3-teramethyluronium tetrafluoroborate (TBTU) (161 mg, 0.5 mmol), N,N-diisopropylethylamine (DIPEA) (0.20 ml, 1.125 mmol) in 1-methylpyrrolidine (1.5 ml) was added and the resultant suspension was agitated at ambient temperature for seventy-two hours. The resin was filtered and was washed with 1-methylpyrrolidine (5 ml) and alternately with methanol (4×5 ml) and dichloromethane (4×5 ml).

The resin (250 mg, 0.1125 mmol) obtained from the third step was placed in a reaction vessel and was swollen by the addition of tetrahydrofuran (2 ml). A 50% wt solution of hydroxylamine in water (0.21 ml, 3.125 mmol) was added and the resultant suspension was agitated at ambient temperature for forty-eight hours. The resin was filtered and washed with a mixture of dioxane and water (1:1, v/v) (5 ml). The filtrates were combined and the solvent was removed under reduced pressure. The crude product obtained was purified by preparative hplc using a 150×21.2 mm 5 μm Hypersil® Elite C$_{18}$ column eluting with 15% ACN/85% H$_2$O+0.2% TFA. The flow rate was 20 mlmin$^{-1}$ and the detector was set at 254 nm. The fractions that contained the desired product were concentrated under reduced pressure and the resultant residue was lyophilised from a mixture of dioxane and water to afford the title compound as a dark brown solid (19.8 mg, 62%), $t_R$ 2.55 (254 nm, 1.5 mlmin$^{-1}$, 15% ACN/85% H$_2$O+0.2%, m/z [ES] 283 [M+H]$^+$.

Example 79

4-Dimethylamino-napthalene-1-carboxylic acid (2-hydroxycarbamoyl-ethyl)-amide (PX082530)

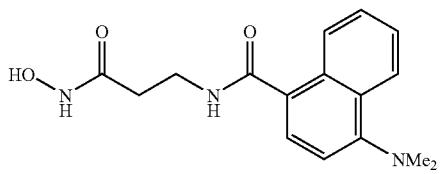

ArgoGel™-OH resin (1.5 g, 0.75 mmol) was placed in a reaction vessel and was swollen by the addition of dichloromethane (7.5 ml). A solution of N-tert-butoxycarbonyl-□-alanine (0.57 g, 3.0 mmol), N,N'-diisopropylcarbodiimide (DIC) (0.94 ml, 6.0 mmol) and 4-(dimethylamino)pyridine (DMAP) (9 mg, 0.075 mmol) in dichloromethane (7.5 ml) was added and the resultant suspension was agitated at ambient temperature for sixteen hours. The resin was filtered and was washed with 1-methylpyrrolidine (10 ml) and alternately with methanol (4×10 ml) and dichloromethane (4×10 ml).

The resin (1.5 g, 0.75 mmol) obtained from the first step was treated with a mixture of dichloromethane/trifluoroacetic acid/triethylsilane (70:25:5, v/v) (15 ml) at ambient temperature for thirty minutes. The resin was filtered and was washed with 1-methylpyrrolidine (10 ml) and alternately with methanol (4×10 ml) and dichloromethane (4×10 ml).

A sample of resin (500 mg, 0.25 mmol) obtained from the second step was placed in a reaction vessel and was swollen by the addition of 1-methylpyrrolidine (2 ml). A solution of 4-dimethylaminonaphthalene-1-carboxylic acid (215 mg, 1.0 mmol), 1-hydroxybenzotriazole (HOBT) (68 mg, 0.5 mmol), 2-(1H-benzotriazole-1-yl)-1,1,3,3-teramethyluronium tetrafluoroborate (TBTU) (321 mg, 1.0 mmol), N,N-diisopropylethylamine (DIPEA) (0.39 ml, 2.25 mmol) in 1-methylpyrrolidine (3 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1656 (amide) and 1735 (ester).

A sample of resin (250 mg, 0.125 mmol) obtained from the third step was placed in a reaction vessel and was swollen by the addition of tetrahydrofuran (3 ml). A 50% wt solution of hydroxylamine in water (0.21 ml, 3.125 mmol) was added and the resultant suspension was agitated at ambient temperature for forty-eight hours. The resin was filtered and washed with methanol (5 ml). The filtrates were combined and the solvent was removed under reduced pressure. The crude product obtained was purified by preparative hplc using a 150×21.2 mm 5 μm Hypersil® Elite $C_{18}$ column eluting with 10% ACN/90% $H_2O$+0.2% TFA. The flow rate was 20 mlmin$^{-1}$ and the detector was set at 254 nm. The fractions that contained the desired product were concentrated under reduced pressure and the resultant residue was lyophilised from a mixture of dioxane and water to afford the title compound as a yellow solid (21.9 mg, 58%), $t_R$ 1.35 (254 nm, 1.5 mlmin$^{-1}$, 10% ACN/90% $H_2O$+0.2% TFA, m/z [ES] 300 [M−H]$^-$.

Example 80

4-Dimethylamino-napthalene-1-carboxylic acid (2-hydroxycarbamoyl-propyl)-amide (PX082533)

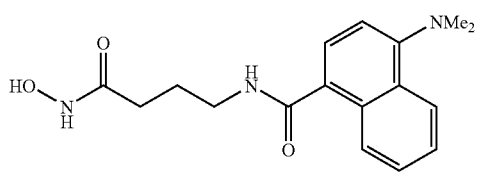

ArgoGel™-OH resin (1.0 g, 0.5 mmol) was placed in a reaction vessel and was swollen by the addition of dichloromethane (5 ml). A solution of N-tert-butoxycarbonyl-4-aminobutyric acid (0.406 g, 2.0 mmol), N,N'-diisopropylcarbodiimide (DIC) (0.16 ml, 1.0 mmol) and 4-(dimethylamino)pyridine (DMAP) (6 mg, 0.05 mmol) in dichloromethane (5 ml) was added and the resultant suspension was agitated at ambient temperature for sixteen hours. The resin was filtered and was washed with 1-methylpyrrolidine (10 ml) and alternately with methanol (4×10 ml) and dichloromethane (4×10 ml).

The resin (1.0 g, 0.5 mmol) obtained from the first step was treated with a mixture of dichloromethane/trifluoroacetic acid/triethylsilane (70:25:5, v/v) (10 ml) at ambient temperature for thirty minutes. The resin was filtered and was washed with 1-methylpyrrolidine (10 ml) and alternately with methanol (4×10 ml) and dichloromethane (4×10 ml).

A sample of resin (500 mg, 0.25 mmol) obtained from the second step was placed in a reaction vessel and was swollen by the addition of 1-methylpyrrolidine (2 ml). A solution of 4-dimethylaminonaphthalene-1-carboxylic acid (215 mg, 1.0 mmol), 1-hydroxybenzotriazole (HOBT) (68 mg, 0.5 mmol), 2-(1H-benzotriazole-1-yl)-1,1,3,3-teramethyluronium tetrafluoroborate (TBTU) (321 mg, 1.0 mmol), N,N-diisopropylethylamine (DIPEA) (0.39 ml, 2.25 mmol) in 1-methylpyrrolidine (3 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1651 (amide) and 1732 (ester).

A sample of resin (250 mg, 0.125 mmol) obtained from the third step was placed in a reaction vessel and was swollen by the addition of tetrahydrofuran (2 ml). A 50% wt solution of hydroxylamine in water (0.21 ml, 3.125 mmol) was added and the resultant suspension was agitated at ambient temperature for forty-eight hours. The resin was filtered and washed with dichloromethane (5 ml). The filtrates were combined and the solvent was removed under reduced pressure. The crude product obtained was purified by preparative hplc using a 150×21.2 mm 5 μm Hypersil® Elite $C_{18}$ column eluting with 30% ACN/70% $H_2O$+0.2% TFA. The flow rate was 20 mlmin$^{-1}$ and the detector was set at 254 nm. The fractions that contained the desired product were concentrated under reduced pressure and the resultant residue was lyophilised from a mixture of dioxane and water to afford the title compound as a brown oil (8.6 mg, 22%), $t_R$ 2.50 (254 nm, 1.5 mlmin$^{-1}$, 30% ACN/70% H$_2$O+0.2% TFA, m/z [ES] 338 [M+Na]$^+$.

Example 81

4-Dimethylamino-napthalene-1-carboxylic acid (4-hydroxycarbamoyl-butyl)-amide (PX082534)

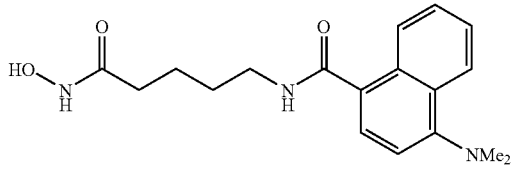

ArgoGel™-OH resin (1.5 g, 0.75 mmol) was placed in a reaction vessel and was swollen by the addition of dichloromethane (7.5 ml). A solution of 5-(tert-butoxycarbonylamino)valeric acid (0.57 g, 3.0 mmol), N,N'-diisopropylcarbodiimide (DIC) (0.23 ml, 1.5 mmol) and 4-(dimethylamino) pyridine (DMAP) (9 mg, 0.075 mmol) in dichloromethane (7.5 ml) was added and the resultant suspension was agitated at ambient temperature for sixteen hours. The resin was filtered and was washed with 1-methylpyrrolidine (10 ml) and alternately with methanol (4×10 ml) and dichloromethane (4×10 ml).

The resin (1.5 g, 0.75 mmol) obtained from the first step was treated with a mixture of dichloromethane/trifluoroacetic acid/triethylsilane (70:25:5, v/v) (15 ml) at ambient temperature for thirty minutes. The resin was filtered and was washed with 1-methylpyrrolidine (10 ml) and alternately with methanol (4×10 ml) and dichloromethane (4×10 ml).

A sample of resin (500 mg, 0.25 mmol) obtained from the second step was placed in a reaction vessel and was swollen by the addition of 1-methylpyrrolidine (2 ml). A solution of 4-dimethylaminonaphthalene-1-carboxylic acid (215 mg, 1.0 mmol), 1-hydroxybenzotriazole (HOBT) (68 mg, 0.5 mmol), 2-(1H-benzotriazole-1-yl)-1,1,3,3-teramethyluronium tetrafluoroborate (TBTU) (321 mg, 1.0 mmol), N,N-diisopropylethylamine (DIPEA) (0.39 ml, 2.25 mmol) in 1-methylpyrrolidine (3 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1652 (amide) and 1732 (ester).

A sample of resin (250 mg, 0.125 mmol) obtained from the third step was placed in a reaction vessel and was swollen by the addition of tetrahydrofuran (3 ml). A 50% wt solution of hydroxylamine in water (0.21 ml, 3.125 mmol) was added and the resultant suspension was agitated at ambient temperature for forty-eight hours. The resin was filtered and washed with dichloromethane (5 ml). The filtrates were combined and the solvent was removed under reduced pressure. The crude product obtained was purified by preparative hplc using a 150×21.2 mm 5 µm Hypersil® Elite C$_{18}$ column eluting with 10% ACN/90% H$_2$O+0.2% TFA. The flow rate was 20 mlmin$^{-1}$ and the detector was set at 254 nm. The fractions that contained the desired product were concentrated under reduced pressure and the resultant residue was lyophilised from a mixture of dioxane and water to afford the title compound as an orange solid (22.0 mg, 54%), $t_R$ 3.80 (254 nm, 1.5 mlmin$^{-1}$, 10% ACN/90% H$_2$O+0.2% TFA, m/z [ES] 330 [M+H]$^+$.

Example 82

4-Dimethylamino-napthalene-1-carboxylic acid (5-hydroxycarbamoyl-pentyl)-amide (PX089275)

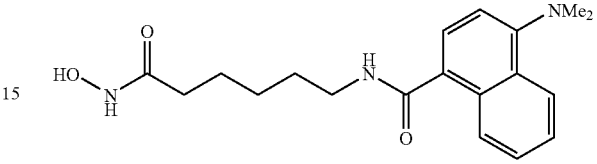

ArgoGel™-OH resin (500 mg, 0.245 mmol) was placed in a reaction vessel and was swollen by the addition of dichloromethane (2 ml). A solution of N-tert-butoxycarbonylaminohexanoic acid (283 mg, 1.225 mmol), N,N'-diisopropylcarbodiimide (DIC) (192 µl, 1.225 mmol) and 4-(dimethylamino)pyridine (DMAP) (3 mg, 0.0245 mmol) in dichloromethane (2 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1711 (urethane) and 1733 (ester).

The resin (500 mg, 0.245 mmol) obtained from the first step was treated with a mixture of dichloromethane/trifluoroacetic acid/triethylsilane (70:25:5, v/v) (4 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1735 (ester).

The resin (500 mg, 0.25 mmol) obtained from the second step was placed in a reaction vessel and was swollen by the addition of 1-methylpyrrolidine (2 ml). A solution of 4-dimethylaminonaphthalene-1-carboxylic acid (211 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1654 (amide) and 1731 (ester).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure. The crude product obtained was purified by preparative hplc using a 150×21.2 mm 5 µm Hypersil® Elite C$_{18}$ column eluting with a gradient of 5% ACN/95% H$_2$O+0.2% TFA to 95% ACN/5% H$_2$O+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the title compound as a brown oil (10.4 mg, 12%), $t_R$ 0.32 (254 nm, 3.0 mlmin$^{-1}$, 5% ACN/95% H$_2$O+0.2% TFA to 95% ACN/5% H$_2$O+0.2% TFA over 3.5 min then 2.5 min at 95% ACN/5% H$_2$O+0.2% TFA), m/z [ES] 344 [M+H]$^+$.

Example 83

Dimethylamino-N-(3-hydroxycarbamoyl-propyl)-benzamide (PX082531)

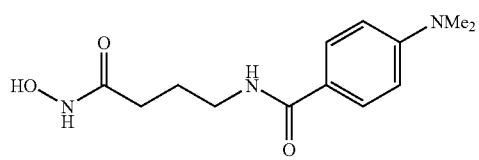

ArgoGel™-OH resin (1.0 g, 0.5 mmol) was placed in a reaction vessel and was swollen by the addition of dichloromethane (5 ml). A solution of N-tert-butoxycarbonyl-4-aminobutyric acid (406 mg, 2.0 mmol), N,N'-diisopropylcarbodiimide (DIC) (0.16 ml, 1.0 mmol) and 4-(dimethylamino)pyridine (DMAP) (6 mg, 0.05 mmol) in dichloromethane (5 ml) was added and the resultant suspension was agitated at ambient temperature for sixteen hours. The resin was filtered and was washed with 1-methylpyrrolidine (10 ml) and alternately with methanol (4×10 ml) and dichloromethane (4×10 ml). The resin was dried and a sample was analysed by IR spectroscopy (IR(resin/cm$^{-1}$) 1714 (urethane).

The resin obtained from the first step was treated with a mixture of dichloromethane/trifluoroacetic acid/triethylsilane (70:25:5, v/v) (15 ml) at ambient temperature for thirty minutes. The resin was filtered and was washed with 1-methylpyrrolidine (10 ml) and alternately with methanol (4×10 ml) and dichloromethane (4×10 ml). The resin was dried and a sample was analysed by IR spectroscopy (IR(resin/cm$^{-1}$) 1737 (ester).

A sample of the resin (100 mg, 0.05 mmol) obtained from the second step was placed in a reaction vessel and was swollen by the addition of 1-methylpyrrolidine (0.5 ml). A solution of 4-dimethylaminobenzoic acid (33 mg, 0.2 mmol), 1-hydroxybenzotriazole (HOBT) (14 mg, 0.1 mmo), 2-(1H-benzotriazole-1-yl)-1,1,3,3-teramethyluronium tetrafluoroborate (TBTU) (64 mg, 0.2 mmol), N,N-diisopropylethylamine (DIPEA) (0.08 ml, 0.45 mmol) in 1-methylpyrrolidine (0.5 ml) was added and the resultant suspension was agitated at ambient temperature for sixteen hours. The resin was filtered and was washed with 1-methylpyrrolidine (2 ml) and alternately with methanol (4×2 ml) and dichloromethane (4×2 ml). The resin was dried and a sample was analysed by IR spectroscopy (IR(resin/cm$^{-1}$) 1651 (amide) and 1732 (ester).

The resin obtained from the third step was placed in a reaction vessel and was swollen by the addition of either tetrahydrofuran (1 ml). A 50% wt solution of hydroxylamine in water (0.9 ml) was added and the resultant suspension was agitated at ambient temperature for forty-eight hours. The resin was filtered and was washed with a mixture of dioxane and water (1:1, v/v) (2 ml). The filtrates were combined and the solvent was removed under reduced pressure. The crude product obtained was purified by preparative hplc using a 150×21.2 mm 5 μm Hypersil® Elite C$_{18}$ column eluting with 30% ACN/70% H$_2$O+0.2% TFA. The flow rate was 20 mlmin$^{-1}$ and the detector was set at 254 nm. The fractions that contained the desired product were concentrated under reduced pressure and the resultant residue was lyophilised from a mixture of dioxane and water to afford the title compound as a yellow oil (3.4 mg, 26%), $t_R$ 1.69 (254 nm, 1.5 mlmin$^{-1}$, 30% ACN/70% H$_2$O+0.2% TFA, m/z [ES] 388 [M+Na]$^+$.

Example 84

N-(5-Hydroxycarbamoyl-pentyl)-benzamide (PX083449)

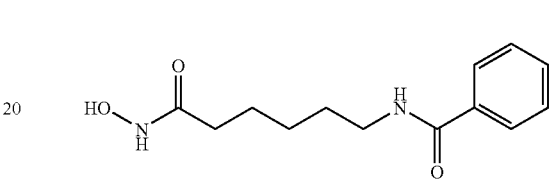

ArgoGel™-OH resin (500 mg, 0.245 mmol) was placed in a reaction vessel and was swollen by the addition of dichloromethane (2 ml). A solution of N-tert-butoxycarbonylaminohexanoic acid (283 mg, 1.225 mmol), N,N'-diisopropylcarbodiimide (DIC) (192 μl, 1.225 mmol) and 4-(dimethylamino)pyridine (DMAP) (3 mg, 0.0245 mmol) in dichloromethane (2 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1713 (urethane) and 1732 (ester).

The resin (500 mg, 0.245 mmol) obtained from the first step was treated with a mixture of dichloromethane/trifluoroacetic acid/triethylsilane (70:25:5, v/v) (4 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1735 (ester).

The resin (500 mg, 0.245 mmol) obtained from the second step was placed in a reaction vessel and was swollen by the addition of 1-methylpyrrolidine (2 ml). A solution of benzoic acid (120 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure. The crude product obtained was purified by preparative hplc using a 150×21.2 mm 5 μm Hypersil® Elite C$_{18}$ column eluting with a gradient of 5% ACN/95% H$_2$O+0.2% TFA to 95% ACN/5% H$_2$O+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the title compound as a pale brown solid (15.9 mg, 26%), t$_R$ 3.24 (254 nm, 3.0 mlmin$^{-1}$, 5% ACN/95% H$_2$O+0.2% TFA to 95% ACN/5% H$_2$O+0.2% TFA over 3.5 min then 2.5 min at 95% ACN/5% H$_2$O+0.2% TFA), m/z [ES] 251 [M+H]$^+$.

Example 85

N-(4-Hydroxycarbamoyl-butyl)-4-methoxy-benzamide (PX089048)

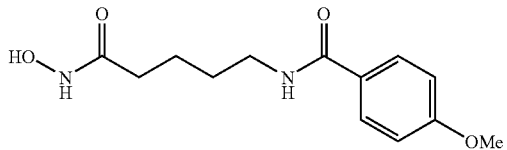

ArgoGel™-OH resin (500 mg, 0.245 mmol) was placed in a reaction vessel and was swollen by the addition of dichloromethane (2 ml). A solution of N-tert-butoxycarbonylaminovaleric acid (266 mg, 1.225 mmol), N,N'-diisopropylcarbodiimide (DIC) (192 μl, 1.225 mmol) and 4-(dimethylamino)pyridine (DMAP) (3 mg, 0.0245 mmol) in dichloromethane (2 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1711 (urethane) and 1733 (ester).

The resin (500 mg, 0.245 mmol) obtained from the first step was treated with a mixture of dichloromethane/trifluoroacetic acid/triethylsilane (70:25:5, v/v) (4 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1735 (ester).

The resin (500 mg, 0.245 mmol) obtained from the second step was placed in a reaction vessel and was swollen by the addition of 1-methylpyrrolidine (2 ml). A solution of 4-methoxybenzoic acid (149 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure. The crude product obtained was purified by preparative hplc using a 150×21.2 mm 5 μm Hypersil® Elite C$_{18}$ column eluting with a gradient of 5% ACN/95% H$_2$O+0.2% TFA to 95% ACN/5% H$_2$O+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the title compound as a pale brown solid (15.9 mg, 26%), t$_R$ 3.43 (254 nm, 3.0 mlmin$^{-1}$, 5% ACN/95% H$_2$O+0.2% TFA to 95% ACN/5% H$_2$O+0.2% TFA over 3.5 min then 2.5 min at 95% ACN/5% H$_2$O+0.2% TFA), m/z [ES] 267 [M+H]$^+$.

Example 86

N-(4-Hydroxycarbamoyl-butyl)-benzamide (PX089049)

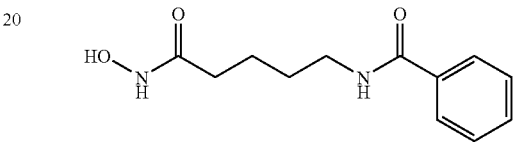

ArgoGel™-OH resin (500 mg, 0.245 mmol) was placed in a reaction vessel and was swollen by the addition of dichloromethane (2 ml). A solution of N-tert-butoxycarbonylaminovaleric acid (266 mg, 1.225 mmol), N,N'-diisopropylcarbodiimide (DIC) (192 μl, 1.225 mmol) and 4-(dimethylamino)pyridine (DMAP) (3 mg, 0.0245 mmol) in dichloromethane (2 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1711 (urethane) and 1733 (ester).

The resin (500 mg, 0.245 mmol) obtained from the first step was treated with a mixture of dichloromethane/trifluoroacetic acid/triethylsilane (70:25:5, v/v) (4 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1735 (ester).

The resin (500 mg, 0.245 mmol) obtained from the second step was placed in a reaction vessel and was swollen by the addition of 1-methylpyrrolidine (2 ml). A solution of benzoic acid (120 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure. The crude product obtained was purified by preparative hplc using a 150×21.2 mm 5 μm Hypersil® Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the title compound as a pale brown solid (15.9 mg, 26%), $t_R$ 3.31 (254 nm, 3.0 mlmin$^{-1}$, 5% ACN/95% $H_2O$+0.2% TFA to 95% ACN/5% $H_2O$+0.2% TFA over 3.5 min then 2.5 min at 95% ACN/5% $H_2O$+0.2% TFA), m/z [ES] 249 [M+TFA]$^-$.

Example 87

4-Dimethylamino-N-(5-hydroxycarbamoyl-pentyl)-benzamide (PX089274)

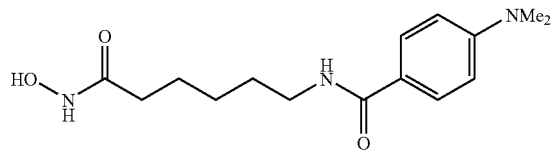

ArgoGel™-OH resin (500 mg, 0.245 mmol) was placed in a reaction vessel and was swollen by the addition of dichloromethane (2 ml). A solution of N-tert-butoxycarbonylaminohexanoic acid (283 mg, 1.225 mmol), N,N'-diisopropylcarbodiimide (DIC) (192 μl, 1.225 mmol) and 4-(dimethylamino)pyridine (DMAP) (3 mg, 0.0245 mmol) in dichloromethane (2 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1713 (urethane) and 1732 (ester).

The resin (500 mg, 0.245 mmol) obtained from the first step was treated with a mixture of dichloromethane/trifluoroacetic acid/triethylsilane (70:25:5, v/v) (4 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1735 (ester).

The resin (500 mg, 0.245 mmol) obtained from the second step was placed in a reaction vessel and was swollen by the addition of 1-methylpyrrolidine (2 ml). A solution of 4-dimethylaminobenzoic acid (162 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure. The crude product obtained was purified by preparative hplc using a 150×21.2 mm 5 μm Hypersil® Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the title compound as a brown oil (10.2 mg, 12%), $t_R$ 3.25 (254 nm, 3.0 mlmin$^{-1}$, 5% ACN/95% $H_2O$+0.2% TFA to 95% ACN/5% $H_2O$+0.2% TFA over 3.5 min then 2.5 min at 95% ACN/5% $H_2O$+0.2% TFA), m/z [ES] 344 [M+H]$^+$.

Example 88

N-(5-Hydroxycarbamoyl-pentyl)-4-methoxy-benzamide (PX089276)

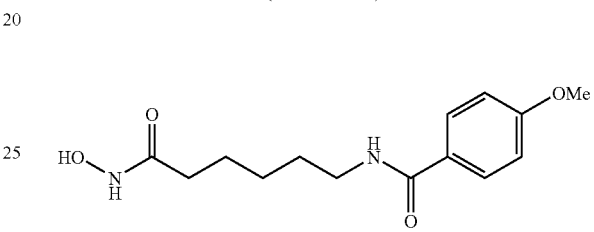

ArgoGel™-OH resin (500 mg, 0.245 mmol) was placed in a reaction vessel and was swollen by the addition of dichloromethane (2 ml). A solution of N-tert-butoxycarbonylaminohexanoic acid (283 mg, 1.225 mmol), N,N'-diisopropylcarbodiimide (DIC) (192 μl, 1.225 mmol) and 4-(dimethylamino)pyridine (DMAP) (3 mg, 0.0245 mmol) in dichloromethane (2 ml) was added and the resultant suspension was agitated at ambient temperature for four hours. The resin was filtered and was washed with 1-methylpyrrolidine (5 ml) and alternately with methanol (4×5 ml) and dichloromethane (5×5 ml). The resin was dried and a sample was analysed by IR spectroscopy (IR(resin/cm$^{-1}$) 1713 (urethane) and 1732 (ester).

The resin (500 mg, 0.245 mmol) obtained from the first step was treated with a mixture of dichloromethane/trifluoroacetic acid/triethylsilane (70:25:5, v/v) (4 ml) at ambient temperature for thirty minutes. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1735 (ester).

The resin (500 mg, 0.245 mmol) obtained from the second step was placed in a reaction vessel and was swollen by the addition of 1-methylpyrrolidine (2 ml). A solution of 4-methoxybenzoic acid (149 mg, 0.98 mmol), 1-hydroxybenzotriazole (HOBT) (66 mg, 0.49 mmol), 2-(1H-benzotriazole-1-yl)-1,1,3,3-teramethyluronium tetrafluoroborate (TBTU) (315 mg, 0.98 mmol), N,N-diisopropylethylamine (DIPEA) (0.38 ml, 2.205 mmol) in 1-methylpyrrolidine (2 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml).

The resin (500 mg, 0.245 mmol) obtained from the third step was placed in a reaction vessel and was swollen by the addition of dioxane (4 ml). A 50% wt solution of hydroxylamine in water (0.4 ml, 6.125 mmol) was added and the resultant suspension was agitated at ambient temperature for forty-eight hours. The resin was filtered and washed with a mixture of dioxane and water (1:1) (5 ml). The filtrates were combined and the solvent was removed under reduced pressure. The crude product obtained was purified by preparative hplc using a 150×21.2 mm 5 μm Hypersil® Elite $C_{18}$ column eluting with a gradient of 5% ACN/95% $H_2O$+0.2% TFA to 95% ACN/5% $H_2O$+0.2% TFA over 10 minutes. The flow rate was 25 mlmin$^{-1}$ and the detector was set at 254 nm. The fractions that contained the desired product were concentrated under reduced pressure and the resultant residue was lyophilised from a mixture of dioxane and water to afford the title compound as a brown oil (9.8 mg, 14%), $t_R$ 0.71 (254 nm, 3.0 mlmin$^{-1}$, 5% ACN/95% $H_2O$+0.2% TFA to 95% ACN/5% $H_2O$+0.2% TFA over 3.5 min then 2.5 min at 95% ACN/5% $H_2O$+0.2% TFA), m/z [ES] 281 [M+H]$^+$.

Example 89

4-(2-(4-Dimethylamino-phenyl)-acetylamino)-N-hydroxy-butyramide (PX082532)

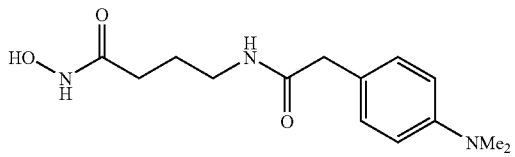

ArgoGel™-OH resin (1.0 g, 0.5 mmol) was placed in a reaction vessel and was swollen by the addition of dichloromethane (5 ml). A solution of N-tert-butoxycarbonyl-aminobutyric acid (460 mg, 2.0 mmol), N,N'-diisopropylcarbodiimide (DIC) (0.16 ml, 1.0 mmol) and 4-(dimethylamino)pyridine (DMAP) (6 mg, 0.005 mmol) in dichloromethane (5 ml) was added and the resultant suspension was agitated at ambient temperature for sixteen hours. The resin was filtered and was washed with 1-methylpyrrolidine (10 ml) and alternately with methanol (4×10 ml) and dichloromethane (4×10 ml). The resin was dried and a sample was analysed by IR spectroscopy (IR(resin/cm$^{-1}$) 1714 (ester).

The resin (1.0 g, 0.5 mmol) obtained from the first step was treated with a mixture of dichloromethane/trifluoroacetic acid/triethylsilane (70:25:5, v/v) (15 ml) at ambient temperature for thirty minutes. The resin was filtered and was washed with 1-methylpyrrolidine (10 ml) and alternately with methanol (4×10 ml) and dichloromethane (4×10 ml).

A sample of resin (500 mg, 0.25 mmol) obtained from the second step was placed in a reaction vessel and was swollen by the addition of 1-methylpyrrolidine (2 ml). A solution of 4-dimethylaminophenylacetic acid (179 mg, 1.0 mmol), 1-hydroxybenzotriazole (HOBT) (68 mg, 0.5 mmol), 2-(1H-benzotriazole-1-yl)-1,1,3,3-teramethyluronium tetrafluoroborate (TBTU) (321 mg, 1.0 mmol), N,N-diisopropylethylamine (DIPEA) (0.39 ml, 2.25 mmol) in 1-methylpyrrolidine (3 ml) was added and the resultant suspension was agitated at ambient temperature for sixteen hours. The resin was filtered and was washed with 1-methylpyrrolidine (5 ml) and alternately with methanol (4×5 ml) and dichloromethane (4×5 ml). The resin was dried and a sample was analysed by IR spectroscopy (IR(resin/cm$^{-1}$) 1650 (amide) and 1732 (ester).

A sample of resin (250 mg, 0.125 mmol) obtained from the third step was placed in a reaction vessel and was swollen by the addition of tetrahydrofuran (2 ml). A 50% wt solution of hydroxylamine in water (0.21 ml, 3.125 mmol) was added and the resultant suspension was agitated at ambient temperature for forty-eight hours. The resin was filtered and washed with methanol (5 ml). The filtrates were combined and the solvent was removed under reduced pressure. The crude product obtained was purified by preparative hplc using a 150×21.2 mm 5 μm Hypersil® Elite $C_{18}$ column eluting with 30% ACN/70% $H_2O$+0.2% TFA. The flow rate was 20 mlmin$^{-1}$ and the detector was set at 254 nm. The fractions that contained the desired product were concentrated under reduced pressure and the resultant residue was lyophilised from a mixture of dioxane and water to afford the title compound as an orange oil (5.9 mg, 17%), $t_R$ 1.64 (254 nm, 1.5 mlmin$^{-1}$, 30% ACN/70% $H_2O$+0.2% TFA, m/z [ES] 302 [M+H]$^+$.

Example 90

3-Benzo[1,3]dioxol-5-yl-acryloyl chloride (2a)

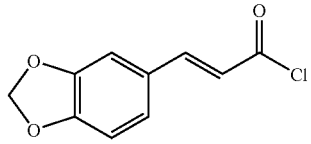

(Method G2) To a suspension of 3-benzo[1,3]dioxol-5-yl-acrylic acid (1a) (0.38 g, 1.98 mmol) in dichloromethane (8.0 ml) oxalyl chloride (0.62 ml, 7.08 mmol) and one drop of dimethylformamide were added. The reaction mixture was stirred at 40° C. for one hour and concentrated under reduced pressure to give crude title compound (0.41 g, 98%).

Example 91

3-[3-[[(E)-3-(1,3-Benzodioxol-5-yl)-1-oxo-2-propenyl]amino]phenyl]-(E)-2-propenoic acid methyl ester (3a)

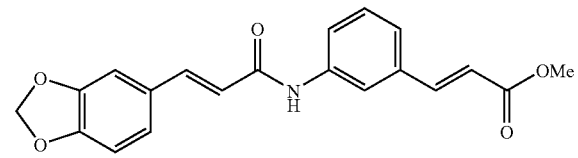

(Method G3) A solution of 3-benzo[1,3]dioxol-5-yl-acryloyl chloride (2a) (0.41 g, 1.95 mmol) in tetrahydrofuran (8.0 ml) was added to a mixture of m-aminophenylacrylic acid methyl ester (0.35 g, 1.97 mmol) in tetrahydrofuran (12.0 ml) and NaHCO$_3$ (0.25 g, 3.00 mmol) in water (7.0 ml), and the resultant solution was stirred at room temperature for one hour. The reaction mixture was evaporated and the residue was partitioned between ethyl acetate and 2N HCl. The organic layer was washed successively with water, saturated NaCl, and dried (Na$_2$SO$_4$). The solvent was removed and the residue was chromatographed on silica gel with dichlormethane-methanol (40:1, v/v) as eluent. The obtained product was washed with diethyl ether to give the title compound (0.50 g, 71%). $^1$H NMR (DMSO-d$_6$, HMDSO), δ: 3.73 (3H, s); 6.09 (2H, s); 6.49 (1H, d, J=16.0 Hz); 6.67 (1H, d, J=16.0 Hz); 6.89-7.83 (8H, m); 7.98 (1H, br s); 10.23 ppm (1H, br s)

Example 92

3-[3-[[(E)-3-(1,3-Benzodioxol-5-yl)-1-oxo-2-propenyl]amino]phenyl]-(E)-2-propenoic acid (4a)

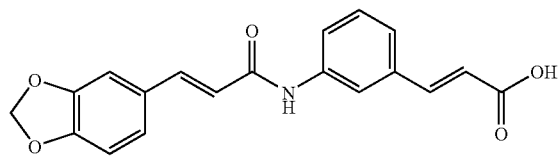

(Method G4) 1N NaOH solution (2.56 ml, 2.56 mmol) was added to a solution of 3-[3-[[(E)-3-(1,3-benzodioxol-5-yl)-1-oxo-2-propenyl]amino]phenyl]-(E)-2-propenoic acid methyl ester (3a) (0.30 g, 0.85 mmol) in tetrahydrofuran (4.0 ml), and the resultant mixture was stirred at ambient temperature overnight. The reaction mixture was partitioned between ethyl acetate and water. The aqueous layer was acidified with 2N HCl solution and extracted with ethyl acetate. The organic layer was washed successively with water, saturated NaCl, and dried ($Na_2SO_4$). The solvent was removed and the residue was washed with diethyl ether. The title compound was obtained as a white solid (0.24 g, 84%). $^1$H NMR (DMSO-$d_6$, HMDSO), δ: 6.09 (2H, s); 6.43 (1H, d, J=16.0 Hz); 6.60 (1H, d, J=16.0 Hz); 6.89-7.76 (8H, m).; 7.92 (1H, br s); 10.16 (1H, br s); 12.38 ppm (1H, br s).

Example 93

(E)-3-(1,3-Benzodioxol-5-yl)-N-{3-[(E)-3-(hydroxyamino)-3-oxo-1-propenyl]phenyl}-2-propenamide (5a) (PX117711)

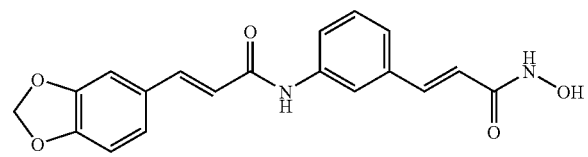

(Method G5) To a solution of 3-[3-[[(E)-3-(1,3-benzodioxol-5-yl)-1-oxo-2-propenyl]amino]phenyl]-(E)-2-propenoic acid (4a) (0.24 g, 0.71 mmol) in tetrahydrofuran (5.0 ml) at 0° C. temperature iso-butylchloroformate (0.1 ml, 0.80 mmol) and triethylamine (0.12 ml, 0.88 mmol) were added, and the mixture was stirred for 15 min. To a solution of KOH (0.084 g, 1.43 mmol) in methanol (0.40 ml) at 0° C. hydroxylamine hydrochloride (0.10 g, 1.43 mmol) in methanol (1.0 ml) was added and the reaction mixture was stirred for 15 min. The precipitated KCl was removed and the filtrate was added to the first solution. The reaction mixture was stirred at room temperature for 1 hour and then the mixture was partitioned between 1N $KH_2PO_4$ and ethyl acetate. The organic layer was washed with water, saturated NaCl, and dried ($Na_2SO_4$). The solvent was evaporated and the residue was washed with hot ethyl acetate and hot methanol affording pure title compound (0.13 g, 52%). M.p. 128° C. $^1$H NMR (DMSO-$d_6$, HMDSO) δ: 6.49 (d, 1H, J=16.0 Hz); 6.67 (d, 1H, J=16.0 Hz); 6.87-7.76 (m, 8 H); 7.98 (br s, 1H); 9.03 (br s, 1H); 10.18 (br s, 1H); 10.80 (br s, 1H). HPLC analysis on Symmetry $C_{18}$ column: impurities 3.2% (column size 3.9× 150 mm; mobile phase acetonitrile–0.1M phosphate buffer (pH 2.5), 50:50; sample concentration 0.5 mg/ml; flow rate 1.0 ml/min; detector UV 254 nm). Anal. Calcd for $C_{19}H_{16}N_2O_5$*$H_2O$, %: C, 61.62; H, 4.90; N, 7.56. Found, %: C, 61.93; H, 5.03; N, 7.24.

Example 94

5-Phenyl-(2E,4E)-pentadienoyl chloride (2b)

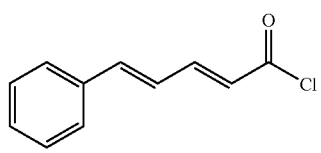

Using an analogous method (G2), the title compound was obtained from 5-phenyl-(2E,4E)-pentadienoic acid (1b) and oxalyl chloride, ca. yield of the crude product 100% (yellow oil).

Example 95

3-[3-[[(2E,4E)-1-Oxo-5-phenyl-2,4-pentadienyl]amino]phenyl]-(2E)-propenoic acid methyl ester (3b)

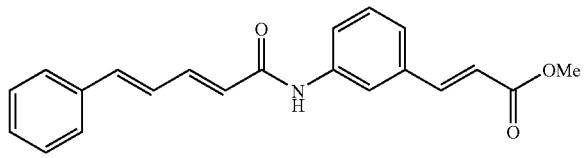

Using an analogous method (G3), the title compound was obtained from 5-phenyl-(2E,4E)-pentadienoyl chloride (2b) and 3-(3-aminophenyl)acrylic acid methyl ester as a white solid, yield 67%. $^1$H NMR (DMSO-$d_6$, HMDSO), δ: 3.74 (3H, s); 6.35 (1H, d, J=15.0 Hz); 6.53 (1H, d, J=16.0 Hz); 7.00-7.15 (2H, m); 7.28-7.73 (10H, m); 7.95 (1H, s); 10.24 (1H, s).

Example 96

3-[3-[[(2E,4E)-1-Oxo-5-phenyl-2,4-pentadienyl]amino]phenyl]-(2E)-propenoic acid (4b)

Using an analogous method (G4), the title compound was obtained from 3-[3-[[(2E,4E)-1-oxo-5-phenyl-2,4-pentadienyl]amino]phenyl]-(2E)-propenoic acid methyl ester (3b) and sodium hydroxide, ca. yield of a crude product 87%. $^1$H NMR (DMSO-$d_6$, HMDSO), δ: 6.35 (1H, d, J=15.4 Hz); 6.44

(1H, d, J=16.0 Hz); 7.02 (1H, m); 7.30-7.55 (8H, m); 7.58-7.80 (2H, m); 7.96 (1H, s); 10.22 (1H, s), 12.48 (1H, br s).

Example 97

N-{3-[(E)-3-(Hydroxyamino)-3-oxo-1-propenyl]phenyl}-5-phenyl-(2E,4E)-pentadienamide (5b) (PX117706)

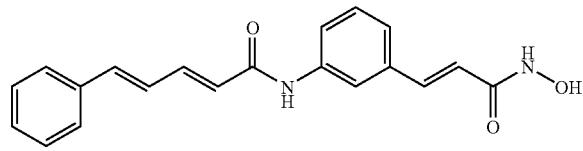

Using an analogous method (G5), the title compound was obtained from 3-[3-[[(2E,4E)-1-oxo-5-phenyl-2,4-pentadienyl]amino]phenyl]-(2E)-propenoic acid (4b), isobutylchloroformate, and hydroxylamine hydrochloride, yield 27%. M.p. 192° C. (dec.). $^1$H NMR (DMSO-$d_6$, HMDSO) δ: 6.38 (d, 1H, J=14.6 Hz); 6.45 (d, 1H, J=15.2 Hz); 6.99-7.19 (m, 2H); 7.20-7.52 (m, 7H); 7.55-7.68 (m, 3H); 8.01 (s, 1H); 9.09 (s, 1H); 10.28 (s, 1H); 10.84 (s, 1H). HPLC analysis on Zorbax SB-$C_{18}$ column: impurities 8% (the presence of other Z,E-isomers in minor quantities is possible) (column size 4.6×150 mm; mobile phase methanol—0.1% $H_3PO_4$, gradient from 50:50 to 90:10; detector UV 270 nm; flow rate 1.5 ml/min; sample concentration 0.15 mg/ml). Anal. Calcd for $C_{20}H_{18}N_2O_3$*0.25 EtOAc, %: C, 70.77; H, 5.66; N, 7.86. Found, %: C, 70.77; H, 5.59; N, 7.65.

Example 98

5-Phenyl-4-methyl-(2E,4E)-pentadienoyl chloride (2c)

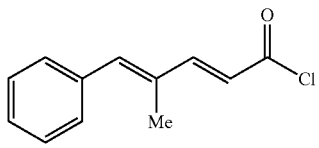

Using an analogous method (G2), the title compound was obtained from 5-phenyl-4-methyl-(2E,4E)-pentadienoic acid (1c) and oxalyl chloride, ca. yield of the crude product 100% (yellow oil).

Example 99

3-[3-[[(2E,4E)-4-Methyl-1-oxo-5-phenyl-2,4-pentadienyl]amino]phenyl]-(2E)-propenoic acid methyl ester (3c)

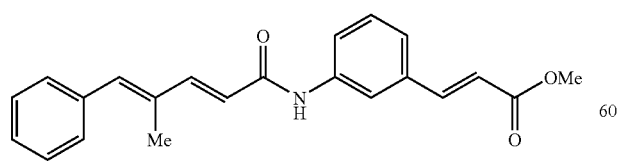

Using an analogous method (G3), the title compound was obtained from 5-phenyl-4-methyl-(2E,4E)-pentadienoyl chloride (2c) and 3-(3-aminophenyl)acrylic acid methyl ester as a white solid, yield 58%.

Example 100

3-[3-[[(2E,4E)-4-Methyl-1-oxo-5-phenyl-2,4-pentadienyl]amino]phenyl]-(2E)-propenoic acid (4c)

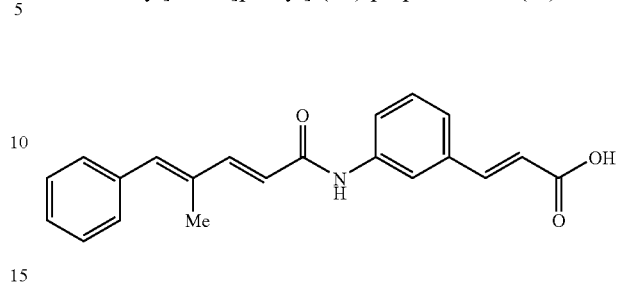

Using an analogous method (G4), the title compound was obtained from 3-[3-[[(2E,4E)-4-methyl-1-oxo-5-phenyl-2,4-pentadienyl]amino]phenyl]-(2E)-propenoic acid methyl ester (3c) and sodium hydroxide, ca. yield of a crude product 79%.

Example 101

N-{3-[(E)-3-(Hydroxyamino)-3-oxo-1-propenyl]phenyl}-4-methyl-5-phenyl-(2E,4E)-pentadienamide (5c) (PX117707)

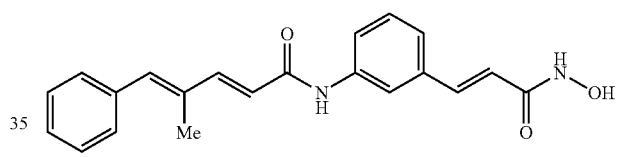

Using an analogous method (G5), the title compound was obtained from 3-[3-[[(2E,4E)-4-methyl-1-oxo-5-phenyl-2,4-pentadienyl]amino]phenyl]-(2E)-propenoic acid (4c), isobutylchloroformate, and hydroxylamine hydrochloride, yield 45%. M.p. 145-148° C. $^1$H NMR (DMSO-$d_6$, HMDSO) δ: 2.07 (s, 3H); 6.35 (d, 1H, J=15.5 Hz); 6.44 (d, 1H, J=15.7 Hz); 7.00 (s, 1H); 7.19-7.49 (m, 9H); 7.61 (d, 1H, J=8.2 Hz); 8.01 (s, 1H); 9.09 (s, 1H); 10.26 (s, 1H); 10.84 (s, 1H). HPLC analysis on Zorbax SB-$C_{18}$ column: impurities 7.7% (the presence of other Z,E-isomers in minor quantities is possible) (column size 4.6×150 mm; mobile phase acetonitrile—0.1M phosphate buffer (pH 2.5), 50:50; detector UV 270 nm; flow rate 1.25 ml/min; sample concentration 0.5 mg/ml). Anal. Calcd for $C_{21}H_{20}N_2O_3$*0.3 EtOAc, %: C, 71.14; H, 6.02; N, 7.47. Found, %: C, 70.91; H, 5.93; N, 7.42.

Example 102

4-Phenylbutyryl chloride (2d)

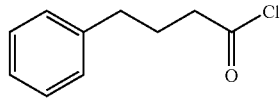

Using an analogous method (G2), the title compound was obtained from 4-phenylbutyric acid (1d) and oxalyl chloride, ca. yield of the crude product 100% (yellow oil).

Example 103

3-[3-(4-Phenylbutyrylamino)-phenyl]-acrylic acid methyl ester (3d)

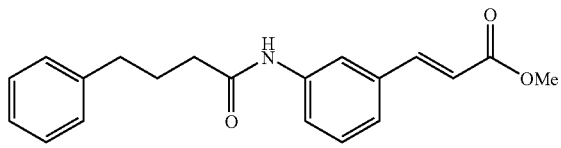

Using an analogous method (G3), the title compound was obtained from 4-phenylbutyryl chloride (2d) and 3-(3-aminophenyl)acrylic acid methyl ester as yellowish crystals, yield 83%. $^1$H NMR (DMSO-d$_6$, HMDSO), δ: 1.77-2.49 (4H, m); 2.72 (2H, t, J=7.0 Hz); 3.78 (3H, s); 6.43 (1H, d, J=16.0 Hz); 7.05-7.56 (9H, m); 7.61 (1H, d, J=16.0 Hz); 7.69 (1H, s).

Example 104

(E)-N-Hydroxy-3-{3-[(4-phenylbutanoyl)amino]phenyl}-2-propenamide (5d)

(PX116212)

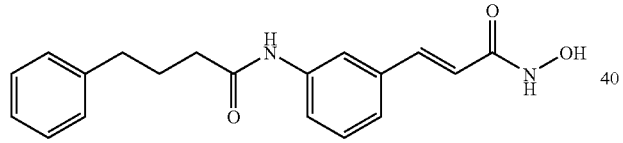

(Method G6) To a mixture of 3-[3-(4-phenyl-butyrylamino)-phenyl]-acrylic acid methyl ester (3d) (0.323 g, 1.0 mmol) and hydroxylamine (0.278 g, 4.0 mmol) in methanol (7 ml) a 3.43 N solution of sodium methylate (1.75 ml, 6.0 mmol) in methanol was added. The resulting mixture was stirred at ambient temperature for 7 hours, diluted with saturated NaH$_2$PO$_4$ (50 ml) and extracted with ethyl acetate (3×25 ml). The organic layer was washed with saturated NaCl and dried (Na$_2$SO$_4$). The solvent was evaporated and the residue was crystallized from acetonitrile affording the title compound as reddish crystals (0.122 g, 38%). M.p. 152-153° C. (from acetonitrile). $^1$H NMR (DMSO-d$_6$, HMDSO) δ: 1.69-2.11 (m, 2H); 2.35 (t, 2H, J=7.4 Hz); 2.64 (t, 2H, J=7.0 Hz); 6.45 (d, 1H, J=15.6 Hz); 7.12-7.66 (m, 9H); 7.94 (s, 1H); 9.07 (br s, 1H); 9.98 (s, 1H); 10.81 (br s, 1H). HPLC analysis on Symmetry C$_{18}$ column: impurities <1% (column size 3.9× 150 mm; mobile phase acetonitrile–0.1M phosphate buffer (pH 2.5), 40:60; detector UV 254 nm; flow rate 1.0 ml/min; sample concentration 0.5 mg/ml). Anal. Calcd for C$_{19}$H$_{20}$N$_2$O$_3$, %: C, 70.35; H, 6.21; N, 8.64. Found, %: C, 70.21; H, 6.20; N, 8.61.

Example 105

3-(4-Nitro-phenyl)-acrylic acid methyl ester (2)

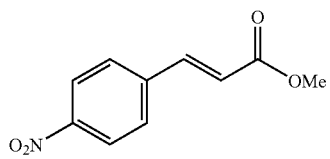

Thionyl chloride (28.8 ml, 0.4 mol) was added dropwise to methanol (450 ml) at −10° C. temperature. To the obtained solution was added 3-(4-nitrophenyl)-acrylic acid (1) (38.63 g, 0.2 mol) and the reaction mixture was stirred at 0° C. for 3 hours, at ambient temperature for 24 hours and at 40° C. for 1 hour. The resulting precipitate was filtered, washed with methanol (2×10 ml) and dried affording the title compound in a form of yellow crystals (39.55 g, 96%). $^1$H NMR (DMSO-d$_6$, HMDSO), δ: 3.69 (2H, br s); 3.77 (3H, s); 6.87 (1H, d, J=16.0 Hz); 7.67-8.39 (5H, m).

Example 106

3-(4-Amino-phenyl)-acrylic acid methyl ester (3)

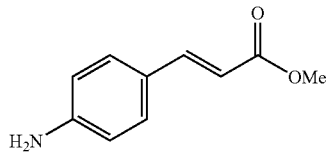

A mixture of 3-(4-nitro-phenyl)-acrylic acid methyl ester (2) (39.54 g, 0.191 mol) and SnCl$_2$.2H$_2$O (220 g, 0.98 mol) in anhydrous ethanol (300 ml) was heated at 50° C. for 1 hour and at 75° C. for 1 hour. The reaction mixture was allowed to cool to 10° C., treated with 20% NaOH solution to pH 8-9, and extracted with ethyl acetate (3×200 ml). The organic extract was washed with saturated NaCl (3×150 ml), dried (MgSO$_4$), and evaporated under reduced pressure. Recrystallization from isopropanol (180 ml) afforded pure title compound in a form of yellowish crystals (17.938 g, 53%). $^1$H NMR (DMSO-d$_6$, HMDSO), δ: 3.64 (3H, s); 5.73 (2H, s);

6.22 (1H, d, J=16.0 Hz); 6.57 (2H, d, J=8.0 Hz); 7.38 (2H, d, J=8.0 Hz); 7.50 (1H, d, J=16.0 Hz).

Example 107

3-(4-Benzoylamino-phenyl)-acrylic acid methyl ester (4b)

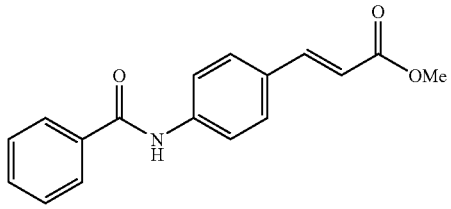

(Method H4) To a suspension of 3-(4-amino-phenyl)-acrylic acid methyl ester (3) (1.740 g, 6.18 mmol) in methylene chloride (10 ml) benzoyl chloride (1.260 g, 9 mmol) and pyridine (0.563 g, 7.00 mmol) were added. The resulting suspension was stirred at 15° C. for 24 hours and filtrated. The precipitate was washed with methylene chloride (10 ml), NaHCO₃ solution (10 ml), and water (2×20 ml). The obtained solid was dried to give the title compound in a form of white crystals (1.675 g, 73%). M.p. 164-165° C. (from isopropanol). ¹H NMR (DMSO-$d_6$, HMDSO), δ: 3.73 (3H, s); 6.58 (1H, d, J=16.0 Hz); 7.51-8.07 (10H, m); 10.44 (1H, s).

Example 108

3-(4-Benzoylamino-phenyl)-acrylic acid (5b)

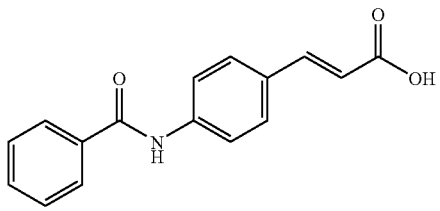

(Method H5) A mixture of 3-(4-benzoylamino-phenyl)-acrylic acid methyl ester (4b) (1.650 g, 5.87 mmol) and LiOH (0.630 g, 15 mmol) in water (30 ml) and methanol (30 ml) was stirred at ambient temperature for 24 hours. Methanol was evaporated and the residue was treated with hydrochloric acid to pH 4. The resulting precipitate was filtered off, washed with water (3×20 ml), and dried to give the title compound as a white solid (1.443 g, 92%). ¹H NMR (DMSO-$d_6$, HMDSO), δ: 6.44 (1H, d, J=16.0 Hz); 7.33-8.11(10H, m); 10.40 (1H, s).

Example 109

3-(4-Benzoylamino-phenyl)-propionic acid (6b)

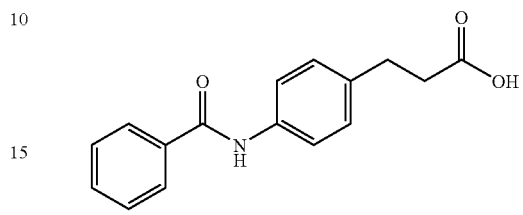

(Method H6) To a solution of 3-(4-benzoylamino-phenyl)-acrylic acid (5b) (1.350 g, 5.05 mmol) in 90% ethanol 10% Pd/C (0.03 g) was added and the mixture was stirred under hydrogen atmosphere at 50° C. for 2 hours. The catalyst was filtered off, the solution was evaporated, and the residue was washed with hot water (20 ml) to give the title compound as a white solid (1.306 g, 96%). ¹H NMR (DMSO-$d_6$, HMDSO), δ: 2.38-2.64 (2H, m, overlapped with a signal of DMSO), 2.65-2.96 (2H, m); 7.21 (2H, d, J=8.6 Hz); 7.44-8.08 (7H, m); 10.16 (1H, s); 12.09 (1H, s).

Example 110

N-[4-(2-Hydroxycarbamoyl-ethyl)-phenyl]-benzamide (PX117232)

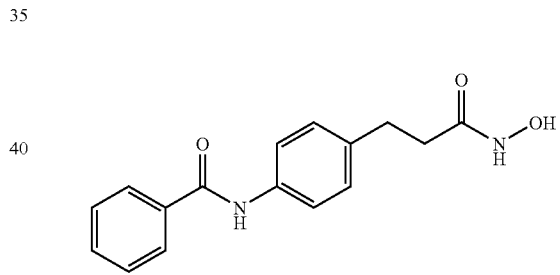

(Method H7) To a solution of 3-(4-benzoylamino-phenyl)-propionic acid (6b) (1.04 g, 3.86 mmol) in tetrahydrofuran (30 ml) under argon atmosphere 1,1'-carbonyldiimidazole (0.814 g, 5.0 mmol), was added and the mixture was stirred at room temperature for 1 hour. In an another vessel, a solution of hydroxylamine hydrochloride (0.805 g, 11.6 mmol) in dimethylformamide (10 ml) was treated with ethyl amine (1.62 ml, 11.6 mmol), the precipitate was filtered off and both solutions were mixed together. The resultant mixture was stirred at ambient temperature for 24 hours, concentrated under reduced pressure and diluted with 3% hydrochloric acid (15 ml). The resulting precipitate was filtered, washed with water (3×20 ml), and crystallized from acetonitrile to give the title compound as a white solid (0.790 g, 72%). M.p. 189-191° C. ¹H NMR (DMSO-$d_6$, HMDSO) δ: 2.26 (t, 2H, J=7.5 Hz); 2.79 (t, 2H, J=7.5 Hz); 7.17 (d, 2H, J=8.4 Hz); 7.45-7.60 (m, 3H); 7.67 (d, 2H, J=8.4 Hz); 7.88-8.02 (m, 2H); 8.73 (s, 1H); 10.18 (s, 1H); 10.38 ppm (s, 1H). HPLC analysis on Symmetry $C_{18}$ column: impurities 1.8% (column size 3.9× 150 mm; mobile phase acetonitrile–0.1M phosphate buffer (pH 2.5), 28:72; sample concentration 0.25 mg/ml; detector UV 220 nm). Anal. Calcd for $C_{16}H_{16}N_2O_3$, %: C, 67.59; H, 5.67; N, 9.85. Found, %: C, 67.46; H, 5.61; N, 9.87.

Example 111

N-[4-(2-Hydroxycarbamoyl-vinyl)-phenyl]-benzamide (PX117231)

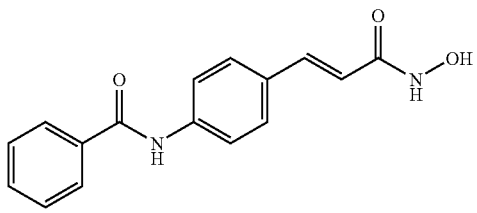

Using an analogous method (H5, H6, H7), the title compound was prepared from 3-(4-benzoylamino-phenyl)-acrylic acid (5b) (0.946 g, 3.54 mmol) in a form of white solid (0.370 g, 37%). M.p. 232-234° C. $^1$H NMR (DMSO-$d_6$, HMDSO) δ: 6.40 (d, 1H, J=16.0 Hz); 7.44 (d, 1H, J=16.0 Hz); 7.40-7.73 (m, 5H); 7.77-8.03 (m, 4H); 9.03 (s, 1H); 10.41 (s, 1H); 10.74 ppm (s, 1H). HPLC analysis on Symmetry $C_{18}$ column: impurities 3% (column size 3.9×150 mm; mobile phase acetonitrile–0.1M phosphate buffer (pH 2.5), 35:65; sample concentration 0.046 mg/ml; flow rate 1.0 ml/min.; detector UV 220 nm). Anal. Calcd for $C_{16}H_{14}N_2O_3$, %: C, 68.08; H, 5.00; N, 9.92. Found, %: C, 67.45; H, 5.54; N, 9.80.

Example 112

3-{4-[(Naphthalene-2-carbonyl)-amino]-phenyl}-acrylic acid methyl ester (4c)

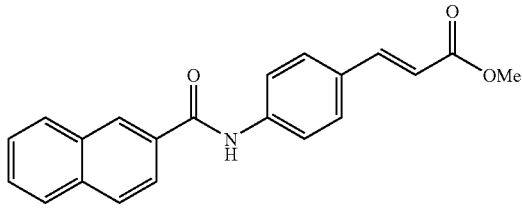

Using an analogous method (H4), the title compound was prepared from 2-naphthalenecarbonyl chloride (0.557 g, 2.91 mmol) and 3-(4-amino-phenyl)-acrylic acid methyl ester (3) in a form of white solid (0.950 g, 75%). $^1$H NMR (DMSO-$d_6$, HMDSO), δ: 3.65 (3H, s); 6.51 (1H, d, J=16.0 Hz); 7.47-8.25 (12H, m); 10.63 (1H, s).

Example 113

3-{4-[(Naphthalene-2-carbonyl)-amino]-phenyl}-acrylic acid (5c)

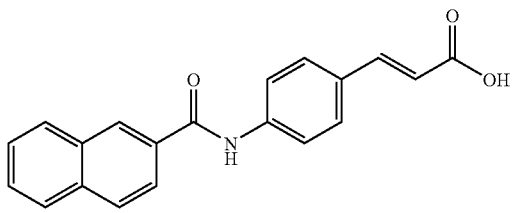

Using an analogous method (H5), the title compound was prepared from 3-{4-[(naphthalene-2-carbonyl)-amino]-phenyl}-acrylic acid methyl ester (4c) (0.940 g, 2.16 mmol) and LiOH in a form of white solid (0.757 g, 83%). $^1$H NMR (DMSO-$d_6$, HMDSO), δ: 6.51 (1H, d, J=16.0 Hz); 7.44-8.22 (12H, m); 8.63 (1H, s); 10.64 (1H, s).

Example 114

Naphthalene-2-carboxylic acid [4-(2-hydroxycarbamoyl-vinyl)-phenyl]-amide (PX116246)

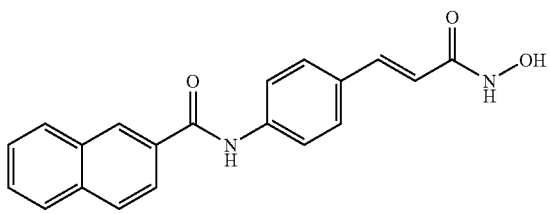

(Method H8) To a suspension of 3-{4-[(naphthalene-2-carbonyl)-amino]-phenyl}-acrylic acid (5c) (0.740 g, 1.75 mmol) in methylene chloride (8 ml) oxalyl chloride (0.54 ml, 6.14 mmol) and one drop of dimethylformamide were added. The mixture was stirred for 30 min. at room temperature and for 1 hour at 40° C. Then the mixture was concentrated under reduced pressure and the residue was diluted with tetrahydrofuran (8.0 ml). In an another vessel, to a suspension of hydroxylamine hydrochloride (0.695 g, 10.0 mmol) in tetrahydrofuran (12 ml) saturated NaHCO$_3$ solution (8.0 ml) was added and the mixture was stirred at room temperature for 5 min. The both mixtures were combined and vigorously stirred at room temperature for 30 min. The solvents were evaporated and the residue was acidified with 3% HCl to pH 5. The resulting precipitate was filtered off and washed with water (3×10 ml). The crystallization from methanol/water provided the title compound as a white solid (0.262 g, 45%). M.p. 231-233° C. $^1$H NMR (DMSO-$d_6$, HMDSO) δ: 6.41 (d, 1H, J=15.8 Hz); 7.45 (d, 1H, J=15.8 Hz); 7.52-7.70 (m, 4H); 7.82-8.16 (m, 6H); 8.59 (s, 1H); 9.02 (s, 1H); 10.58 (s, 1H); 10.73 (s, 1H). HPLC analysis on Zorbax SB-C18 column: impurities <1% (column size 4.6×150 mm; mobile phase methanolx-0.1% $H_3PO_4$, gradient from 50:50 to 90:10; sample concentration 0.05 mg/ml; flow rate 1.5 ml/min.; detector UV 220 nm). Anal. Calcd for $C_{20}H_{16}N_2O_3$ containing 1% of inorganic impurities, %: C, 71.55; H, 4.80; N, 8.34. Found, %: C, 71.60; H, 4.78; N, 8.39.

Example 115

3-[4-(2-Naphthalen-1-yl-acetylamino)-phenyl]-acrylic acid methyl ester (4d)

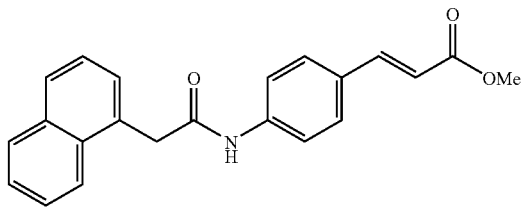

Using an analogous method (H4), the title compound was prepared from 1-naphthalenyl-acetyl chloride (3.070 g, 15 mmol) and 3-(4-amino-phenyl)-acrylic acid methyl ester (3) in a form of yellow solid (1.380 g, 14%). $^1$H NMR (DMSO-d$_6$, HMDSO), δ: 3.70 (3H, s); 4.07 (2H, s); 6.51 (1H, d, J=16.0 Hz); 7.40-8.22 (12H, m); 10.53 (1H, s).

Example 116

3-[4-(2-Naphthalen-1-yl-acetylamino)-phenyl]-acrylic acid (5d)

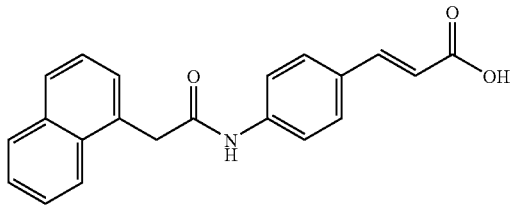

Using an analogous method (H5), the title compound was prepared from 3-[4-(2-naphthalen-1-yl-acetylamino)-phenyl]-acrylic acid (4d) (1.360 g, 3.03 mmol) and LiOH in a form of white solid (1.214 g, 92%). $^1$H NMR (DMSO-d$_6$, HMDSO), δ: 4.05 (2H, s); 6.51 (1H, d, J=16.0 Hz); 7.41-8.24 (12H, m); 8.65 (1H, s); 10.59 (1H, s).

Example 117

(E)-N-Hydroxy-3-(4-{[2-(1-naphthyl)acetyl]amino}phenyl)-2-propenamide (PX116244)

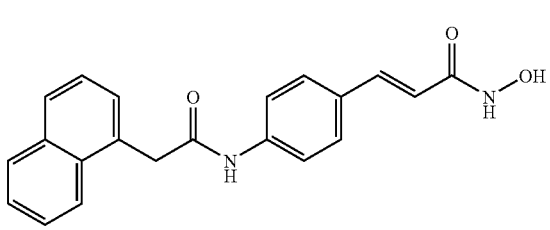

Using an analogous method (H8), the title compound was prepared from 3-[4-(2-naphthalen-1-yl-acetylamino)-phenyl]-acrylic acid (5d) (1.200 g, 2.76 mmol) in a form of white solid (0.691 g, 62%). M.p. 222-224° C. $^1$H NMR (DMSO-d$_6$, HMDSO) δ: 64.17 (s, 2H); 6.36 (d, 1H, J=15.6 Hz); 7.40 (d, 1H, J=15.6 Hz); 7.42-8.02 (m, 9H); 8.12 (d, 1H, J=8.4 Hz); 9.03 (s, 1H); 10.51 (s, 1H); 10.72 (s, 1H). HPLC analysis on Zorbax SB-C18 column: impurities <1% (column size 4.6× 150 mm; mobile phase methanol −0.1% H$_3$PO$_4$, gradient from 30:70 to 100:0; sample concentration 1.0 mg/ml; flow rate 1.5 ml/min.; detector UV 220 nm). Anal. Calcd C$_{21}$H$_{18}$N$_2$O$_3$ containing 6% inorganic impurities, %: C, 68.45; H, 4.92; N, 7.60. Found, %: C, 68.48; H, 4.87; N, 7.51.

Example 118

(2E)(4E)-6-(5-Phenylpenta-2,4-dienoylamino)hexanoic acid methyl ester (3/1)

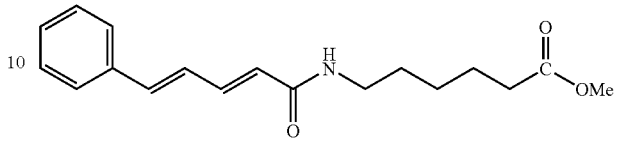

(Method J1A) 1,1'-Carbonyidiimidazole (0.36 g, 2.2 mmol) was added to a solution of 5-phenyl-penta-2E,4E-dienoic acid (1/1) (0.35 g, 2 mmol) in dry tetrahydrofuran (10 ml) and the obtained mixture was stirred for 1 hour at ambient temperature. To the mixture triethylamine (0.30 g 3.0 mmol) and methyl 6-aminohexanoate hydrochloride (2c) (0.40 g, 2.2 mmol) were added and the resultant suspension was stirred for 6 hours at ambient temperature. The solvent was removed under reduced pressure, to the residue water (15 ml) was added and the precipitate was filtered off, washed with water and dried. The title compound (0.36 g, 60%) was obtained as a white solid. M. p. 125-127° C. $^1$H NMR (DMSO-d$_6$, HMDSO), δ: 1.05-1.72 (6H, m, CH$_2$); 2.29 (2H, t, J=7.3 Hz, CH$_2$); 3.12 (2H, q, J=6.0 Hz, CH$_2$N); 3.58 (3H, s, CH$_3$); 6.12 (1H, d, J=14.8 Hz, CH); 6.91-7.16 (2H, m, CH—CH); 7.23-7.66 (6H, m, C$_6$H$_5$, CH); 8.05 (1H, t, J=5.8 Hz, NH).

Example 119

(2E)(4E)-5-Phenylpenta-2,4-dienoic acid (5-hydroxycarbamoylpentyl)amide (4/1) (PX105553)

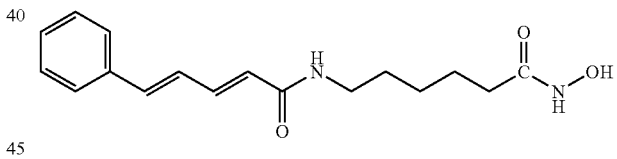

(Method J1B) A solution of sodium methylate (6 mmol) in methanol (5 ml) was added to a solution of hydroxylamine hydrochloride (0.28 g, 4 mmol) in methanol (8 ml). A mixture was stirred for 10 min. and the precipitate was filtered off. (2E)(4E)-6-(5-Phenylpenta-2,4-dienoylamino)hexanoic acid methyl ester (3/1) (0.30 g, 1 mmol) was added to the filtrate and the mixture was heated to the complete dissolving. The resultant mixture was stirred for 4 hours at ambient temperature and the solvent was removed under reduced pressure. The product was dissolved in water (10 ml) and acidified with 3% HCl. Precipitate was filtered off and crystallized from methanol. The title compound (0.23 g, 66%) was obtained as a white solid. M. p 160-161° C.° C. $^1$H NMR (DMSO-d$_6$, HMDSO), δ: 1.05-1.69 (6H, m, CH$_2$); 1.81-2.07 (2H, m, CH$_2$); 3.12 (2H, q, J=5.8 Hz, CH$_2$N); 6.14 (1H, d, J=14.8 Hz, CH); 6.89-7.14 (2H, m, CH—CH); 7.23-7.65 (6H, m, C$_6$H$_5$, CH); 8.05 (1H, t, J=6.0 Hz, NH); 8.63 (1H, s, NH), 10.34 (1H, s, OH). HPLC analysis on Symmetry C$_{18}$: impurities 1.0% (column size 3.9×150 mm; mobile phase acetonitrile−0.1 M phosphate buffer (pH 2.5), 30:70; detector UV 230 nm;

sample concentration 0.1 mg/ml). Anal. Calcd for $C_{17}H_{22}N_2O_3$: C, 65.68; H, 6.61; N, 10.21. Found: C, 65.63; H, 6.60; N, 10.17.

Example 120

6-(3-Phenyl-propionylamino)-hexanoic acid methyl ester (3/2)

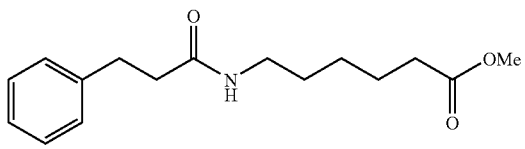

Using an analogous method (J1A), the title compound was obtained from 3-phenyl-propionic acid (1/2) and methyl 6-aminohexanoate hydrochloride (2c). Yield 76%, m.p. 34-35° C. $^1$H NMR (CDCl$_3$, HMDSO), δ: 0.99-1.77 (6H, m, CH$_2$); 2.27 (2H, t, J=7.2 Hz, CH$_2$); 2.44 (2H, t, J=7.5 Hz, CH$_2$); 2.95 (2H, t, J=7.5 Hz, CH$_2$); 3.18 (2H, q, J=6.0 Hz, CH$_2$N); 3.64 (3H, s, CH$_3$); 5.47 (1H, br s, NH); 7.22 (5H, s, C$_6$H$_5$).

Example 121

6-(3-Phenylpropionylamino)hexanoic acid hydroxyamide (4/2) (PX106516)

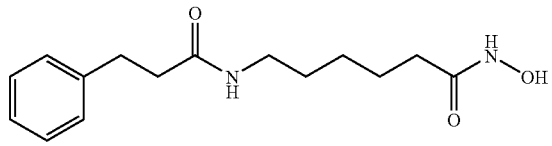

Using an analogous method (J1B), the title compound was obtained. Yield 95%, m.p. 107° C. $^1$H NMR (DMSO-d$_6$, HMDSO), δ: 1.08-1.64 (6H, m); 1.91 (2H, t, J=6.6 Hz); 2.33 (2H, m); 2.66-3.12 (4H, m); 7.08-7.36 (5H, m); 7.73 (2H, unresolv. t); 8.61 (1H, br s); 10.29 (1H, br s). HPLC analysis on Symmetry C$_{18}$ column: impurities 1% (column size 3.9×150 mm; mobile phase acetonitrile–0.1M phosphate buffer (pH 2.5), 25:75; detector UV 220 nm; sample concentration 0.33 mg/ml; flow rate 1.0 ml/min). Anal. Calcd for $C_{15}H_{22}N_2O_3$, %: C, 64.73; H, 7.97; N, 10.06. Found, %: C, 64.85; H, 8.07; N, 9.94.

Example 122

4-[(2E)(4E)-5-(4-Chlorophenyl)penta-2,4-dienoylamino]butyric acid methyl ester (3/3)

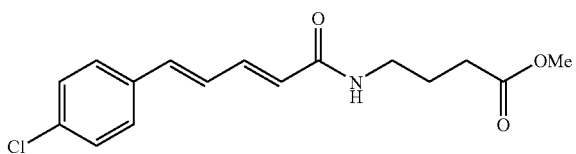

Using an analogous method (J1A), the title compound was obtained from 5-(4-chloro-phenyl)-penta-2E,4E-dienoic acid (1/3) and methyl 4-aminobutyrate hydrochloride (2a). Yield (66%), m.p. 140-142° C. $^1$H NMR (90 MHz, DMSO-d$_6$) δ: 1.38-1.87 (2H, m, CH$_2$); 2.25 (2H, t, J=7.0 Hz, CH$_2$); 3.09 (2H, q, J=5.6 Hz, CH$_2$); 3.55 (3H, s, CH$_3$); 6.05 (1H, d, J=15.0 Hz, CH); 6.61-7.32 (3H, m, CH=CH—CH); 7.32 (2H, d, J=8.0 Hz, C$_6$H$_2$); 7.49 (2H, d, J=8.0 Hz, C$_6$H$_2$); 7.98 (1H, t, J=5.3 Hz, NH).

Example 123

(2E)(4E)-5-(4-Chlorophenyl)-penta-2,4-dienoic acid (3-hydroxycarbamoylpropyl)-amide (4/3) (PX105845)

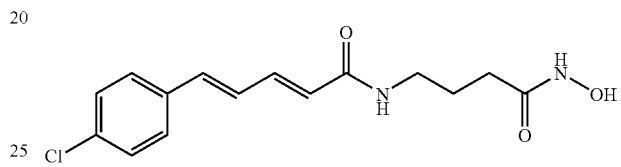

Using an analogous method (J1B), the title compound was obtained. Yield 58%, m.p. 164-166° C. $^1$H NMR (90 MHz, DMSO-d$_6$) δ: 1.41-1.85 (2H, m, CH$_2$); 2.01 (2H, t, J=7.0 Hz, CH$_2$); 3.61 (2H, q, J=5.6 Hz, CH$_2$); 6.16 (1H, d, J=14.8 Hz, CH); 6.72-7.29 (3H, m, CH=CH—CH); 7.38 (2H, d, J=7.6 Hz, C$_6$H$_2$); 7.56 (2H, d, J=7.6 Hz, C$_6$H$_2$); 8.09 (1H, unresolv. t, NH); 8.69 (1H, br s, NH); 10.38 (1H, br s, OH). HPLC analysis on Symmetry C$_{18}$: impurities <1% (column size 3.9×150 mm; mobile phase acetonitrile–0.1 M phosphate buffer (pH 2.5), 25:75; detector UV 220 nm; sample concentration 0.33 mg/ml). Anal. Calcd for $C_{15}H_{17}ClN_2O_3$: C, 58.35; H, 5.55; N, 9.07. Found: C, 57.99; H, 5.50; N, 8.87.

Example 124

4-[(2E)(4E)-5-(4-Bromophenyl)penta-2,4-dienoylamino]butyric acid methyl ester (3/4)

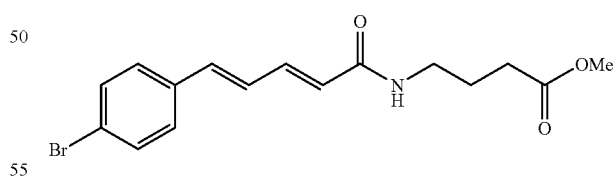

Using an analogous method (J1A), the title compound was obtained from 5-(4-bromo-phenyl)-penta-2E,4E-dienoic acid (1/4) and methyl 4-aminobutyrate hydrochloride (2a). Yield (56%), m.p. 149-151° C. $^1$H NMR (90 MHz, DMSO-d$_6$) δ: 1.40-1.86 (2H, m, CH$_2$); 2.30 (2H, t, J=6.9 Hz, CH$_2$); 3.27 (2H, q, J=5.9 Hz, CH$_2$); ); 3.58 (3H, s, CH$_3$); 6.12 (1H, d, J=15.0 Hz, CH); 6.70-7.41 (3H, m, CH=CH—CH); 7.57 (4H, s, C$_6$H$_4$); 8.10 (1H, t, J=5.0 Hz, NH).

Example 125

(2E)(4E)-5-(4-Bromophenyl)penta-2,4-dienoic acid (3-hydroxycarbamoylpropyl)amide (4/4) (PX105816)

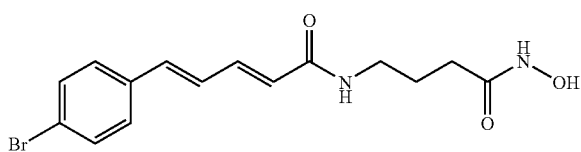

Using an analogous method (J1B), the title compound was obtained. Yield 63%, m.p. 173-175° C. $^1$H NMR (90 MHz, DMSO-$d_6$) δ: 1.38-1.83 (2H, m, $CH_2$); 1.98 (2H, t, J=7.0 Hz, $CH_2$); 2.93-3.28 (2H, m, $CH_2$); 6.14 (1H, d, J=14.9 Hz, CH); 6.72-7.38 (3H, m, CH=CH—CH); 7.54 (4H, s, $C_6H_4$); 8.07 (1H, unresolv. t, NH); 8.72 (1H, br s, NH), 10.18 (1H, br s, OH). HPLC analysis on Symmetry $C_{18}$: impurities <1% (column size 3.9×150 mm; mobile phase acetonitrile–0.1M phosphate buffer (pH 2.5), 40:60; detector UV 220 nm; sample concentration 0.5 mg/ml). Anal. Calcd for: $C_{15}H_{17}BrN_2O_3$: C, 51.01; H, 4.85; N, 7.93. Found: C, 50.87; H, 4.83; N, 7.83.

Example 126

4-[(2Z)(4E)-5-(4-Bromophenyl)penta-2,4-dienoylamino]butyric acid methyl ester (3/5)

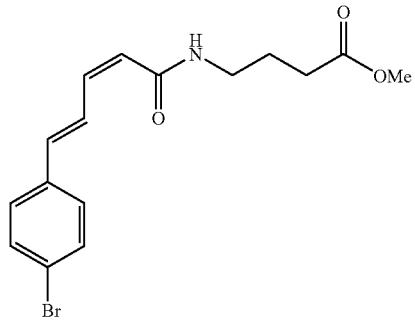

Using an analogous method (J1A), the title compound was obtained from 5-(4-bromo-phenyl)-penta-2Z,4E-dienoic acid (1/5) and methyl 4-aminobutyrate hydrochloride (2a). Yield 56%, m.p. 74-76° C. $^1$H NMR (90 MHz, DMSO-$d_6$) δ: 1.42-1.85 (2H, m, $CH_2$); 2.15 (2H, t, J=6.8 Hz, $CH_2$); 3.15 (2H, q, J=5.6 Hz, $CH_2$); 3.56 (3H, s, $CH_3$); 5.83 (1H, d, J=11.1 Hz, CH); 6.58 (1H, t, J=11.0 Hz, CH); 6.75 (1H, d, J=16.0 Hz, CH); 7.38 (2H, d, J=7.0 Hz, $C_6H_2$); 7.55 (2H, d, J=7.0 Hz, $C_6H_2$); 8.26 (1H, dd, J=11.0 Hz, and 16.0 Hz, CH); 8.12 (1H, t, J=5.2 Hz, NH).

Example 127

(2Z)(4E)-5-(4-Bromophenyl)penta-2,4-dienoic acid (3-hydroxycarbamoyl-propyl)amide (4/5) (PX105846)

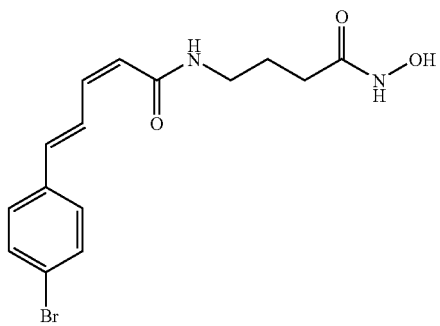

Using an analogous method (J1B), the title compound was obtained. Yield 79%, m.p. 172-174° C. $^1$H NMR (90 MHz, DMSO-$d_6$) δ: 1.41-1.83 (2H, m, $CH_2$); 1.98 (2H, t, J=7.0 Hz, $CH_2$); 3.12 (2H, q, J=5.4 Hz, $CH_2$); 5.78 (1H, d, J=11.2 Hz, CH); 6.56 (1H, t, J=11.0 Hz, CH); 6.72 (1H, d, J=15.8 Hz, CH); 7.36 (2H, d, J=7.0 Hz, $C_6H_2$); 7.54 (2H, d, J=7.0 Hz, $C_6H_2$); 8.24 (1H, dd, J=11.0 Hz, and 15.8 Hz, CH); 8.09 (1H, unresolv. t, NH); 8.65 (1H, br s, NH), 10.32 (1H, br s, OH). HPLC analysis on Symmetry $C_{18}$: impurities 1.3% (column size 3.9×150 mm; mobile phase acetonitrile–0.1 M phosphate buffer (pH 2.5), 35:65; detector UV 220 nm; sample concentration 1.0 mg/ml). Anal. Calcd for $C_{15}H_{17}BrN_2O_3$: C, 51.01; H, 4.85; N 7.93. Found: C, 50.91; H, 4.74; N, 7.84.

Example 128

6-[(2E)(4E)-5-Phenylpenta-2,4-dienoylamino]pentanoic acid methyl ester (3/6)

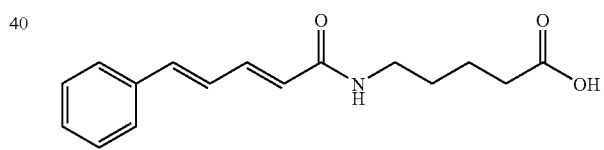

Using an analogous method (J1A), the title compound was obtained from 5-phenyl-penta-2E,4E-dienoic acid (1/6) and methyl 5-aminopentanoate hydrochloride (2b). Yield 71%, m.p. 113-115° C. $^1$H NMR (90 MHz, DMSO-$d_6$): δ: 1.05-1.72 (6H, m, $CH_2$); 2.29 (2H, t, J=7.1 Hz, $CH_2$); 3.14 (2H, q, J=6.0 Hz, $CH_2N$); 3.58 (3H, s, $CH_3$); 6.11 (1H, d, J=15.0 Hz, CH); 6.61-7.74 (8H, m, $C_6H_5CH$=CH—CH); 8.07 (1H, t, J=5.2 Hz, NH).

Example 129

(2E)(4E)-5-Phenylpenta-2,4-dienoic acid (4-hydroxycarbamoyl-butyl)amide (4/6) (PX105832)

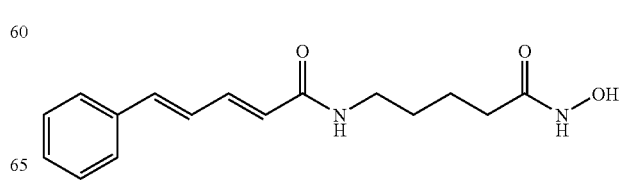

Using an analogous method (J1B), the title compound was obtained. Yield 77%, m.p. 168-170° C. ¹H NMR (200 MHz, DMSO-d₆) δ: 1.01-1.72 (4H, m, CH₂); 1.72-2.09 (2H, m, CH₂); 2.94-3.36 (2H, m, CH₂N); 6.12 (1H, d, J=14.8 Hz, CH); 6.61-7.74 (8H, m, C₆H₅CH=CH—CH); 8.05 (1H, unresolv. t, NH); 8.72 (1H, s, NH); 10.29 (1H, s, OH). HPLC analysis on Symmetry C₁₈: impurities 1.5% (column size 3.9×150 mm; mobile phase acetonitrile–0.1M phosphate buffer (pH 2.5), 30:70; detector UV 254 nm; sample concentration 0.08 mg/ml). Anal. Calcd for C₁₆H₂₀N₂O₃: C, 66.65; H, 7.00; N, 9.72. Found: C, 67.15; H, 7.18; N, 9.33.

Example 130

6-[(4-Aminofurazan-3-carbonyl)amino]hexanoic acid methyl ester (3/7)

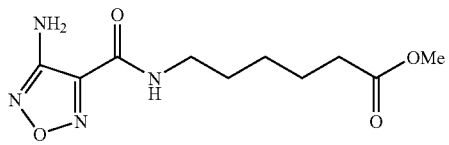

Using an analogous method (J1A), the title compound was obtained from 4-amino-furazan-3-carboxylic acid (1/7) and methyl 6-aminohexanoate hydrochloride (2c). Yield 70%, m.p. 82-84° C. ¹H NMR (90 MHz, DMSO-d₆) δ: 1.05-1.76 (6H, m, CH₂); 2.29 (2H, t, J=7.0 Hz, CH₂); 3.19 (2H, q, J=6.0 Hz, CH₂N); 3.52 (3H, s, CH₃); 6.32 (2H, s, NH₂); 9.01 (1H, t, J=5.2 Hz, NH).

Example 131

4-Aminofurazan-3-carboxylic acid (5-hydroxycarbamoylpentyl)amide (4/7) (PX106519)

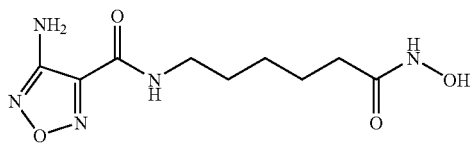

Using an analogous method (J1B), the title compound was obtained. Yield 50%, m.p. 150-152° C. ¹H NMR (90 MHz, DMSO-d₆) δ: 1.05-1.72 (6H, m, CH₂); 1.94 (2H, t, J=7.5 Hz, CH₂); 3.23 (2H, q, J=6.0 Hz, CH₂N); 6.61 (2H, s, NH₂); 8.63 (1H, s, NH), 9.01 (1H, t, J=5.5 Hz, NH); 10.29 (1H, s, OH). HPLC analysis on Symmetry C₁₈: impurities <1% (column size 3.9×150 mm; mobile phase acetonitrile–0.1M phosphate buffer (pH 2.5), 15:85; detector UV 220 nm; sample concentration 0.5 mg/ml). Anal. Calcd for C₉H₁₅N₅O₄: C, 42.02; H, 5.88; N, 27.22. Found: C, 42.06; H, 5.85; N, 27.01.

Example 132

6-(4-Phenyl-butyrylamino)-hexanoic acid methyl ester (3/8)

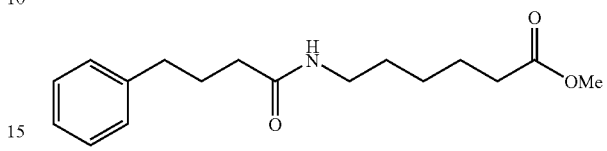

Using an analogous method (J1A), the title compound was obtained from 4-phenyl-butyric acid (1/8) and methyl 6-aminohexanoate hydrochloride (2c). Yield 76%, oil. ¹H NMR (CDCl₃, HMDSO), δ: 1.11-2.43 (12H, m, CH₂); 2.65 (2H, t, J=7.0 Hz, CH₂); 3.23 (2H, br q, J=5.4 Hz, CH₂N); 3.64 (3H, s, CH₃); 5.56 (1H, br s, NH); 7.21 (5H, s, Ph).

Example 133

N-Hydroxy-6-[(4-phenylbutanoyl)amino]hexanamide (4/8) (PX116210)

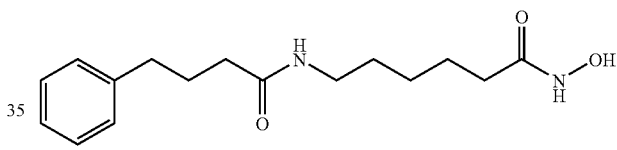

Using an analogous method (J1 B), the title compound was obtained. Yield 73%, m.p. 92-93° C. (from ethyl acetate). ¹H NMR (DMSO-d₆, HMDSO) δ: 1.11-2.21 (m, 12H); 2.88-3.16 (m, 2H); 7.23 (br s, 5H); 7.74 (unresolv. t, 1H); 8.63 (br s, 1H); 10.32 (br s, 1H). HPLC analysis on Symmetry C₁₈: impurities <1% (column size 3.9×150 mm; mobile phase acetonitrile–0.1M phosphate buffer (pH 2.5), 25:75; detector UV 220 nm; sample concentration 1.0 mg/ml). Anal. Calcd for C₁₆H₂₄N₂O₃: C, 65.73; H, 8.27; N, 9.58. Found: C, 65.79; H, 8.34; N, 9.56.

Example 134

6-(E-3-Naphthalen-2-ylacryloylamino)hexanoic acid methyl ester (3/10)

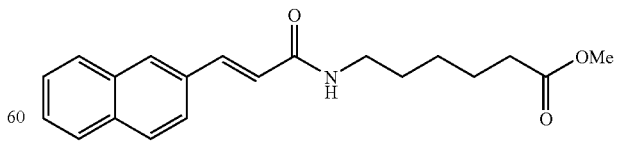

Using an analogous method (J1A), the title compound was obtained from 3-naphthalen-2-yl-acrylic acid (1/10) and methyl 6-aminohexanoate hydrochloride (2c). Yield 94%, m.p.74-76° C. ¹H NMR (90 MHz, DMSO-d₆): δ: 1.10-1.78 (6H, m, CH₂); 2.25 (2H, t, J=6.5 Hz, CH₂); 3.21 (2H, q, J=5.6

Hz, CH₂N); 3.58 (3H, s, CH₃); 6.78 (1H, d, J=15.5 Hz, CH); 7.46-8.23 (9H, m, C₁₀H₇, CH, NH).

Example 135

E-N-(5-Hydroxycarbamoylpentyl)-3-naphthalen-2-yl-acrylamide (4/10) (PX116232)

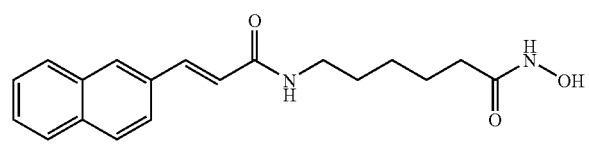

Using an analogous method (J1 B), the title compound was obtained. Yield 74%, m.p. 161-163° C. ¹H NMR (90 MHz, DMSO-d₆): δ: 1.07-1.74 (6H, m, CH₂); 1.81-2.14 (2H, unresolv. t, CH₂); 3.03-3.41 (2H, m, CH₂N); 6.74 (1H, d, J=16.0 Hz, CH); 7.43-8.21 (9H, m, C₁₀H₇, CH, NH); 8.63 (1H, s, NH), 10.32 (1H, s, OH). HPLC analysis on Symmetry C₁₈ column: impurities <1% (column size 3.9×150 mm; mobile phase acetonitrile–0.1 M phosphate buffer (pH 2.5), 35:65; detector UV 230 nm; sample concentration 0.125 mg/ml). Anal. Calcd for C₁₉H₂₂N₂O₅*H₂O: C, 66.26; H, 7.02; N, 8.13. Found: C, 66.51; H, 7.11; N, 8.01.

Example 136

6-[(2E)(4E)-5-Naphthalen-1-yl-penta-2,4-dienoylamino]hexanoic acid methyl ester (3/11)

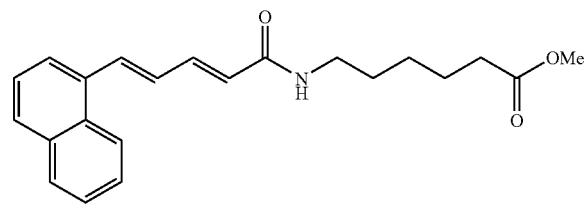

Using an analogous method (J1A), the title compound was obtained from 5-naphthalen-1-yl-penta-2E,4E-dienoic acid (1/11) and methyl 6-aminohexanoate hydrochloride (2c). Yield 77%, m.p. 131-134° C. ¹H NMR (90 MHz, DMSO-d₆) δ: 1.01-1.78 (6H, m, CH₂); 1.96 (2H, t, J=7.0 Hz, CH₂); 3.18 (2H, q, J=5.6 Hz, CH₂N); 3.57 (3H, s, CH₃); 6.24 (1H, d, J=16.0 Hz, CH); 6.87-7.47 (2H, m, CH=CH); 7.47-7.71 (3H, m, C₁₀H₃); 7.71-8.18 (5H, m, C₁₀H₃, CH, NH); 8.18-8.45 (1H, m, C₁₀H).

Example 137

(2E)(4E)-5-Naphthalen-1-yl-penta-2,4-dienoic acid (5-hydroxycarbamoylpentyl)amide (4/11) (PX117237)

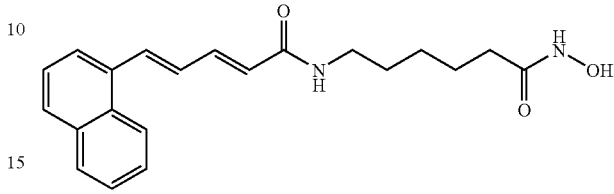

Using an analogous method (J1B), the title compound was obtained. Yield 71%, m.p. 143-145° C. ¹H NMR (90 MHz, DMSO-d₆) δ: 1.01-1.78 (6H, m, CH₂); 1.96 (2H, t, J=7.0 Hz, CH₂); 3.18 (2H, q, J=5.6 Hz, CH₂N); 6.24 (1H, d, J=16.0 Hz, CH); 6.87-7.47 (2H, m, CH=CH); 7.47-7.71 (3H, m, C₁₀H₃); 7.71-8.18 (5H, m, C₁₀H₃, CH, NH); 8.18-8.45 (1H, m, C₁₀H); 8.72 (1H, s, NH); 10.31 (1H, s, OH). HPLC analysis on Symmetry C₁₈ column: impurities 2.5% (column size 3.9×150 mm; mobile phase acetonitrile–0.1M phosphate buffer (pH 2.5), 35:65; detector UV 270 nm; sample concentration 0.5 mg/ml). Anal. Calcd for C₂₁H₂₄N₂O₃: C, 71.57; H, 6.86; N, 7.95. Found: C, 71.38; H, 6.91; N, 7.98.

Example 138

6-{E-3-[1-(4-Chlorophenyl)-1H-pyrrol-2-yl]acryloylamino}hexanoic acid methyl ester (3/12)

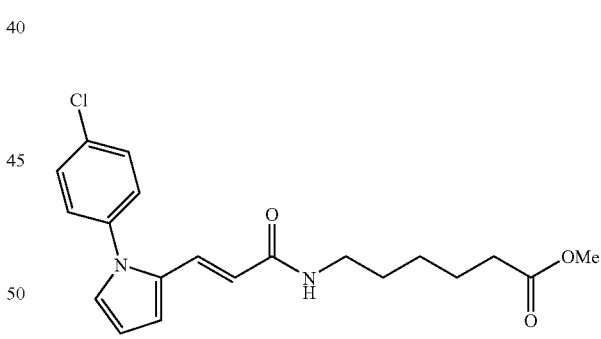

Using an analogous method (J1A), the title compound was obtained from 3-[1-(4-chloro-phenyl)-1H-pyrrol-2-yl]-acrylic acid (1/12) and methyl 6-aminohexanoate hydrochloride (2c). Yield 81%, an oil. ¹H NMR (90 MHz, DMSO-d₆) δ: 1.02-1.72 (6H, m, CH₂); 2.28 (2H, t, J=6.7 Hz, CH₂); 3.14 (2H, q, J=5.6 Hz, CH₂N); 3.57 (3H, s, CH₃); 6.26-6.46 (1H, m, C₄HN); 6.33 (1H, d, J=15.5 Hz, CH); 6.60-6.78 (1H, m, C₄HN); 7.09 (1H, d, J=15.5 Hz, CH); 7.10-7.25 (1H, m, C₄HN); 7.37 (2H, d, J=8.4 Hz, C₆H₂); 7.61 (2H, d, J=8.4 Hz, C₆H₂); 7.95 (1H, t, J=5.0 Hz, NH).

Example 139

E-3-[1-(4-Chlorophenyl)-1H-pyrrol-2-yl]-N-(5-hydroxycarbamoylpentyl)acrylamide (4/12) (PX116235)

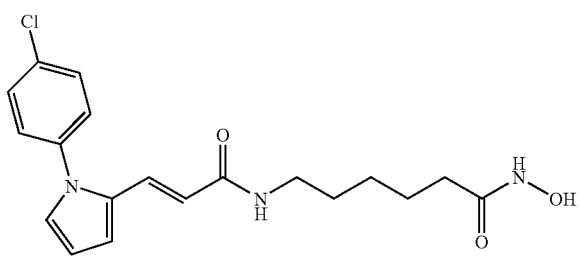

Using an analogous method (J1B), the title compound was obtained. Yield 85%, m.p 167-169° C. $^1$H NMR (90 MHz, DMSO-$d_6$) δ: 1.01-1.69 (6H, m, CH$_2$); 1.78-2.07 (2H, m, CH$_2$); 3.12 (2H, q, J=6.0 Hz, CH$_2$N); 6.27-6.45 (1H, m, C$_4$HN); 6.31 (1H, d, J=15.4 Hz, CH); 6.63-6.76 (1H, m, C$_4$HN); 7.07 (1H, d, J=15.4 Hz, CH); 7.08-7.23 (1H, m, C$_4$HN); 7.36 (2H, d, J=8.4 Hz, C$_6$H$_2$); 7.63 (2H, d, J=8.4 Hz, C$_6$H$_2$); 7.93 (1H, unresolv. t, NH); 8.65 (1H, s, NH), 10.33 (1H, s, OH). HPLC analysis on Symmetry C$_{18}$ column: impurities 2.8% (column size 3.9×150 mm; mobile phase acetonitrile–0.1 M phosphate buffer (pH 2.5), 35:65; detector UV 230 nm; sample concentration 0.4 mg/ml). Anal. Calcd for C$_{19}$H$_{22}$ClN$_3$O$_3$: C, 60.72; H, 5.90; N, 11.18. Found: C, 60.69; H, 5.87; N, 11.27.

Example 140

6-{3-[5-(3,5-Bis-trifluoromethyl-phenyl)-furan-2-yl]-acryloylamino}hexanoic acid methyl ester (3/13)

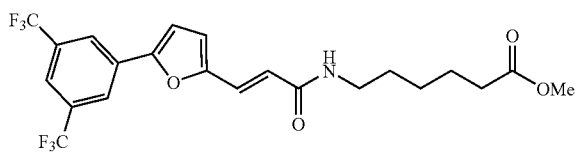

Using an analogous method (J1 A), the title compound was obtained from 3-[5-(3,5-bis-trifluoromethyl-phenyl)-furan-2-yl]-acrylic acid (1/13) and methyl 6-aminohexanoate hydrochloride (2c). Yield 73%, white solid. $^1$H NMR (CDCl$_3$, HMDSO), δ: 1.07-1.85 (6H, m, CH$_2$); 2.33 (2H, t, J=6.6 Hz, CH$_2$); 3.42 (2H, q, J=6.0 Hz, CH$_2$N); 3.68 (3H, s, CH$_3$); 5.82 (1H, br t, J=5.6 Hz, NH); 6.51 (1H, d, J=15.7 Hz, CH=); 6.62 (1H, d, J=3.4 Hz, CH=); 6.88 (1H, d, J=3.4 Hz, CH=); 7.46 (1H, d, J=15.7 Hz, CH=); 7.77 (1H, s, C$_6$H); 8.08 (2H, s, C$_6$H$_2$).

Example 141

(E)-3-{5-[3,5-bis(trifluoromethyl)phenyl]-2-furyl}-N-[6-(hydroxyamino)-6-oxohexyl]2-propenamide (4/13) (PX117224)

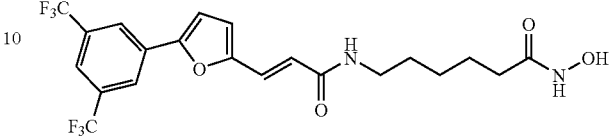

Using an analogous method (J1B), the title compound was obtained. Yield 61%, m.p 186° C. (dec.). $^1$H NMR (DMSO-$d_6$, HMDSO) δ: 1.20-1.36 (m, 2H); 1.36-1.58 (m, 4H); 1.95 (t, 2H, J=7.6 Hz); 3.08-3.23 (m, 2H); 6.64 (d, 1H, J=15.7 Hz); 6.96 (d, 1H, J=3.4 Hz); 7.27 (d,1H, J=15.7 Hz); 7.56 (d,1H, J=3.4 Hz); 8.04 (s, 1H); 8.21 (t, 1H, J=5.4 Hz); 8.37 (s, 2H); 8.66 (d, 1H, J=1.6 Hz); 10.34 (s, 1H). HPLC analysis on Symmetry C$_8$ column: impurities <1% (column size 3.9×150 mm; mobile phase acetonitrile–0.1 M phosphate buffer (pH 2.5), 50:50; detector UV 230 nm; sample concentration 0.15 mg/ml). Anal. Calcd for C$_{21}$H$_{20}$F$_6$N$_2$O$_4$: C, 52.73; H, 4.21; N, 5.86. Found: C, 52.75; H, 4.11; N, 5.82.

Example 142

6-(E-3-Phenylbut-2-enoylamino)hexanoic acid methyl ester (3/14)

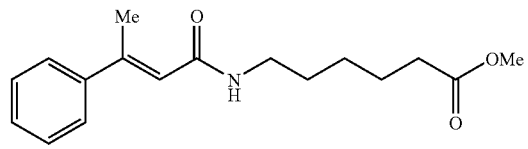

Using an analogous method (J1A), the title compound was obtained from 3-phenyl-but-2E-enoic acid (1/14) and methyl 6-aminohexanoate hydrochloride (2c). Yield 51%, m.p. 131-133° C. $^1$H NMR (90 MHz, DMSO-$d_6$): δ: 0.93-1.66 (6H, m, CH$_2$); 2.29 (2H, t, J=6.5 Hz, CH$_2$); 2.47 (3H, c, CH$_3$, overlapped with DMSO); 3.09 (2H, q, J=5.5 Hz, CH$_2$N); 6.18 (1H, s, CH); 7.07-7.65 (5H, m, C$_6$H$_5$), 7.97 (1H, t, J=5.5, NH).

Example 143

E-3-Phenylbut-2-enoic acid (5-hydroxycarbamoylpentyl)-amide (4/14) (PX117254)

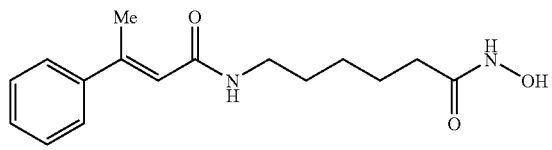

Using an analogous method (J1B), the title compound was obtained. Yield 82%, m.p. 131-133° C. $^1$H NMR (90 MHz, DMSO-d$_6$) δ: 0.83-1.69 (6H, m, CH$_2$); 1.78-2.12 (2H, m, CH$_2$); 2.47 (3H, c, CH$_3$, overlapped with DMSO); 2.89-3.34 (2H, m, CH$_2$N); 6.23 (1H, s, CH); 7.05-7.62 (5H, m, C$_6$H$_5$); 7.97 (1H, unresolv. t, NH); 8.76 (1H, br s, NH), 10.31 (1H, br s, OH). HPLC analysis on Symmetry C$_{18}$ column: impurities <1% (column size 3.9×150 mm; mobile phase acetonitrile–0.1M phosphate buffer (pH 2.5), 30:70; detector UV 270 nm; sample concentration 0.1 mg/ml). Anal. Calcd for C$_{16}$H$_{22}$N$_2$O$_3$: C, 66.19; H, 7.64; N, 9.65. Found: C, 66.19; H, 7.66; N, 9.68.

Example 144

6-[E-3-(1-Methyl-1H-pyrrol-2-yl)acryloylamino]hexanoic acid methyl ester (3/15)

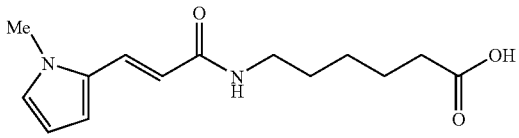

Using an analogous method (J1A), the title compound was obtained from 3-(1-methyl-1H-pyrrol-2-yl)-acrylic acid (1/5) and methyl 6-aminohexanoate hydrochloride (2c). Yield 64%, an oil. $^1$H NMR (90 MHz, DMSO-d$_6$) δ: 1.03-1.74 (6H, m, CH$_2$); 2.29 (2H, t, J=6.5 Hz, CH$_2$); 3.14 (2H, q, J=5.6 Hz, CH$_2$N); 3.58 (3H, s, CH$_3$); 3.65 (3H, s, CH$_3$); 6.05 (1H, dd, J=2.4 Hz, J=3.8 Hz, CH); 6.27 (1H, d, J=15.0 Hz, CH); 6.47 (1H, dd, J=1.8 Hz, J=3.8 Hz, CH); 6.87 (1H, t, J=2.0 Hz, CH); 7.32 (1H, d, J=15.0 Hz, CH); 7.87 (1H, t, J=5.0 Hz, NH).

Example 145

E-3-(1-Methyl-1H-pyrrol-2-yl)-N-(5-hydroxycarbamoylpentyl)-acrylamide (4/15) (PX117239)

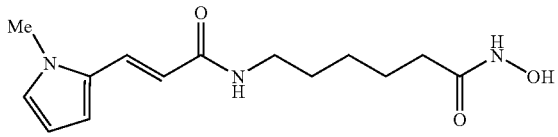

Using an analogous method (J1B), the title compound was obtained. Yield 48%, m.p. 103-105° C. $^1$H NMR (90 MHz, DMSO-d$_6$) δ: 1.05-1.72 (6H, m, CH$_2$); 1.94 (2H, t, J=6.5 Hz, CH$_2$); 3.14 (2H, q, J=5.7 Hz, CH$_2$N); 3.66 (3H, s, CH$_3$); 6.07 (1H, dd, J=2.4 Hz, J=3.8 Hz, CH); 6.27 (1H, d, J=16.0 Hz, CH); 6.49 (1H, dd, J=1.8 Hz, J=3.8 Hz, CH); 6.89 (1H, t, J=2.0 Hz, CH); 7.16 (1H, d, J=16.0 Hz, CH); 7.89 (1H, t, J=5.0 Hz, NH); 8.65 (1H, s, NH), 10.34 (1H, s, OH). HPLC analysis on Symmetry C$_{18}$ column: impurities 3% (column size 3.9×150 mm; mobile phase acetonitrile–0.1 M phosphate buffer (pH 2.5), 20:80; detector UV 220 nm; sample concentration 0.5 mg/ml). Anal. Calcd for C$_{14}$H$_{21}$N$_3$O$_3$: C, 60.20; H, 7.58; N, 15.04. Found: C, 60.07; H, 7.54; N, 15.20.

Example 146

6-(E-4-Phenylbut-2-enoylamino)hexanoic acid methyl ester (3/16)

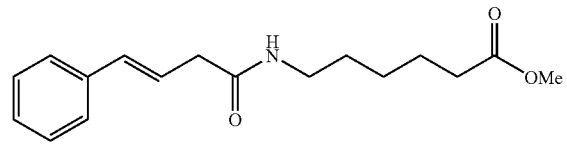

Using an analogous method (J1A), the title compound was obtained from 4-phenyl-but-2E-enoic acid (1/16) and methyl 6-aminohexanoate hydrochloride (2c). Yield 49%, m.p. 49-51° C. $^1$H NMR (90 MHz, DMSO-d$_6$) δ: 0.98-1.70 (6H, m, CH$_2$); 2.25 (2H, t, J=6.7 Hz, CH$_2$); 2.91-3.13 (4H, m, CH$_2$); 3.57 (3H, s, CH$_3$); 6.09-6.58 (2H, m, CH=CH); 7.03-7.75 (5H, m, C$_6$H$_5$); 7.85 (1H, unresolv. t, NH).

Example 147

E-4-Phenylbut-2-enoic acid (5-hydroxycarbamoylpentyl)-amide (4/16) (PX116211)

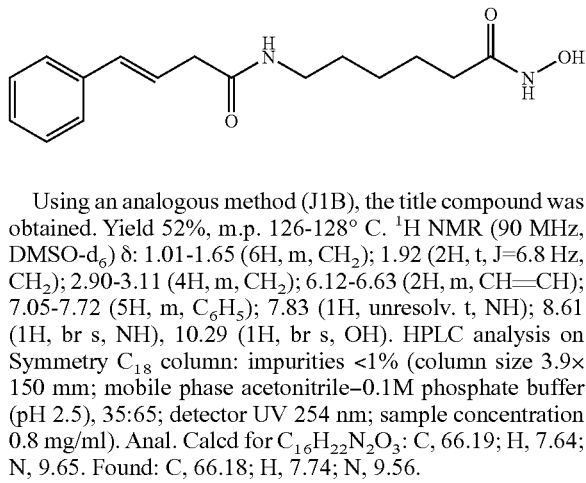

Using an analogous method (J1B), the title compound was obtained. Yield 52%, m.p. 126-128° C. $^1$H NMR (90 MHz, DMSO-d$_6$) δ: 1.01-1.65 (6H, m, CH$_2$); 1.92 (2H, t, J=6.8 Hz, CH$_2$); 2.90-3.11 (4H, m, CH$_2$); 6.12-6.63 (2H, m, CH=CH); 7.05-7.72 (5H, m, C$_6$H$_5$); 7.83 (1H, unresolv. t, NH); 8.61 (1H, br s, NH), 10.29 (1H, br s, OH). HPLC analysis on Symmetry C$_{18}$ column: impurities <1% (column size 3.9×150 mm; mobile phase acetonitrile–0.1M phosphate buffer (pH 2.5), 35:65; detector UV 254 nm; sample concentration 0.8 mg/ml). Anal. Calcd for C$_{16}$H$_{22}$N$_2$O$_3$: C, 66.19; H, 7.64; N, 9.65. Found: C, 66.18; H, 7.74; N, 9.56.

Example 148

4-[(2E)(4E)-5-(2-Chlorophenyl)penta-2,4-dienoylamino]butyric acid methyl ester (3/17)

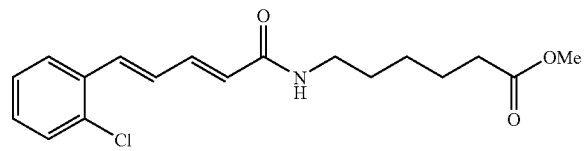

Using an analogous method (J1A), the title compound was obtained from 5-(2-chloro-phenyl)-penta-2E,4E-dienoic acid (1/17) and methyl 6-aminohexanoate hydrochloride (2c). Yield 61%, m.p. 110-112° C. $^1$H NMR (90 MHz, DMSO-$d_6$) δ: 1.10-1.70 (6H, m, $CH_2$); 2.29 (2H, t, J=6.5 Hz, $CH_2$); 3.16 (2H, q, J=5.7 Hz, $CH_2$N); 3.56 (3H, s, $CH_3$); 6.25 (1H, d, J=15.7 Hz, CH); 7.03-7.64(6H, m, CH=CH—CH, $C_6H_3$); 7.72-7.96 (1H, m, $C_6$H); 8.09 (1H, d, J=5.7 Hz, NH).

Example 149

(2E)(4E)-5-(2-Chlorophenyl)penta-2,4-dienoic acid (5-hydroxycarbamoylpentyl)amide (4/17) (PX117255)

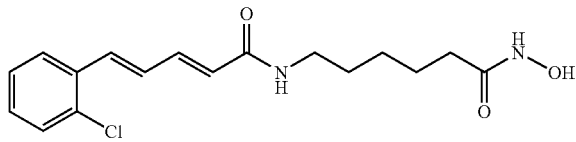

Using an analogous method (J1B), the title compound was obtained. Yield 87%, m.p. 129-131° C. $^1$H NMR (90 MHz, DMSO-$d_6$) δ: 1.05-1.67 (6H, m, $CH_2$); 1.95 (2H, t, J=6.6 Hz, $CH_2$); 3.14 (2H, q, J=5.8 Hz, $CH_2$N); 6.22 (1H, d, J=15.8 Hz, CH); 7.01-7.61(6H, m, CH=CH—CH, $C_6H_3$); 7.74-7.94 (1H, m, $C_6$H); 8.07 (1H, d, J=5.5 Hz, NH); 8.61 (1H, s, NH); 10.29 (1H, s, OH). HPLC analysis on Symmetry $C_{18}$ column: impurities 2.5% (column size 3.9×150 mm; mobile phase acetonitrile—0.1M phosphate buffer (pH 2.5), 40:60; detector UV 270 nm; sample concentration 0.7 mg/ml). Anal. Calcd for $C_{17}H_{21}ClN_2O_3$: C, 60.62; H, 6.28; N, 8.32. Found: C, 60.37; H, 6.22; N, 8.07.

Example 150

6-[E-3-(3-Phenoxyphenyl)acryloylamino]hexanoic acid methyl ester (3/18)

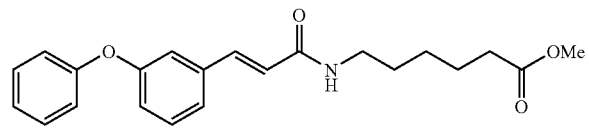

Using an analogous method (J1A), the title compound was obtained from 3-(3-phenoxy-phenyl)-acrylic acid (1/18) and methyl 6-aminohexanoate hydrochloride (2c). Yield 84%, an oil. $^1$H NMR (90 MHz, DMSO-$d_6$) δ: 1.01-1.71 (6H, m, $CH_2$); 2.29 (2H, t, J=6.6 Hz, $CH_2$); 3.18 (2H, q, J=5.7 Hz, $CH_2$N); 3.59 (3H, s, $CH_3$); 6.53 (1H, d, J=15.7 Hz, CH); 6.78-7.60 (10H, m, $C_6H_5$, CH); 8.01 (1H, t, J=5.2 Hz, NH).

Example 151

E-N-(5-Hydroxycarbamoylpentyl)-3-(3-phenoxyphenyl)acrylamide (4/18) (PX117430)

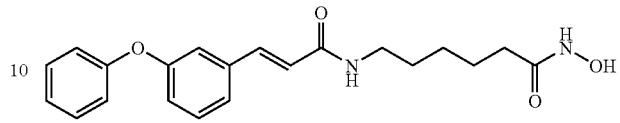

Using an analogous method (J1B), the title compound was obtained. Yield 45%, m.p. 113-115° C. $^1$H NMR (90 MHz, DMSO-$d_6$) δ: 1.03-1.68 (6H, m, $CH_2$); 1.93 (2H, t, J=6.5 Hz, $CH_2$); 3.14 (2H, q, J=5.8 Hz, $CH_2$N); 6.57 (1H, d, J=15.8 Hz, CH); 6.81-7.58 (10H, m, $C_6H_5$, CH); 8.04 (1H, t, J=5.3 Hz, NH); 8.79 (1H, s, NH), 10.33 (1H, s, OH). HPLC analysis on Symmetry $C_{18}$ column: impurities 1.0% (column size 3.9×150 mm; mobile phase acetonitrile–0.1M phosphate buffer (pH 2.5), 45:55; detector UV 230 nm; sample concentration 0.5 mg/ml). Anal. Calcd for $C_{21}H_{24}N_2O_4$: C, 68.46; H, 6.57; N, 7.60. Found: C, 68.28; H, 6.57; N, 7.60.

Example 152

6-(E-3,3-Diphenyl-acryloylamino)hexanoic acid methyl ester (3/19)

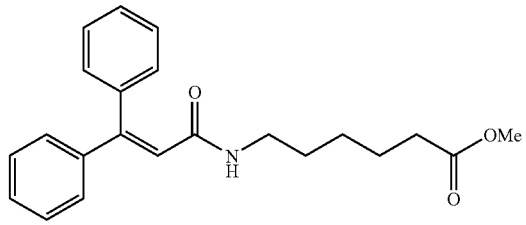

Using an analogous method (J1A), the title compound was obtained from 3,3-diphenyl-acrylic acid (1/19) and methyl 6-aminohexanoate hydrochloride (2c). Yield 82%, an oil. $^1$H NMR (90 MHz, DMSO-$d_6$) δ: 0.91-1.70 (6H, m, $CH_2$); 2.30 (2H, t, J=6.9 Hz, $CH_2$); 3.01 (2H, q, J=5.6 Hz, $CH_2$N); 3.59 (3H, s, $CH_3$); 6.45 (1H, s, CH); 7.03-7.50 (10H, m, $C_6H_5$); 7.80 (1H, t, J=5.0 Hz, NH).

Example 153

E-N-(5-Hydroxycarbamoylpentyl)-3,3-diphenylacrylamide (4/19) (PX117436)

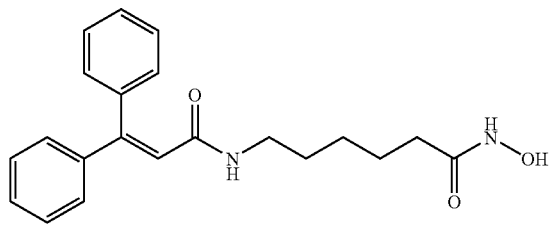

Using an analogous method (J1B), the title compound was obtained. Yield 63%, m.p. 123-125° C. $^1$H NMR (90 MHz, DMSO-d$_6$) δ: 0.90-1.63 (6H, m, CH$_2$); 2.01 (2H, t, J=7.0 Hz, CH$_2$); 2.97 (2H, q, J=5.5 Hz, CH$_2$N); 6.43 (1H, s, CH); 7.01-7.47 (10H, m, C$_6$H$_5$); 7.78 (1H, t, J=5.0 Hz, NH); 8.63 (1H, s, NH), 10.32 (1H, s, OH). HPLC analysis on Symmetry C$_{18}$ column: impurities 1.0% (column size 3.9×150 mm; mobile phase acetonitrile–0.1 M phosphate buffer (pH 2.5), 30:70; detector UV 230 nm; sample concentration 0.5 mg/ml). Anal. Calcd for C$_{21}$H$_{24}$N$_2$O$_3$: C, 71.57; H, 6.86; N, 7.95. Found: C, 71.56, H, 6.87; N, 7.98.

Example 154

2E-6-(5,5-Diphenylpenta-2,4-dienoylamino)hexanoic acid methyl ester (3/20)

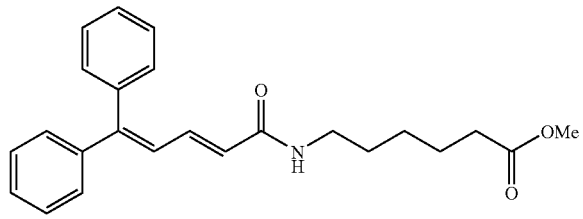

Using an analogous method (J1A), the title compound was obtained from 5,5-diphenyl-penta-2E,4-dienoic acid (1/20) and methyl 6-aminohexanoate hydrochloride (2c). Yield 84%, an oil. $^1$H NMR (90 MHz, DMSO-d$_6$) δ: 1.00-1.61 (6H, m, CH$_2$); 2.25 (2H, t, J=7.0 Hz, CH$_2$); 3.06 (2H, q, J=5.8 Hz, CH$_2$N); 3.59 (3H, s, CH$_3$); 6.16-6.36 (1H, m, CH); 6.86-7.04 (2H, m, CH—CH); 7.11-7.60 (5H, m, C$_6$H$_5$); 8.03 (1H, t, J=5.5 Hz, NH).

Example 155

2E-5,5-Diphenylpenta-2,4-dienoic acid (5-hydroxycarbamoylpentyl)amide (4/20) (PX117437)

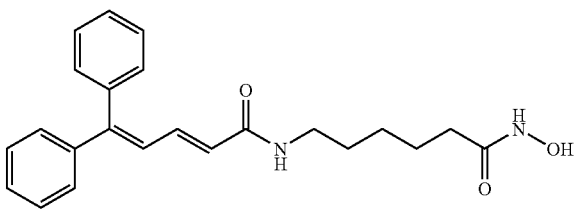

Using an analogous method (J1B), the title compound was obtained. Yield 91%, m.p. 167-169° C. $^1$H NMR (90 MHz, DMSO-d$_6$) δ: 1.02-1.58 (6H, m, CH$_2$); 1.93 (2H, t, J=7.1Hz, CH$_2$); 3.06 (2H, q, J=5.8 Hz, CH$_2$N); 6.15-6.35 (1H, m, CH); 6.88-7.02 (2H, m, CH—CH); 7.10-7.58 (5H, m, C$_6$H$_5$); 8.07 (1H, t, J=5.0 Hz, NH); 8.67 (1H, s, NH); 10.34 (1H, s, OH). HPLC analysis on Symmetry C$_{18}$ column: impurities <1% (column size 3.9×150 mm; mobile phase acetonitrile–0.1 M phosphate buffer (pH 2.5), 35:65; detector UV 254 nm; sample concentration 0.5 mg/ml). Anal. Calcd for C$_{23}$H$_{26}$N$_2$O$_3$: C, 72.99; H, 6.92; N, 7.40. Found: C, 72.64; H, 6.89; N, 7.32.

Example 156

6-(E-2-Methyl-5-phenylpent-2-en-4-ynoylamino)hexanoic acid methyl ester (3/21)

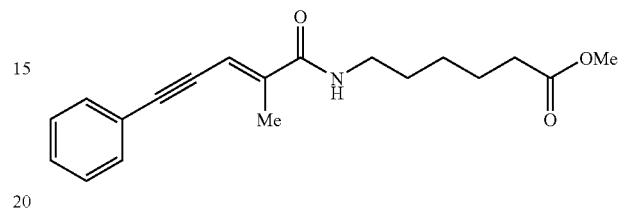

Using an analogous method (J1A), the title compound was obtained from 2-methyl-5-phenyl-pent-2E-en-4-ynoic acid (1/21) and methyl 6-aminohexanoate hydrochloride (2c). Yield 62%, m.p. 62-64° C. $^1$H NMR (90 MHz, DMSO-d$_6$) δ: 1.03-1.70 (6H, m, CH$_2$); 2.26 (2H, t, J=6.6 Hz, CH$_2$); 2.09 (3H, s, CH$_3$); 3.14 (2H, q, J=5.6 Hz, CH$_2$N); 3.56 (3H, s, CH$_3$); 6.50 (1H, s, CH); 7.30-7.74 (5H, m, C$_6$H$_5$); 8.06 (1H, t, J=5.0 Hz, NH).

Example 157

E-2-Methyl-5-phenylpent-2-en-4-ynoic acid (5-hydroxycarbamoyl-pentyl)amide (4/21) (PX117451)

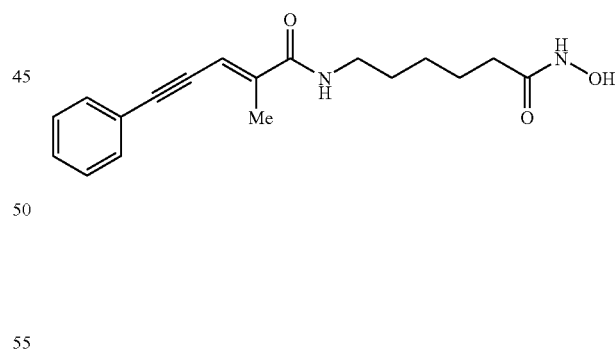

Using an analogous method (J1B), the title compound was obtained. Yield 85%, m.p. 135-137° C. $^1$H NMR (90 MHz, DMSO-d$_6$) δ: 1.01-1.72 (6H, m, CH$_2$); 1.96 (2H, t, J=6.5 Hz, CH$_2$); 2.08 (3H, s, CH$_3$); 3.15 (2H, q, J=5.5 Hz, CH$_2$N); 6.49 (1H, s, CH); 7.33-7.72 (5H, m, C$_6$H$_5$); 8.03 (1H, t, J=5.0 Hz, NH); 9.52 (2H, br s, NH, OH). HPLC analysis on Symmetry C$_{18}$ column: impurities 1.4% (column size 3.9×150 mm; mobile phase acetonitrile–0.1M phosphate buffer (pH 2.5), 35:65; detector UV 230 nm; sample concentration 0.3 mg/ml). Anal. Calcd for C$_{18}$H$_{22}$N$_2$O$_3$: C, 68.77; H, 7.05; N, 8.91. Found: C, 68.61; H, 7.12; N, 8.84.

Example 158

6-(E-4,4-Diphenylbut-3-enoylamino)hexanoic acid methyl ester (3/22)

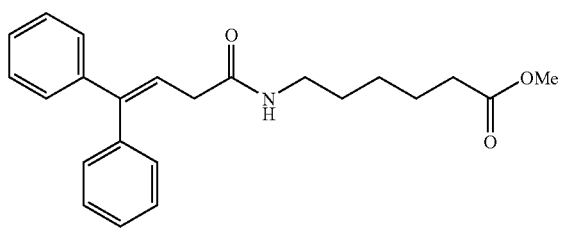

Using an analogous method (J1A), the title compound was obtained from 4,4-diphenyl-but-3-enoic acid (1/22) and methyl 6-aminohexanoate hydrochloride (2c). Yield 60%, an oil. $^1$H NMR (90 MHz, DMSO-$d_6$) δ: 0.94-1.65 (6H, m, CH$_2$); 2.25 (2H, t, J=6.9 Hz, CH$_2$); 2.94 (2H, d, J=7.0 Hz, CH$_2$); 3.04 (2H, q, J=6.0 Hz, CH$_2$N); 3.58 (3H, s, CH$_3$); 6.27 (1H, t, J=7.0 Hz, CH); 6.94-7.69 (11H, m, C$_6$H$_5$, CH); 7.76 (1H, unresolv t, NH).

Example 159

E-4,4-Diphenylbut-3-enoic acid (5-hydroxycarbamoylpentyl)amide (4/22) (PX117454)

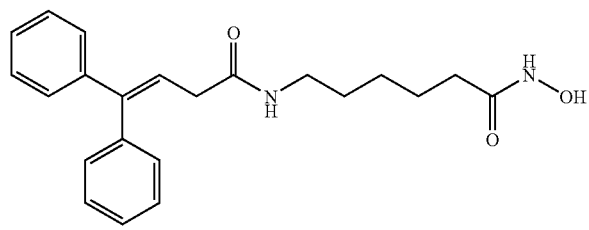

Using an analogous method (J1B), the title compound was obtained. Yield 63%, m.p. 101-103° C. $^1$H NMR (90 MHz, DMSO-$d_6$) δ: 0.94-1.65 (6H, m, CH$_2$); 1.92 (2H, t, J=7.0 Hz, CH$_2$); 2.72-3.16 (4H, m, CH$_2$); 6.24 (1H, t, J=7.5 Hz, CH); 6.98-7.56 (11H, m, C$_6$H$_5$, CH); 7.79 (1H, t, J=5.0 Hz, NH); 9.49 (1H, br s, NH, OH). HPLC analysis on Symmetry C$_{18}$ column: impurities 1.0% (column size 3.9×150 mm; mobile phase acetonitrile–0.1M phosphate buffer (pH 2.5), 35:65; detector UV 230 nm; sample concentration 0.5 mg/ml). Anal. Calcd for C$_{22}$H$_{26}$N$_2$O$_3$: C, 71.57; H, 6.86; N, 7.95. Found: C, 71.56, H, 6.87; N, 7.98.

Example 160

6-(E-2-Methyl-3-phenylbut-2-enoylamino)hexanoic acid methyl ester (3/23)

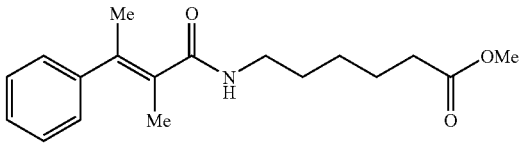

Using an analogous method (J1A), the title compound was obtained from 2-methyl-3-phenyl-but-2E-enoic acid (1/23) and methyl 6-aminohexanoate hydrochloride (2c). Yield 52%, m.p 104-106° C. $^1$H NMR (90 MHz, DMSO-$d_6$) δ: 1.07-1.76 (6H, m, CH$_2$); 1.72 (3H, q, J=1.0 Hz, CH$_3$); 2.01 (3H, q, J=1.0 Hz, CH$_3$); 2.34 (2H, t, J=6.8 Hz, CH$_2$); 3.15 (2H, q, J=5.6 Hz CH$_2$N); 3.63 (3H, s, CH$_3$); 7.15-7.64 (5H, m, C$_6$H$_5$); 7.98 (1H, t, J=5.0 Hz, NH).

Example 161

E-2-Methyl-3-phenylbut-2-enoic acid (5-hydroxycarbamoylpentyl)amide (4/23) (PX117737)

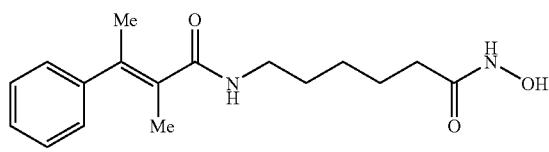

Using an analogous method (J1B), the title compound was obtained. Yield 71%, m.p 129-131° C. $^1$H NMR (90 MHz, DMSO-$d_6$) δ: 1.07-1.69 (6H, m, CH$_2$); 1.63 (3H, q, J=1.0 Hz, CH$_3$); 1.78-2.05 (2H, m, CH$_2$); 1.94 (3H, q, J=1.0 Hz, CH$_3$); 3.13 (2H, q, J=5.5 Hz CH$_2$N); 7.07-7.58 (5H, m, C$_6$H$_5$); 7.93 (1H, t, J=5.5 Hz, NH); 8.61 (1H, s, NH), 10.31 (1H, s, OH). HPLC analysis on Symmetry C$_{18}$ column: impurities 1.5% (column size 3.9×150 mm; mobile phase acetonitrile—0.1M phosphate buffer (pH 2.5), 35:65; detector UV 254 nm; sample concentration 0.5 mg/ml). Anal. Calcd for C$_{17}$H$_{24}$N$_2$O$_3$: C, 67.08; H, 7.95; N, 9.20. Found: C, 66.74; H, 7.98; N, 9.20.

Example 162

6-[(2E)(4E)-2,4-Dimethyl-5-phenylpenta-2,4-dienoylamino]hexanoic acid methyl ester (3/24)

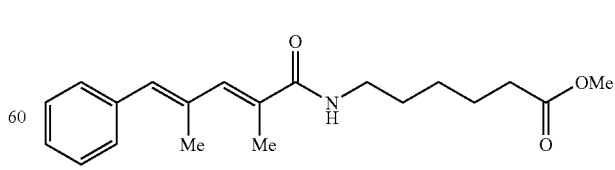

Using an analogous method (J1A), the title compound was obtained from 2,4-dimethyl-5-phenyl-penta-2E,4E-dienoic acid (1/24) and methyl 6-aminohexanoate hydrochloride (2c). Yield 92%, m.p. 58-60° C. $^1$H NMR (90 MHz, DMSO-d$_6$) δ: 1.05-1.74 (6H, m, CH$_2$); 1.94-2.09 (6H, m, CH$_3$); 2.29 (2H, t, J=6.6 Hz, CH$_2$); 3.14 (2H, q, J=5.8 Hz CH$_2$N); 3.61 (3H, s, CH$_3$); 6.55 (1H, s, CH); 6.77 (1H, s, CH); 7.21-7.49 (5H, m, C$_6$H$_5$); 7.87 (1H, t, J=5.2 Hz, NH).

Example 163

(2E)(4E)-2,4-Dimethyl-5-phenylpenta-2,4-dienoic acid (5-hydroxycarbamoyl-pentyl)amide (4/24) (PX117738)

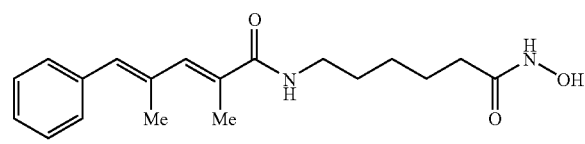

Using an analogous method (J1B), the title compound was obtained. Yield 86%, m.p. 120-122° C. $^1$H NMR (200 MHz, DMSO-d$_6$) δ: 1.10-1.34 (2H, m, CH$_2$); 1.34-1.58 (4H, m, CH$_2$); 1.95 (2H, t, J=7.4 Hz, CH$_2$); 2.00 (3H, s, CH$_3$); 2.04 (3H, s, CH$_3$); 3.11 (2H, q, J=6.1Hz CH$_2$N); 6.55 (1H, s, CH); 6.77 (1H, s, CH); 7.20-7.46 (5H, m, C$_6$H$_5$); 7.89 (1H, t, J=5.3 Hz, NH); 8.67 (1H, s, NH), 10.34 (1H, s, OH). HPLC analysis on Symmetry C$_{18}$ column: impurities 1.5% (column size 3.9×150 mm; mobile phase acetonitrile–0.1M phosphate buffer (pH 2.5), 50:50; detector UV 254 nm; sample concentration 0.5 mg/ml). Anal. Calcd for C$_{19}$H$_{26}$N$_2$O$_3$: C, 69.06; H, 7.93; N, 8.48. Found C, 68.63; H, 7.91; N, 8.58.

Example 164

6-(2-Fluoren-9-ylideneacetylamino)hexanoic acid methyl ester (3/25)

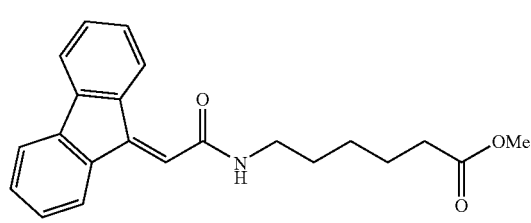

Using an analogous method (J1A), the title compound was obtained from fluoren-9-ylidene-acetic acid (1/25) and methyl 6-aminohexanoate hydrochloride (2c). Yield 73%, m.p. 54-56° C. $^1$H NMR (90 MHz, DMSO-d$_6$) δ: 1.05-1.76 (6H, m, CH$_2$); 2.28 (2H, t, J=7.3 Hz, CH$_2$); 3.27 (2H, q, J=6.1 Hz, CH$_2$); 3.59 (3H, s, CH$_3$); 7.11 (1H, s, CH); 7.22-7.59 (4H, m, C$_{13}$H$_4$); 7.64-7.95 (3H, m, C$_{13}$H$_3$); 8.51 (1H, t, J=5.2 Hz, NH); 8.62-8.84 (1H, m, C$_{13}$H).

Example 165

6-(2-Fluoren-9-ylideneacetylamino)hexanoic acid hydroxyamide (4/25) (PX117456)

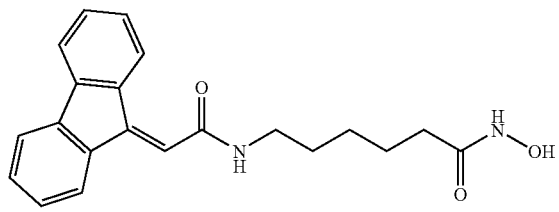

Using an analogous method (J1B), the title compound was obtained. Yield 84%, m.p. 174-176° C. $^1$H NMR (90 MHz, DMSO-d$_6$) δ: 1.02-1.74 (6H, m, CH$_2$); 1.97 (2H, t, J=7.5 Hz, CH$_2$); 3.25 (2H, q, J=6.0 Hz, CH$_2$); 7.09 (1H, s, CH); 7.21-7.56 (4H, m, C$_{13}$H$_4$); 7.69-7.94 (3H, m, C$_{13}$H$_3$); 8.49 (1H, t, J=5.0 Hz, NH); 8.59-8.81 (1H, m, C$_{13}$H); 8.65 (1H, s, NH), 10.34 (1H, s, OH). HPLC analysis on Symmetry C$_{18}$ column: impurities 2.0% (column size 3.9×150 mm; mobile phase acetonitrile–0.1M phosphate buffer (pH 2.5), 45:55; detector UV 254 nm; sample concentration 0.25 mg/ml). Anal. Calcd for C$_{21}$H$_{22}$N$_2$O$_3$: C, 71.98; H, 6.33; N, 7.99. Found: C, 71.91; H, 6.37; N, 8.03.

Example 166

6-(E-3-Pyridin-3-yl-acryloylamino)hexanoic acid methyl ester (3/26)

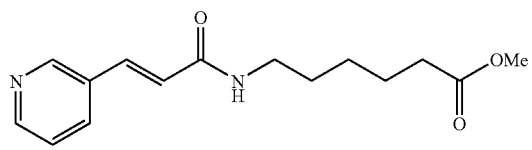

Using an analogous method (J1A), the title compound was obtained from 3-pyridin-3-yl-acrylic acid (1/26) and methyl 6-aminohexanoate hydrochloride (2c). Yield 52%, m.p. 75-77° C. $^1$H NMR (90 MHz, DMSO-d$_6$) δ: 1.01-1.78 (6H, m, CH$_2$); 225 (2H, t, J=7.2 Hz, CH$_2$); 3.16 (2H, q, J=6.0 Hz, CH$_2$N); 3.57 (3H, s, CH$_3$); 6.75 (1H, d, J=16.0 Hz, CH); 7.49 (1H, d, J=16.0 Hz, CH); 7.49 (1H, dd, J=3.2 Hz and J=8.6 Hz, C$_5$HN); 7.98 (1H, dt, J=3.2 Hz and J=8.6 Hz, C$_5$HN); 8.14 (1H, t, J=5.3 Hz, NH); 8.56 (1H, dd, J=1.6 Hz and J=4.4 Hz, C$_5$HN); 8.76 (1H, d, J=1.6 Hz, C$_5$HN).

Example 167

E-N-(5-Hydroxycarbamoyl-pentyl)-3-pyridin-3-yl-acrylamide oxalate (4/26) (PX116231)

(Isolated in the Form of a Salt with Oxalic Acid)

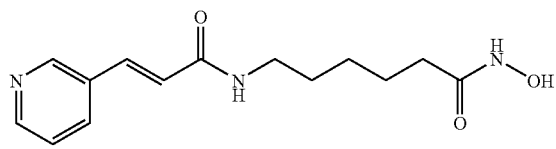

A solution of sodium methylate (6 mmol) in methanol (5 ml) was added to a solution of hydroxylamine hydrochloride (0.28 g, 4 mmol) in methanol (8 ml). The mixture was stirred for 10 min, and NaCl was filtered off. 6-(E-3-Pyridin-3-yl-acryloylamino)hexanoic acid methyl ester (3/26) (0.28 g, 1 mmol) was added to the filtrate and the resultant mixture was stirred for 4 hours at ambient temperature. The solvent was removed under reduced pressure, product was dissolved in ethanol (10 ml), and then oxalic acid (0.36 g, 4 mmol) was added to the solution. The precipitate was filtered off and crystallized from water. The title compound (0.22 g, 68%) was obtained as a white solid. M.p. 157-159° C. $^1$H NMR (200 MHz, DMSO-$d_6$) δ: 1.03-1.72 (6H, m, $CH_2$); 1.96 (2H, t, J=7.2 Hz, $CH_2$); 3.18 (2H, q, J=6.0 Hz, $CH_2$N); 6.74 (1H, d, J=15.8 Hz, CH); 7.45 (1H, d, J=15.8 Hz, CH); 7.49 (1H, dd, J=3.0 Hz and J=8.5 Hz, $C_5$HN); 7.98 (1H, dt, J=3.0 Hz and J=8.5 Hz, $C_5$HN); 8.18 (1H, t, J=5.2 Hz, NH); 8.54 (1H, dd, J=1.6 Hz and J=4.4 Hz, $C_5$HN); 8.75 (1H, d, J=1.6 Hz, $C_5$HN); 10.34 (1H, s, OH). HPLC analysis on Zorbax SB-C18 column: impurities 2.0% (column size 4.6×150 mm; mobile phase gradient 10 min 5-100% acetonitrile –0.1% $H_3PO_4$; detector UV 220 nm; sample concentration 1.0 mg/ml). Anal. Calcd for $C_{14}H_{19}N_3O_3$*0.5(COOH)$_2$* 2H$_2$O: C, 50.27; H, 6.75; N, 11.73. Found: C, 50.28; H, 6.71; N, 11.60.

Example 168

6-{Methyl-[(2E)(4E)-5-phenylpenta-2,4-dienoyl]amino}hexanoic acid methyl ester (3/27)

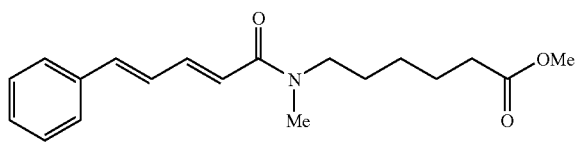

Using an analogous method (J1A), the title compound was obtained was prepared from 5-phenyl-penta-2E,4E-dienoic acid (1/1) and methyl 6-N-methylaminohexanoate hydrochloride (2d) by the method of example 1. Yield 69%, oil. $^1$H NMR (90 MHz, DMSO-$d_6$): δ: 0.98-1.77 (6H, m, $CH_2$); 2.29 (2H, t, J=6.5 Hz, $CH_2$); 2.87 and 3.03 (3H, s,s, $CH_3$); 3.38 (2H, unresolv. t, $CH_2$N); 3.56 (3H, s, $CH_3$); 6.78 (1H, d, J=15.5 Hz, CH); 6.85-7.75 (8H, m, $C_6H_5$, CH—CH=CH).

Example 169

[(2E)(4E)-5-Phenylpenta-2,4-dienoic acid (5-hydroxycarbamoylpentyl)methylamide (4/28) (PX116234)

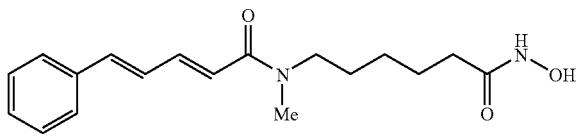

Using an analogous method (J1B), the title compound was obtained was prepared from 6-{methyl-[(2E)(4E)-5-phenyl-penta-2,4-dienoyl]amino}hexanoic acid methyl ester (3/27) by the method of example 1. Yield (40%), m.p. 145-147° C. $^1$H NMR (90 MHz, DMSO-$d_6$): 6:0.96-1.74 (6H, m, $CH_2$); 1.78-2.06 (2H, m, $CH_2$); 2.89 and 3.05 (3H, s,s, $CH_3$); 3.35 (2H, unresolv. t, $CH_2$N); 6.64 (1H, d, J=14.5 Hz, CH); 6.83-7.72 (8H, m, $C_6H_5$, CH—CH=CH); 8.69 (1H, s, NH), 10.36 (1H, s, OH). HPLC analysis on Symmetry $C_{18}$ column: impurities <1% (column size 3.9×150 mm; mobile phase acetonitrile–0.1M phosphate buffer (pH 2.5), 35:65; detector UV 230 nm; sample concentration 0.25 mg/ml). Anal. Calcd for $C_{18}H_{24}N_2O_3$: C, 68.33, H, 7.65; N, 8.85. Found C, 68.15; H, 7.67; N, 8.88.

Example 170

6-(2-1H-Indol-3-yl-acetylamino)-hexanoic acid methyl ester (3/33)

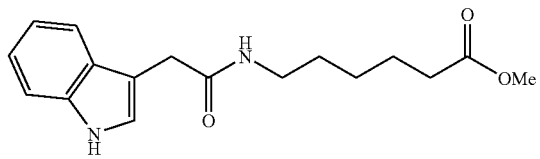

The title compound was obtained from (1H-indol-3-yl)-acetic acid (1/33) using the following method. Yield 83%. $^1$H NMR (CDCl$_3$, HMDSO), δ: 1.15-1.78(m, 6H); 2.29(t, J=7.0 Hz, 2H); 3.37(q, J=6.0 Hz, 2H); 3.46(s, 2H); 3.63(s, 3H); 6.00(br s, 1H); 6.97-8.15(m, 6H).

(Method J4A) A solution of carboxylic acid 1/33-1/52 (2.75 mmol) in dry dimethylformamide (3 ml) under argon atmosphere was cooled in ice bath and 1,1'-carbonyldiimidazole (490 mg, 3.01 mmol) was added. The mixture was stirred for 30 min, and then triethylamine (1.0 ml, 7.2 mmol) followed by a solution of methyl 6-aminohexanoate hydrochloride (2c) (2.75 mmol) in dry dimethylformamide (3 ml) were added. The reaction mixture was stirred at ice bath temperature for 1 hour and 20 hours at room temperature, diluted with 50 ml of brine and extracted with ethyl acetate (3×25 ml). The organic phase was washed with brine, 5% NaHCO$_3$, brine, saturated KH$_2$PO$_4$, and brine. The organic layer was dried (Na$_2$SO$_4$) and the solvent was evaporated. The residue was purified on silica gel (20 g) with chloroform-ethyl acetate as eluent affording the corresponding amidoester derivative 3/33-3/52.

Example 171

6-(2-1H-lndol-3-yl-acetylamino)-hexanoic acid hydroxyamide (PX116214)

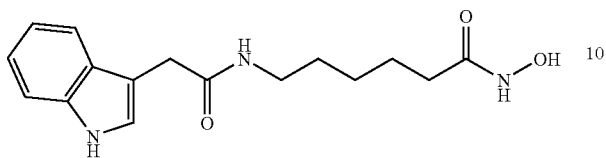

The title compound was obtained from 6-(2-1H-indol-3-yl-acetylamino)-hexanoic acid methyl ester (3/33) using the following method. M.p. 130-131.5° C. $^1$H NMR (DMSO-d$_6$, HMDSO), δ: 1.13-1.53(m, 6H); 1.91(t, J=7.2 Hz, 2H); 3.01 (q, J=6.0 Hz, 2H); 6.91-7.09(m, 4H); 7.16(d, J=2.2 Hz, 1H); 7.32(d, J=7.4 Hz, 1H); 7.52(d, J=7.4 Hz, 1H); 7.85(t, J=5.4 Hz, 1H); 8.65(s, 1H); 10.32(s, 1H); 10.83(s, 1H). HPLC analysis on Zorbax SB-C18 column: impurities 2.6% (column size 4.6×150 mm; mobile phase gradient 10 min 30-100% acetonitrile +0.1% H$_3$PO$_4$; detector UV 220 nm; sample concentration 0.56 mg/ml). Anal. Calcd for C$_{16}$H$_{21}$N$_3$O$_3$: C, 63.35; H, 6.98; N, 13.85. Found: C, 63.27; H, 6.99; N, 13.89.

(Method J4B) An appropriate amidoester 3/33-3/52 (1 mmol) was dissolved in methanol (3-5 ml), and solutions of hydroxylamine hydrochloride (278 mg, 4 mmol) in methanol (3 ml), and NaOH (320 mg, 8 mmol) in water (1 ml) were added. After stirring for 15-45 min. at ambient temperature, the resultant mixture was acidified with 1 N HCl to pH 3 and extracted with ethyl acetate (3×30 ml). The organic phase was evaporated under reduced pressure by adding several times of benzene to remove traces of water. The crude product was washed with a small amount of ethyl acetate and crystallized from acetonitrile to give the corresponding hydroxamic acid.

Example 172

6-(4-Bromo-benzoylamino)-hexanoic acid methyl ester (3/34)

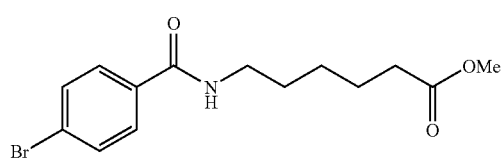

Using an analogous method (J4A), the title compound was obtained from 4-bromo-benzoic acid (1/34), yield 60%. $^1$H NMR (CDCl$_3$, HMDSO), δ: 1.15-1.89(m, 6H); 2.33 (t, J=7.0 Hz, 2H); 3.45(q, J=6.0 Hz, 2H); 3.63(s, 3H); 6.30(bs, 1H); 7.70(d, J=9.0 Hz, 2H); 8.02(d, J=9.0 Hz, 2H).

Example 173

4-Bromo-N-(5-hydroxycarbamoyl-pentyl)-benzamide (PX116215)

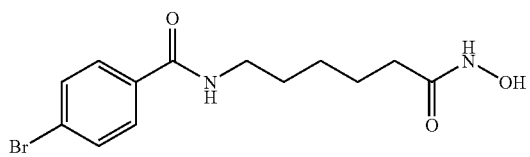

Using an analogous method (J4B), the title compound was obtained from 6-(4-bromo-benzoylamino)-hexanoic acid methyl ester (3/34), m.p. 164-166° C. $^1$H NMR (DMSO-d$_6$, HMDSO), δ: 1.18-1.38(m, 2H); 1.40-1.62(m, 4H); 1.94(t, J=7.2 Hz, 2H); 3.22(q, J=6.0 Hz, 2H); 7.62-7.82(m, 4H); 8.53(t, J=5.4 Hz, 1H); 8.67(d, J=1.2 Hz, 1H); 10.34(s, 1H). HPLC analysis on Zorbax SB-C18 column: impurities 2% (column size 4.6×150 mm; mobile phase gradient 10 min 30-100% acetonitrile +0.1% H$_3$PO$_4$; detector UV 230 nm; sample concentration 0.4 mg/ml). Anal. Calcd for C$_{13}$H$_{17}$BrN$_2$O$_3$: C, 47.43; H, 5.21; N, 8.51. Found: C, 47.46; H, 5.16; N, 8.32.

Example 174

6-(4-Iodo-benzoylamino)-hexanoic acid methyl ester (3/35)

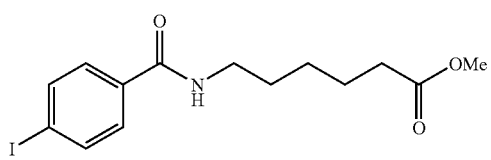

Using an analogous method (J4A), the title compound was obtained from 4-iodo-benzoic acid (1/35), yield 68%. $^1$H NMR (CDCl$_3$, HMDSO), δ: 1.18-1.87(m, 6H); 2.32(t, J=7.0 Hz, 2H); 3.43(q, J=6.0 Hz, 2H); 3.65(s, 3H); 6.32(bs, 1H); 7.49(d, J=8.0 Hz, 2H); 7.78(d, J=8.0 Hz, 2H).

Example 175

N-(5-Hydroxycarbamoylpentyl)-4-iodobenzamide (PX106494)

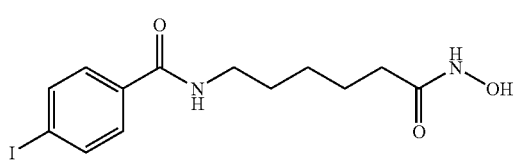

Using an analogous method (J4B), the title compound was obtained from 6-(4iodo-benzoylamino)-hexanoic acid methyl ester (3/35), m.p. 168-169° C. $^1$H NMR (DMSO-d$_6$, HMDSO), δ: 1.20-1.38(m, 2H); 1.40-1.65(m, 4H); 1.94(t, J=7.2 Hz, 2H); 3.28(q, J=6.0 Hz, 2H); 7.61(d, J=8.4 Hz, 2H); 7.83(d, J=8.4 Hz, 2H); 8.50(t, J=6.0 Hz, 1H); 8.67(s, 1H); 10.33(s, 1H). HPLC analysis on Zorbax SB-C18 column: impurities <1% (column size 4.6×150 mm; mobile phase gradient 10 min 30-100% acetonitrile +0.1% $H_3PO_4$; detector UV 254 nm; sample concentration 0.9 mg/ml; flow rate 1.5 ml/min). Anal. Calcd for $C_{13}H_{17}IN_2O_3$: C, 41.51; H, 4.55; N, 7.45. Found: C, 41.51; H, 4.49; N, 7.38.

Example 176

6-(4-Nitro-benzoylamino)-hexanoic acid methyl ester (3/36)

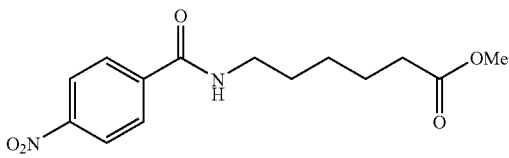

Using an analogous method (J4A), the title compound was obtained from 4-nitrobenzoic acid (1/36), yield 56%. $^1$H NMR (CDCl$_3$, HMDSO), δ: 1.18-1.89(m, 6H); 2.34(t, J=7.0 Hz, 2H); 3.38(q, J=6.0 Hz, 2H); 3.65(s, 3H); 4.49(bs, 1H); 7.94(d, J=9.0 Hz, 2H); 8.29(d, J=9.0 Hz, 2H).

Example 177

N-(5-Hydroxycarbamoylpentyl)-4-nitrobenzamide (PX106495)

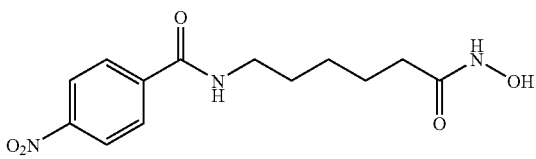

Using an analogous method, the title compound was obtained from 6-(4-nitro-benzoylamino)-hexanoic acid methyl ester (3/36), m.p. 139.5-141° C. $^1$H NMR (DMSO-d$_6$, HMDSO), δ: 1.20-1.38(m, 2H); 1.40-1.64(m, 4H); 1.95(t, J=7.2 Hz, 2H); 3.20-3.30(m, 2H); 8.06(d, J=9.0 Hz, 2H); 8.30(d, J=9.0 Hz, 2H); 8.67(s, 1H); 8.79(t, J=6.0 Hz, 1H); 10.34(s, 1H). HPLC analysis on Symmetry C$_{18}$ column: impurities <1% (column size 3.9×150 mm; mobile phase 25% acetonitrile –75% 0.1 M phosphate buffer (pH 2.5); detector UV 270 nm; sample concentration 1.0 mg/ml; flow rate 0.8 ml/min). Anal. Calcd for $C_{13}H_{17}N_3O_5$: C, 52.88; H, 5.80; N, 14.23. Found: C, 52.81; H, 5.73; N, 14.24.

Example 178

6-(4-tret-Butyl-benzoylamino)-hexanoic acid methyl ester (3/37)

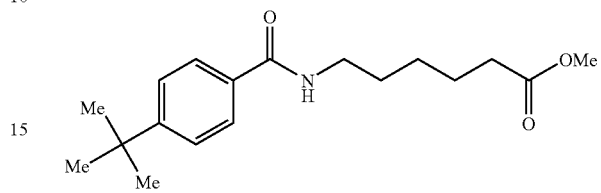

Using an analogous method (J4A), the title compound was obtained from 4-tert-butyl-benzoic acid (1/37), yield 66%. $^1$H NMR (CDCl$_3$, HMDSO), δ: 1.18-1.78(m, 6H); 1.25(s, 9H); 2.29(t, J=7.0 Hz, 2H); 3.43(q, J=6.0 Hz, 2H); 3.63(s, 3H); 6.43(bs, 1H); 7.43(d, J=8.0 Hz, 2H); 7.74(d, J=8.0 Hz, 2H).

Example 179

4-tert-Butyl-N-(5-hydroxycarbamoylpentyl)benzamide (PX106496)

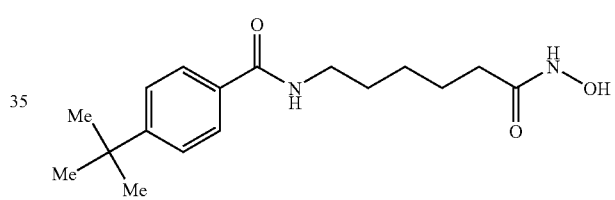

Using an analogous method (J4B), the title compound was obtained from 6-(4-tret-butyl-benzoylamino)-hexanoic acid methyl ester (3/37), m.p. 150-151.5° C. $^1$H NMR (DMSO-d$_6$, HMDSO), δ: 1.20-1.38(m, 11H); 1.40-1.64(m, 4H); 1.94(t, J=7.2 Hz, 2H); 3.21(q, J=6.0 Hz, 2H); 7.45(d, J=8.6 Hz, 2H); 7.76(d, J=8.6 Hz, 2H); 8.36(t, J=6.0 Hz, 1H); 8.66 (s, 1H); 10.33(s, 1H). HPLC analysis on Symmetry C$_{18}$ column: impurities <1% (column size 3.9×150 mm; mobile phase 35% acetonitrile –65% 0.1 M phosphate buffer (pH 2.5); detector UV 230 nm; sample concentration 1.0 mg/ml; flow rate 1.0 ml/min). Anal. Calcd for $C_{17}H_{26}N_2O_3$: C, 66.64; H, 8.55; N, 9.14. Found: C, 66.02; H, 8.56; N, 9.08.

Example 180

6-(4-Cyano-benzoylamino)-hexanoic acid methyl ester (3/38)

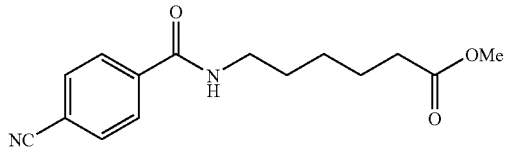

Using an analogous method (J4A), the title compound was obtained from 4-cyano-benzoic acid (1/38), yield 75%. ¹H NMR (CDCl₃, HMDSO), δ: 1.16-1.92(m, 6H); 2.34(t, J=7.0 Hz, 2H); 3.47(q, J=6.0 Hz, 2H); 3.65(s, 3H); 6.43(bs, 1H); 7.72(d, J=9.0 Hz, 2H); 7.89(d, J=9.0 Hz, 2H).

Example 181

4-Cyano-N-(5-hydroxycarbamoylpentyl)-benzamide (PX106497)

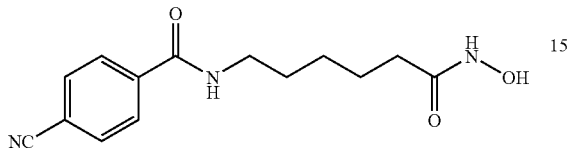

Using an analogous method (J4B), the title compound was obtained from 6-(4-cyano-benzoylamino)-hexanoic acid methyl ester (3/38), m.p. 234-236° C. ¹H NMR (DMSO-d₆, HMDSO), δ: 1.20-1.38(m, 2H); 1.40-1.64(m, 4H); 1.94(t, J=7.2 Hz, 2H); 3.25(q, J=6.0 Hz, 2H); 7.90-8.15(m, 4H); 8.62-8.78(m, 2H); 10.34(s, 1H). HPLC analysis on Zorbax SB-C18 column: impurities 2.5% (column size 4.6×150 mm; mobile phase gradient 10 min 30-100% acetonitrile +0.1% H₃PO₄; detector UV 230 nm; sample concentration 0.9 mg/ml; flow rate 1.5 ml/min). Anal. Calcd for C₁₄H₁₇N₃O₃: C, 61.08; H, 6.22; N, 15.26. Found: C, 60.62; H, 6.23; N, 14.82.

Example 182

6-[(Furan-3-carbonyl)-amino]-hexanoic acid methyl ester (3/39)

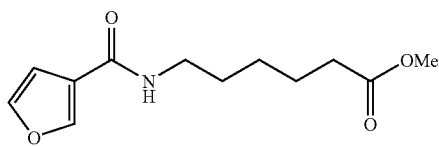

Using an analogous method (J4A), the title compound was obtained from furan-3-carboxylic acid (1/39), yield 78%. ¹H NMR (CDCl₃, HMDSO), δ: 1.20-1.87(m, 6H); 2 94(t, J=7.0 Hz, 2H); 3.41 (q, J=6.0 Hz, 2H);3.67(s, 3H); 6.65(dd, J=1.8 and 1.0 Hz, 1H); 7.45(t, J=1.8 Hz, 1H); 7.94(m, 1H).

Example 183

Furan-3-carboxylic acid (5-hydroxycarbamoyl-pentyl)-amide (PX116219)

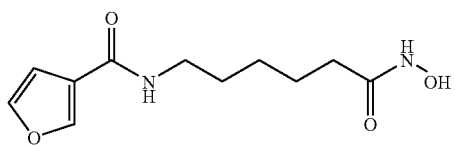

Using an analogous method (J4B), the title compound was obtained from 6[(furan-3-carbonyl)-amino]-hexanoic acid methyl ester (3/39), yield 33%, m.p. 139.5-140.5° C. ¹H NMR (DMSO-d₆, HMDSO), δ: 1.14-1.40(m, 2H); 1.37-1.60 (m, 4H); 1.94(t, J=7.0 Hz, 2H); 3.10-3.24(m, 2H); 6.82(m, 1H); 7.70(t, J=1.6 Hz, 1H); 8.06-8.20(m, 2H); 8.66(s, 1H); 10.33(s, 1H). HPLC analysis on Zorbax SB-C18 column: impurities 4% (column size 4.6×150 mm; mobile phase gradient 10 min 30-100% acetonitrile +0.1% H₃PO₄; detector UV 220 nm; sample concentration 0.55 mg/ml; flow rate 1.5 ml/min). Anal. Calcd for C₁₁H₁₆N₂O₃: C, 54.99; H, 6.71; N, 11.66. Found: C, 54.86; H, 6.76; N, 11.55.

Example 184

6-(3-1H-Indol-3-yl-acryloylamino)-hexanoic acid methyl ester (3/40)

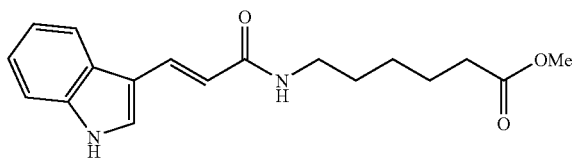

Using an analogous method (J4A), the title compound was obtained from 3-(1H-indol-3-yl)-acrylic acid (1/40), yield 42%. ¹H NMR (CDCl₃, HMDSO), δ: 1.01-1.69(m, 6H); 2 27(t, J=7.0 Hz, partly overlapped with DMSO signal); 3.00-3.32(m, overlapped with H₂O signal); 3.51 (s, 3H); 6.58(d, J=16.0 Hz, 1H); 6.00-7.45(m, 3H); 7.58(d, J=16.0 Hz, 1H); 7.69-7.94(m. 3H); 10.47(s, 1H).

Example 185

N-(5-Hydroxycarbamoyl-pentyl)-3-(1-N-indol-3-yl)-acrylamide (PX116220)

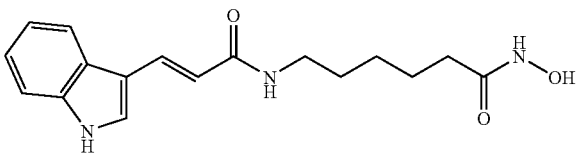

Using an analogous method (J4B), the title compound was obtained from 6-(3-1H-indol-3-yl-acryloylamino)-hexanoic acid methyl ester (3/40), yield 32%, m.p. 92-94° C. ¹H NMR (DMSO-d₆, HMDSO), δ: 1.20-1.62(m, 6H); 1.95(t, J=7.0 Hz, 2H); 3.16(q, J=6.0 Hz, 2H); 6.60(d, J=15.8 Hz, 1H); 7.10-7.24(m, 2H); 7.39-7.50(m. 1H); 7.58(d, J=15.8 Hz, 1H); 7.73 (d, J=2.6 Hz, 1H); 7.80-7.94(m, 2H); 8.66(d, J=1.6 Hz, 1H); 10.34(s, 1H); 11.52(s, 1H). HPLC analysis on Symmetry C₈ column: impurities 3.4% (column size 3.9×150 mm; mobile phase 25% acetonitrile–75% 0.1 M phosphate buffer (pH 2.5); detector UV 220 nm; sample concentration 0.25 mg/ml; flow rate 1.3 ml/min). Anal. Calcd for C₁₇H₂₁N₃O₃* H₂O: C, 61.25; H, 6.95; N, 12.60. Found: C, 61.49; H, 6.84; N, 13.04.

Example 186

6-[(5-Bromo-furan-2-carbonyl)-amino]-hexanoic acid methyl ester (3/41)

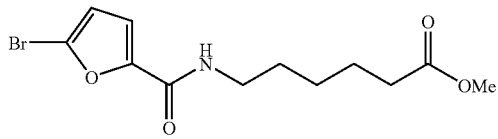

Using an analogous method (J4A), the title compound was obtained from 5-bromo-furan-2-carboxylic acid (1/41), yield 59%. $^1$H NMR (CDCl$_3$, HMDSO), δ: 1.14-1.98(m, 6H);2.34 (t, J=7.0 Hz, 2H); 3.43(q, J=6.0 Hz, 2H); 3.67(s, 3H); 6.34(br s, 1H); 6.45(d, J=4.0 Hz, 1H); 7.07(d, J=4.0 Hz, 1H).

Example 187

5-Bromo-furan-2-carboxylic acid (5-hydroxycarbamoyl-pentyl)-amide (PX116221)

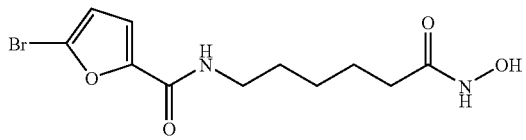

Using an analogous method (J4B), the title compound was obtained from 6-[(5-bromo-furan-2-carbonyl)-amino]-hexanoic acid methyl ester (3/41), yield 60%, m.p. 122-124° C. $^1$H NMR (DMSO-d$_6$, HMDSO), δ: 1.14-1.60(m, 6H); 1.93(t, J=7.0 Hz, 2H); 3.17(q, J=6.2 Hz, 2H); 6.31(d, J=3.6 Hz, 1H); 7.10(d, J=3.6 Hz, 1H); 8.40(t, J=5.8 Hz, 1H); 8.66(s, 1H); 10.32(s, 1H). HPLC analysis on Symmetry C$_8$ column: impurities <1% (column size 3.9×150 mm; mobile phase 25% acetonitrile–75% 0.1 M phosphate buffer (pH 2.5); detector UV 254 nm; sample concentration 0.8 mg/ml; flow rate 1.0 ml/min). Anal. Calcd for C$_{11}$H$_{15}$BrN$_2$O$_4$: C, 41.40; H, 4.74; N, 8.78. Found: C, 41.39; H, 4.67; N, 8.77.

Example 188

6-(3-Thiophen-2-yl-acryloylamino)-hexanoic acid methyl ester (3/42)

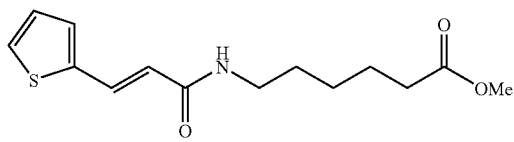

Using an analogous method (J4A), the title compound was obtained from 3-thiophen-2-yl-acrylic acid (1/42), yield 63%. $^1$H NMR (CDCl$_3$, HMDSO), δ: 1.16-1.75(m, 6H); 2.31 (t, J=7.0 Hz, 2H); 3.37(q, J=6.0 Hz, 2H); 3.65(s, 3H); 5.92(br s, 1H); 6.42(d, J=16.0 Hz, 1H); 7.10(dd, J=4 and 2.0 Hz, 1H); 7.38(d, J=4.0 Hz, 1H); 7.58(d, J=2.0 Hz, 1H); 7.81(d, J=16.0 Hz, 1H).

Example 189

N-(5-Hydroxycarbamoyl-pentyl)-3-thiophen-2-yl-acrylamide (PX117247)

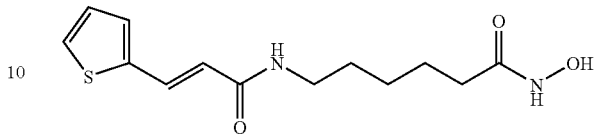

Using an analogous method (J4B), the title compound was obtained from 6-(3-thiophen-2-yl-acryloylamino)-hexanoic acid methyl ester (3/42), yield 73%, m.p. 151-153° C. $^1$H NMR (DMSO-d$_6$, HMDSO), δ: 1.16-1.60(m, 6H); 1.94(t, J=7.2 Hz, 2H); 3.13(q, J=5.8 Hz, 2H); 6.37(d, J=15.6 Hz, 1H); 7.09(dd, J=5.2 and 3.5 Hz, 1H); 7.35(d, J=3.5 Hz, 1H); 7.54(d, J=15.6 Hz, 1H); 7.58(d, J=5.2 Hz, 1H); 8.08(t, J=5.6 Hz, 1H); 8.67(s, 1H); 10.34(s, 1H). HPLC analysis on Symmetry C$_8$ column: impurities 4% (column size 3.9×150 mm; mobile phase 30% acetonitrile–70% 0.1 M phosphate buffer (pH 2.5); detector UV 270 nm; sample concentration 0.5 mg/ml; flow rate 1.0 ml/min). Anal. Calcd for C$_{13}$H$_{18}$N$_2$O$_3$S: C, 55.30; H, 6.43; N, 9.92. Found: C, 55.56; H, 6.41; N, 9.75.

Example 190

6-(3-Phenyl-propynoylamino)-hexanoic acid methyl ester (3/43)

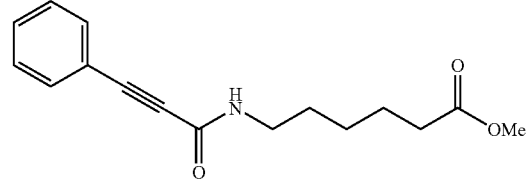

Using an analogous method (J4A), the title compound was obtained from phenylpropynoic acid (1/43), yield 89%. $^1$H NMR (CDCl$_3$, HMDSO), δ: 1.25-1.92(m, 6H); 2.34(t, J=7.0 Hz, 2H); 3.34(q, J=6.0 Hz, 2H); 3.65(s, 3H); 7.27-7.63(m, 5H).

Example 191

3-Phenyl-propynoic acid (5-hydroxycarbamoyl-pentyl)-amide (PX117415)

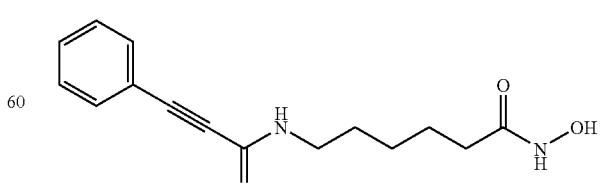

Using an analogous method (J4B), the title compound was obtained from 6-(3-phenyl-propynoylamino)-hexanoic acid methyl ester (3/43), yield 70%, m.p. 112-113° C. $^1$H NMR (DMSO-d$_6$, HMDSO), δ: 1.15-1.55(m, 6H); 1.94(t, J=7.2 Hz, 2H); 3.10(q, J=6.2 Hz, 2H); 7.39-7.61(m, 5H); 8.66(s, 1H); 8.76(t, J=5.4 Hz, 1H); 10.33(s, 1H). HPLC analysis on Symmetry C$_{18}$ column: impurities 1.5% (column size 3.9×150 mm; mobile phase 30% acetonitrile–70% 0.1 M phosphate buffer (pH 2.5); detector UV 220 nm; sample concentration 0.5 mg/ml; flow rate 1.0 ml/min). Anal. Calcd for C$_{15}$H$_{18}$IN$_2$O$_3$: C, 65.68; H, 6.61; N, 10.21. Found: C, 65.49; H, 6.61; N, 10.24.

Example 192

6-(4-Isopropyl-benzoylamino)-hexanoic acid methyl ester (3/44)

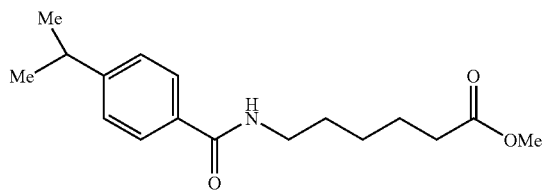

Using an analogous method (J4A), the title compound was obtained from 4-isopropyl-benzoic acid (1/44), yield 68%. $^1$H NMR (CDCl$_3$, HMDSO), δ: 1.23(d, J=7.0 Hz, 6H); 1.36-1.85(m, 6H); 2.32(t, J=7.0 Hz, 2H); 2.92(dq, J=7.0 Hz, 1H); 3.43(q, J=6.0 Hz, 1H); 3.63(s, 3H); 6.20(br s, 1H); 7.25(d, J=8.0 Hz, 2H); 7.69(d, J=8.0 Hz, 2H).

Example 193

N-[6-(Hydroxyamino)-6-oxohexyl]-4-isopropylbenzamide (PX117421)

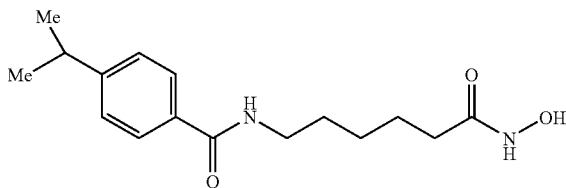

Using an analogous method (J4B), the title compound was obtained from 6-(4-isopropyl-benzoylamino)-hexanoic acid methyl ester (3/44), yield 81%, m.p. 127.5-128° C. $^1$H NMR (DMSO-d$_6$, HMDSO), δ: 1.14-1.35(m, 2H); 1.20(d, J=6.8 Hz, 6H); 1.38-1.60(m, 4H); 1.94(t, J=7.2 Hz, 2H); 2.93(hept, J=6.8 Hz, 1H); 3.24(q, J=6.2 Hz, 2H); 7.31 (d, J=8.2 Hz, 2H); 7.75(d, J=8.2 Hz, 2H); 8.43(t, J=5.6 Hz, 1H); 8.66(s, 1H); 10.33(s, 1H). HPLC analysis on Symmetry C$_8$ column: impurities 1.7% (column size 3.9×150 mm; mobile phase 40% acetonitrile–60% 0.1 M phosphate buffer (pH 2.5); detector UV 254 nm; sample concentration 0.5 mg/ml; flow rate 1.0 ml/min). Anal. Calcd for C$_{16}$H$_{24}$N$_2$O$_3$: C, 65.73; H, 8.27; N, 9.58. Found: C, 65.54; H, 8.29; N, 9.55.

Example 194

6-(3-Naphtalen-1-yl-acryloylamino)-hexanoic acid methyl ester (3/45)

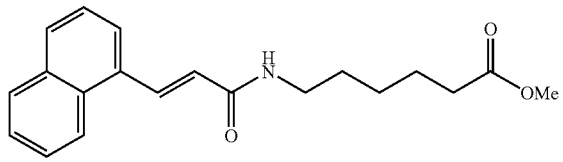

Using an analogous method (J4A), the title compound was obtained from 3-naphthalen-1-yl-acrylic acid (1145), yield 65%. $^1$H NMR (CDCl$_3$, HMDSO), δ: 1.13-1.87(m, 6H); 2.29 (t, J=7.0 Hz, 2H); 3.90(q, J=6.0 Hz, 2H); 3.63(s, 3H); 6.00(br s, 1H); 6.47(d, J=16.0 Hz, 1H); 7.29-7.94(m, 6H); 8.00-8.27 (m, 1H); 8.43(d, J=16.0 Hz, 1H).

Example 195

N-(5-Hydroxycarbamoyl-pentyl)-3-naphthalen-1-yl-acrylamide (PX117441)

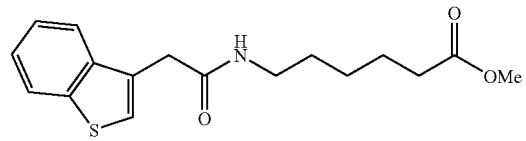

Using an analogous method (J4B), the title compound was obtained from 6-(3-naphtalen-1-yl-acryloylamino)-hexanoic acid methyl ester (3/45), yield 89%, m.p. 135-137° C. $^1$H NMR (DMSO-d$_6$, HMDSO), δ: 1.19-1.37(m, 2H); 1.39-1.62 (m, 4H); 1.96(t, J=7.1Hz, 2H); 3.12-3.27(m, 2H); 6.68(d, J=15.6 Hz, 1H); 7.50-7.68(m, 3H); 7.77(d, J=7.0 Hz, 1H); 7.92-8.20(m, 2H); 8.19(d, J=15.6 Hz, 1H); 8.12-8.31(m, 2H); 8.70(s, 1H); 10.37(s, 1H). HPLC analysis on Zorbax SB-C18 column: impurities 3.2% (column size 4.6×150 mm; mobile phase 50%-100% MeOH+0.1% H$_3$PO$_4$; detector UV 230 nm; sample concentration 1.0 mg/ml; flow rate 1.0 ml/min). Anal. Calcd for C$_{19}$H$_{22}$N$_2$O$_3$: C, 69.92; H, 6.79; N, 8.58. Found: C, 69.73; H, 6.78; N, 8.54.

Example 196

6-(2-Benzo[b]thiophen-3-yl-acetylamino)-hexanoic acid methyl ester (3/46)

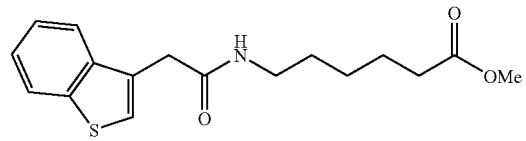

Using an analogous method (J4A), the title compound was obtained from benzo[b]thiophen-3-yl-acetic acid (1/46), yield 82%. $^1$H NMR (CDCl$_3$, HMDSO), δ: 0.94-1.74(m, 6H); 2.20(t, J=7.0 Hz, 2H); 3.16(q, J=6.0 Hz, 2H); 3.63(s, 3H); 3.78(s, 2H); 5.49(br s, 1H); 7.29-7.49(m, 3H); 7.74-8.20(m, 2H).

Example 197

6-(2-Benzothiophen-3-yl-acetylamino)-hexanoic acid hydroxyamide (PX117442)

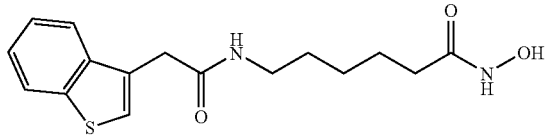

Using an analogous method (J4B), the title compound was obtained from 6-(2-benzo[b]thiophen-3-yl-acetylamino)-hexanoic acid methyl ester (3146), yield 57%, m.p. 113-115° C. $^1$H NMR (DMSO-d$_6$, HMDSO), δ: 1.12-1.56(m, 6H); 1.91(t, J=7.3 Hz, 2H); 3.04(q, J=6.4 Hz, 2H); 3.66(s, 2H); 7.30-7.51(m, 3H); 7.78-7.88(m, 1H); 7.90-8.00(m, 1H); 8.14 (t, J=5.6 Hz, 1H); 8.67(d, J=1.4 Hz, 1H); 10.34(s, 1H). HPLC analysis on Symmetry C$_8$ column: impurities 2% (column size 3.9×150 mm; mobile phase 30% acetonitrile–70% 0.1 M phosphate buffer (pH 2.5); detector UV 230 nm; sample concentration 1.0 mg/ml; flow rate 1.5 ml/min). Anal. Calcd for C$_{16}$H$_{20}$N$_2$O$_3$S: C, 59.98; H, 6.29; N, 8.47. Found: C, 59.95; H, 6.25; N, 8.77.

Example 198

6{-2-[1-(4-Fluoro-benzyl)-1H-indol-3-yl]-acetylamino}-hexanoic acid methyl ester (3/47)

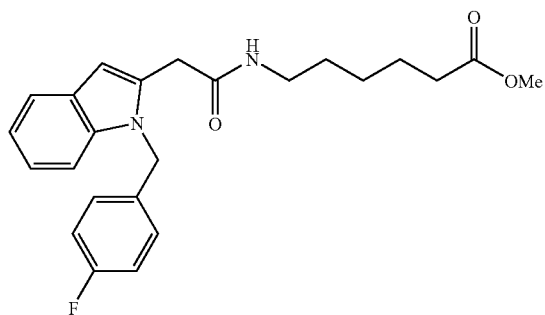

Using an analogous method (J4A), the title compound was obtained from [1-(4-fluoro-benzyl)-1H-indol-3-yl]-acetic acid (1/47), yield 92%. $^1$H NMR (CDCl$_3$, HMDSO), δ: 0.98-1.72(m, 6H); 2.20(t, J=7.0 Hz, 2H); 3.16(q, J=6.0 Hz, 2H); 3.36(s, 3H); 3.69(s, 2H); 5.27(s, 2H); 5.63(br s, 1H); 6.87-7.67(m, 9H).

Example 199

6-{2-[1-(4-Fluorobenzyl)-1H-indol-3-yl]-acetylamino}-hexanoic acid hydroxyamide (PX117721)

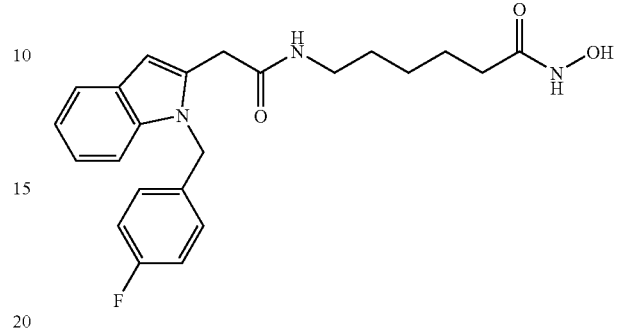

Using an analogous method (J4B), the title compound was obtained from 6-{2-[1-(4-fluoro-benzyl)-1H-indol-3-yl]-acetylamino}-hexanoic acid methyl ester (3/47), yield 51%, m.p. 74-76° C. $^1$H NMR (DMSO-d$_6$, HMDSO), δ: 1.12-1.55 (m, 6H); 1.91(t, J=7.3 Hz, 2H); 3.02(q, J=7.4 Hz, 2H); 3.48(s, 2H); 5.35(s, 2H); 6.94-7.34(m, 7H); 7.41 (br d, J=6.6 Hz, 1H); 7.55(dd, J=6.6 and 1.2 Hz, 1H); 7.91 (t, J=4.8 Hz, 1H); 8.65(s, 1H); 10.32(s, 1H). HPLC analysis on Symmetry C$_8$ column: impurities 1% (column size 3.9×150 mm; mobile phase 35% acetonitrile–65% 0.1 M phosphate buffer (pH 2.5); detector UV 230 nm; sample concentration 0.5 mg/ml; flow rate 1.5 ml/min). Anal. Calcd for C$_{23}$H$_{26}$FN$_3$O$_3$: C, 67.14; H, 6.37; N, 10.21. Found: C, 66.29; H, 6.28; N, 10.15.

Example 200

6-(3-Benzyloxycarbonylamino-3-p-tolyl-propionylamino)-hexanoic acid methyl ester (3/48)

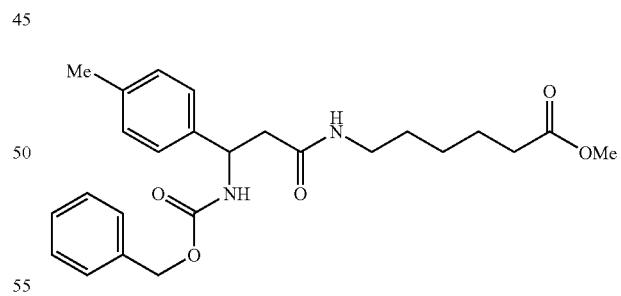

Using an analogous method (J4A), the title compound was obtained from 3-benzyloxycarbonylamino-3-p-tolyl-propionic acid (1/48), yield 78%. $^1$H NMR (CDCl$_3$, HMDSO), δ: 0.94-1.74(m, 6H); 2.25(t, J=7.0 Hz, 2H); 2.32(s, 3H); 2.63 (dd, J=6.0 and 4.0 Hz, 2H); 3.12(q, J=6.0 Hz, 2H); 3.65(s, 3H); 4.87-5.16(m, 1H); 5.07(s, 2H); 5.49(br s, 1H);6.27-6.52 (m, 1H); 7.14(s, 4H); 7.34(s, 5H).

Example 201

[2-(5-Hydroxycarbamoyl-pentylcarbamoyl)-1-p-tolyl-ethyl]-carbamic acid benzyl ester (PX117729)

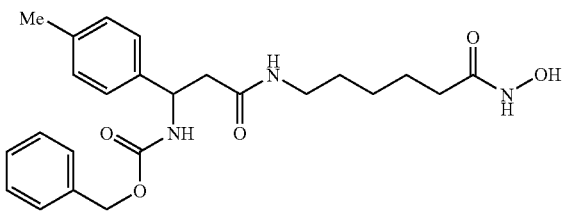

Using an analogous method (J4B), the title compound was obtained from 6-(3-benzyloxycarbonylamino-3-p-tolyl-propionylamino)-hexanoic acid methyl ester (3/48), yield 69%, m.p. 146-148° C. $^1$H NMR (DMSO-d$_6$, HMDSO), δ: 1.02-1.50(m, 6H); 1.89(t, J=7.6 Hz, 2H); 2.25(s, 3H); 2.34-2.60(m, overlapped with a signal of DMSO, 2H); 2.86-3.01(m, 2H); 4.84-4.98(m, 1H); 4.95(d, J=12.8 Hz, 1H); 4.98(d, J=12.8 Hz, 1H); 7.09(d, J=8.4 Hz, 2H); 7.16(d, J=8.4 Hz, 2H); 7.32(s, 5H); 7.72(t, J=5.7 Hz, 1H); 7.77(d, J=8.8 Hz, 1H); 8.64(s, 1H); 10.31 (s, 1H). HPLC analysis on Symmetry C$_8$ column: impurities 4.5% (column size 3.9×150 mm; mobile phase 40% acetonitrile–60% 0.1 M phosphate buffer (pH 2.5); detector UV 220 nm; sample concentration 0.5 mg/ml; flow rate 1.5 ml/min). Anal. Calcd for C$_{24}$H$_{31}$N$_3$O$_5$: C, 65.29; H, 7.08; N, 9.52. Found: C, 65.64; H, 7.10; N, 9.17.

Example 202

6-[2-(4-Chloro-phenyl)-2-methyl-propionylamino]-hexanoic acid methyl ester (3/49)

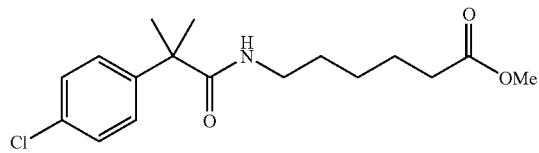

Using an analogous method (J4A), the title compound was obtained from 2-(4-chloro-phenyl)-2-methyl-propionic acid (1/49), yield 87%. $^1$H NMR (CDCl$_3$, HMDSO), δ: 1.07-1.76 (m, 6H); 1.43(s, 6H); 2.27(t, J=7.0 Hz, 2H); 3.14(q, J=6.0 Hz, 2H); 3.65(s, 3H); 5.14(br s, 1H); 7.62(s, 4H).

Example 203

6-[2-(4-Chlorophenyl)-2-methyl-propionylamino]-hexanoic acid hydroxyamide (PX117722)

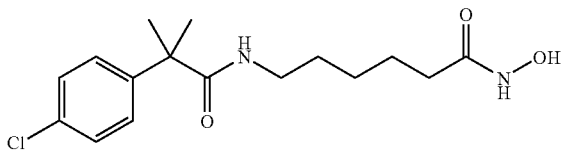

Using an analogous method (J4B), the title compound was obtained from 6-[2-(4-chloro-phenyl)-2-methyl-propionylamino]-hexanoic acid methyl ester (3/49), yield 79%, m.p. 102-104° C. $^1$H NMR (DMSO-d$_6$, HMDSO), δ: 1.03-1.22(m, 2H); 1.25-1.54(m, 4H); 1.41(s, 6H); 1.90(t, J=7.0 Hz, 2H); 2.99(q, J=6.2 Hz, 2H); 7.25-7.40(m, 5H); 8.64(s, 1H); 10.31 (s, 1H). HPLC analysis on Symmetry C$_8$ column: impurities 3% (column size 3.9×150 mm; mobile phase 35% acetonitrile–65% 0.1 M phosphate buffer (pH 2.5); detector UV 220 nm; sample concentration 0.5 mg/ml; flow rate 1.5 ml/min). Anal. Calcd for C$_{16}$H$_{23}$ClN$_2$O$_3$: C, 58.80; H, 7.09; N, 8.57. Found: C, 58.56; H, 7.06; N, 8.57.

Example 204

6-(5-Phenyl-pentanoylamino)-hexanoic acid methyl ester (3/50)

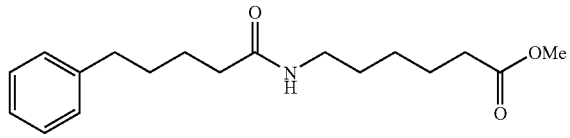

Using an analogous method (J4A), the title compound was obtained from 5-phenyl-pentanoic acid (1/50), yield 35%. $^1$H NMR (CDCl$_3$, HMDSO), δ: 1.22-1.81 (m, 10H); 2.02-2.41 (m, 4H); 2.49-2.75 (m, 2H); 3.22 (q, J=6.0 Hz, 2H); 3.65 (s, 3H); 5.52 (br s, 1H); 7.05-7.38 (m, 5H).

Example 205

6-(5-Phenyl-pentanoylamino)-hexanoic acid hydroxyamide (PX117261)

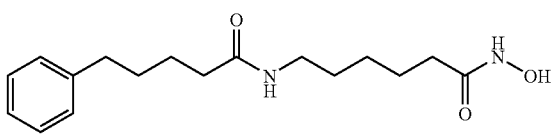

Using an analogous method (J4B), the title compound was obtained from 6-(5-phenyl-pentanoylamino)-hexanoic acid methyl ester (3/50), yield 52%, m.p. 97-98° C. $^1$H NMR (DMSO-d$_6$, HMDSO), δ: 1.09-1.61 (10H, m, CH$_2$); 1.91 (2H, t, J=7.3 Hz, CH$_2$); 2.06 (2H, t, J=6.7 Hz, CH$_2$); 2.56 (2H, t, J=7.2 Hz, CH$_2$, overlapped with a signal of DMSO); 2.99 (2H, q, J=6.3 Hz, NCH$_2$); 7.11-7.34 (5H, m, C$_6$H$_5$); 7.75 (1H, t, J=5.4 Hz, NH); 8.67 (1H, s, NH); 10.33 (1H, s, OH). HPLC analysis on Symmetry C$_{18}$ column: impurities <1% (column size 3.9×150 mm; mobile phase acetonitrile–0.1 M phosphate buffer (40:60), pH 2.5; detector UV 220 nm; sample

Example 206

6-(5-Phenyl-pent-4Z-enoylamino)-hexanoic acid methyl ester (3/51)

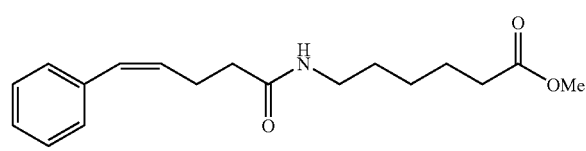

Using an analogous method (J4A), the title compound was obtained from 5-phenyl-pent-4Z-enoic acid (1/51), yield 29%. $^1$H NMR (CDCl$_3$, HMDSO), δ: 1.14-1.81 (m, 6H); 2.16-2.38 (m, 4H); 2.52-2.83 (m, 2H); 3.22 (q, J=6.0 Hz, 2H); 3.65 (s, 3H); 5.63 (dt, 1H, J=11.4 and 7.0 Hz); 6.47 (d, 1H, J=11.4 Hz); 7.17-7.38 (m, 5H).

Example 207

(Z)-N-[6-(Hydroxyamino)-6-oxohexyl]-5-phenyl4-pentenamide (PX117444)

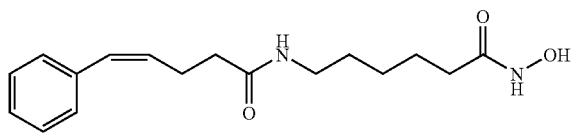

Using an analogous method (J4B), the title compound was obtained from 6-(5-phenyl-pent-4Z-enoylamino)-hexanoic acid methyl ester (3/51), yield 50%, m.p. 101-103° C. $^1$H NMR (DMSO-d$_6$, HMDSO), δ: 1.12-1.56 (8H, m, CH$_2$); 1.92 (2H, t, J=6.8 Hz, CH$_2$); 2.19 (2H, t, J=7.6 Hz, CH$_2$); 3.00 (2H, q, J=6.0 Hz, NCH$_2$); 5.60 (1H, dt, J=11.6 and 5.8 Hz, CH=); 6.41 (1H, d, J=11.6 Hz, CH=); 7.18-7.42 (5H, m, C$_6$H$_5$); 7.84 (1H, t, J=5.2 Hz, NH); 8.67 (1H, s, NH); 10.34 (1H, s, OH). HPLC analysis on Symmetry C$_{18}$ column: impurities ~1% (column size 3.9×150 mm; mobile phase acetonitrile–0.1 M phosphate buffer (40:60), pH 2.5; detector UV 230 nm; sample concentration 0.5 mg/ml; flow rate 0.8 ml/min). Anal. Calcd for C$_{17}$H$_{24}$N$_2$O$_3$: C, 67.08; H, 7.95; N, 9.20. Found: C, 66.96; H, 7.91; N, 9.10.

Example 208

6-(5-Phenyl-pent-4E-enoylamino)-hexanoic acid methyl ester (3/52)

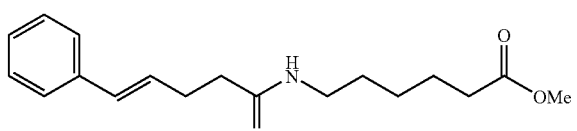

Using an analogous method (J4A), the title compound was obtained from 5-phenyl-pent-4E-enoic acid (1/52), yield 82%. $^1$H NMR (CDCl$_3$, HMDSO), δ: 1.10-1.78 (m, 6H); 2.07-2.69 (m, 6H); 3.25 (q, J=6.0 Hz, 2H); 3.65 (s, 3H); 5.53 (br s, 1H); 6.20 (dt, 1H, J=16.0 and 6.0 Hz); 6.49 (d, 1H, J=16.0 Hz); 7.07-7.45 (m, 5H).

Example 209

(E)-N-[6-(Hydroxyamino)-6-oxohexyl]-5-phenyl-4-pentenamide (PX117797)

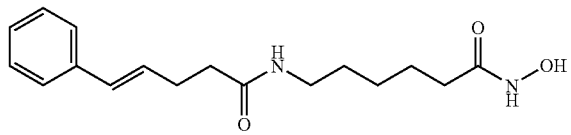

Using an analogous method (J4B), the title compound was obtained from 6-(5-phenyl-pent-4E-enoylamino)-hexanoic acid methyl ester (3/52), yield 10%, m.p. 131-133° C. $^1$H NMR (DMSO-d$_6$, HMDSO), δ: 1.12-1.54 (8H, m, 4CH$_2$); 1.90 (2H, t, J=6.8 Hz, CH$_2$); 2.10-2.40 (2H, m, CH$_2$); 3.00 (2H, m, NCH$_2$); 6.25-6.50 (2H, m, 2CH=); 7.18-7.42 (5H, m, C$_6$H$_5$); 7.81 (1H, t, J=5.2 Hz, NH); 8.65 (1H, s, NH); 10.32 (1H, s, OH). HPLC analysis on Symmetry C$_{18}$ column: impurities ~1% (column size 3.9×150 mm; mobile phase acetonitrile–0.1 M phosphate buffer (40:60), pH 2.5; detector UV 220 nm; sample concentration 0.5 mg/ml; flow rate 1.0 ml/min). Anal. Calcd for C$_{17}$H$_{24}$N$_2$O$_3$: C, 67.08; H, 7.95; N, 9.20. Found: C, 66.67; H, 7.94; N, 9.17.

Example 210

6-[(Naphthalene-2-carbonyl)amino]hexanoic acid methyl ester (3/53)

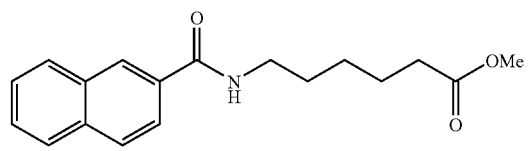

(Method J5A) To a solution of 6-aminocaproic acid methyl ester hydrochloride (2c) (0.500 g, 2.75 mmol) and diisopropyl ethylamine (0.96 ml, 5.5 mmol) in dry dimethylformamide (3 ml) 2-naphthoyl chloride (1/53) (0.524 g, 2.75 mmol) in dry dimethylformamide (3 ml) was added. The mixture was stirred for three hours at room temperature, then diluted with saturated NaCl (30 ml) and extracted with ethyl acetate (3×25 ml). The organic phase was washed with saturated NaCl (2×15 ml) and dried (Na$_2$SO$_4$). The solvent was evaporated to give crude title compound (0.825 g) which was used in the next step without further purification.

Example 211

6-[(Naphthalene-2-carbonyl)-amino]hexanoic acid (4/53)

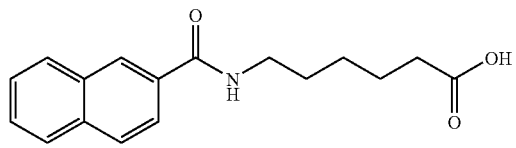

(Method J5B) The crude 6-[(naphthalene-2-carbonyl)amino]hexanoic acid methyl ester (3/53) was dissolved in tetrahydrofuran (5 ml) and 1 N LiOH (5.5 ml, 5 mmol) was added. The reaction mixture was stirred for three hours at room temperature and acidified with 2N HCl up to pH 3. The mixture was extracted with ethyl acetate (3×20 ml) the organic layer was washed with saturated NaCl (3×10 ml) and dried ($Na_2SO_4$). The solvent was evaporated and the residue was chromatographed on silica gel with ethyl acetate as eluent to give pure title compound (0.618 g, 79%). $^1$H NMR ($CDCl_3$, HMDSO), δ: 1.11-1.77 (6H, m); 2.22-2.39 (2H, m); 3.47 (2H, dd, J=7.0 Hz); 6.26 (1H, br s); 7.17(1H, s); 7.33-7.57 (2H, m); 7.64-7.93 (4H, m); 8.22 (1H, s).

Example 212

Naphthalene-2-carboxylic acid (5-hydroxycarbamoylpentyl)amide (PX105687)

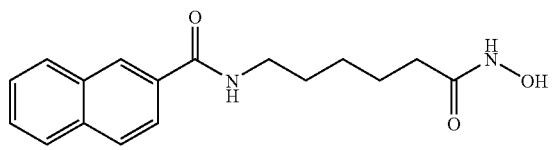

(Method J5C) A solution of 6-[(naphthalene-2-carbonyl)amino]hexanoic acid (4/53) (0.618 g, 2.17 mmol) in dry tetrahydrofuran (6 ml) was cooled in ice bath under argon atmosphere and 1,1'-carbonyldiimidazole (0.422 g, 2.6 mmol) was added. The mixture was stirred for 30 min. and a solution of hydroxylamine (4.35 mmol) in dry dimethylformamide (3 ml) [the solution of hydroxylamine was made from hydroxylamine hydrochloride (0.302 g, 4.35 mmol) and triethylamine (0.61 ml) in dimethylformamide (3 ml) and filtered] was added. After stirring overnight the reaction mixture was diluted with saturated $NaH_2PO_4$ (30 ml) and extracted with ethyl acetate (3×30 ml). The organic phase was evaporated under reduced pressure by adding several times of benzene to remove traces of water. The crude product was crystallized successively from ethyl acetate and acetonitrile to give of the title compound (0.260 g, 40%), m.p. 96-98° C. $^1$H NMR (DMSO-$d_6$, HMDSO), δ: 1.21-1.45 (2H, m); 1.46-1.73 (4H, m); 1.89-2.05 (2H, m); 3.25-3.37 (2H, m); 7.65-7.81 (2H, m); 7.86-8.04 (4H, m); 8.42 (1H, s); 8.56-8.72 (2H, m); 10.32 (1H, s). HPLC analysis on Symmetry $C_8$ column: impurities <1% (column size 3.9×150 mm; mobile phase 40% acetonitrile +60% 0.1% $H_3PO_4$; detector UV 220 nm; sample concentration 0.145 mg/ml). Anal. Calcd, %: C, 67.98; H, 6.71; N, 9.33. Found, %: C, 68.29; H, 6.97; N, 8.99.

Example 213

Naphthalene-2-carboxylic acid (4-hydroxycarbamoyl-butyl)-amide (PX106492)

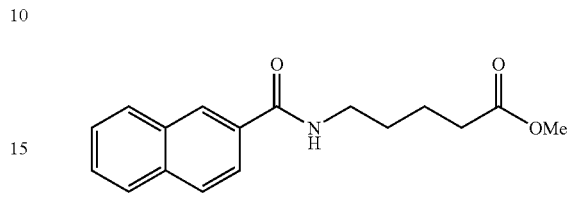

5-[Naphthalene-2-carbonyl)-amino]pentanoic acid methyl ester (3/54) was obtained from 2-naphthoyl chloride (1/53) and methyl 5-aminopentanoate hydrochloride (2b) by the following method. Yield 83%. $^1$H NMR ($CDCl_3$, HMDS), δ: 1.41-1.89(m, 4H); 2.23-2.52(m, 2H); 3.32-3.60(M, 2H); 3.67 (s, 3H); 6.60(br s, 1H); 7.36-7.63(m, 2H); 7.72-8.00(m, 4H); 8.27(s, 1H).

(Method J6) To a solution of ω-amino acid methyl ester hydrochloride (2b, 2c, 2f or 2g) (2.75 mmol) and diisopropyl ethylamine (0.96 ml, 5.5 mmol) in anhydrous N,N-dimethylformamide (3 ml) an appropriate carboxylic acid chloride (1/53 or 1/57) (2.75 mmol) in dimethylformamide (3 ml) was added. The mixture was stirred for 3 hours at room temperature, diluted with brine (30 ml) and extracted with ethyl acetate (3×25 ml). The organic phase was washed with brine (2×15 ml), dried ($Na_2SO_4$) and the solvent was evaporated. The residue was purified on silica gel (20 g) with chloroform-ethyl acetate as eluent, affording the corresponding amidoester derivative 3/54-3/57.

Example 214

Naphthalene-2-carboxylic acid (4-hydroxycarbamoyl-butyl)-amide (PX106492)

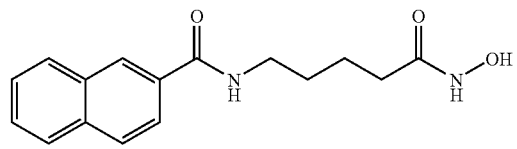

Using an analogous method (J4B), the title compound was obtained from 5-[naphthalene-2-carbonyl)-amino]pentanoic acid methyl ester (3/54).

Yield 92%. M.p. 155-156° C. $^1$H NMR (DMSO-$d_6$, HMDSO), δ: 1.44-1.62(m, 4H); 1.94-2.06(m, 2H); 3.20-3.30 (m, 2H); 7.52-7.64(m, 2H); 7.86-8.08(m, 4H); 8.43(s, 1H); 8.58-8.75(m, 2H); 10.36(s, 1H). HPLC analysis on Symmetry $_{18}$ column: impurities <1% (column size 3.9×150 mm; mobile phase 30% acetonitrile+70% 0.1 M phosphate buffer (pH 2.5); detector UV 230 nm; sample concentration 0.4 mg/ml). Anal. Calcd for C_{16}H_{18}N_2O_3: C, 67.12; H, 6.34; N, 9.78. Found: C, 67.00; H, 6.33; N, 9.83.

Example 215

7-[Naphthalene-2-carbonyl)-amino]heptanoic acid methyl ester (3/55)

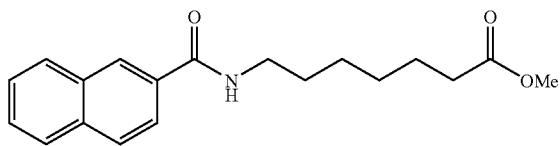

Using an analogous method (J6), the title compound was obtained from 2-naphthoyl chloride (1/53) and methyl 7-aminoheptanoate hydrochloride (2f). Yield 85%. $^1$H NMR (CDCl$_3$, HMDS), δ: 1.16-1.83(m, 8H); 2.32(t, J=7.0 Hz, 2H); 3.49(q, J=6.0 Hz, 2H); 3.63(s, 3H); 6.32(br s, 1H); 7.40-7.56 (m, 2H); 7.72-8.05(m, 4H); 8 27(s, 1H).

Example 216

Naphthalene-2-carboxylic acid (6-hydroxycarbamoyl-hexyl)-amide (PX106493)

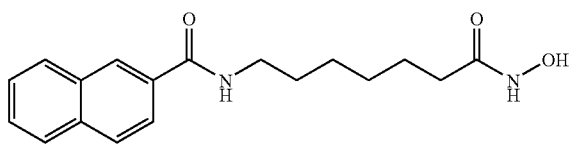

Using an analogous method (J4B), the title compound was obtained from 7-[(naphthalene-2-carbonyl)-amino]-heptanoic acid methyl ester (3/55). Yield 97%. M.p. 136-137° C. $^1$H NMR (DMSO-d$_6$, HMDSO), δ: 1.48-1.62(m, 8H); 1.95(t, J=6.8 Hz, 2H); 3.20-3.30(m, 2H); 7.52-7.64(m, 2H); 7.86-8.08(m, 4H); 8.43(s, 1H); 8.52-8.68(m, 2H); 10.33(s, 1H). HPLC analysis on Symmetry$_{18}$ column: impurities <1% (column size 3.9×150 mm; mobile phase 35% acetonitrile +65% 0.1 M phosphate buffer (pH 2.5); detector UV 230 nm; sample concentration 0.4 mg/ml). Anal. Calcd for C$_{18}$H$_{22}$N$_2$O$_3$: C, 68.77; H, 7.05; N, 8.91. Found: C, 68.50; H, 7.08; N, 8.96.

Example 217

8-[(Naphthalene-2-carbonyl)-amino]-octanoic acid methyl ester (3/56)

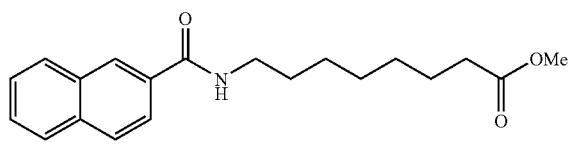

Using an analogous method (J6), the title compound was obtained from 2-naphthoyl chloride (1/53) and methyl 8-amino octanoate hydrochloride (2g). Yield 93%. $^1$H NMR (CDCl$_3$, HMDS), δ: 0.98-1.89(m, 10H); 2.34(t, J=7.0 Hz, 2H); 3.47(q, J=6.0 Hz, 2H); 3.63(s, 3H); 6.31 (br s, 1H); 7.40-7.52(m, 2H); 7.72-8.00(m 4H); 8.27(s, 1H).

Example 218

Naphthalene-2-carboxylic acid (7-hydroxycarbamoyl-heptyl)-amide (PX106515)

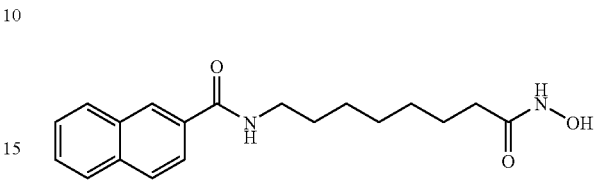

Using an analogous method (J4B), the title compound was obtained from 8-[(naphthalene-2-carbonyl)-amino]-octanoic acid methyl ester (3/56). Yield 84%. M.p. 138-139° C. $^1$H NMR (DMSO-d$_6$, HMDSO), δ: 1.14-1.66(m, 10H); 1.95(t, J=7.2 Hz, 2H); 3.22-3.30(m, 2H); 7.53-7.65(m, 2H); 7.87-8.08(m, 4H); 8.43(s, 1H); 8.55-8.71(m, 2H); 10.33(s, 1H). HPLC analysis on Zorbax SB-C18 column: impurities 2% (column size 4.6×150 mm; mobile phase gradient 10 min 30-100% acetonitrile+0.1% H$_3$PO$_4$; detector UV 230 nm; sample concentration 0.5 mg/ml, flow rate 1.5 ml/min). Anal. Calcd for C$_{19}$H$_{24}$N$_2$O$_3$: C, 69.49; H, 7.37; N, 8.53. Found: C, 69.20; H, 7.40; N, 8.52.

Example 219

6-(4-Phenyl-but-3-enoylamino)-hexanoic acid methyl ester (3/57)

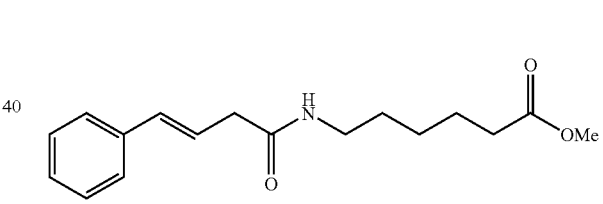

Using an analogous method (J6), the title compound was obtained from 4-phenylbut-3-enoyl chloride (1/57) and methyl 6-amino hexanoate hydrochloride (2c). Yield 48%. $^1$H NMR (CDCl$_3$, HMDSO), δ: 1.12-1.81 (6H, m); 2.29 (2H, t, J=7.0 Hz); 3.14 (2H, d, J=6.2 Hz); 3.26 (2H, q, J=6.5 Hz); 3.64 (3H, s); 5.65 (1H, br s); 6.27 (1H, dt, J=6.2 and 16.0 Hz); 6.57 (1H, d, J=16.0 Hz); 7.21-7.52 (5H, m).

Example 220

(E)-N-[6-(Hydroxyamino)-6-oxohexyl]-4-phenyl-3-butenamide (PX116211)

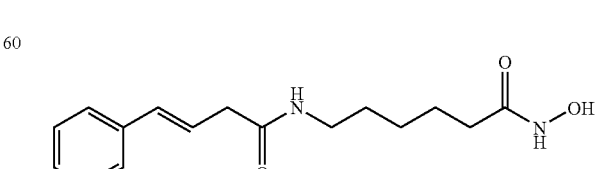

(Method J7) To a mixture of 6-(4-phenyl-but-3-enoylamino)-hexanoic acid methyl ester (3/57) (100 mg, 0.35 mmol) and hydroxylamine hydrochloride (96 mg, 1.38 mmol) in methanol (1 ml) the 3.43 N solution of sodium methylate (0.61 ml, 2.1 mmol) in methanol was added. The mixture was stirred for 1 hour at room temperature, diluted with saturated $NaH_2PO_4$ (10 ml), and extracted with ethyl acetate (2×20 ml). The organic extracts were combined, washed with brine, and dried ($Na_2SO_4$). The solvent was evaporated and the residue was crystallized from ethyl acetate to give the title product, yield 66%. M.p. 127-128° C. (from ethyl acetate). $^1$H NMR (DMSO-$d_6$, HMDSO), δ: 1.07-1.68 (m, 6H); 1.78-2.06 (m, 2H); 2.03 (t, 2H, J=6.6 Hz); 2.85-3.18 (m, 4H); 6.30 (dd, 1H, J=16.1 and 6.0 Hz); 6.48 (d, 1H, J=16.1 Hz); 7.14-7.53 (m, 5H); 7.85 (t, 1H, J=5.8 Hz); 8.63 (br s, 1H); 10.32 (br s, 1H). HPLC analysis on Zorbax SB-C18 column: impurities 2% (column size 4.6×150 mm; mobile phase 0.1% $H_3PO_4$, gradient from 50:50 to 90:10; detector UV 254 nm; sample concentration 0.75 mg/ml, flow rate 1.5 ml/min). Anal. Calcd for $C_{16}H_{22}N_2O_3$: C, 66.19; H, 7.64; N, 9.65. Found: C, 66.19; H, 7.69; N, 9.67.

Example 221

6-[2-(4-Dimethylamino-phenyl)-acetylamino]-hexanoic acid methyl ester (3/58)

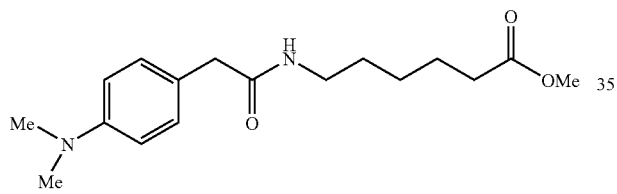

The title compound was obtained from (4-dimethylamino-phenyl)-acetic acid (1/58) and methyl 6-aminohexanoate hydrochloride (2c) by the following method. Yield 73%. $^1$H NMR (CDCl$_3$, HMDSO), δ: 1.16-1.92(m, 6H); 2.34(t, J=7.0 Hz, 2H); 3.03(s, 6H); 3.22(s, 2H); 3.43(q, J=6.0 Hz, 2H); 3.65(s, 3H); 6.00(bs, 1H); 6.69(d, J=9.0 Hz, 2H); 7.79(d, J=9.0 Hz, 2H).

(Method J8) To a solution of appropriate carboxylic acid 1/58, 1/59, 1/60, 1/61 (2.0 mmol) in anhydrous tetrahydrofuran (5 ml) under argon atmosphere triethylamine (0.36 ml, 2.6 mmol) was added and the mixture was cooled in an ice bath. Then to the reaction mixture iso-butylchloroformate (0.3 ml, 2.3 mmol) was added and the resulting mixture was stirred for 20 min at ice bath temperature. At the same time, a suspension of methyl 6-aminocaproate hydrochloride (2c) (364 mg, 2 mmol), anhydrous tetrahydrofuran (3 ml) and triethylamine (0.31 ml, 2.2 mmol) was prepared and stirred for 20 min at room temperature. This suspension to the above prepared reaction mixture of activated ester was added. The resulting mixture was stirred at ice bath temperature for 15 min and 1 hour at room temperature, then diluted with brine (50 ml) and extracted with ethyl acetate (3×25 ml). The organic phase was washed with brine, 5% $NaHCO_3$, brine, saturated $KH_2PO_4$ and brine. The organic layer was dried ($Na_2SO_4$) and the solvent was evaporated. The residue was purified on silica gel (20 g) with chloroform-ethyl acetate as eluent affording title products 3/58, 3159, 3/60, 3/61.

Example 222

6-[2-(4-Dimethylamino-phenyl)-acetylamino]-hexanoic acid hydroxyamide (PX117458)

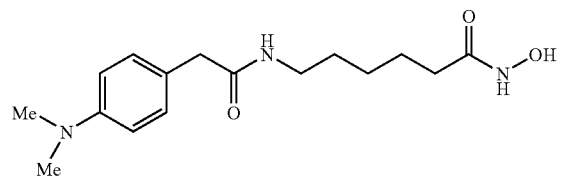

Using an analogous method (J4B), the title compound was obtained from 6-[2-(4-dimethylamino-phenyl)-acetylamino]-hexanoic acid mathyl ester (3/58). Yield 39%. M.p. 124-126° C. $^1$H NMR (DMSO-$d_6$, HMDSO), δ: 1.11-1.56(m, 6H); 1.91(t, J=7.4 Hz, 2H); 2.84 (s, 6H); 2.98(q, J=6.4 Hz, 2H); 3.22(s, 2H); 6.64 (d, J=8.6 Hz, 2H); 7.04(d, J=8.6 Hz, 2H); 7.85(t, J=5.4 Hz, 1H); 8.66(s, 1H); 10.33(s, 1H). HPLC analysis on Symmetry $_{18}$ column: impurities 1.2% (column size 3.9×150 mm; mobile phase 5% acetonitrile–95% 0.1 M phosphate buffer (pH 2.5); detector UV 215 nm; sample concentration 0.5 mg/ml, flow rate 1.2 ml/min). Anal. Calcd for $C_{16}H_{25}N_3O_3$: C, 62.52; H, 8.20; N, 13.67. Found: C, 62.32; H, 8.21; N, 13.68.

Example 223

6-[3-(4-Trifluoromethyl-phenyl)acryloylamino]-hexanoic acid methyl ester (3/59)

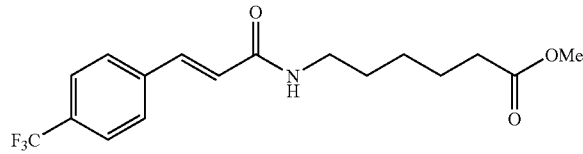

Using an analogous method (J8), the title compound was obtained from (3-(4-trifluoromethyl-phenyl)-acrylic acid (1/59) and methyl 6-aminohexanoate hydrochloride (2c). Yield 80%. $^1$H NMR (CDCl$_3$, HMDSO), δ: 1.14-1.87(m, 6H); 2.32(t, J=7.0 Hz, 2H); 3.38(q, J=6.0 Hz, 2H); 3.65(s, 3H); 5.78(bs, 1H); 6.45(d, J=16.0 Hz, 1H); 7.56-7.72(m, 4H); 7.63(d, J=16.0 Hz, 1H).

Example 224

N-(5-Hydroxycarbamoyl-pentyl)-3-(4-trifluoromethyl-phenyl)-acrylamide (PX117717)

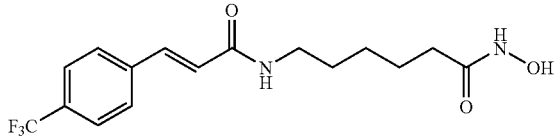

Using an analogous method (J4B), the title compound was obtained from 6-[3-(4-trifluoromethyl-phenyl)acryloylamino]-hexanoic acid methyl ester (3/59). Yield 37%. M.p. 132-134° C. $^1$H NMR (DMSO-d$_6$, HMDSO), δ: 1.15-1.62(m, 6H); 1.94(t, J=7.4 Hz, 2H); 3.16(q, J=6.2 Hz, 2H); 6.74(d, J=16.2 Hz, 1H); 7.47(d, J=16.2 Hz, 1H); 7.77(s, 4H); 8.20(t, J=5.4 Hz, 1H); 8.66(d, J=1.4 Hz, 1H); 10.34(s, 1H). HPLC analysis on Symmetry $_{18}$ column: impurities 1.2% (column size 3.9×150 mm; mobile phase 40% acetonitrile–60% 0.1 M phosphate buffer (pH 2.5); detector UV 254 nm; sample concentration 0.5 mg/ml, flow rate 1.0 ml/min). Anal. Calcd for C$_{16}$H$_{19}$F$_3$N$_2$O$_3$: C, 55.81; H, 5.56; N, 8.14. Found: C, 55.50; H, 5.58; N, 8.19.

Example 225

6-[3-(3-Trifluoromethoxy-phenyl)-acryloylamino]-hexanoic acid methyl ester (3/60)

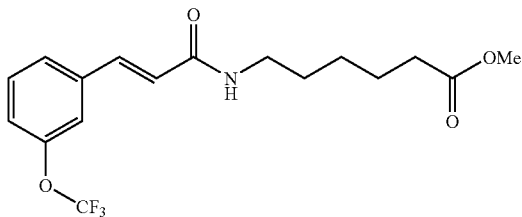

Using an analogous method (J8), the title compound was obtained from 3-(3-trifluoromethoxy-phenyl)-acrylic acid (1/60) and methyl 6-aminohexanoate hydrochloride (2c). Yield 83%. $^1$H NMR (CDCl$_3$, HMDSO), δ: 1.20-1.85(m, 6H); 2.29(t, J=7.0 Hz, 2H); 3.38(q, J=6.0 Hz, 2H); 3.60(s, 3H); 5.88(bs, 1H); 6.41(d, J=16.0 Hz, 1H); 7.18-7.49(m, 4H); 7.63(d, J=16.0 Hz, 1H).

Example 226

N-(5-Hydroxycarbamoyl-pentyl)-3-(3-trifluoromethoxy-phenyl)-acrylamide (PX117718)

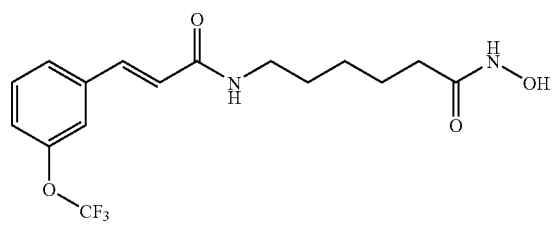

Using an analogous method (J4B), the title compound was obtained from 6-[3-(3trifluoromethoxy-phenyl)-acryloylamino]-hexanoic acid methyl ester (3/60). Yield 30%. M.p. 109-111° C. $^1$H NMR (DMSO-d$_6$, HMDSO), δ: 1.14-1.62(m, 6H); 1.94(t, J=7.0 Hz, 2H); 3.15(q, J=6.2 Hz, 2H); 6.70(d, J=16.2 Hz, 1H); 7.30-7.44(m, 1H); 7.44(d, J=16.2 Hz, 1H); 7.46-7.66(m, 3H); 8.13(t, J=5.4 Hz, 1H); 8.67(s, 1H); 10.34 (s, 1H). HPLC analysis on Symmetry $_{18}$ column: impurities 1.2% (column size 3.9×150 mm; mobile phase 40% acetonitrile–60% 0.1 M phosphate buffer (pH 2.5); detector UV 215 nm; sample concentration 0.5 mg/ml, flow rate 1.0 ml/min). Anal. Calcd for C$_{16}$H$_{19}$F$_3$N$_2$O$_4$: C, 53.33; H, 5.31; N, 7.77. Found: C, 53.47; H, 5.45; N, 7.77.

Example 227

6-[3-(4-Chloro-2-fluoro-phenyl)-acryloylamino]-hexanoic acid methyl ester (3/61)

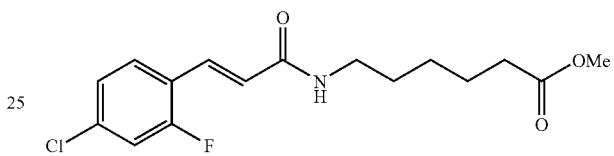

Using an analogous method (J8), the title compound was obtained from 3-(4-chloro-2-fluoro-phenyl)-acrylic acid (1/61) and methyl 6-aminohexanoate hydrochloride (2c). Yield 76%. $^1$H NMR (CDCl$_3$, HMDSO), δ: 1.16-1.85(m, 6H); 2.32(t, J=7.0 Hz, 2H); 3.40(q, J=6.0 Hz, 2H); 3.65(s, 3H); 5.80(bs, 1H); 6.52(d, J=16.0 Hz, 1H); 7.00-7.54(m, 3H); 7.56(d, J=7.0 Hz, 1H).

Example 228

3-(4-Chloro-2-fluoro-phenyl)-N-(5-hydroxycarbamoyl-pentyl)-acrylamide (PX117719)

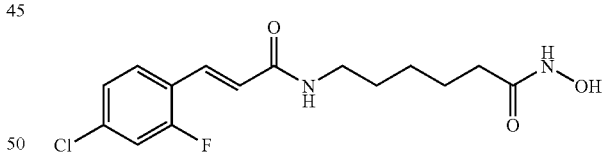

Using an analogous method (J4B), the title compound was obtained from 6-[3-(4-chloro-2-fluoro-phenyl)-acryloylamino]-hexanoic acid methyl ester (3/61). Yield 27%. M.p. 155-157° C. $^1$H NMR (DMSO-d$_6$, HMDSO), δ: 1.16-1.60(m, 6H); 1.94(t, J=7.3 Hz, 2H); 3.15(q, J=6.2 Hz, 2H); 6.72(d, J=16.0 Hz, 1H); 7.35(dd, J=8.4 and 2.2 Hz, 1H); 7.42(d, J=16.0 Hz, 1H); 7.53(dd, J=11.0 and 2.2 Hz, 1H); 7.68(t, J=8.4 Hz, 1H); 8.23(t, J=5.4 Hz, 1H); 8.67(d, J=1.8 Hz, 1H); 10.34(s, 1H). HPLC analysis on Symmetry $_{18}$ column: impurities 1.2% (column size 3.9×150 mm; mobile phase 50-100% acetonitrile +0.1% H$_3$PO$_4$; detector UV 270 nm; sample concentration 1.0 mg/ml, flow rate 1.0 ml/min). Anal. Calcd for C$_{15}$H$_{18}$ClFN$_2$O$_3$: C, 54.80; H, 5.52; N, 8.52. Found: C, 54.60; H, 5.55; N, 8.60.

Example 229

5-[[[4-(Dimethylamino)-1-naphthalenyl]carbonyl]
amino]-pentanoic acid methyl ester (3/62)

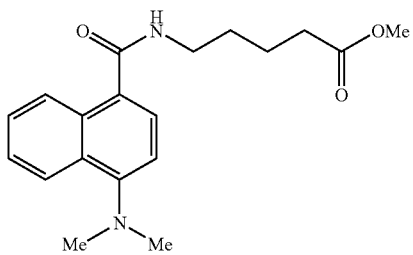

(Method J9A) To the mixture of 4-(dimethylamino)-1-naphthalenecarboxylic acid (1/62) (0.32 g, 1.5 mmol) and N-hydroxysuccinimide (0.21 g, 1.8 mmol) in methylene chloride (10 ml), dicyclohexylcarbodiimide (0.37 g, 1.8 mmol) in methylene chloride (2 ml) was added. A white precipitate appeared. The reaction mixture was after 0.5 h filtered through a pad of Celite® into the solution of methyl 5-aminopentanoate hydrochloride (2b) (0.33 g, 1.9 mmol) in methylene chloride, followed by the addition of triethylamine (2.6 ml, 19 mmol). The reaction mixture was stirred at room temperature overnight, evaporated, suspended in water and extracted with 3 portions of ethyl acetate. The organic layer was washed with brine and dried ($Na_2SO_4$). The solvent was removed and the residue (0.55 g) was purified on silica gel with light petrol—ethyl acetate (2:1) as eluent to give the title compound (0.31 g, 63%), $R_f$ 0.48 (light petrol-ethyl acetate 1:1). $^1$H NMR (200 MHz, DMSO-$d_6$, TMS) δ: 1.51-1.59 (4H, m), 2.38 (2H, t, 6.9 Hz), 2.85 (6H, s), 3.26-3.36 (m, overlapped with a signal from DMSO), 3.61 (3H, s), 7.08 (1H, d, 7.6 Hz), 7.48-7.57 (3H, m), 8.15-8.27 (2H, m), 8.43 (1H, t, br).

Example 230

4-(Dimethylamino)-N-[5-(hydroxyamino)-5-oxopentyl]-1-naphthamide (PX082534)

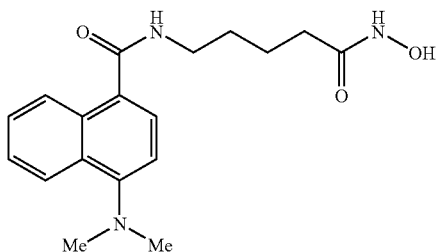

(Method J9B) To the solution of 5-[[[4-(dimethylamino)-1-naphthalenyl]carbonyl]amino]-pentanoic acid methyl ester (3/62) (0.31 g, 0.94 mmol) and hydroxylamine hydrochloride (0.26 g, 3.8 mmol) in absolute methanol was added NaOMe solution made by dissolving Na (0.18 g, 8 mmol) in absolute methanol. A white precipitate immediately appeared. After 0.5 h the reaction was complete (TLC), and the reaction mixture was evaporated, suspended in 1M phosphate buffer (pH 4), and extracted with 3 portions of methylene chloride. The organic phase became turbid, therefore the solvent was removed, and the residue was dried under reduced pressure yielding the crude product (0.27 g). Recrystallisation from acetonitrile gave the title product (0.06 g, 19%) of acceptable purity. $R_f$ 0.50 (CHCl$_3$-MeOH 4:1). M.p. 129° C. $^1$H NMR (DMSO-$d_6$, TMS) δ: 1.53-1.57 (4H, m), 1.97-2.01 (2H, m), 2.84 (6H, s), 3.32-3.33 (m, overlapped with a signal from DMSO), 7.08 (1H, d, J=8.2 Hz), 7.46-7.56 (3H, m), 8.14-8.24 (2H, m), 8.39 (1H, br t, J=5.2 Hz), 8.69 (1H, br s), 10.37 (1H, br s). HPLC analysis on Symmetry $_{18}$ column: impurities <1% (column size 3.9×150 mm; mobile phase acetonitrile–0.1M phosphate buffer (pH 2.5), 10:90; detector UV 220 nm; flow rate 1.3 ml/min). Anal. Calcd for $C_{18}H_{23}N_3O_3$: C, 65.63; H, 7.04; N, 12.76. Found: C, 65.50; H, 6.90; N, 12.73.

Example 231

5-[[[4-(Dimethylamino)-1-naphthalenyl]carbonyl]
amino]-hexanoic acid methyl ester (3/63)

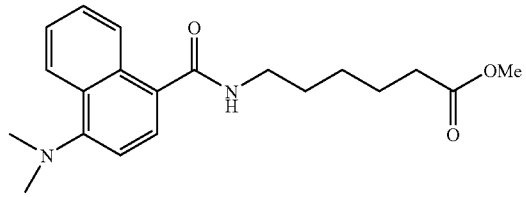

Using an analogous method (J9A), the title compound was obtained from 4-(dimethylamino)-1-naphthalenecarboxylic acid (1/62) and methyl 6-aminohexanoate hydrochloride (2c). Yield 86%. $R_f$ 0.31 (light petrol-ethyl acetate 1:1). $^1$H nMR (200 MHz, DMSO-$d_6$, TMS) δ: 1.30-1.37 (2H, m), 1.50-1.62 (4H, m), 2.33 (2H, t, 7.2 Hz), 2.84 (6H, s), 3.22-3.33 (m, overlapped with a signal of DMSO), 3.56 (3H, s), 7.07 (1H, d, 8.0 Hz), 7.46-7.56 (3H, m), 8.14-8.24 (2H, m), 8.38 (1H, t, br).

Example 232

4-(Dimethylamino)-N-[5-(hydroxyamino)5-oxohexyl]-1-naphthamide (PX089275)

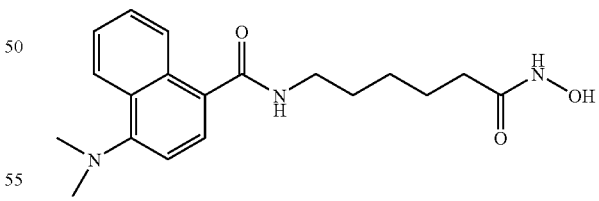

Using an analogous method (J9B), the title compound was obtained from 5-[[[4(dimethylamino)-1-naphthalenyl]carbonyl]amino]-hexanoic acid methyl ester (3/63). Yield 38%. M.p. 135-136° C. $^1$H NMR (DMSO-$d_6$, TMS) δ: 1.31-1.36 (2H, m), 1.50-1.59 (4H, m), 1.97 (2H, t, J=7.2 Hz), 2.84 (6H, s), 3.22-3.33 (m, overlapped with a signal from DMSO), 7.08 (1H, d, J=7.6 Hz), 7.46-7.58 (3H, m), 8.14-8.24 (2H, m), 8.38 (1H, br t, J=5.3 Hz), 8.69 (1H, br s), 10.36 (1H, br s). HPLC analysis on Symmetry $_{18}$ column: impurities ~1% (column size 3.9×150 mm; mobile phase acetonitrile–0.1M phosphate buffer (pH 2.5), 20:80; detector UV 220 nm; flow rate 1.3 ml/min). Anal. Calcd for $C_{19}H_{25}N_3O_3$: C, 66.45; H, 7.34; N, 12.28. Found: C, 66.12; H, 7.33; N, 12.27.

Example 233

6-[(3,4-Dimethoxybenzoyl)amino]hexanoic acid methyl ester (3/64)

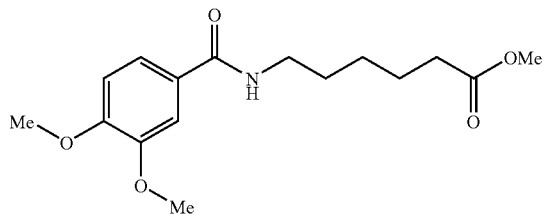

Using an analogous method (J9A), the title compound was obtained from veratric acid (1/64) and methyl 6-aminohexanoate hydrochloride (2c). Yield 86%. $R_f$ 0.53 (ethyl acetate-MeOH 12:1). $^1$H NMR (200 MHz, $d_6$-DMSO, TMS) δ: 1.21-1.33 (2H, m), 1.43-1.60 (4H, m), 2.31 (2H, t, 7.4 Hz), 3.19-3.25 (2H, m), 3.57 (3H, s), 7.00 (1H, d, 8.0 Hz), 7.42-7.48 (2H, m), 8.32 (1H, t, br, ~5 Hz).

Example 234

N-[6-(Hydroxyamino)-6-oxohexyl]-3,4-dimethoxy-benzamide (PX116213)

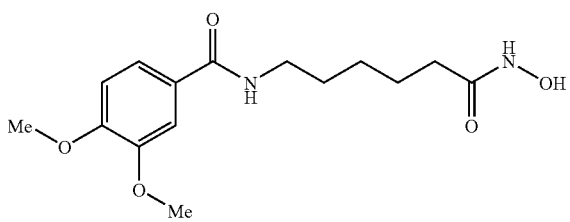

Using an analogous method (J9B), the title compound was obtained from 6-[(3,4-dimethoxybenzoyl)amino]hexanoic acid methyl ester (3/64). Yield 50%. M.p. 133° C. $^1$H NMR (DMSO-$d_6$, TMS) δ: (DMSO-$d_6$, TMS) δ: 1.21-1.33 (2H, m), 1.43-1.54 (4H, m), 1.95 (2H, t, J=7.1 Hz), 3.19-3.25 (2H, m), 3.80 (6H, s), 7.00 (1H, d, J=80 Hz), 7.42-7.49 (2H, m), 8.32 (1H, br t, J=5.3 Hz), 8.68 (1H, br s), 10.34 (1H, br s). HPLC analysis on Symmetry $_{18}$ column: impurities <1% (column size 3.9×150 mm; mobile phase acetonitrile–0.1M phosphate buffer (pH 2.5), 20:80; detector UV 220 nm; flow rate 1.0 ml/min). Anal. Calcd for $C_{15}H_{22}N_2O_5$: C, 58.05; H, 7.15; N, 9.03. Found: C, 57.89; H, 7.08; N, 9.00.

Example 235

6-(4-Methoxy-benzoylamino)-hexanoic acid methyl ester (3/65)

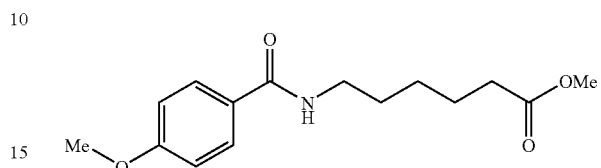

Using an analogous method (J4A), the title compound was obtained from 4-methoxy-benzoic acid (1/65) and methyl 6-aminohexanoate hydrochloride (2c). Yield 85%. $^1$H NMR (CDCl$_3$, HMDSO), δ: 1.35-1.47(m, 2H); 1.55-1.74(m, 4H); 2.29-2.36(m. 2H); 3.38-3.48(m, 2H); 3.66(s, 3H); 3.84(s, 3H); 6.32(bs, 1H); 6.88-6.94(m, 2H); 7.71-7.78(m, 2H).

Example 236

6-(4-Methoxy-benzoylamino)-hexanoic acid (4/65)

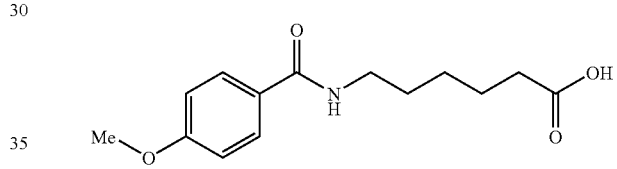

Using an analogous method (J5B), the title compound was obtained from 6-(4-methoxy-benzoylamino)-hexanoic acid methyl ester (3/65). Yield 98%. $^1$H NMR (CDCl$_3$, HMDSO), δ: 1.35-1.47(m, 2H); 1.55-1.74(m, 4H); 2.29-2.36(m. 2H); 3.38-3.48(m, 2H); 3.84(s, 3H); 6.32(bs, 1H); 6.88-6.94(m, 2H); 7.71-7.78(m, 2H).

Example 237

N-(5-Hydroxycarbamoylpentyl)-4-methoxybenzamide (PX089276)

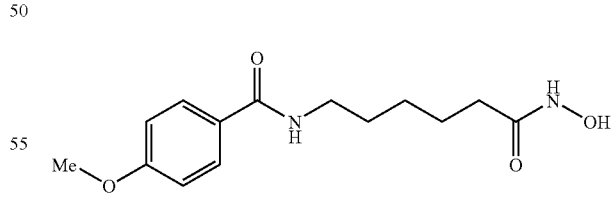

Using an analogous method (J5C), the title compound was obtained from 6-(4-methoxy-benzoylamino)-hexanoic acid (4/65). Yield 63%. M.p. 131-132° C. (from acetonitrile). $^1$H NMR (DMSO-$d_6$, HMDSO), δ: 1.18-1.34 (m, 2H), 1.38-1.58 (m, 4H), 1.92 (t, 2H, J=7.0 Hz), 3.13-3.26 (m, 2H), 3.79 (s, 3H), 6.97 (d, 2H, J=8.6 Hz), 7.80 (d, 2H, J=8.6 Hz), 8.27 (t, 1H, J=5.45 Hz), 8.65 (s, 1H), 10.32 (s, 1H). HPLC analysis on Zorbax SB-C18 column: impurities <1% (column size 4.6× 150 mm; mobile phase gradient 10 min 30-100% acetonitrile+0.1% $H_3PO_4$; detector UV 220 nm; sample concentration 1.0 mg/ml, flow rate 1.5 ml/min). Anal. Calcd for $C_{14}H_{20}N_2O_4$: C, 59.99; H, 7.19; N, 9.99; Found: C, 60.55; H, 7.42; N, 9.62.

Example 238

6-(4-Dimethylamino-benzoylamino)-hexanoic acid methyl ester (3/66)

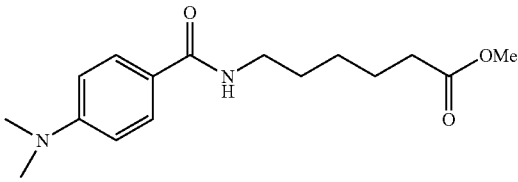

Using an analogous method (J4A), the title compound was obtained from 4-dimethylamino-benzoic acid (1/66) and methyl 6-aminohexanoate hydrochloride (2c). Yield 67%. $^1$H NMR (CDCl$_3$, HMDSO), δ: 1.16-1.92(m, 6H); 2.34(t, J=7.0 Hz, 2H); 3.03(s, 6H); 3.43(q, J=6.0 Hz, 2H); 3.65(s, 3H); 6.00(bs, 1H); 6.69(d J=9.0 Hz, 2H); 7.79(d, J=9.0 Hz, 2H).

Example 239

6-(4-Dimethylamino-benzoylamino)-hexanoic acid (4/66)

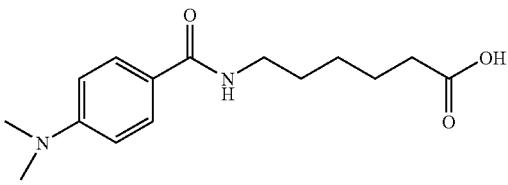

Using an analogous method (J5B), the title compound was obtained from 6-(4-dimethylamino-benzoylamino)-hexanoic acid methyl ester (3/66). Yield 87%. $^1$H NMR (CDCl$_3$, HMDSO), δ: 1.16-1.92(m, 6H); 2.34(t, J=7.0 Hz, 2H); 3.03(s, 6H); 3.43(q, J=6.0 Hz, 2H); 5.97 (bs, 1H); 6.69(d, J=9.0 Hz, 2H); 7.79(d, J=9.0 Hz, 2H).

Example 240

4-Dimethylamino-N-(5-hydroxycarbamoylpentyl) benzamide (PX089274)

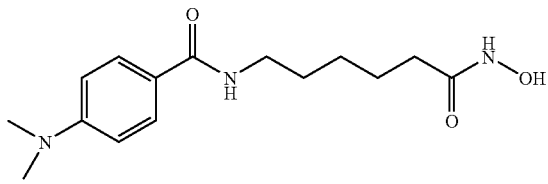

Using an analogous method (J5C), the title compound was obtained from 6-(4dimethylamino-benzoylamino)-hexanoic acid (4/66). Yield 71%. M.p. 137-138° C. (from acetonitrile).

$^1$H NMR (DMSO-d$_6$, HMDSO), δ: 1.17-1.1.33 (m, 2H), 1.35-1.56 (m, 4H), 1.93 (t, 2H, J=7.5 Hz), 2.95 (s, 6H), 3.11-3.25 (m, 2H)), 6.68 (d, 2H, J=8.8 Hz), 7.69 (d, 2H, J=8.8 Hz), 8.01 (t, 1H, J=5.45 Hz), 8.65 (s, 1H), 10.32 (s, 1H). HPLC analysis on Symmetry C$_8$ column: impurities <1% (column size 3.9×150 mm; mobile phase 25% acetonitrile-75% 0.1% $H_3PO_4$; detector UV 220 nm; sample concentration 1.0 mg/ml, flow rate 0.8 ml/min). Anal. Calcd for $C_{15}H_{23}N_3O_3$: C, 61.41; H, 7.90; N, 14.32; Found: C, 61.87; H, 8.08; N, 14.01.

Example 241

6-Benzoylamino-hexanoic acid (4/67)

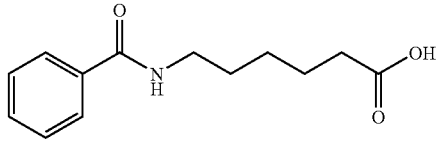

(Method J10) To the solution of 6-aminocaproic acid (2h) (0.982 g, 7.5 mmol) in water/dioxane (1:1) mixture (30 ml) NaOH (0.8 g, 20 mmol) in $H_2O$ (2 ml) and benzoyl chloride (1/67) (1.16 ml, 10 mmol) were added. The mixture was stirred for 6 h at room temperature and diluted with brine (150 ml). The mixture was washed with diethyl ether (2×25 ml), acidified with conc. HCl to pH 4, and extracted with ethyl acetate (4×25 ml). The organic solution was washed with brine (3×25 ml), dried (Na$_2$SO$_4$) and evaporated. The crude title compound (1.589 g, 90%) was purified by column chromatography on silica gel with chloroform -ethyl acetate (1:2) as eluent. $^1$H NMR (CDCl$_3$, HMDS) δ: 1.18-1.85(m, 6H); 2.34(t, J=7.0 Hz, 2H); 3.45(q, J=6.0 Hz, 2H); 6.27(bs, 1H); 7.29-7.52(m, 3H); 7.61-7.85(m, 2H); 10.41(bs, 1H).

Example 242

N-(5-Hydroxycarbamoylpentyl)-benzamide (PX083449)

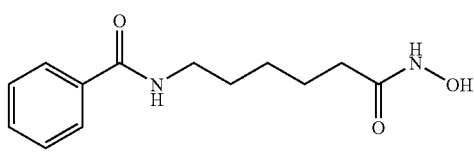

Using an analogous method (J5C), the title compound was obtained from 6-benzoylamino-hexanoic acid (4/67) by the method of example 5, yield 26%. M.p. 102-104° C. (from acetonitrile). $^1$H NMR (DMSO-d$_6$, HMDSO), δ: 1.15-1.1.30 (m, 2H), 1.42-1.50 (m, 4H), 1.87 (t, 2H, J=7.0 Hz), 3.16 (dd, 2H, J=7.0 and 5.85 Hz), 7.34-7.50 (m, 3H), 7.70-7.80 (m, 2H), 8.37 (t, 1H, J=5.45 Hz), 8.60 (s, 1H), 10.27 (s, 1H). HPLC analysis on Zorbax SB-C18 column: impurities 1.5% (column size 4.6×150 mm; mobile phase gradient 10 min 30-100% acetonitrile+0.1% $H_3PO_4$; detector UV 220 nm;

sample concentration 0.5 mg/ml, flow rate 1.5 ml/min). Anal. Calcd for $C_{13}H_{18}N_2O_3$: C, 62.38; H, 7.25; N, 11.19; Found: C, 62.96; H, 7.47; N, 10.65.

Example 243

Methyl 6-[(1H-benzimidazol-2-ylcarbonyl)amino]hexanoate (3/68)

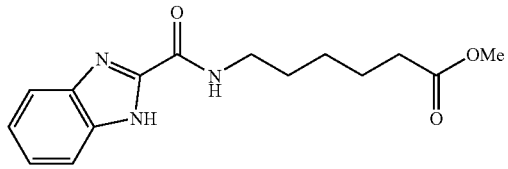

Using the following method, the title compound was obtained from 1H-benzimidazole-2-carboxylic acid (1/68) and methyl 6-aminohexanoate hydrochloride (2c), yield 47% (white solid). TLC: single spot at $R_f$ 0.64 (ethyl acetate, detection—UV-254 nm).

(Method J9A) A solution of carboxylic acid 1/68-1/73 (2.75 mmol) in dry dimethylformamide (3 ml) under argon atmosphere was cooled in ice bath and 1,1'-carbonyldiimidazole (490 mg, 3.01 mmol) was added. The mixture was stirred for 30 min, and then triethylamine (1.0 ml, 7.2 mmol) followed by a solution of methyl 6-aminohexanoate hydrochloride (2c) (2.75 mmol) in dry dimethylformamide (3 ml) were added. The reaction mixture was stirred at ice bath temperature for 1 hour and 20 hours at room temperature, diluted with 50 ml of brine and extracted with ethyl acetate (3×25 ml). The organic phase was washed with brine, 5% $NaHCO_3$, brine, saturated $KH_2PO_4$, and brine. The organic layer was dried ($Na_2SO_4$) and the solvent was evaporated. The residue was purified on silica gel (20 g) with chloroform-ethyl acetate as eluent affording the corresponding amidoester derivative 3/68-3/73.

Example 244

6-[(1H-Benzimidazol-2-ylcarbonyl)amino]hexanoic acid (4/68)

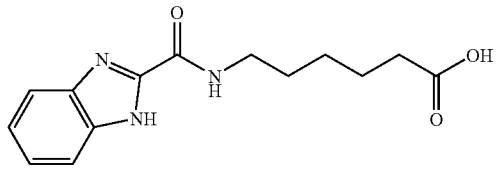

Using the following method, the title compound was obtained from methyl 6-[(1H-benzimidazol-2-ylcarbonyl)amino]hexanoate (3/68), yield 79%. TLC: single spot at $R_f$ 0.10 (ethyl acetate, detection—UV-254 nm).

(Method J9B) The crude ester 3/68-3/73 (1.5-2 mmol) was dissolved in 5 ml tetrahydrofuran and to the mixture the aqueous solution of 1M LiOH (2 equiv) was added. The resulting mixture was stirred for 3 h at room temperature and acidified with 2M HCl to pH 3. The crude product was extracted with ethyl acetate (3×20 ml). The organic layer was washed with brine (3×10 ml) and dried ($Na_2SO_4$). The solvent was evaporated and the residue was chromatographed on silica gel with ethyl acetate as eluent to give the title compounds 4/68-4/73.

Example 245

N-{6-[(Benzyloxy)amino]-6-oxohexyl}-1H-benzimidazole-2-carboxamide (5/68)

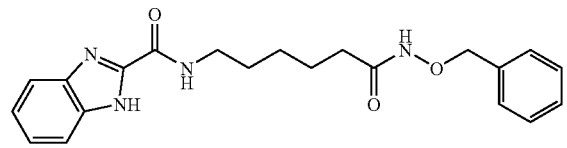

Using the following method, the title compound was obtained from 6-[(1H-benzimidazol-2-ylcarbonyl)amino] hexanoic acid (4/68) and O-benzylhydroxylamine hydrochloride, yield 54% (white solid). TLC: single spot at $R_f$ 0.43 (chloroform-methanol, 10:1, detection—UV-254 nm).

(Method J9C) A solution of appropriate amido acid 4/68-4/73 (1 mmol/1 ml) in anhydrous dimethylformamide under argon atmosphere was cooled in ice bath and carbonyldiimidazole (1.1 eq.) was added. The resulting mixture was stirred for 30 min at ice bath temperature and then triethylamine (4.5 eq.) followed by a solution of O-benzylhydroxylamine hydrochloride (1.5 equiv.) in anhydrous dimethylformamide were added. The mixture was stirred at ice bath temperature for 1 h and for 20 h at room temperature. The reaction mixture was diluted with brine, compounds 5/72 and 5/73 were filtered off and chromatographed on silica gel. In the case of other products 5/68-5/71 the mixture was extracted with ethyl acetate (3×25 ml). The organic phase was washed with brine, 5% $NaHCO_3$, brine, saturated $KH_2PO_4$ and brine. The organic layer was dried ($Na_2SO_4$) and the solvent was evaporated. The residue was purified on silica gel with ethyl acetate as eluent, to give the title compounds 5/68-5/73.

Example 246

1H-Benzimidazole-2-carboxylic acid (5-hydroxycarbamoylpentyl)amide (PX05824)

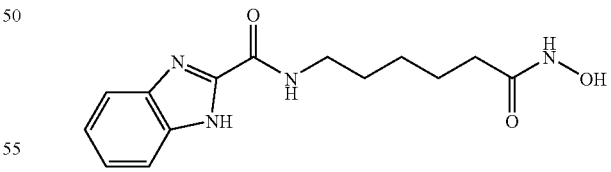

Using the following method, the title compound was obtained from N-{6-[(benzyloxy)amino]-6-oxohexyl}-1H-benzimidazo-2-carboxamide (5/68), yield 79%. M.p. 201° C. (dec.). $^1H$ NMR (DMSO-$d_6$, HMDSO), δ: 1.07-1.68 (m, 6H); 1.78-2.04 (m, 2H); 3.05-3.48 (m, 2H); 7.14-7.35 (m, 2H); 7.44-7.76 (m, 2H); 8.01 (s, 1H); 8.83 (t, 1H, J=6.0 Hz); 10.30 (s, 1H); 13.14 (s, 1H). HPLC analysis on Zorbax SB $C_{18}$ column: impurities 3.5% (column size 4.6×150 mm; mobile phase acetonitrile–0.1% $H_3PO_4$, 15:85; sample concentration 0.05 mg/ml; flow rate 1.5 ml/min.; detector: UV 220 nm).

Anal. Calcd for $C_{14}H_{18}N_4O_3$, %: C, 57.92; H, 6.25; N, 19.29; Found, %: C, 57.28; H, 6.30; N, 18.53.

(Method J9D) Benzyloxyamides 5/68-5/73 (1 mmol) were dissolved in methanol (10 ml) and 50 mg of 5% Pd/C catalyst was added. The suspension was vigorously stirred under hydrogen atmosphere for 1-2 hours (control by TLC). The resultant reaction mixture was filtered through a small amount of silica gel, the sorbent was washed with methanol and the combined filtrates were evaporated in vacuum. The crude product was crystallized from acetonitrile to give corresponding hydroxamic acids.

Example 247

6-[(Furan-2-carbonyl)-amino]-hexanoic acid methyl ester (3/69)

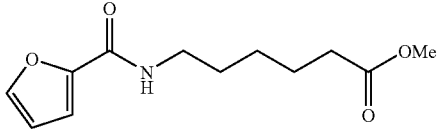

Using an analogous method ( ), the title compound was obtained from furan-2-carboxylic acid (1/69) and methyl 6-aminohexanoate hydrochloride (2c), yield 89% (white solid). $^1$H NMR (CDCl$_3$, HMDSO) δ: 1.15-1.80(m, 6H); 2.34(t, J=7.0 Hz, 2H); 3.36(q, J=6.0 Hz, 2H); 3.63(s, 3H); 6.25(br s, 1H); 6.50(dd, J=4.0 and 2.0 Hz, 1H); 7.10(d, J=4.0 Hz, 1H); 7.45(d, J=2.0 Hz, 1H).

Example 248

6-[(Furan-2-carbonyl)-amino]-hexanoic acid (4/69)

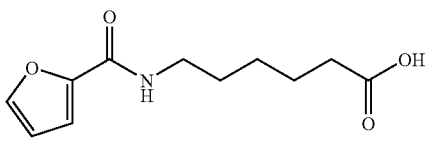

Using an analogous method ( ), the title compound was obtained from 6-[(furan-2-carbonyl)-amino]-hexanoic acid methyl ester (3/69), yield 97%. 1H NMR (CDCl$_3$, HMDSO) δ: 1.20-1.78(m, 6H); 2.37(t, J=7.0 Hz, 2H); 3.36(q, J=6.0 Hz, 2H); 6.30 (br s, 1H); 6.51(dd, J=4.0 and 2.0 Hz, 1H); 7.07(d, J=4.0 Hz, 1H); 7.40(d, J=2.0 Hz, 1H)

Example 249

6-[(Furan-2-carbonyl)-amino]-hexanoic acid benzyloxy-amide (5/69)

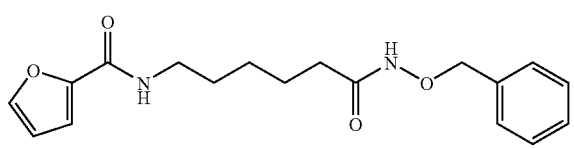

Using an analogous method ( ), the title compound was obtained from 6-[(furan-2-carbonyl)-amino]-hexanoic acid (4/69) and O-benzylhydroxylamine hydrochloride, yield 84% (white solid). $^1$H NMR (CDCl$_3$, HMDSO) δ: 1.18-1.78 (m, 6H); 1.92-2.20(m,2H); 3.36(q, J=6.0 Hz, 2H); 4.87(s, 2H); 6.38(br s, 1H); 6.45(dd, J=4.0 and 2.0 Hz, 1H); 7.07(d, J=4.0 Hz, 1H); 7.36(s, 5H); 7.40(d, J=2.0 Hz, 1H)).

Example 250

Furan-2-carboxylic acid (5-hydroxycarbamoyl-pentyl)-amide (PX105826)

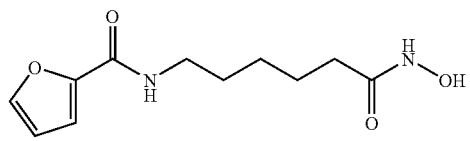

Using an analogous method ( ), the title compound was obtained from 6-[(furan-2-carbonyl)-amino]-hexanoic acid benzyloxy-amide (5/69), yield 82%. M.p. 113.5-115° C. (from acetonitrile). $^1$H NMR (DMSO-d$_6$, HMDSO), δ: 1.12-1.60(m, 6H); 1.85-2.0(m, 2H); 3.09-3.22(m, 2H); 6.60(dd, J=1.6 and 3.4 Hz, 1H); 7.05(dd, J=0.8 and 3.6 Hz, 1H), 7.80(s, 1H); 8.26-8.40(m, 1H); 8.66(s, 1H); 10.33(s, 1H). HPLC analysis on Zorbax SB C$_{18}$ column: impurities 1% (column size 4.6×150 mm; mobile phase 15% acetonitrile+85% 0.1% H$_3$PO$_4$; sample concentration 1.0 mg/ml; flow rate 1.5 ml/min.; detector: UV 220 nm). Anal. Calcd for $C_{11}H_{16}N_2O_4$, %: C, 54.99; H, 6.71; N, 11.66. Found, %: C, 55.89; H, 7.06; N, 11.23.

Example 251

6-(3-Furan-2-yl-propionylamino)-hexanoic acid methylester (3/70)

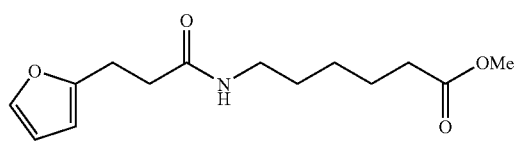

Using an analogous method ( ), the title compound was obtained from 3furan-2-yl-propionic acid (1/70) and methyl 6-aminohexanoate hydrochloride (2c), yield 92% (white solid). $^1$H NMR (CDCl$_3$, HMDSO) δ: 1.38-2.18(m, 8H); 2.49(t, J=7.0 Hz, 2H); 2.89(t, J=7.0 Hz, 2H); 3.43(q, J=6.0

Hz, 2H); 3.63(s, 3H); 5.70(br s, 1H); 6.00(d, J=4.0 Hz, 1H); 6.30(dd, J=4.0 and 2.0 Hz, 1H); 7.31(m, 1H).

Example 252

6-(3-Furan-2-yl-propionylamino)-hexanoic acid (4/70)

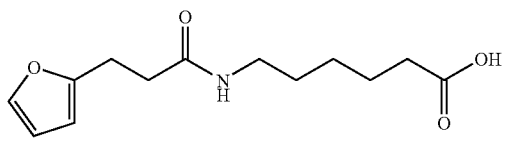

Using an analogous method ( ), the title compound was obtained from 6-(3-furan-2-yl-propionylamino)-hexanoic acid methylester (3/70), yield 74%. $^1$H NMR (CDCl$_3$, HMDSO) δ: 1.35-2.12(m, 8H); 2.50(t, J=7.0 Hz, 2H); 2.90(t, J=7.0 Hz, 2H); 3.43(q, J=6.0 Hz, 2H); 5.80(br s, 1H); 6.02(d, J=4.0 Hz, 1H); 6.33(dd, J=4.0 and 2.0 Hz, 1H); 7.51-7.80(m, 1H).

Example 253

6-(3-furan-2-yl-propionylamino)-hexanoic acid benzyloxy-amide (5/70)

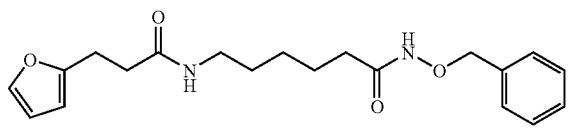

Using an analogous method ( ), the title compound was obtained from 6-(3-furan-2-yl-propionylamino)-hexanoic acid (4/70) and O-benzylhydroxylamine hydrochloride, yield 81% (white solid). 1H NMR (CDCl$_3$, HMDSO) δ: 1.56-2.27 (m, 8H); 2.49(t, J=7.0 Hz, 2H); 2.96(t, J=7.0 Hz, 2H); 3.23(q, J=6.0 Hz, 2H); 4.92(s, 2H); 5.81 (br s, 1H); 6.00(d, J=4.0 Hz, 1H); 6.25(dd, J=4.0 and 2.0 Hz, 1H); 7.29(d, J=2.0 Hz, 1H); 7.40(s, 5H).

Example 254

6-(3-Furan-2-yl-propionylamino)-hexanoic acid hydroxyamide (PX105827)

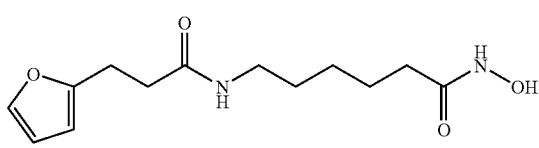

Using an analogous method ( ), the title compound was obtained from 6-(3-furan-2-yl-propionylamino)-hexanoic acid benzyloxy-amide (5/70), yield 50%. M.p. 127-128° C. (from acetonitrile). $^1$H NMR (DMSO-d$_6$, HMDSO), δ: 1.12-1.55(m, 6H); 1.92(t, J=6.8Hz, 2H); 2.36(t, J=7.6 Hz, 2H); 2.81(t, J=7.6 Hz, 2H); 2.90-3.10(m, 2H); 6.05(dd, J=1.0 and 3.0 Hz, 1H); 6.33(dd, J=1.8 and 3.0 Hz, 1H); 7.48(d, J=1.0 Hz,1H); 7.71-7.93(m, 1H); 8.67(s, 1H); 10.33(s, 1H). HPLC analysis on Zorbax SB C$_{18}$ column: impurities 2.3% (column size 4.6×150 mm; mobile phase 20% acetonitrile+80% 0.1% H$_3$PO$_4$; sample concentration 1.0 mg/ml; flow rate 1.5 ml/min.; detector: UV 220 nm). Anal. Calcd for C$_{13}$H$_{20}$N$_2$O$_4$, %: C, 58.19; H, 7.51; N, 10.44. Found, %: C, 58.65; H, 7.91; N, 10.11.

Example 255

6-[(Naphthalene-1-carbonyl-amino]-hexanoic acid methyl ester (3/71)

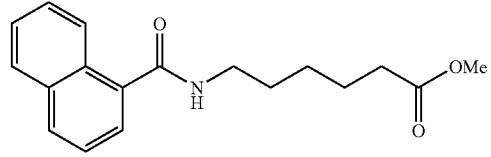

Using an analogous method ( ), the title compound was obtained from naphthalene-1-carboxylic acid (1/71) and methyl 6-aminohexanoate hydrochloride (2c), yield 68% (white solid). $^1$H NMR (CDCl$_3$, HMDSO) δ: 1.25-1.89(m, 6H); 2.32(t, J=7.0 Hz, 2H); 3.49(q, J=6.0 Hz, 2H); 3.61 (s, 3H); 6.03(br s, 1H); 7.27-7.65(m, 4H); 7.72-7.96(m, 2H); 8.18-8.40(m, 1H).

Example 256

6-[(Naphthalene-1-carbonyl-amino]-hexanoic acid (4/71)

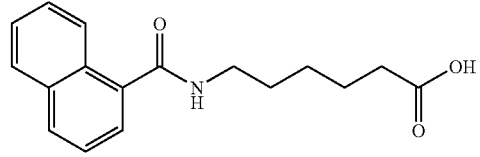

Using an analogous method ( ), the title compound was obtained from 6-[(naphthalene-1-carbonyl-amino]-hexanoic acid methyl ester (3/71), yield 83%. $^1$H NMR (CDCl$_3$, HMDSO) δ: 1.25-1.89(m, 6H); 2.31(t, J=7.0 Hz, 2H); 3.47(q, J=6.0 Hz, 2H); 5.97(br s, 1H); 7.27-7.65(m, 4H); 7.72-7.97 (m, 2H); 8.20-8.40(m, 1H).

Example 257

6-[(Naphthalene-1-carbonyl-amino]-hexanoic acid benzyloxy-amide (5/71)

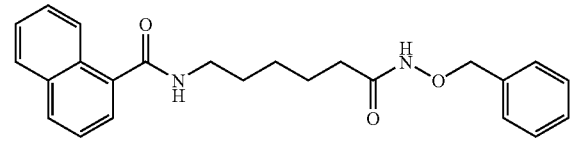

Using an analogous method ( ), the title compound was obtained from 6[(naphthalene-1-carbonyl-amino]-hexanoic acid (4/71) and O-benzylhydroxylamine hydrochloride, yield 64% (white solid). ¹H NMR (CDCl₃, HMDSO) δ: 1.14-1.83 (m, 6H); 1.89-2.29(m, 2H); 3.47(q, J=6.0 Hz, 2H); 4.85(s, 2H); 6.05(br s, 1H); 7.27-7.67(m, 9H); 7.74-8.00(m, 2H); 8.12-8.38(m,1H).

Example 258

Naphthalene-1-carboxylic acid (5-hydroxycarbamoyl-pentyl)-amide (PX105828)

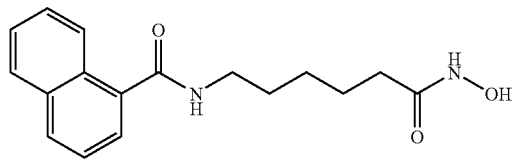

Using an analogous method ( ), the title compound was obtained from 6-[(naphthalene-1-carbonyl-amino]-hexanoic acid benzyloxy-amide (5/71), yield 84%. M.p. 118-119° C. (from acetonitrile). ¹H NMR (DMSO-d₆, HMDSO), δ: 1.25-1.46(m, 2H); 1.47-1.74(m, 4H); 1.94-2.06(m, 2H); 3.35(dd, J=6.2 and 12.6 Hz, 2H); 7.46-7.60(m, 4H); 7.86-7.95(m, 2H); 8.14-8.24(m, 2H); 8.45(br s, 1H); 10.39(s, 1H). HPLC analysis on Zorbax SB C₁₈ column: impurities 2.2% (column size 4.6×150 mm; mobile phase 25% acetonitrile+75% 0.1% H₃PO₄; sample concentration 1.0 mg/ml; flow rate 1.5 ml/min.; detector: UV 220 nm). Anal. Calcd for C₁₇H₂₀N₂O₃, %: C, 67.98; H, 6.71; N, 9.33. Found, %: C, 68.18; H, 6.91; N, 9.07.

Example 259

6-(2-Biphenyl-4-yl-acetylamino)-hexanoic acid methyl ester (3/72)

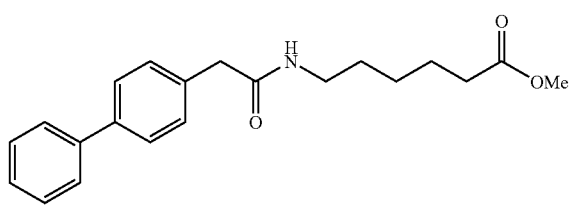

Using an analogous method ( ), the title compound was obtained from biphenyl-4-yl-acetic acid (1/72) and methyl 6-aminohexanoate hydrochloride (2c), yield 79% (white solid). ¹H NMR (CDCl₃, HMDSO) δ: 1.09-1.89(m, 6H); 1,27(t, J=7.0 Hz, 2H); 3.20(q, J=6.0 Hz, 2H); 3.58(s, 2H); 3.65(s, 3H); 5.43(br s, 1H); 7.18-7.74(m 9H).

Example 260

6-(2-Biphenyl-4-yl-acetylamino)-hexanoic acid (4/72)

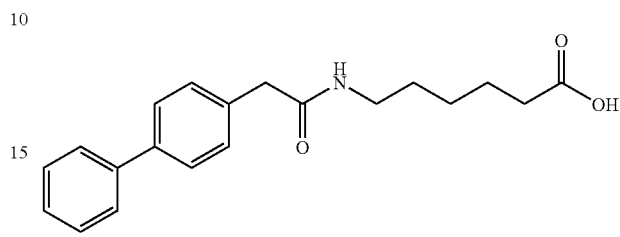

Using an analogous method ( ), the title compound was obtained from 6-(2-biphenyl-4-yl-acetylamino)-hexanoic acid methyl ester (3/72), yield 87%. ¹H NMR (CDCl₃, HMDSO) δ: 1.09-1.69(m, 6H); 2.32(t, J=7.0 Hz, 2H); 3.20(q, J=6.0 Hz, 2H); 3.61 (s, 2H); 5.43(br s, 1H); 7.29-7.69(m, 9H).

Example 261

6-(2-Biphenyl-4-yl-acetylamino)-hexanoic acid benzyloxy-amide (5/72)

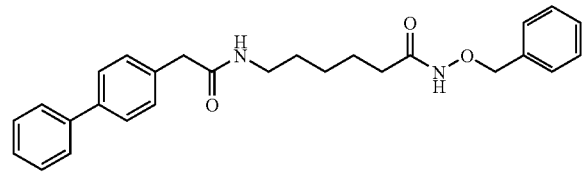

Using an analogous method ( ), the title compound was obtained from 6-(2-biphenyl-4-yl-acetylamino)-hexanoic acid (4/72) and O-benzylhydroxylamine hydrochloride, yield 67% (white solid). ¹H NMR (CDCl₃, HMDSO) δ: 1.07-1.69 (m, 6H); 1.85-2.23(m, 2H); 3.18(q, J=6.0 Hz, 2H); 3.58(s, 2H); 4.87(s, 2H); 5.56(br s, 1H); 7.29-7.65(m, 14H).

Example 262

6-(2-Biphenyl-4-yl-acetylamino)-hexanoic acid hydroxyamide (PX106488)

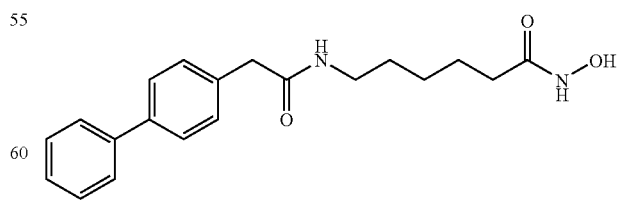

Using an analogous method ( ), the title compound was obtained from 6-(2-biphenyl-4-yl-acetylamino)-hexanoic acid benzyloxy-amide (5/72), yield 73%. M.p. 226-227° C. ¹H NMR (DMSO-d₆, HMDSO), δ: 11.25-1.48(m, 6H); 1.92

(t, J=7.2 Hz, 2H); 3.35(q, J=6.0 Hz, 2H); 3.42(s, 2H); 7.26-7.54(m, 5H); 7.56-7.69(m, 4H); 8.04(t, J=6.0 Hz, 1H); 8.65(s, 1H); 10.33(s, 1H). HPLC analysis on Zorbax SB C$_{18}$ column: impurities 3.5% (column size 4.6×150 mm; mobile phase gradient 10 min 40-100% acetonitrile+0.1% H$_3$PO$_4$; sample concentration 0.3 mg/ml; flow rate 1.5 ml/min.; detector: UV 254 nm). Anal. Calcd for C$_{20}$H$_{24}$N$_2$O$_3$, %: C, 70.57; H, 7.11; N, 8.23. Found, %: C, 69.33; H, 7.24; N, 8.15.

Example 263

6-Diphenylacetylamino-hexanoic acid methyl ester (3/73)

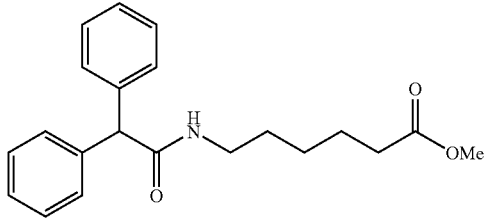

Using an analogous method ( ), the title compound was obtained from diphenylacetic acid (1/73) and methyl 6-aminohexanoate hydrochloride (2c), yield 79% (white solid). $^1$H NMR (CDCl$_3$, HMDSO) δ: 1.05-1.81 (m, 6H); 2.27(t, J=7.0 Hz, 2H); 3.25(q, J=6.0 Hz, 2H); 3.65(s, 3H); 4.94(s, 1H); 5.63(br s, 1H); 7.09-7.54(m 10H).

Example 264

6-Diphenylacetylamino-hexanoic acid (4/73)

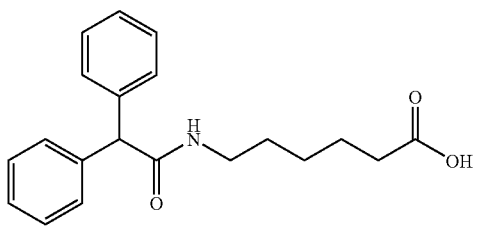

Using an analogous method ( ), the title compound was obtained from 6-diphenylacetylamino-hexanoic acid methyl ester (3/73), yield 80%. $^1$H NMR (CDCl$_3$, HMDSO) δ: 1.01-1.81(m, 6H); 2.27(t, J=7.0 Hz, 2H); 3.27(q, J=6.0 Hz, 2H); 4.92(s, 1H); 5.60(br s, 1H); 7.07-7.56(m, 1 OH); 9.69(br s, 1H).

Example 265

6-Diphenylacetylamino-hexanoic acid benzyloxy-amide (5/73)

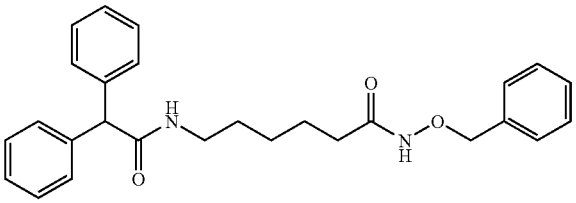

Using an analogous method ( ), the title compound was obtained from 6-diphenylacetylamino-hexanoic acid (4/73) and O-benzylhydroxylamine hydrochloride, yield 73% (white solid). $^1$H NMR (CDCl$_3$, HMDSO) δ: 1.03-1.74(m, 6H); 1.78-2.20(m, 2H); 3.23(q, J=6.0 Hz, 2H); 4.83(s, 2H); 4.87(s, 1H); 5.69(br s, 1H); 7.05-7.52(m, 15H).

Example 266

6-Diphenylacetylamino-hexanoic acid hydroxyamide (PX106489)

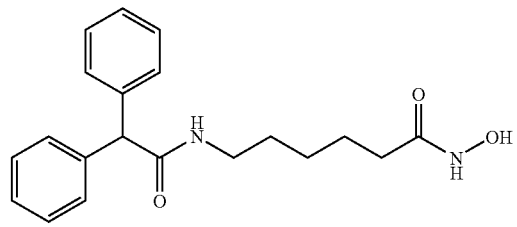

Using an analogous method ( ), the title compound was obtained from 6-diphenylacetylamino-hexanoic acid benzyloxy-amide (5/73), yield 80%. M.p. 55-56° C. $^1$H NMR (DMSO-d$_6$, HMDSO), δ: 1.15-1.6(m, 6H); 1.90(t, J=7.2 Hz, 2H); 3.05(q, J=6,0 Hz, 2H); 4.90(s, 1H); 7.12-7.34(m, 10H); 8.23(t, J=6.0 Hz, 1H); 8.65(s, 1H); 10.32(s, 1H). HPLC analysis on Zorbax SB C$_{18}$ column: impurities 2% (column size 4.6×150 mm; mobile phase gradient 10 min 40-100% acetonitrile+0.1% H$_3$PO$_4$; sample concentration 1.0 mg/ml; flow rate 1.5 ml/min.; detector: UV 254 nm). Anal. Calcd for C$_{20}$H$_{24}$N$_2$O$_3$, %: C, 70.57; H, 7.11; N 8.23. Found, %: C, 70.23; H, 7.19; N 7.91.

Example 267

7-[2-(1H-Indol-3-yl)-ethylcarbamoyl]-heptanoic acid methyl ester (7/74)

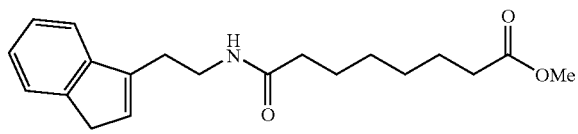

Using the following method, the title compound was obtained from suberic acid monomethyl ester (6c) and 2-(1H-indol-3-yl)-ethylamine (1/74) by the method of example 12, yield 84%. $^1$H NMR (CDCl$_3$, HMDSO) δ: 1.05-1.81(m, 8H); 2.07(t, J=8.0 Hz, 2H); 2.27(t, J=8.0 Hz, 2H); 2.96(t, J=7.0 Hz, 2H); 3,56(t, J=7.0 Hz, 2H); 3.65(s, 3H); 5.52(br s, 1H); 6.98-7.72(m, 5H); 8.38(s, 1H).

(Method J12A) A solution of dicarbonic acid monomethyl (or ethyl) ester 6a, 6b or 6c (2.75 mmol) in anhydrous dimethylformamide (3 ml) under argon atmosphere was cooled in ice bath and to the solution carbonyldiimidazole (490 mg, 3.01 mmol) was added. The mixture was stirred for 30 min. at ice bath temperature, then a solution of appropriate amine 1/74, 1/76-1/82 (2.75 mmol) in dimethylformamide (3 ml) was added (1.0 ml triethylamine additionally was added in the case of 7/79 synthesis). The reaction mixture was stirred for 1 hour at ice bath temperature and 20 hours at room temperature. Then the mixture was supplemented with brine (50 ml) and extracted with ethyl acetate (3×25 ml). The organic phase was washed with brine, 5% NaHCO$_3$, brine, saturated KH$_2$PO$_4$, and brine. The organic layer was dried (Na$_2$SO$_4$) and the solvent was evaporated. The residue was purified on silica gel (20 g) with chloroform-ethyl acetate as eluent affording the corresponding reaction product 7/74-7/83.

Example 268

Octanedioic acid hydroxyamide [2-(1H-indol-3-yl)-ethyl]-amide (PX116216)

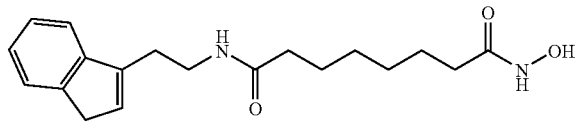

Using the following method, the title compound was obtained from 7-[2-(1H-indol-3-yl)-ethylcarbamoyl]-heptanoic acid methyl ester (7/74) by the method of example 12, yield 49%. M.p. 118.5-120° C. $^1$H NMR (DMSO-d$_6$, HMDSO), δ: 1.12-1.32(m, 4H); 1.46(br t, J=6.5 Hz, 4H); 1.93(t, J=7.0 Hz, 2H); 2.04(t, J=7.0 Hz, 2H); 2.79(t, J=7.4 Hz, 2H); 3.25-3.40(m, overlapped with a signal from H$_2$O); 6.90-7.16(m, 3H); 7.32(d, J=7.4 Hz, 1H); 7.52(d, J=7.4 Hz, 1H); 7.86(t, J=5.9 Hz, 1H); 8.65(s, 1H); 10.33(s, 1H); 10.78(s, 1H). HPLC analysis on Zorbax SB-C18 column: impurities 1.3% (column size 4.6×150 mm; mobile phase gradient 10 min 30-100% acetonitrile+0.1% H$_3$PO$_4$; detector UV 220 nm; sample concentration 0.75 mg/ml, flow rate 1.5 ml/min). Anal. Calcd for C$_{18}$H$_{25}$N$_3$O$_3$: C, 65.24; H, 7.60; N, 12.68. Found: C, 65.20; H, 7.60; N, 12.71.

(Method J12B) Appropriate amido ester 7/74-7/83 (1 mmol) was dissolved in methanol (3-5 ml) and to the obtained mixture solutions of hydroxylamine hydrochloride (278 mg, 4 mmol) in methanol (3 ml) and NaOH (320 mg, 8 mmol) in water (1 ml) were added. After stirring for 15-45 min. (TLC control) the resultant mixture was acidified with 1N HCl to pH 3 and extracted with ethyl acetate (3×30 ml). The organic phase was evaporated under reduced pressure by adding several times of benzene to remove traces of water. The crude product was washed with a small amount of ethyl acetate and crystallized from acetonitrile to give the corresponding hydroxamic acid.

Example 269

5-[2-(1H-Indol-3-yl)-ethylcarbamoyl]-pentanoic acid methyl ester (7/75)

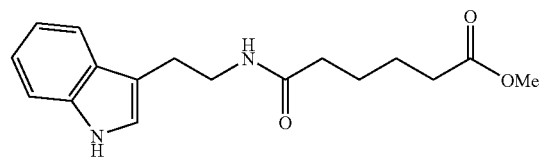

Using an analogous method ( ), the title compound was obtained from adipic acid monomethyl ester (6a) and 2-(1H-indol-3-yl)-ethylamine (1/74) by the method of example 12, yield 73%. $^1$H NMR (CDCl$_3$, HMDSO) δ: 1.34-1.78(m, 4H); 1.92-2.41(m, 4H); 2.94(t, J=6.0 Hz, 2H); 3.54(t, J=6.0 Hz, 2H); 3.63(s, 3H); 5.63(br s, 1H); 6.94-7.69(m, 5H); 8.36(s, 1H).

Example 270

Hexanedioic acid hydroxyamide [2-(1H-indol-3-yl)-ethyl]-amide (PX116217)

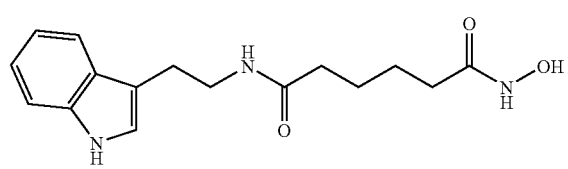

Using an analogous method ( ), the title compound was obtained from 5-[2-(1H-indol-3-yl)-ethylcarbamoyl]-pentanoic acid methyl ester (7/75) by the method of example 12, yield 68%. M.p. 121-122.5° C. $^1$H NMR (DMSO-d$_6$, HMDSO), δ: 1.38-1.58(m, 4H); 1.86-2.18(m, 4H); 2.72-2.88 (m, 2H); 3.28-3.38(m, overlapped with a signal from H$_2$O); 6.80-7.25(m, 3H); 7.32(d, J=7.4 Hz, 1H); 7.52(d, J=7.4 Hz, 1H); 7.82-7.95(m, 1H); 8.67(s, 1H); 10.34(s, 1H); 10.79(s, 1H). HPLC analysis on Zorbax SB-C18 column: impurities 1.3% (column size 4.6×150 mm; mobile phase gradient 10 min 30-100% acetonitrile+0.1% H$_3$PO$_4$; detector UV 230 nm; sample concentration 0.6 mg/ml, flow rate 1.5 ml/min).

Anal. Calcd for $C_{16}H_{21}N_3O_3$: C, 63.35; H, 6.98; N, 13.85. Found: C, 63.29; H, 6.99; N, 13.91.

Example 271

7-(2-Naphthalen-1-yl-ethylcarbamoyl)-heptanoic acid methyl ester (7/76)

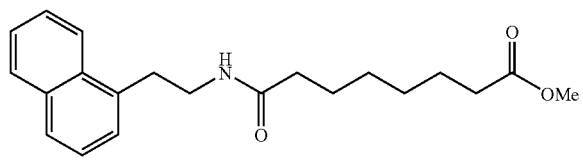

Using an analogous method ( ), the title compound was obtained from suberic acid monomethyl ester (6c) and 2-naphthalen-1-yl-ethylamine (1/76) by the method of example 12, yield 70%. $^1$H NMR (CDCl$_3$, HMDSO) δ: 1.12-1.82(m, 8H); 2.16(t, J=7.0 Hz, 2H); 2.25(t, J=7.0 Hz, 2H); 2.78(t, J=7.0 Hz, 2H); 3.52(q, J=6.0 Hz, 2H); 3.63(s, 3H); 5.56(br s, 1H); 7.32-7.67(m, 4H); 7.67-8.11(m, 3H).

Example 272

Octanedioic acid hydroxyamide (2-naphthalen-1-yl-ethyl)-amide (PX116224)

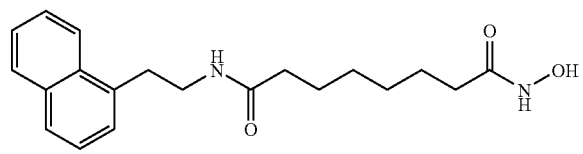

Using an analogous method ( ), the title compound was obtained from 7-(2-naphthalen-1-yl-ethylcarbamoyl)-heptanoic acid methyl ester (7/76) by the method of example 12, yield 63%. M.p. 120-121.5° C. $^1$H NMR (DMSO-d$_6$, HMDSO), δ: 1.12-1.30(m, 4H); 1.48-1.58(m, 4H); 1.93(t, J=7.0 Hz, 2H); 2.04(t, J=7.2 Hz, 2H); 3.08-3.26(m, 2H); 3.28-3.42(m, 2H); 7.30-7.62(m, 4H); 7.78(d, J=7.8 Hz, 1H); 7.86-8.20(m, 2H); 8.14-8.22(m, 1H); 8.66(d, J=1.2 Hz, 1H); 10.33(s, 1H). HPLC analysis on Symmetry C$_8$ column: impurities 1.3% (column size 3.9×150 mm; mobile phase 35% acetonitrile–65% 0.1 M phosphate buffer (pH 2.5); detector UV 220 nm; sample concentration 0.4 mg/ml, flow rate 1.3 ml/min). Anal. Calcd for $C_{20}H_{26}N_2O_3$: C, 70.15; H, 7.65; N, 8.18. Found: C, 69.76; H, 7.63; N, 8.22.

Example 273

7-(2-Hydroxy-2-phenyl-ethylcarbamoyl)-heptanoic acid methyl ester (7/77)

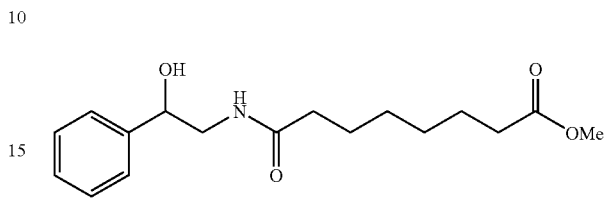

Using an analogous method ( ), the title compound was obtained from suberic acid monomethyl ester (6c) and 2-amino-1-phenyl-ethanol (1/77) by the method of example 12, yield 47%. $^1$H NMR (CDCl$_3$, HMDSO) δ: 1.03-1.76(m, 8H); 2.16(t, J=7.0 Hz, 2H); 2.29(t, J=7.0 Hz, 2H); 3.01-3.92 (m, 2H); 3.63(s, 3H); 4.81(q, J=3.5 Hz, 1H); 6.09(br s, 1H); 7.32(s, 5H).

Example 274

Octanedioic acid hydroxyamide (2-hydroxy-2-phenyl-ethyl)-amide (PX116226)

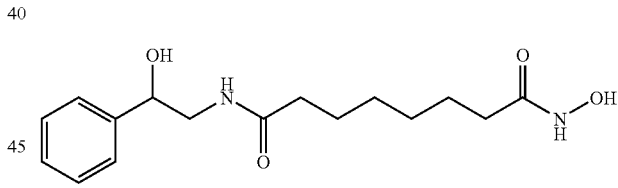

Using an analogous method ( ), the title compound was obtained from 7-(2-hydroxy-2-phenyl-ethylcarbamoyl)-heptanoic acid methyl ester (7/77) by the method of example 12, yield 55%. M.p. 100-102° C. $^1$H NMR (DMSO-d$_6$, HMDSO), δ: 1.12-1.30(m, 4H); 1.36-1.56(m, 4H); 1.92(t, J=7.2 Hz, 2H); 2.04(t, J=7.2 Hz, 2H); 3.00-3.16(m, 1H); 3.18-3.38(m, overlapped with a signal from H$_2$O); 4.52-4.64 (m, 1H); 5.43(d, J=4.4 Hz, 1H); 7.18-7.36(m, 5H); 7.82(t, J=5.2 Hz, 1H); 8.65(s, 1H); 10.32(s, 1H). HPLC analysis on Symmetry C$_{18}$ column: impurities 1.8% (column size 3.9× 150 mm; mobile phase 20% acetonitrile–80% 0.1 M phosphate buffer (pH 2.5); detector UV 220 nm; sample concentration 0.5 mg/ml, flow rate 1.0 ml/min). Anal. Calcd for $C_{16}H_{24}N_2O_4$: C, 62.32; H, 7.84; N, 9.08. Found: C, 62.23; H, 7.84; N, 8.97.

Example 275

7-(2,2-Diphenyl-ethylcarbamoyl)-heptanoic acid methyl ester (7/78)

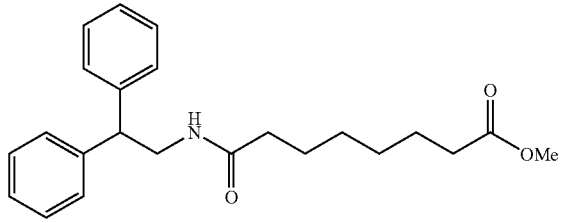

Using an analogous method ( ), the title compound was obtained from suberic acid monomethyl ester (6c) and 2,2-diphenyl-ethylamine (1/78) by the method of example 12, yield 83%. $^1$H NMR (CDCl$_3$, HMDSO) δ: 1.05-1.16(m, 8H); 2.03(t, J=7.0 Hz, 2H); 2.25(t, J=7.0 Hz, 2H); 3.63(s, 3H); 3.73-4.01(m, 2H); 4.18(t, J=7.0 Hz, 1H); 5.45(t, J=6.0 Hz, 1H); 7.16-7.36(m, 10H).

Example 276

Octanedioic acid (2,2-diphenyl-ethyl)-amide hydroxyamide (PX117249)

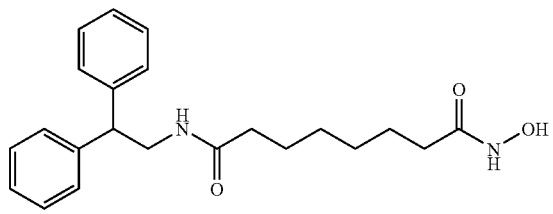

Using an analogous method ( ), the title compound was obtained from 7-(2,2diphenyl-ethylcarbamoyl)-heptanoic acid methyl ester (7/78) by the method of example 12, yield 83%. M.p. 123-123.5° C. $^1$H NMR (DMSO-d$_6$, HMDSO), δ: 0.95-1.22(m, 4H); 1.24-1.50(m, 4H); 1.89(t, J=7.2 Hz, 2H); 1.92(t, J=7.4 Hz, 2H); 3.67(dd, J=5.6 and 7.8 Hz, 2H); 4.18(t, J=7.8 Hz, 1H); 7.11-7.33(m, 10H); 7.82(t, J=5.6 Hz, 1H); 8.66(d, J=1.6 Hz, 1H); 10.32(s, 1H). HPLC analysis on Symmetry C$_8$ column: impurities 1.6% (column size 3.9×150 mm; mobile phase 40% acetonitrile–60% 0.1 M phosphate buffer (pH 2.5); detector UV 220 nm; sample concentration 0.8 mg/ml, flow rate 1.2 ml/min). Anal. Calcd for $C_{22}H_{28}N_2O_3$: C, 71.71; H, 7.66; N, 7.60. Found: C, 71.63; H, 7.68; N, 7.57.

Example 277

7-(3-Phenyl-allylcarbamoyl)-heptanoic acid methyl ester (7/79)

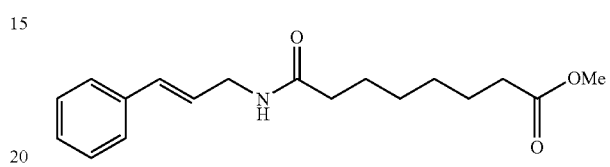

Using an analogous method ( ), the title compound was obtained from suberic acid monomethyl ester (6c) and 3-phenyl-allylamine (1/79) by the method of example 12, yield 64%. $^1$H NMR (CDCl$_3$, HMDSO) δ: 1.16-1.83(m, 8H); 2.21 (t, J=8.0 Hz, 2H); 2.29(t, J=8.0 Hz, 2H); 3.63(s, 3H); 4.03(t, J=6.0 Hz, 2H); 5.56(br s, 1H); 6.14(dt, J=16.0 and 6.0 Hz, 1H); 6.52(d, J=16.0 Hz, 1H); 7.29(s, 5H).

Example 278

Octanedioic acid hydroxyamide (3-phenyl-allyl)-amide (PX117416)

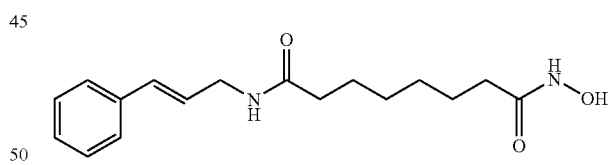

Using an analogous method ( ), the title compound was obtained from 7-(3-phenyl-allylcarbamoyl)-heptanoic acid methyl ester (7/79) by the method of example 12, yield 64%. M.p. 133-133.5° C. $^1$H NMR (DMSO-d$_6$, HMDSO), δ: 1.26-1.35(m, 4H); 1.37-1.59(m, 4H); 1.93(t, J=7.4 Hz, 2H); 2.10(t, J=7.4 Hz, 2H); 3.84(t, J=5.6 Hz, 2H); 6.22(dt, J=16.0 and 5.6 Hz, 1H); 6.46(d, J=16.0 Hz, 1H); 7.18-7.44(m, 5H); 8.04(t, J=5.6 Hz, 1H); 8.66(d, J=1.8 Hz, 1H); 10.33(s, 1H). HPLC analysis on Symmetry C$_8$ column: impurities 1.6% (column size 3.9×150 mm; mobile phase 35% acetonitrile–65% 0.1 M phosphate buffer (pH 2.5); detector UV 254 nm; sample concentration 0.4 mg/ml, flow rate 1.1 ml/min). Anal. Calcd for $C_{17}H_{24}N_2O_3 \cdot 0.5\ H_2O$ containing 1% of inorganic material: C, 64.50; H, 7.96; N, 8.85. Found: C, 64.31; H, 7.54; N, 8.88.

Example 279

7-Benzylcarbamoyl-heptanoic acid methyl ester (7/80)

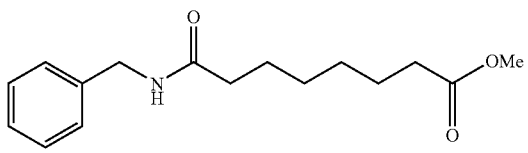

Using an analogous method ( ), the title compound was obtained from suberic acid monomethyl ester (6c) and benzylamine (1/80) by the method of example 12, yield 80%. $^1$H NMR (CDCl$_3$, HMDSO) δ: 1.14-1.83(m, 8H); 2.21(t, J=7.0 Hz, 2H); 2.27(t, J=7.0 Hz, 2H); 3.63(s, 3H); 4.43(d, J=6.0 Hz, 2H); 5.69(br s, 1H); 7.29(s, 5H).

Example 280

Octanedioic acid benzylamide hydroxyamide (PX117418)

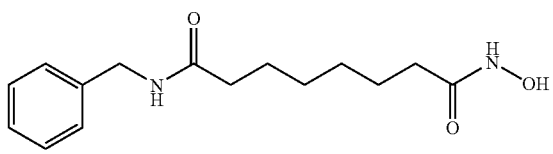

Using an analogous method ( ), the title compound was obtained from 7-benzylcarbamoyl-heptanoic acid methyl ester (7/80) by the method of example 12, yield 60%. M.p. 126-126.5° C. $^1$H NMR (DMSO-d$_6$, HMDSO), δ: 1.16-1.32 (m, 4H); 1.36-1.60(m, 4H); 1.92(t, J=7.2 Hz, 2H); 2.12(t, J=7.4 Hz, 2H); 4.24(d, J=5.6 Hz, 2H); 7.16-7.36(m, 5H); 8.30(t, J=5.6 Hz, 1H); 8.66(s, 1H); 10.33(s, 1H). HPLC analysis on Symmetry C$_{18}$ column: impurities 1% (column size 3.9×150 mm; mobile phase 30% acetonitrile–70% 0.1 M phosphate buffer (pH 2.5); detector UV 220 nm; sample concentration 0.5 mg/ml, flow rate 0.9 ml/min). Anal. Calcd for $C_{15}H_{22}N_2O_3 \cdot 0.5\ H_2O$: C, 62.70; H, 8.07; N, 9.75. Found: C, 62.84; H, 7.83; N, 9.73.

Example 281

7-Phenethylcarbamoyl-heptanoic acid methyl ester (7/81)

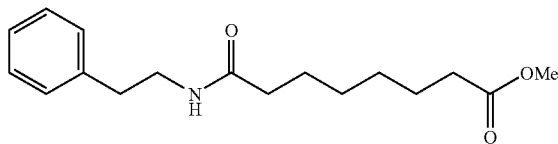

Using an analogous method ( ), the title compound was obtained from suberic acid monomethyl ester (6c) and phenethylamine (1/81) by the method of example 12, yield 63%. $^1$H NMR (CDCl$_3$, HMDSO) δ: 1.05-1.81 (m, 8H); 2.09(t, J=7.0 Hz, 2H); 2.27(t, J=7.0 Hz, 2H); 2.78(t, J=7.0 Hz, 2H); 3.52(q, J=6.0 Hz, 2H); 3.65(s, 3H); 5.56(br s, 1H); 7.00-7.43 (m, 5H).

Example 282

Octanedioic acid hydroxyamide phenethyl-amide (PX117419)

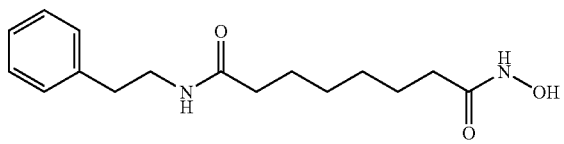

Using an analogous method ( ), the title compound was obtained from 7-phenethylcarbamoyl-heptanoic acid methyl ester (7/81) by the method of example 12, yield 30%. M.p. 113-114° C. $^1$H NMR (DMSO-d$_6$, HMDSO), δ: 1.10-1.30(m, 4H); 1.34-1.56(m, 4H); 1.92(t, J=7.2 Hz, 2H); 2.01(t, J=7.4 Hz, 2H); 2.68(t, J=7.6 Hz, 2H); 3.25 (q, J=6.8 Hz, 2H); 7.12-7.34(m, 5H); 7.85(t, J=5.6 Hz, 1H); 8.66(d, J=1.6 Hz, 1H); 10.33(s, 1H). HPLC analysis on Symmetry C$_{18}$ column: impurities 1% (column size 3.9×150 mm; mobile phase 30% acetonitrile–70% 0.1 M phosphate buffer (pH 2.5); detector UV 220 nm; sample concentration 0.5 mg/ml, flow rate 1.0 ml/min). Anal. Calcd for $C_{16}H_{24}N_2O_3$: C, 65.73; H, 8.27; N, 9.58. Found: C, 65.04; H, 8.25; N, 9.44.

Example 283

7-(3-Phenyl-propylcarbamoyl)-heptanoic acid methyl ester (7/82)

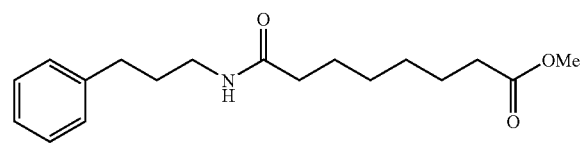

Using an analogous method ( ), the title compound was obtained from suberic acid monomethyl ester (6c) and 3-phenyl-propylamine (1/82) by the method of example 12, yield 80.5%. $^1$H NMR (CDCl$_3$, HMDSO) δ: 1.12-1.78(m, 8H); 1.81(t, J=7.0 Hz, 2H); 2.09(t, J=7.0 Hz, 2H); 2.29(t, J=7.0 Hz, 2H); 2.63(t, J=7.0 Hz, 2H); 3.27(q, J=6.0 Hz, 2H); 3.65(s, 3H); 5.45(br s); 7.05-7.45(m, 5H).

Example 284

Octanedioic acid hydroxyamide (3-phenyl-propyl)-amide (PX117420)

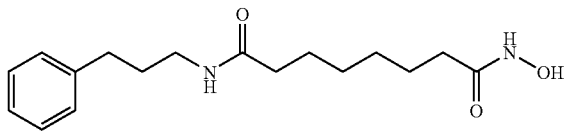

Using an analogous method ( ), the title compound was obtained from 7-(3-phenyl-propylcarbamoyl)-heptanoic acid methyl ester (7/82) by the method of example 12, yield 33%. M.p. 97-98° C. $^1$H NMR (DMSO-d$_6$, HMDSO), δ: 1.14-1.32 (m, 4H); 1.34-1.56(m, 4H); 1.67(quint, J=7.5 Hz, 2H); 1.92(t, J=7.5 Hz, 2H); 2.04(t, J=7.5 Hz, 2H); 2.56(t, overlapped with a signal of DMSO, J=7.5 Hz, 2H); 3.03(q, J=6.5 Hz, 2H); 7.15-7.34(m, 5H); 7.79(t, J=5.4 Hz, 1H); 8.66(s, 1H); 10.32 (s, 1H). HPLC analysis on Symmetry C$_8$ column: impurities 1% (column size 3.9×150 mm; mobile phase 35% acetonitrile–65% 0.1 M phosphate buffer (pH 2.5); detector UV 220 nm; sample concentration 0.5 mg/ml, flow rate 1.1 ml/min). Anal. Calcd for C$_{17}$H$_{26}$N$_2$O$_3$: C, 66.64; H, 8.55; N, 9.14. Found: C, 66.47; H, 8.58; N, 9.08.

Example 285

6-[2-(1H-Indol-3-yl)-ethylcarbamoyl-hexanoic acid ethyl ester (7/83)

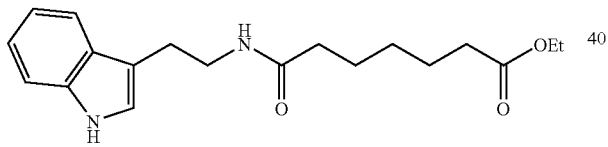

Using an analogous method ( ), the title compound was obtained from pimelic acid monoethyl ester (6c) and 2-(1H-indol-3-yl)-ethylamine (1/74) by the method of example 12, yield 88%. $^1$H NMR (DMSO-d$_6$, HMDSO) δ: 1.10-1.75 (m, 11H); 2.13-3.17 (m, 6H, overlapped woth a signal of DMSO); 4.14 (q, 2H, J=7.2 Hz); 7.00-7.55 (m, 5H); 7.90 (t, 1H, J=5.5 Hz); 10.35 (s, 1H).

Example 286

N$^1$-Hydroxy-N$^7$-[2-(1H-indol-3-yl)ethyl]heptanediamide (PX117408)

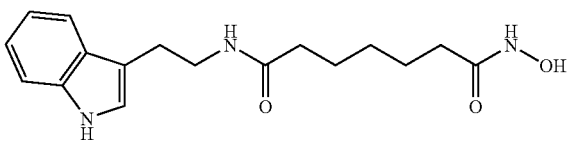

Using an analogous method ( ), the title compound was obtained from 6-[2-(1H-indol-3-yl)-ethylcarbamoyl-hexanoic acid ethyl ester (7/83) by the method of example 7, yield 24%, M.p. 140-142° C. $^1$H NMR (DMSO-d$_6$, HMDSO), δ: 1.10-1.30 (m, 2H); 1.36-1.58 (m, 4H); 1.93 (t, 2H, J=7.3 Hz); 2.04 (t, 2H, J=7.2 Hz); 2.80 (t, 2H, J=7.3 Hz); 3.31 (q, overlapped with a water signal of DMSO, 2H, J=6.7 Hz); 6.90-7.18 (m, 3H); 7.32 (d, 1H, J=7.8 Hz); 7.53 (d, 1H, J=7.4 Hz); 7.89 (t, 1H, J=5.4 Hz); 8.69 (s, 1H); 10.35 (s, 1H); 10.80 ppm (s, 1H). HPLC analysis on Zorbax SB-C18 column: impurities 1.7% (column size 4.6×150 mm; mobile phase methanol–0.1% H$_3$PO$_4$, gradient from 50:50 to 100:0; detector UV 220 nm; sample concentration 0.6 mg/ml, flow rate 1.0 ml/min). Anal. Calcd for C$_{17}$H$_{23}$N$_3$O$_3$: C, 64.33; H, 7.30; N, 13.24. Found: C, 64.24; H, 7.30; N, 13.30.

Example 287

7-(Naphthalen-1-ylcarbamoyl)-heptanoic acid methyl ester (7/84)

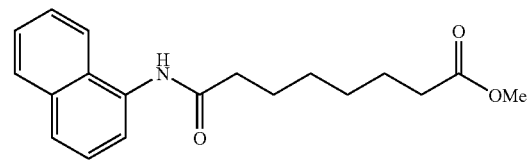

Using the following method, the title compound was obtained from suberic acid monomethyl ester (6c) and naphthalen-1-ylamine (1/84). Yield 60%. $^1$H NMR (CDCl$_3$, HMDSO) δ: 1.12-1.81(m, 8H); 2.16(t, J=8.0 Hz, 2H); 2.25(t, J=8.0 Hz, 2H); 3.63(s, 3H); 4.87(d, J=6.0 Hz, 2H); 5.61(br s, 1H); 7.32-7.63(m, 4H); 7.67-8.09(m, 3H).

(Method J13) To a solution of pimelic or suberic acid monomethyl esters 6b or 6c (2.75 mmol) in anhydrous dichloromethane (10 ml) oxalyl chloride (0.84 ml, 9.63 mmol) and one drop of N,N-dimethylformamide were added, and the resulting mixture was stirred for 30 min at room temperature followed by 1 h at 40° C. The solution was carefully evaporated under reduced pressure and dried. The resulting chloride was dissolved in anhydrous tetrahydrofuran (3 ml), cooled in ice bath and to the solution triethylamine (0.5 ml) was added. A solution of amine 1/84-1/88 (2.75 mmol) and triethylamine (0.5 ml) in N,N-dimethylformamide (3 ml) was added to the above prepared chloride solution and stirring was continued for 1 h at 0° C. followed by 20 h at room temperature. The mixture was diluted with brine (30 ml) and extracted with ethyl acetate (3×25 ml). The organic phase was washed with brine, 5% NaHCO$_3$, brine, 0.1 N HCl and brine, then the organic layer was dried (Na$_2$SO$_4$) and the solvent was evaporated. The residue was purified on silica gel (20 g) with chloroform-ethyl acetate as eluent affording the corresponding amido ester 7/84-7/88.

Example 288

Octanedioic acid hydroxyamide naphthalen-1-ylamide (PX116218)

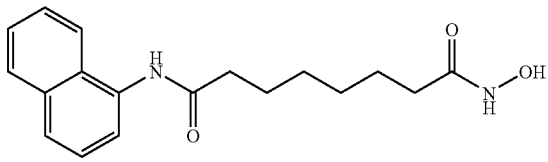

Using an analogous method (J12B), the title compound was obtained from 7-(naphthalen-1-ylcarbamoyl)-heptanoic acid methyl ester (7/84). Yield 64%. M.p. 115-116.5° C. $^1$H NMR (DMSO-d$_6$, HMDSO), δ: 1.24-1.74(m, 8H); 1.96(t, J=7.2 Hz, 2H); 2.37-2.55(m, overlapped with a signal from DMSO-d$_6$); 7.42-7.60(m, 3H); 7.62-7.70(m, 1H); 7.70-7.80 (m, 1H); 7.87-7.98(m, 1H); 8.00-8.09(m, 1H); 8.66(s, 1H); 9.85(s, 1H); 10.34(s, 1H). HPLC analysis on Symmetry C$_8$ column: impurities <1% (column size 3.9×150 mm; mobile phase 35% acetonitrile–65% 0.1 M phosphate buffer (pH 2.5); detector UV 220 nm; sample concentration 0.5 mg/ml, flow rate 1.0 ml/min). Anal. Calcd for C$_{18}$H$_{22}$N$_2$O$_3$: C, 68.77; H, 7.05; N, 8.91. Found: C, 68.45; H, 7.00; N, 8.90.

Example 289

7-(Naphthalen-2-ylcarbamoyl)-heptanoic acid methyl ester (7/85)

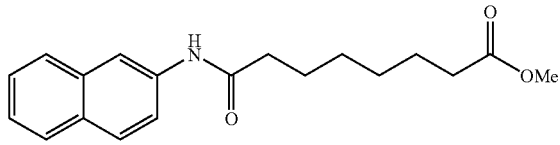

Using an analogous method (J13), the title compound was obtained from suberic acid monomethyl ester (6c) and naphthalen-2-ylamine (1/85). Yield 71%. $^1$H NMR (CDCl$_3$, HMDSO) δ: 1.21-1.94(m, 8H); 2.32(t, J=7.0 Hz, 2H); 2.41(t, J=7.0 Hz, 2H); 3.63(s, 3H); 8.23(s, 1H).

Example 290

Octanedioic acid hydroxyamide naphthalen-2-ylamide (PX116223)

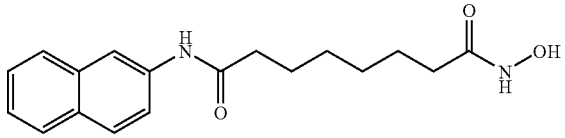

Using an analogous method (J12B), the title compound was obtained from 7-(naphthalen-2-ylcarbamoyl)-heptanoic acid methyl ester (7/85). Yield 62%. M.p. 142.5-144° C. $^1$H NMR (DMSO-d$_6$, HMDSO), δ: 1.20-1.40(m, 4H); 1.42-1.70 (m, 4H); 1.94(t, J=7.2 Hz, 2H); 2.35(t, J=7.0 Hz, 2H); 7.32-7.62(m, 3H); 7.74-7.87(m, 3H); 8.30(d, J=1.8 Hz, 1H); 8.66 (s, 1H); 10.06(s, 1H); 10.33(s, 1H). HPLC analysis on Symmetry C$_8$ column: impurities <1% (column size 3.9×150 mm; mobile phase 35% acetonitrile–65% 0.1 M phosphate buffer (pH 2.5); detector UV 220 nm; sample concentration 0.5 mg/ml, flow rate 1.3 ml/min). Anal. Calcd for C$_{18}$H$_{22}$N$_2$O$_3$: C, 68.77; H, 7.05; N, 8.91. Found: C, 68.74; H, 7.05; N, 9.00.

Example 291

7-(Benzhydryl-carbamoyl)-heptanoic acid methyl ester (7/86)

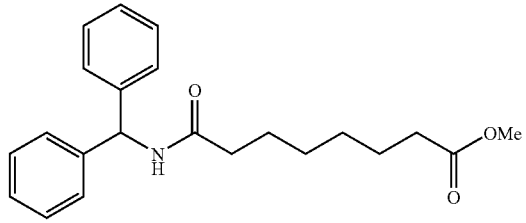

Suberic acid monomethyl ester chloride was obtained from suberic acid monomethyl ester (6c) (518 mg, 2.75 mmol). The crude chloride was dissolved in acetonitrile (3 ml) and the obtained solution was added to the suspension prepared from solutions of diphenyl-methylamine (1/86) (503 mg, 2.75 mmol) in acetonitrile (5 ml) and saturated aq. NaHCO$_3$ (8 ml). The resulting mixture was stirred at room temperature for 6 h and diluted with ethyl acetate (50 ml). The mixture was washed with 1N HCl (20 ml) and brine (4×20 ml), then the organic layer was dried (Na$_2$SO$_4$) and the solvent was evaporated. The residue was purified on silica gel (20 g), with chloroform-ethyl acetate as eluent to give the title compound 7/86 (681 mg, 70%). $^1$H NMR (CDCl$_3$, HMDSO) δ: 1.12-1.76(m, 8H); 2.12-2.38(m, 4H); 3.65(s, 3H); 5.89-6.12(m, 1H); 6.29(d, J=8.0 Hz, 1H); 7.29(s, 10H).

Example 292

N$^1$-benzhydryl-N$^8$-hydroxyoctanediamide (PX117417)

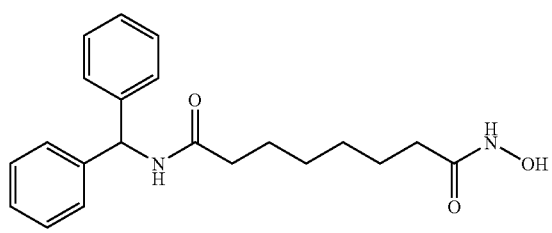

Using an analogous method (J12B), the title compound was obtained from 7-(benzhydryl-carbamoyl)-heptanoic acid methyl ester (7/86). Yield 58%. M.p. 155-156.5° C. $^1$H NMR (DMSO-d$_6$, HMDSO), δ: 1.14-1.31(m, 4H); 1.34-1.60(m, 4H); 1.91(t, J=7.2 Hz, 2H); 2.19(t, J=7.2 Hz, 2H); 6.11(d, J=8.8 Hz, 1H); 7.11-7.38(m, 10H); 8.66(s, 1H); 8.72(d, J=8.8 Hz, 1H); 10.33(s, 1H). HPLC analysis on Symmetry $C_8$ column: impurities 3.7% (column size 3.9×150 mm; mobile phase 35% acetonitrile–65% 0.1 M phosphate buffer (pH 2.5); detector UV 220 nm; sample concentration 0.3 mg/ml, flow rate 1.3 ml/min). Anal. Calcd for $C_{21}H_{26}N_2O_3$: C, 71.16; H, 7.39; N, 7.90. Found: C, 71.04; H, 7.40; N, 7.85.

Example 293

6-(Naphthalen-2-ylcarbamoyl)-hexanoic acid ethyl ester (7/87)

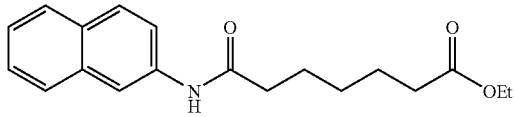

Using an analogous method (J13), the title compound was obtained from pimelic acid monoethyl ester (6b) and naphthalen-2-ylamine (1/87). Yield 65%. $^1$H NMR (CDCl$_3$, HMDSO) δ: 1.23(t, J=7.0 Hz, 3H); 1.32-1.94(m, 6H); 2.32(t, J=7.0 Hz, 2H); 2.38(t, J=7.0 Hz, 2H); 4.12(q, J=7.0 Hz, 2H); 7.27-7.87(m, 7H); 8.21(s, 1H).

Example 294

Heptanedioic acid hydroxyamide naphthalen-2-ylamide (PX117461)

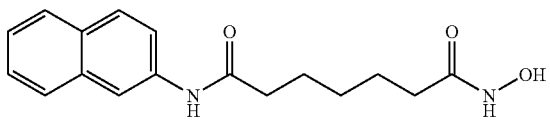

Using an analogous method (J12B), the title compound was obtained from 6-(naphthalen-2-ylcarbamoyl)-hexanoic acid ethyl ester (7/87). Yield 54%. M.p. 142-144° C. $^1$H NMR (DMSO-d$_6$, HMDSO), δ: 1.20-1.40(m, 2H); 1.43-1.73(m, 4H); 1.96(t, J=7.2 Hz, 2H); 2.35(t, J=7.4 Hz, 2H); 7.34-7.60 (m, 3H); 7.75-7.90(m, 3H); 8.31(d, J=1.8 Hz, 1H); 8.68(d, J=1.8 Hz, 1H); 10.08(s, 1H); 10.35(s, 1H). HPLC analysis on Zorbax SB-C18 column: impurities <1% (column size 4.6× 150 mm; mobile phase 30%-100% acetonitrile+0.1% H$_3$PO$_4$ (grad. 15 min); detector UV 254 nm; sample concentration 0.5 mg/ml, flow rate 1.0 ml/min). Anal. Calcd for $C_{17}H_{20}N_2O_3$: C, 67.98; H, 6.71; N, 9.33. Found: C, 67.97; H, 6.72; N, 9.32.

Example 295

7-(Biphenyl-4-ylcarbamoyl)-heptanoic acid ethyl ester (7/88)

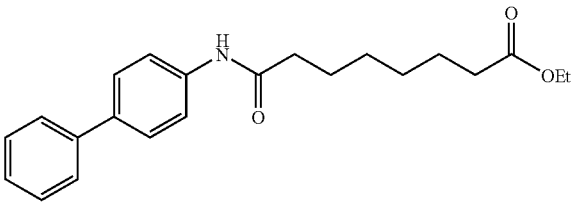

Using an analogous method (J13), the title compound was obtained from suberic acid monoethyl ester (6c, R'=Et) and biphenyl-4-ylamine (1/88). Yield 91%. $^1$H NMR (CDCl$_3$, HMDSO) δ: 1.23(t, J=7.0 Hz, 3H); 1.29-1.85(m, 8H); 2 26(t, J=7.0 Hz, 2H); 2.38(t, J=7.0 Hz, 2H); 4.12(q, J=7.0 Hz, 2H); 7.14-7.81(m, 10H).

Example 296

Octanedioic acid biphenyl-4-ylamide hydroxamide (PX117720)

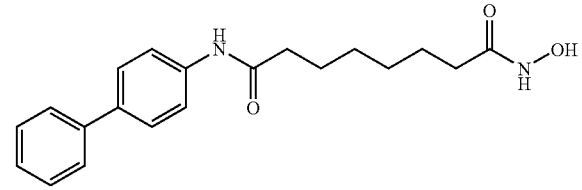

Using an analogous method (J12B), the title compound was obtained from 7-(biphenyl-4-ylcarbamoyl)-heptanoic acid ethyl ester (7/88). Yield 81%. M.p. 227-229° C. $^1$H NMR (DMSO-d$_6$, HMDSO), δ: 1.21-1.38(m, 4H); 1.42-1.68(m, 4H); 1.95(t, J=7.3 Hz, 2H); 2.31(t, J=7.3 Hz, 2H); 7.26-7.49 (m, 3H); 7.55-7.73(m, 6H); 8.66(s, 1H); 9.85(s, 1H); 10.33(s, 1H). HPLC analysis on Zorbax SB-C18 column: impurities 3% (column size 4.6×150 mm; mobile phase 50-100% acetonitrile+0.1% H$_3$PO$_4$; detector UV 254 nm; sample concentration 0.25 mg/ml, flow rate 1.0 ml/min). Anal. Calcd for $C_{20}H_{24}N_2O_3$: C, 70.57; H, 7.11; N, 8.23. Found: C, 70.35; H, 7.14; N, 8.23.

Example 297

7-[(Naphthalen-1-ylmethyl)-carbamoyl]-heptanoic acid methyl ester (7/89)

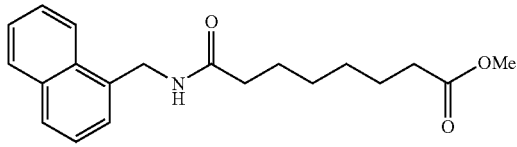

To a solution of suberic acid monomethyl ester 6c (376 mg, 2.0 mmol) in anhydrous tetrahydrofuran (5 ml) under argon atmosphere triethylamine (0.36 ml, 2.6 mmol) was added and the resulting solution was cooled in ice bath. To the mixture iso-butylchloroformate (0.3 ml, 2.3 mmol) was added and the reaction was stirred for 20 min, then a solution of 1-naphthylmethylamine 1/89 (314 mg, 2 mmol) in tetrahydrofuran (1.5 ml) was added. The mixture was stirred at ice bath temperature for 15 min and for 1 h at room temperature, diluted with brine (50 ml) and extracted with ethyl acetate (3×25 ml). The organic phase was washed with brine, 5% $NaHCO_3$, brine, saturated $KH_2PO_4$, and brine. The organic layer was dried ($Na_2SO_4$) and the solvent was evaporated. The residue was purified on silica gel (20 g) with chloroform-ethyl acetate as eluent to give the title compound 7/89, yield 85.4%. $^1$H NMR (CDCl$_3$, HMDSO) δ: 1.12-1.81(m, 8H); 2.16(t, J=8.0 Hz, 2H); 2.25(t, J=8.0 Hz, 2H); 3.63(s, 3H); 4.87(d, J=6.0 Hz, 2H); 5.61(br s, 1H); 7.32-7.63(m, 4H); 7.67-8.09(m, 3H).

Example 298

Octanedioic acid hydroxyamide (naphthalen-1-ylmethyl)-amide (PX117459)

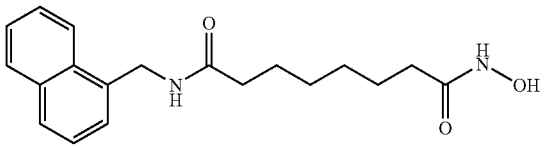

Using an analogous method (J12B), the title compound was obtained from 7-[(naphthalen-1-ylmethyl)-carbamoyl]-heptanoic acid methyl ester (7/89), yield 48%. M.p. 141-143° C. $^1$H NMR (DMSO-d$_6$, HMDSO), δ: 1.12-1.32(m, 4H); 1.36-1.66(m, 4H); 1.91(t, J=7.4 Hz, 2H); 2.13(t, J=7.2 Hz, 2H); 4.71(d, J=5.6 Hz, 2H); 7.38-7.60(m, 4H); 7.80-7.88(m, 1H); 7.89-7.98(m, 1H); 8.00-8.10(m, 1H); 8.31(t, J=5.6 Hz, 1H); 8.65(s, 1H); 10.32(s, 1H). HPLC analysis on Symmetry $C_{18}$ column: impurities 2% (column size 3.9×150 mm; mobile phase 50% acetonitrile–50% 0.1 M phosphate buffer, pH 2.5; detector UV 220 nm; sample concentration 0.5 mg/ml, flow rate 1.0 ml/min). Anal. Calcd for $C_{19}H_{24}N_2O_3$: C, 69.49; H, 7.37; N, 8.53. Found: C, 69.46; H, 7.37; N, 8.50.

Example 299

7-[2-(1H-Benzoimidazol-2-yl)-ethylcarbamoyl]-heptanoic acid methyl ester (3/90)

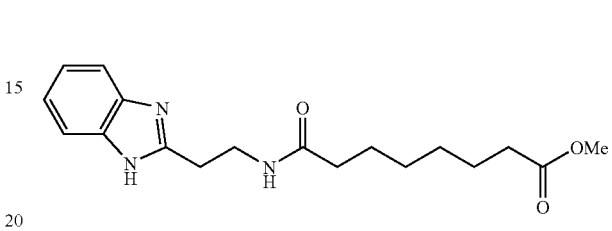

Using an analogous method (J11A), the title compound was obtained from 2-(1H-benzoimidazol-2-yl)-ethylamine (1/90) and suberic acid monomethyl ester (6c). Yield 78% (white solid). TLC: single spot at R$_f$ 0.66 (ethyl acetate-methanol, 13:1; detection—UV-254 nm).

Example 300

7-[2-(1H-Benzoimidazol-2-yl)-ethylcarbamoyl]-heptanoic acid (4/90)

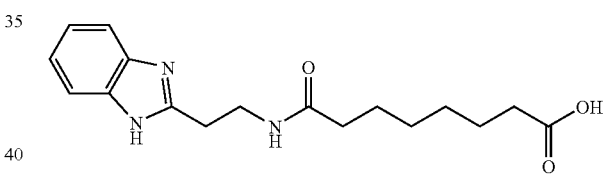

Using an analogous method (J11B), the title compound was obtained from 7-[2-(1H-benzoimidazol-2-yl)-ethylcarbamoyl]-heptanoic acid methyl ester (3/90) and NaOH (instead of LiOH) as a white solid, yield 80%. TLC: single spot at R$_f$ 0.22 (chloroform-methanol, 5:1; detection—UV-254 nm).

Example 301

Octanedioic acid [2-(1H-benzoimidazol-2-yl)-ethyl]-amide benzyloxy-amide (5/90)

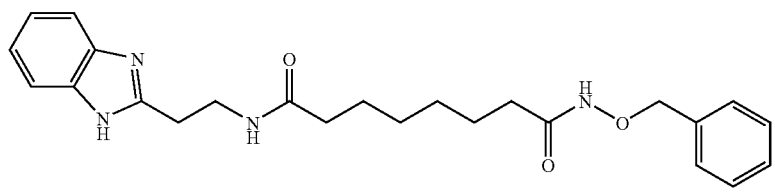

Using an analogous method (J11C), the title compound was obtained from 7-[2-(1H-benzoimidazol-2-yl)-ethylcarbamoyl]-heptanoic acid (4/90) and O-benzylhydroxylamine hydrochloride, yield 81% (white solid). TLC: single spot at $R_f$ 0.45 (chloroform-methanol, 8:1, detection—UV-254 nm).

Example 302

$N^1$-[2-(1H-Benzimidazol-2-yl)ethyl]-$N^8$-hydroxyoctanediamide (PX116241)

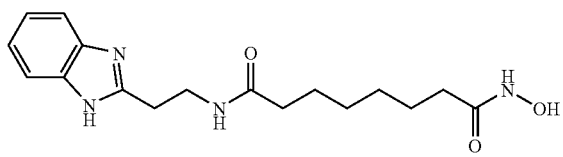

Using an analogous method (J11D), the title compound was obtained from octanedioic acid [2-(1H-benzoimidazol-2-yl)-ethyl]-amide benzyloxy-amide (5/90), yield 78%. M.p. 190° C., (dec.). $^1$H NMR (DMSO-$d_6$, HMDSO), δ: 1.03-1.64 (m, 8H); 1.92 (t, 2H, J=7.0 Hz); 2.03 (t, 2H, J=6.6 Hz); 2.96 (t, 2H, J=6.9 Hz); 3.52 (q, 2H, J=6.4 Hz); 7.05-7.27(m, 2H); 7.39-7.63 (m, 2H); 7.96 (t, 1H, J=5.1 Hz); 8.87 (br s, 1H); 10.36 (br s, 1H). HPLC analysis on Symmetry $C_{18}$ column: impurities 3.6% (column size 3.9×150 mm; mobile phase acetonitrile–0.1M phosphate buffer (pH 2.5), 10:90; sample concentration 0.5 mg/ml; flow rate 1.0 ml/min.; detector: UV 220 nm). Anal. Calcd for $C_{13}H_{17}N_5O_3 \times 0.5H_2O$, %: C, 59.80; H, 7.38; N, 16.41. Found, %: C, 59.74; H, 7.19; N, 16.12.

Example 303

4-Phenyl-butyric acid 2,5-dioxo-pyrrolidin-1-yl ester (15/95)

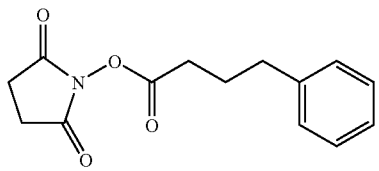

(Method J15A) A solution of 4-phenyl-butyric acid (1/95) (6.570 g, 40 mmol) and N-hydroxysuccinimide (4.830 g, 42 mmol) in acetonitrile (100 ml) was treated with N,N'-dicyclohexylcarbodiimide (8.650 g, 42 mmol) at 0° C. The resulting suspension was allowed to stand for 14 hours at 4° C., the precipitate was filtered off and washed with ethyl acetate (3×30 ml). The solvents were removed in vacuum and the residue was crystallized from isopropanol (50 ml) to give the activated ester 15/95 (7.520 g, 72%) as colorless crystals. $^1$H NMR (DMSO-$d_6$, HMDSO) δ: 1.78-2.20 (2H, m); 2.53-3.00 (8H, m); 6.84-7.67 (5H, m); 10.80 (1H, s).

Example 304

(S)-3-(1H-Indol-3-yl)-2-(4-phenyl-butyrylamino)-propionic acid (16/95)

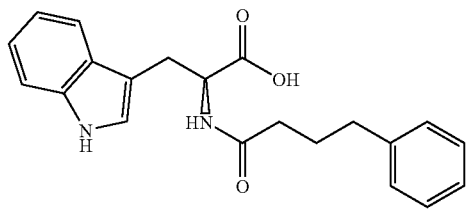

(Method J15B) A suspension of L-tryptophan (2.040 g, 10 mmol) and NaHCO$_3$ in water (15 ml) was treated with 4-phenyl-butyric acid 2,5-dioxo-pyrrolidin-1-yl ester (15/95) (2.610 g, 10 mmol) followed by the addition of acetonitrile (ca. 15 ml) to get a clear solution. The reaction mixture was stirred at ambient temperature for 12 hours and acetonitrile was removed under reduced pressure. The residue was acidified with citric acid to pH 2 and extracted with ethyl acetate (100 ml). The organic layer was washed with water (2×20 ml), brine (20 ml), and dried (MgSO$_4$). The solvents were evaporated to give the crude product 16/95 (3.160 g, 95%). $^1$H NMR (DMSO-$d_6$, HMDSO) δ: 1.51-1.82 (2H, m); 1.96-2.24 (2H, m); 2.33-2.64 (2H, m); 2.80-3.38 (2H, m); 4.38-4.68 (1H, m); 6.82-7.66 (14H, m); 8.11 (1H, d, J=8.0 Hz); 10.87 (1H, m).

Example 305

(S)-6-[3-(1H-Indol-3-yl)-2-(4-phenyl-butyrylamino)-propionylamino]-hexanoic acid 2,5-dioxo-pyrrolidin-1-yl ester (18/95)

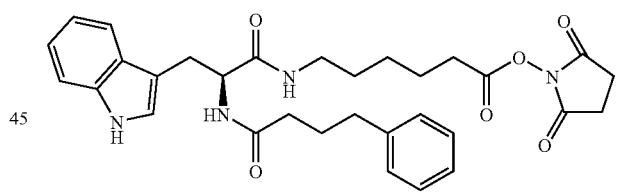

(Method J15C) A solution of 3-(1H-indol-3-yl)-2-(4-phenyl-butyrylamino)-propionic acid (16/95) (1.333 g, 4.01 mmol) and N-hydroxysuccinimide (0.461 g, 4.01 mmol) in acetonitrile (50 ml) was treated with N,N'-dicyclohexylcarbodiimide (0.828 g, 4.02 mmol) at 0° C. The resulting suspension was allowed to stand for 14 hours at 4° C., the precipitate was filtered off and washed with acetonitrile (2×10 ml). To the filtrate a solution of 6-aminohexanoic acid (0.526 g, 4.01 mmol) and NaHCO$_3$ (0.672 g, 4.01 mmol) in water (20 ml) was added and the resulting mixture was stirred for 3 hours at room temperature. Acetonitrile was removed under reduced pressure, the residue was acidified with citric acid to pH 2 and the mixture was extracted with ethyl acetate (100 ml). The organic layer was washed with water (20 ml), brine (20 ml), and dried (MgSO$_4$). The extract was filtered and to the filtrate successively N-hydronxysuccinimide ((0.461 g, 4.01 mmol) and N,N'-dicyclohexylcarbodiimide (0.828 g, 4.02 mmol) were added. The mixture was stirred for 6 hours at room temperature, the precipitate was filtered off and washed with ethyl acetate (3×20 ml). The filtrate was evaporated and the residue was chromatographed on silicagel with ethyl acetate-petroleum ether (1:1) as eluent to give the title product 18/95 (1.217 g, 56%) as a foam. $^1$H NMR (DMSOd-$_6$, HMDSO) δ: 1.11-1.89 (8H, m); 1.96-2.23 (2H, m); 2.31-2.70 (4H, m, partially overlapped with a signal of DMSO); 2.79 (4H, s); 2.89-3.20 (4H, m); 4.40-4.72 (1H, m); 6.87-7.69 (10H, m); 7.75-8.07 (2H, m); 10.78 (1H, s).

Example 306

N-hydroxy-6-({(2S)-3-(1H-indol-3-yl)-2-[(4-phenylbutanoyl)amino]-propanoyl}amino)-hexanamide (PX117407)

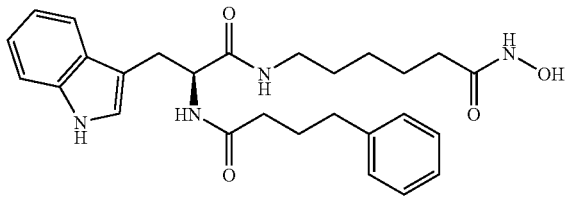

(Method J15D) To a solution of 6-[3-(1H-indol-3-yl)-2-(4-phenyl-butyrylamino)propionylamino]-hexanoic acid 2,5-dioxo-pyrrolidin-1-yl ester (18/95) (1.200 g, 2.2 mmol) in tetrahydrofuran (20 ml) a solution of hydroxylamine hydrochloride (0.695 g, 10 mmol) in saturated NaHCO$_3$ (8.5 ml) was added and the resulting mixture was vigorously stirred for 24 hours at room temperature. The volatile solvents were removed under reduced pressure and the residue was acidified with saturated KHPO$_4$ to pH 6. The precipitate was filtered, washed with water (3×20 ml), and dried. The crude product was crystallized from chloroform (30 ml) to give title hydroxamic acid PX117407 (0.431 g, 41%) as white crystals. M.p. 106-108° C. $^1$H NMR (DMSO-d$_6$, HMDSO), δ: 1.00-1.57 (m, 6H); 1.67 (quint, 2H, J=7.4 Hz); 1.91 (t, 2H, J=7.2 Hz); 2.08 (t, 2H, J=7.2 Hz); 2.42 (t, overlapped with a signal of DMSO, 2H, J=7.6 Hz); 2.77-3.25 (m, 4H); 4.42-4.60 (m, 1H); 6.82-7.40 (m, 9H); 7.59 (d, 1H, J=7.6 Hz); 7.83-8.02 (m, 2H); 8.69 (s, 1H); 10.35 (s, 1H); 10.78 ppm (s, 1H). HPLC analysis on Symmetry C$_{18}$ column: impurities 1.8% (column size 3.9× 150 mm; mobile phase acetonitrile–0.1% H$_3$PO$_4$, 50:50; detector UV 220 nm; sample concentration 0.5 mg/ml, flow rate 1.3 ml/min). Anal. Calcd for C$_{27}$H$_{34}$N$_4$O$_4$: C, 67.76; H, 7.16; N, 11.71. Found: C, 67.52; H, 7.13; N, 11.67.

Example 307

Naphthalen-2-yl-acetic acid 2,5-dioxo-pyrrolidin-1-yl ester (15/96)

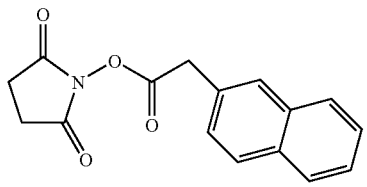

Using an analogous method (J15A), the title compound was prepared from naphthalen-2-yl-acetic acid (1/96) (5.590 g, 30 mmol). Yield 7.394 g (87%). $^1$H NMR (CDCl$_3$, HMDSO) δ: 2.78 (4H, s); 4.10 (2H, s); 7.34-7.96 (7H, m).

Example 308

(S)-3-(1H-Indol-3-yl)-2-(2-naphthalen-2-yl-acetylamino)-propionic acid (16/96)

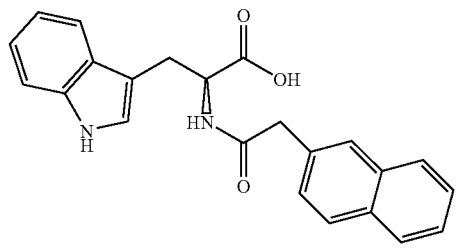

Using an analogous method (J15B), the title compound was prepared from naphthalen-2-yl-acetic acid 2,5-dioxo-pyrrolidin-1-yl ester (15/96) (2.266 g, 8 mmol). Yield 2.920 g (98%). $^1$H NMR (DMSO-d$_6$, HMDSO) δ: 2.87-4.22 (4H, m); 4.33-4.73 (1H, m); 6.89-8.00 (12H, m); 8.47 (1H, d, J=8.0 Hz); 10.89 (1H, s).

Example 309

(S)-6-[3-(1H-Indol-3-yl)-2-(2-naphthalen-2-yl-acetylamino)-propionylamino]-hexanoic acid 2,5-dioxo-pyrrolidin-1-yl ester (18/96)

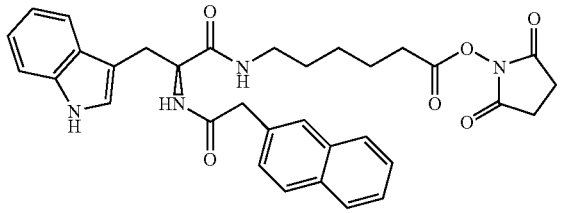

Using an analogous method (J15C), the title compound was prepared from 3-(1H-indol-3-yl)-2-(2-naphthalen-2-yl-acetylamino)-propionic acid (16/96) (1.235 g, 3.32 mmol). Yield 1.603 g (97%). $^1$H NMR (DMSO-d$_6$, HMDSO) δ: 1.11-1.87 (8H, m); 2.81 (4H, s); 2.89-3.17 (4H, m); 3.62 (2H, s); 4.38-4.69 (1H, m); 6.87-8.04 (13H, m); 8.29 (1H, d, J=8.0 Hz); 10.82 (1H, s).

Example 310

N-Hydroxy-6-[((2S)-3-(1H-indol-3-yl)-2-{[2-(2-naphthyl)acetyl]-amino}propanoyl)amino]-hexanamide (PX117406)

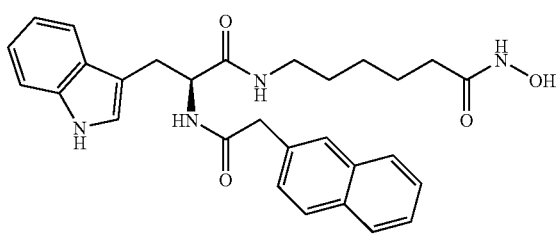

Using an analogous method (J15D), the title compound was prepared from 6-[3(1H-indol-3-yl)-2-(2-naphthalen-2-yl-acetylamino)-propionylamino]-hexanoic acid 2,5-dioxo-pyrrolidin-1-yl ester (18/96) (1.120 g, 1.87 mmol). Yield 0.353 g (37%). M.p. 112-114° C. $^1$H NMR (DMSO-$d_6$, HMDSO), δ: 1.00-1.57 (m, 6H); 1.91 (t, 2H, J=7.0 Hz); 2.82-3.20 (m, 4H); 3.60 (s, 2H); 4.42-4.62 (m, 1H); 6.90-7.90 (m, 12H); 7.97 (t, 1H, J=4.8 Hz); 8.34 (d, 1H, J=8.0 Hz); 8.71 (br s, 1H); 10.35 (br s, 1H); 10.82 ppm (s, 1H). HPLC analysis on Symmetry $C_8$ column: impurities 1.8% (column size 3.9× 150 mm; mobile phase acetonitrile–0.1M phosphate buffer (pH 2.5), 50:50; detector UV 220 nm; sample concentration 0.5 mg/ml, flow rate 1.3 ml/min). Anal. Calcd for $C_{29}H_{32}N_4O_4$*0.5 $H_2O$: C, 68.35; H, 6.53; N, 10.99. Found: C, 68.08; H, 6.39; N, 10.93.

Example 311

4-(1H-Indol-3-yl)-butyric acid 2,5-dioxo-pyrrolidin-1-yl ester (15/97)

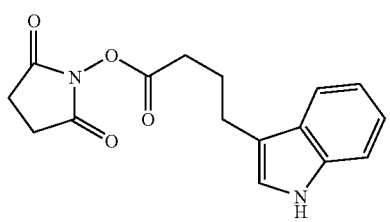

Using an analogous method (J15A), the title compound was prepared from 4-(1H-indol-3-yl)-butyric acid (1/97) (6.100 g, 30 mmol). Yield 7.387 g (82%). $^1$H NMR (DMSO-$d_6$, HMDSO) δ: 1.78-2.20 (2H, m); 2.53-3.00 (8H, m); 6.84-7.67 (5H, m); 10.80 (1H, s).

Example 312

(S)-3-(1H-Indol-3-yl)-2-(4-1H-indol-3-yl-butyrylamino)-propionic acid (16/97)

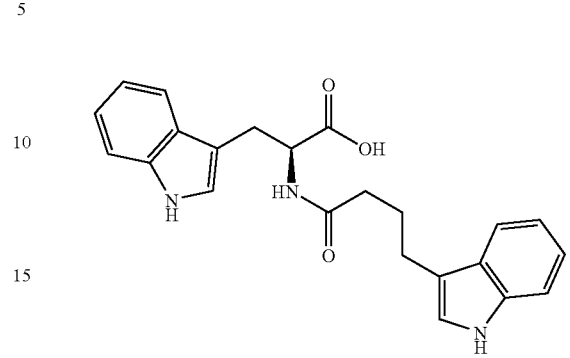

Using an analogous method (J15B), the title compound was prepared from 4-(1H-indol-3-yl)-butyric acid 2,5-dioxo-pyrrolidin-1-yl ester (15/97) (2.402 g, 8 mmol). Yield 3.084 g (99%). $^1$H NMR (DMSO-$d_6$, HMDSO) δ: 2.95-3.38 (4H, m); 3.43-3.75 (4H, m); 4.33-4.64 (1H, m); 6.75-7.60 (11H, m); 8.00 (1H, d, J=8.0 Hz); 10.80 (2H, s).

Example 313

(S)-6-[3-(1H-Indol-3-yl)-2-(4-1H-indol-3-yl-butyrylamino)-propionylamino]-hexanoic acid benzyloxyamide (19/97)

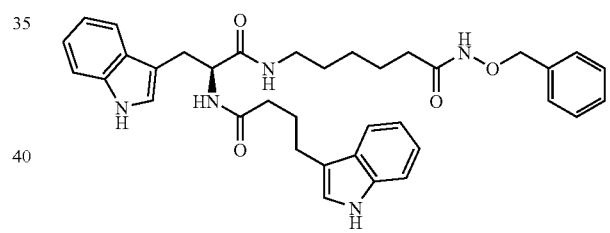

(Method J15E) A solution of 3-(1H-indol-3-yl)-2-(4-1H-indol-3-yl-butyrylamino)-propionic acid (16/97) (2.628 g, 6.75 mmol) and N-hydroxysuccinimide (0.776 g, 6.75 mmol) in acetonitrile at 0° C. was treated with N,N'-dicyclocarbodiimide (1.400 g, 6.8 mmol)The resulting suspension was allowed to stand at 15° C., for 3 hours, the precipitate was filtered off and washed with acetonitrile (2×15 ml). To the filtrate was added a solution of 6-aminohexanoic acid (0.881 g, 6.72 mmol) and $NaHCO_3$ (1.014 g, 13 mmol) in water (20 ml) and the resulting mixture was stirred at room temperature for 3 hours. Acetonitrile was evaporated under reduced pressure, the residue was acidified with citric acid to pH 2 and extracted with ethyl acetate (100 ml). The organic layer was washed with water (2×20 ml), brine (20 ml), and dried ($MgSO_4$). The solvent was evaporated and the residue was dissolved in tetrahydrofuran (100 ml). To the obtained solution under argon atmosphere 1,1'-carbonyldiimidazole was added and the mixture was stirred at room temperature for 40 min. To the reaction mixture a suspension of O-benzylhydroxylamine hydrochloride (1.053 g, 6.60 mmol) and triethylamine (0.666 g, 6.60 mmol) in tetrahydrofuran (30 ml) was added and the resulting suspension was vigorously stirred at room temperature for 24 hours. The mixture was evaporated and the residue was dissolved in ethyl acetate (150 ml). The solution was washed successively with water (2×20 ml), 5% citric acid (20 ml), water (20 ml), brine (20 ml), and dried (MgSO$_4$). The solvent was removed and the residue was crystallized from ethyl acetate to give the title product (2.163 g, 53%). $^1$H NMR (DMSO-d$_6$, HMDSO) δ: 1.02-1.60 (6H, m); 1.64-2.36 (8H, m); 2.80-3.20 (4H, m); 4.33-4.66 (1H, m); 4.78 (2H, s); 6.84-8.03 (17H, m); 10.73 (1H, s); 10.91 (1H, s).

Example 314

N-Hydroxy-6-[((2S)-3-(1H-indol-3-yl)-2-{[4-(1H-indol-3-yl)butanoyl]amino}propanoyl)-amino]hexanamide (PX117767)

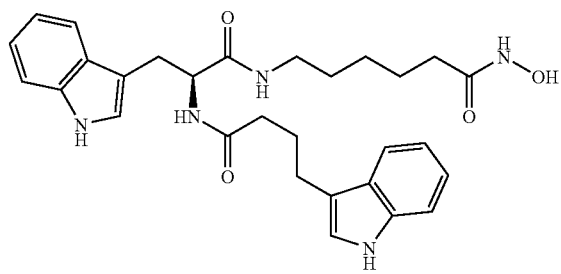

(Method J15F) 6-[3-(1H-Indol-3-yl)-2-(4-1H-indol-3-yl-butyrylamino)-propionylamino]-hexanoic acid benzyloxy-amide (19/97) (1.654 g, 0.274 mmol) was dissolved in ethanol (20 ml), 10% Pd/C (50 mg) was added and the reaction mixture was hydrogenated at room temperature for 4 hours. The catalyst was filtered off, the solvent was evaporated and the residue was chromatographed on silica gel with acetonitrile-acetic acid (60:1) and acetonitrile-acetic acid-water (30:1:1) as eluent to give the title product (0.582 g, 41%) as white powder. M.p. 94-96° C. $^1$H NMR (DMSO-d$_6$, HMDSO), δ: 1.06-1.55 (m, 6H); 1.68-1.97 (m, 4H); 2.04-2.27 (m, 2H); 2.42-2.67 (m, 2H overlapped with DMSO) 2.80-3.15 (m, 4H); 4.44-4.57 (m, 1H); 6.87-7.17 (m, 6H); 7.31 (d, 2H, J=7.6 Hz); 7.44 (d, 1H, J=7.6 Hz); 7.58 (d, 1H, J=7.6 Hz); 7.80-8.03 (m, 2H); 8.67 (s, 1H); 10.33 (s, 1H); 10.72 (s, 1H); 10.76 ppm (s, 1H). HPLC analysis on Symmetry C$_8$ column: impurities 2.5% (column size 3.9×150 mm; mobile phase acetonitrile–0.1M phosphate buffer (pH 2.5), 35:65; detector UV 220 nm; sample concentration 0.5 mg/ml, flow rate 1.0 ml/min). Anal. Calcd for C$_{29}$H$_{35}$N$_5$O$_4$: C, 67.29; H, 6.82; N, 13.53. Found: C, 67.06; H, 6.86; N, 13.66.

Example 315

Naphthalene-2-carboxylic acid 2,5-dioxo-pyrrolidin-1-yl ester (15/98)

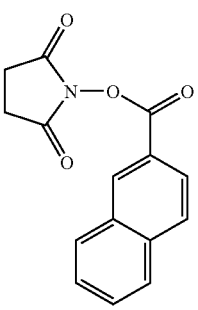

Using an analogous method (J15A), the title compound was prepared from naphthalene-2-carboxylic acid (1/98). Yield 82%. $^1$H NMR (DMSO-d$_6$, HMDSO) δ: 2.79 (4H, s); 7.42-8.05 (7H, m).

Example 316

(S)-3-(1H-Indol-3-yl)-2-[(naphthalene-2-carbonyl)-amino]-propionic acid (16/98)

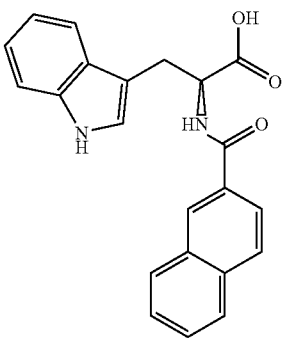

Using an analogous method (J15B), the title compound was prepared from naphthalene-2-carboxylic acid 2,5-dioxo-pyrrolidin-1-yl ester (15/98). Yield 95%. $^1$H NMR (DMSO-d$_6$, HMDSO) δ: 2.83-4.02 (2H, m, overlapped with a water signal of DMSO); 4.33-4.72 (1H, m); 6.87-8.08 (12H, m); 8.49 (1H, d, J=8.0 Hz); 10.88 (1H, s).

Example 317

(S)-Naphthalene-2-carboxylic acid [1-(5-benzyloxy-carbamoyl-pentylcarbamoyl)-2-(1H-indol-3-yl)-ethyl]-amide (19/98)

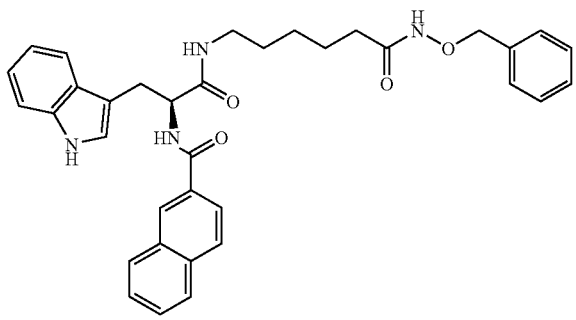

Using an analogous method (J15E), the title compound was prepared from 3-(1H-indol-3-yl)-2-[(naphthalene-2-carbonyl)-amino]-propionic acid (16/98). Yield 49%. ¹H NMR (DMSO-d₆, HMDSO) δ: 1.02-1.67 (6H, m); 1.80-2.11 (2H, m); 2.89-3.36 (4H, m); 4.60-4.93 (3H, m); 6.93-7.33 (4H, m); 7.40 (5H, s); 7.51-7.82 (3H, m); 7.84-8.20 (5H, m); 8.44 (1H, s); 8.60 (1H, d, J=8.0 Hz); 10.78 (1H, s); 10.96 (1H, s).

Example 318

(S)-Naphthalene-2-carboxylic acid [1-(5-hydroxy-carbamoyl-pentylcarbamoyl)-2-(1H-indol-3-yl)-ethyl]-amide (PX117783)

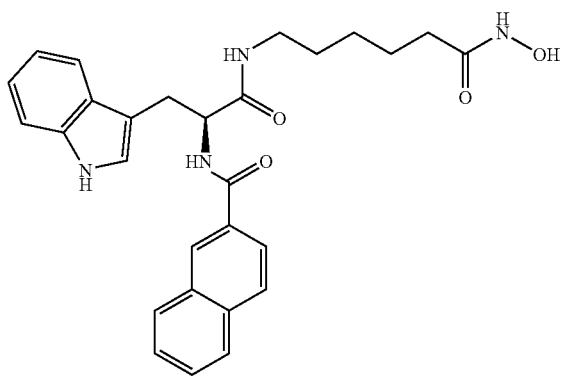

Using an analogous method (J15F), the title compound was prepared from naphthalene-2-carboxylic acid [1-(5-benzy-loxycarbamoyl-pentylcarbamoyl)-2-(1H-indol-3-yl)-ethyl]-amide (19/98). Yield 7%, foam. ¹H NMR (DMSO-d₆, HMDSO), δ: 1.10-1.60 (m, 6H); 1.93 (t, 2H, J=7.4 Hz); 2.95-3.30 (m, 4H); 4.65-4.83 (m, 1H); 6.92-7.10 (m, 2H); 7.23 (s, 1H); 7.30 (d, 1H, J=7.6 Hz); 7.53-7.66 (m, 2H); 7.71 (d, 1H, J=7.0 Hz); 7.84-8.04 (m, 4H); 8.09 (br t, 1H, J=5.2 Hz); 8.42 (s, 1H); 8.60 (d, 1H, J=8.2 Hz); 8.68 (br s, 1H); 10.34 (s, 1H); 10.77 (s, 1H). HPLC analysis on Symmetry C₈ column: impurities 2.5% (column size 3.9×150 mm; mobile phase acetonitrile–0.1M phosphate buffer (pH 2.5), 40:60; detector UV 220 nm; sample concentration 0.25 mg/ml, flow rate 1.5 ml/min). Anal. Calcd for $C_{28}H_{30}N_4O_4 \cdot H_2O$: C, 66.65; H, 6.39; N, 11.10. Found: C, 66.69; H, 6.00; N, 11.01.

Example 319

4-Benzyloxycarbonylamino-butyric acid 2,5-dioxo-pyrrolidin-1-yl ester (15/99)

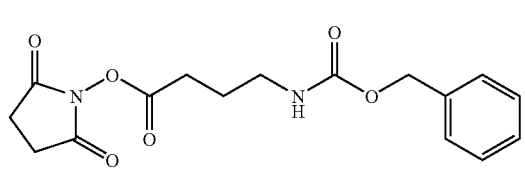

Using an analogous method (J15A), the title compound was prepared from 4-benzyloxycarbonylamino-butyric acid (1/99). Yield 90%. ¹H NMR (CDCl₃, HMDSO) δ: 1.74-2.12 (2H, m); 2.64 (2H, t, J=7.3 Hz); 2.77 (4H, s); 3.28 (2H, q, J=7.2 Hz); 5.09 (3H, s) 7.23-7.48 (5H, m).

Example 320

(S)-2-(4-Benzyloxycarbonylamino-butyrylamino)-3-(1H-indol-3-yl)-propionic acid (16/99)

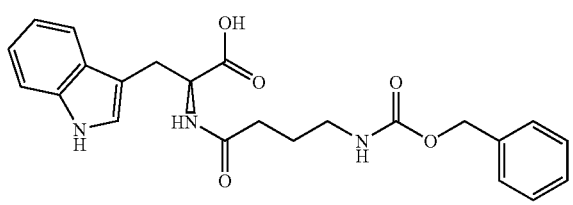

Using an analogous method (J15B), the title compound was prepared from 4-benzyloxycarbonylamino-butyric acid 2,5-dioxo-pyrrolidin-1-yl ester (15/99). Yield 98%. ¹H NMR (CDCl₃, HMDSO) δ: 1.37-2.14 (4H, m); 2.65-3.44 (4H, m); 4.69-5.29 (3H, m); 6.40-7.64 (12H, m); 8.05 (1H, s); 10.18 (1H, s).

Example 321

(S)-6-[2-(4-Benzyloxycarbonylamino-butyrylamino)-3-(1H-indol-3-yl)-propionylamino]-hexanoic acid 2,5-dioxo-pyrrolidin-1-yl ester (18/99)

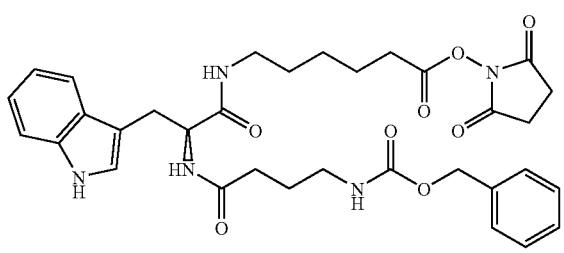

Using an analogous method (J15C), the title compound was prepared from 2-(4-benzyloxycarbonylamino-butyrylamino)-3-(1H-indol-3-yl)-propionic acid (16/99). Yield 46%. $^1$H NMR (DMSO-d$_6$, HMDSO) δ: 0.98-1.78 (10H, m); 1.93-2.31 (2H, m); 2.80 (4H, s); 2.84-3.10 (6H, m); 4.27-4.62 (1H, m); 5.00 (2H, s); 6.82-7.67 (10H, m); 7.71-8.04 (2H, m); 10.78 (2H, m).

Example 322

(S)-Carbamic acid, [4-[[2-[[6-(hydroxyamino)-6-oxohexyl]amino]-1-(1H-indol-3-ylmethyl)-2-oxoethyl]amino]-4-oxobutyl]-, phenylmethyl ester (PX117785)

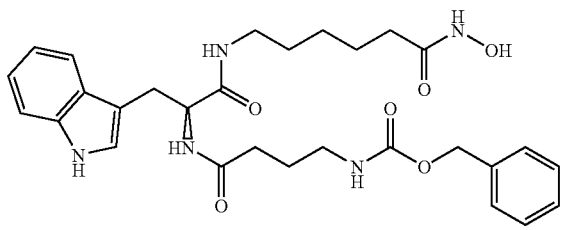

Using an analogous method (J15D), the title compound was prepared from 6-[2-(4-benzyloxycarbonylamino-butyrylamino)-3-(1H-indol-3-yl)-propionylamino]-hexanoic acid 2,5-dioxo-pyrrolidin-1-yl ester (18/99). Yield 37%, foam. $^1$H NMR (DMSO-d$_6$, HMDSO), δ: 1.91 (t, 2H, J=7.2 Hz); 2.08 (br t, 2H, J=6.6 Hz); 2.80-3.15 (m, 6H); 4.40-4.57 (m, 1H); 5.00 (s, 2H); 6.90-7.14 (m, 3H); 7.18-7.43 (m, 7H); 7.58 (d, 1H, J=7.4 Hz); 7.84-8.02 (m, 2H); 8.70 (s, 1H); 10.35 (s, 1H); 10.77 ppm (s, 1H). HPLC analysis on Symmetry C$_8$ column: impurities 1.8% (column size 3.9×150 mm; mobile phase acetonitrile–0.1 M phosphate buffer (pH 2.5), 70:30; detector UV 220 nm; sample concentration 0.5 mg/ml, flow rate 1.0 ml/min). Anal. Calcd for C$_{29}$H$_{37}$N$_5$O$_6$*0.2H$_2$O: C, 62.73; H, 6.79; N, 12.61. Found: C, 62.53; H, 6.75; N, 12.54.

Biological Activity

Candidate compounds were assessed for their ability to inhibit deacetylase activity (biochemical assays) and to inhibit cell proliferation (cell-based antiproliferation assays), as described below.

Primary Assay: Deacetylase Activity

Briefly, this assay relies on the release of radioactive acetate from a radioactively labelled histone fragment by the action of HDAC enzyme. Test compounds, which inhibit HDAC, reduce the yield of radioactive acetate. Signal (e.g., scintillation counts) measured in the presence and absence of a test compound provide an indication of that compound's ability to inhibit HDAC activity. Decreased activity indicates increased inhibition by the test compound.

The histone fragment was an N-terminal sequence from histone H4, and it was labelled with radioactively labelled acetyl groups using tritiated acetylcoenzyme A (coA) in conjunction with an enzyme which is the histone acetyltransferase domain of the transcriptional coactivator p300. 0.33 mg of peptide H4 (the N-terminal 20 amino acids of histone H4, synthesised using conventional methods) were incubated with His6-tagged p300 histone acetyltransferase domain (amino acids 1195-1673, expressed in E. coli strain BLR (DE3)pLysS (Novagen, Cat. No. 69451-3) and 3H-acetyl coA (10 μL of 3.95 Ci/mmol; from Amersham) in a total volume of 300 μL of HAT buffer (50 mM TrisCl pH 8, 5% glycerol, 50 mM KCl, 0.1 mM ethylenediaminetetraacetic acid (EDTA), 1 mM dithiothreitol (DTT) and 1 mM 4-(2-aminoethyl)-benzenesulfonylfluoride (AEBSF)). The mixture was incubated at 30° C. for 45 min after which the His-p300 was removed using nickel-trinitriloacetic acid agarose (Qiagen, Cat No. 30210). The acetylated peptide was then separated from free acetyl coA by size exclusion chromatography on Sephadex G-15 (Sigma G-15-120), using distilled H$_2$O as the mobile phase.

After purification of the radiolabelled histone fragment, it was incubated with a source of HDAC (e.g., an extract of HeLa cells (a rich source of HDAC), recombinantly produced HDAC1 or HDAC2) and any released acetate was extracted into an organic phase and quantitatively determined using scintillation counting. By including a test compound with the source of HDAC, that compound's ability to inhibit the HDAC was determined.

HeLa Cell Extract

The HeLa cell extract was made from HeLa cells (ATCC Ref. No. CCL-2) by freeze-thawing three times in 60 mM TrisCl pH 8.0, 450 mM NaCl, 30% glycerol. Two cell volumes of extraction buffer were used, and particulate material was centrifuged out (20800 g, 4° C., 10 min). The supernatant extract having deacetylase activity was aliquotted and frozen for storage.

Recombinantly Produced HDAC1 and HDAC2

Recombinant plasmids were prepared as follows.

Full length human HDAC1 was cloned by PCR using a λgt11 Jurkat cDNA library (Clontech-HL5012b). The amplified fragment was inserted into the EcoRI-SalI sites of pFlag-CTC vector (Sigma-E5394), in frame with the Flag tag. A second PCR was carried out in order to amplify a fragment containing the HDAC1 sequence fused to the Flag tag. The resulting fragment was subcloned into the EcoRI-Sac1 sites of the baculovirus transfer vector pAcHTL-C (Pharmingen-21466P).

Full length human HDAC2 was subcloned into pAcHLT-A baculovirus transfer vector (Pharmingen-21464P) by PCR amplification of the EcoRI-Sac1 fragment from a HDAC2-pFlag-CTC construct.

Recombinant protein expression and purification was performed as follows.

HDAC1 and HDAC2 recombinant baculoviruses were constructed using BaculoGold Transfection Kit (Pharmingen-554740). Transfer vectors were co-transfected into SF9 insect cells (Pharmingen-21300C). Amplification of recombinant viruses was performed according to the Pharmingen Instruction Manual. SF9 cells were maintained in serum-free SF900 medium (Gibco 10902-096).

For protein production, 2×10$^7$ cells were infected with the appropriate recombinant virus for 3 days. Cells were then harvested and spun at 3,000 rpm for 5 minutes. They were then washed twice in PBS and resuspended in 2 pellet volumes of lysis buffer (25 mM HEPES pH 7.9, 0.1 mM EDTA, 400 mM KCl, 10% glycerol, 0.1% NP-40, 1 mM AEBSF). Resuspended cells were frozen on dry ice and thawed at 37° C. 3 times and centrifuged for 10 minutes at 14,000 rpm. The supernatant was collected and incubated with 300 μl of 50% Ni-NTA agarose bead slurry (Qiagen-30210). Incubation was carried out at 4° C. for 1 hour on a rotating wheel. The slurry was then centrifuged at 500 g for 5 minutes. Beads were washed twice in 1 ml of wash buffer (25 mM HEPES pH7.9, 0.1 mM EDTA, 150 mM KCl, 10% glycerol, 0.1% NP-40, 1 mM AEBSF). Protein was eluted 3 times in 300 μl elution buffer (25 mM HEPES pH 7.9, 0.1 mM EDTA, 250 mM KCl, 10% glycerol, 0.1% NP-40, 1 mM AEBSF) containing increasing concentrations of imidazole: 0.2 M, 0.5 M and 1

M. Each elution was performed for 5 minutes at room temperature. Eluted protein was kept in 50% glycerol at −70° C.

Assay Method

A source of HDAC (e.g., 2 μL of crude HeLa extract, 5 μL of HDAC1 or HDAC2; in elution buffer, as above) was incubated with 3 μL of radioactively labelled peptide along with appropriate dilutions of candidate compounds (1.5 μL) in a total volume of 150 μL of buffer (20 mM Tris pH 7.4, 10% glycerol). The reaction was carried out at 37° C. for one hour, after which the reaction was stopped by adding 20 μL of 1 M HCl/0.4 M sodium acetate. Then, 750 μL of ethyl acetate was added, the samples vortexed and, after centrifugation (14000 rpm, 5 min), 600 μL from the upper phase were transferred to a vial containing 3 mL of scintillation liquid (UltimaGold, Packard, Cat. No. 6013329). Radioactivity was measured using a Tri-Carb 2100TR Liquid Scintillation Analyzer (Packard).

Percent activity (% activity) for each test compound was calculated as:

% activity=$\{(S^C-B)/(S^o-B)\} \times 100$ wherein $S^C$ denotes signal measured in the presence of enzyme and the compound being tested, $S^o$ denotes signal measured in the presence of enzyme but in the absence of the compound being tested, and B denotes the background signal measured in the absence of both enzyme and compound being tested. The IC50 corresponds to the concentration which achieves 50% activity.

IC50 data for several compounds of the present invention, as determined using this assay, are also shown in Table 1, below.

Measurement of cell viability in the presence of increasing concentration of test compound at different time points is used to assess both cytotoxicity and the effect of the compound on cell proliferation.

Secondary Assay: Cell Proliferation

Compounds with HDAC inhibition activity, as determined using the primary assay, were subsequently evaluated using secondary cell-based assays. The following cell lines were used:

HeLa—Human cervical adenocarcinoma cell line (ATCC ref. No. CCL-2).

K11—HPV E7 transformed human keratinocyte line provided by Pidder Jansen-Duerr, Institut für Biomedizinische Alternsforschung, Innsbruck, Austria.

NHEK-Ad—Primary human adult keratinocyte line (Cambrex Corp., East Rutherford, N.J., USA).

JURKAT—Human T-cell line (ATCC no. TIB-152).

Assay Method

Cells were cultured, exposed to candidate compounds, and incubated for a time, and the number of viable cells was then assessed using the Cell Proliferation Reagent WST-1 from Boehringer Mannheim (Cat. No. 1 644 807), described below.

Cells were plated in 96-well plates at 3-10×$10^3$ cells/well in 100 μL of culture medium. The following day, different concentrations of candidate compounds were added and the cells incubated at 37° C. for 48 h. Subsequently, 10 μL/well of WST-1 reagent was added and the cells reincubated for 1 hour. After the incubation time, absorbance was measured.

WST-1 is a tetrazolium salt which is cleaved to formazan dye by cellular enzymes. An expansion in the number of viable cells results in an increase in the overall activity of mitochondrial dehydrogenases in the sample. This augmentation in the enzyme activity leads to an increase in the amount of formazan dye formed, which directly correlates to the number of metabolically active cells in the culture. The formazan dye produced is quantified by a scanning multiwell spectrophotometer by measuring the absorbance of the dye solution at 450 nm wavelength (reference wavelength 690 nm).

Percent activity (% activity) in reducing the number of viable cells was calculated for each test compound as:

% activity=$\{(S^C-B)/(S^o-B)\} \times 100$ wherein $S^C$ denotes signal measured in the presence of the compound being tested, $S^o$ denotes signal measured in the absence of the compound being tested, and B denotes the background signal measured in blank wells containing medium only. The IC50 corresponds to the concentration which achieves 50% activity.

IC50 values were calculated using the software package Prism 3.0 (GraphPad software Inc., San Diego, Calif.), setting top value at 100 and bottom value at 0.

IC50 data for several compounds of the present invention, as determined using this assay, are also shown in Table 2, below.

Measurement of cell viability in the presence of increasing concentration of test compound at different time points is used to assess both cytotoxicity and the effect of the compound on cell proliferation.

Biological Data

IC50 (or percent activity) data for several compounds of the present invention, as determined using the assays described above are summarised in Table 1 and Table 2, below.

TABLE 1-A

Biochemical Assay Data

| Compound | | HDAC Inhibition (IC50 unless otherwise specified) | | |
|---|---|---|---|---|
| No. | Ref. | HeLa | HDAC1 | HDAC2 |
|  | TSA | 5 | 15 | 17 |
| 1 | PX082530 | 13% @ 1 μM |  | 18% @ 5 μM |
| 2 | PX082531 | 16% @ 1 μM |  |  |
| 3 | PX082533 | 2% @ 1 μM |  |  |
| 4 | PX082534 | 1500 |  |  |
| 5 | PX082546 | 36% @ 1 μM |  |  |
| 6 | PX082548 | 41% @ 1 μM |  |  |
| 7 | PX082549 | 43% @ 1 μM |  |  |
| 8 | PX083449 | 238 |  | 688 |
| 9 | PX089048 | 34% @ 1 μM |  |  |
| 10 | PX089049 | >1000 |  |  |
| 11 | PX089274 | 109 |  | 206 |
| 12 | PX089275 | 466 | 175 | 480 |
| 13 | PX089276 | 165 | 250 | 312 |
| 14 | PX105687 | 21 | 33 | 29 |
| 15 | PX105824 | 69 | 69 |  |
| 16 | PX105826 | 396 |  |  |
| 17 | PX105828 | 333 |  |  |
| 18 | PX106492 | 42% @ 500 nM |  |  |
| 19 | PX106493 | 20 | 25 |  |
| 20 | PX106494 | 100 |  |  |
| 21 | PX106495 | 34% @ 500 nM |  |  |
| 22 | PX106496 | 82 |  |  |
| 23 | PX106497 | 30% @ 500 nM |  |  |
| 24 | PX106515 | 27.7 |  |  |
| 25 | PX106519 | 46% @ 500 nM |  |  |
| 26 | PX116213 | 48% @ 500 nM |  |  |
| 27 | PX116215 | 70% @ 500 nM |  |  |
| 28 | PX116218 | 33 |  |  |
| 29 | PX116219 | 26% @ 500 nM |  |  |
| 30 | PX116221 | 72% @ 500 nM |  |  |
| 31 | PX116223 | <12.5 |  |  |
| 32 | PX116246 | 52% @ 500 nM |  |  |

TABLE 1-A-continued

Biochemical Assay Data

| Compound | | HDAC Inhibition (IC50 unless otherwise specified) | | |
|---|---|---|---|---|
| No. | Ref. | HeLa | HDAC1 | HDAC2 |
| 33 | PX117231 | 72% @ 500 nM | | |
| 34 | PX117232 | 43% @ 500 nM | | |
| 35 | PX117421 | 85 | | |
| 36 | PX117461 | 20 | | |
| 37 | PX117720 | 40 | | |
| 38 | PX117723 | 46% @ 500 nM | | |
| 39 | PX117726 | 35% @ 500 nM | | |

TABLE 1-B

Biochemical Assay Data

| Compound | | HDAC Inhibition (IC50 unless otherwise specified) | | |
|---|---|---|---|---|
| No. | Ref. | HeLa | HDAC1 | HDAC2 |
| 40 | PX082532 | 21% @ 1 μM | | |
| 41 | PX106488 | 51% @ 500 nM | | |
| 42 | PX106489 | 3300 | 4000 | |
| 43 | PX116214 | 35% @ 500 nM | | |
| 44 | PX116244 | 22 | | |
| 45 | PX117417 | 56% @ 500 nM | | |
| 46 | PX117418 | 39% @ 500 nM | | |
| 47 | PX117442 | 31% @ 500 nM | | |
| 48 | PX117458 | 9% @ 500 nM | | |
| 49 | PX117459 | 63% @ 500 nM | | |
| 50 | PX117721 | 10% @ 100 nM | | |
| 51 | PX117722 | >100 | | |
| 52 | PX117728 | >100 | | |

TABLE 1-C

Biochemical Assay Data

| Compound | | HDAC Inhibition (IC50 unless otherwise specified) | | |
|---|---|---|---|---|
| No. | Ref. | HeLa | HDAC1 | HDAC2 |
| 53 | PX083447 | 15% @ 1 μM | | |
| 54 | PX083448 | >1000 | | |
| 55 | PX083803 | 15% @ 1 μM | | |
| 56 | PX083804 | 14% @ 1 μM | | |
| 57 | PX083806 | 19% @ 1 μM | | |
| 58 | PX083807 | 9% @ 1 μM | | |
| 59 | PX083808 | 20000 | | |
| 60 | PX089283 | 21% @ 1 μM | | |
| 61 | PX099268 | 18% @ 10 μM | | |
| 62 | PX105552 | 500 | | 967 |
| 63 | PX105553 | 18 | 38 | 47 |
| 64 | PX105554 | 21900 | | 31000 |
| 65 | PX105668 | >10000 | | |
| 66 | PX105669 | | | 28000 |
| 67 | PX105670 | 29% @ 1 μM | | |
| 68 | PX105816 | 20% @ 500 nM | | |
| 69 | PX105827 | 34% @ 500 nM | | |
| 70 | PX105829 | 54 | 31 | 38 |
| 71 | PX105830 | 82 | | |
| 72 | PX105831 | 33 | 64 | 69 |
| 73 | PX105832 | 438 | | |
| 74 | PX105845 | 22% @ 500 nM | | |
| 75 | PX105846 | 46% @ 500 nM | | |
| 76 | PX105847 | 75 | | |
| 77 | PX105848 | 22 | 25 | 56 |
| 78 | PX105849 | 29 | 50 | 63 |
| 79 | PX105850 | 28 | 25 | 75 |

TABLE 1-C-continued

Biochemical Assay Data

| Compound | | HDAC Inhibition (IC50 unless otherwise specified) | | |
|---|---|---|---|---|
| No. | Ref. | HeLa | HDAC1 | HDAC2 |
| 80 | PX105851 | 18 | 12 | 50 |
| 81 | PX106491 | 83 | | |
| 82 | PX106513 | 43% @ 500 nM | 438 | |
| 83 | PX106516 | 27% @ 500 nM | | |
| 84 | PX106517 | 83 | | |
| 85 | PX106518 | 62 | | |
| 86 | PX106520 | 63 | | |
| 87 | PX106521 | 138 | | |
| 88 | PX106524 | 57% @ 500 nM | | |
| 89 | PX106525 | 28 | 37 | |
| 90 | PX106526 | 9.1 | | |
| 91 | PX106527 | 24 | | |
| 92 | PX106528 | 67% @ 500 nM | | |
| 93 | PX116210 | 19% @ 500 nM | | |
| 94 | PX116211 | 53% @ 500 nM | | |
| 95 | PX116212 | 72% @ 500 nM | | |
| 96 | PX116216 | 100 | | |
| 97 | PX116217 | 17% @ 500 nM | | |
| 98 | PX116220 | 6.3 | | |
| 99 | PX116224 | 78% @ 500 nM | | |
| 100 | PX116226 | 562 | | |
| 101 | PX116230 | insoluble | | |
| 102 | PX116231 | 51% @ 500 nM | | |
| 103 | PX116232 | 10 | | |
| 104 | PX116234 | 15 | | |
| 105 | PX116235 | 10 | | |
| 106 | PX116241 | 39% @ 500 nM | | |
| 107 | PX117224 | 81% @ 500 nM | | |
| 108 | PX117237 | 63 | | |
| 109 | PX117239 | 85% @ 500 nM | | |
| 110 | PX117247 | 19 | | |
| 111 | PX117249 | 64% @ 500 nM | | |
| 112 | PX117254 | 40 | | |
| 113 | PX117255 | 50 | | |
| 114 | PX117261 | 51% @ 500 nM | | |
| 115 | PX117406 | 48% @ 500 nM | | |
| 116 | PX117407 | 40% @ 500 nM | | |
| 117 | PX117408 | 41% @ 500 nM | | |
| 118 | PX117415 | 62 | | |
| 119 | PX117416 | 75% @ 500 nM | | |
| 120 | PX117419 | 46% @ 500 nM | | |
| 121 | PX117420 | 73% @ 500 nM | | |
| 122 | PX117430 | 85 | | |
| 123 | PX117436 | 64% @ 500 nM | | |
| 124 | PX117437 | 95% @ 500 nM | | |
| 125 | PX117441 | 48 | | |
| 126 | PX117444 | 688 | | |
| 127 | PX117451 | 31 | | |
| 128 | PX117454 | 263 | | |
| 129 | PX117456 | 3 | | |
| 130 | PX117706 | 320 | | |
| 131 | PX117707 | 235 | | |
| 133 | PX117711 | 440 | | |
| 134 | PX117717 | 22 | | |
| 135 | PX117718 | 67 | | |
| 136 | PX117719 | 15 | | |
| 137 | PX117729 | 13% @ 100 nM | | |
| 138 | PX117737 | 1200 | | |
| 139 | PX117738 | 131 | | |
| 140 | PX117767 | 90 | | |
| 141 | PX117783 | 100 | | |
| 142 | PX117785 | 192 | | |
| 143 | PX117797 | 688 | | |

TABLE 2-A

Cell-Based Antiproliferation Assay Data

| Compound | | Cell Proliferation Inhibition WST-1 (IC50 unless otherwise specified) | | | |
|---|---|---|---|---|---|
| No. | Ref. | HeLa | K11 | NHEK-AD | Jurkat |
| | TSA | 0.350 | 0.38 | 0.2 | 0.042 |
| | Oxamflatin | 1.1 | 4.56 | 3.53 | 0.260 |
| | MS-275 | | 9.16 | 3.1 | 0.365 |
| | SAHA | 2.2 | 6.82 | 5.3 | 0.750 |
| 4 | PX082534 | 24 | | | |
| 8 | PX083449 | 6.3 | | | |
| 11 | PX089274 | 4.4 | | | |
| 12 | PX089275 | 2.3 | | | |
| 13 | PX089276 | 6.3 | | | |
| 14 | PX105687 | 1.1 | 2.6 | | 0.40 |
| 15 | PX105824 | 5.2 | | | |
| 16 | PX105826 | 18 | | | |
| 17 | PX105828 | 17 | | | |
| 19 | PX106493 | 0.36 | 2.1 | | 0.20 |
| 22 | PX106496 | 5.8 | | | |
| 24 | PX106515 | 3.6 | 1.8 | | 2.7 |
| 31 | PX116223 | <0.310 | 1.7 | 1.3 | 0.22 |
| 35 | PX117421 | 3.1 | | | |
| 36 | PX117461 | >5 | | | |
| 37 | PX117720 | 1.8 | 2.5 | | 0.26 |
| 38 | PX117723 | | 10.0 | | 1.2 |
| 39 | PX117726 | | 4.1 | | 9.9 |

TABLE 2-B

Cell-Based Antiproliferation Assay Data

| Compound | | Cell Proliferation Inhibition WST-1 (IC50 unless otherwise specified) | | | |
|---|---|---|---|---|---|
| No. | Ref. | HeLa | K11 | NHEK-AD | Jurkat |
| 42 | PX106489 | 60 | | | |
| 44 | PX116244 | <0.310 | | | |
| 50 | PX117721 | 20 | 12 | | 1.2 |
| 51 | PX117722 | | >30 | | 8.8 |
| 52 | PX117728 | | 28 | | 4.1 |

TABLE 2-C

Cell-Based Antiproliferation Assay Data

| Compound | | Cell Proliferation Inhibition WST-1 (IC50 unless otherwise specified) | | | |
|---|---|---|---|---|---|
| No. | Ref. | HeLa | K11 | NHEK-AD | Jurkat |
| 62 | PX105552 | 10 | 10 | | 7.9 |
| 63 | PX105553 | 5.7 | 7.5 | 2.4 | 3.7 |
| 64 | PX105554 | 114 | | | 20 |
| 70 | PX105829 | 3.8 | | | |
| 71 | PX105830 | 14 | | | |
| 72 | PX105831 | 9 | | | |
| 76 | PX105847 | 8.3 | | | |
| 77 | PX105848 | 4.3 | | | |
| 78 | PX105849 | 5.3 | | | |
| 79 | PX105850 | 6.3 | | | |
| 80 | PX105851 | 4.2 | | | |
| 81 | PX106491 | 0.52 | | | |
| 84 | PX106517 | 0.47 | | | |
| 85 | PX106518 | 0.65 | | | |
| 86 | PX106520 | 8.4 | | | |
| 87 | PX106521 | 46 | | | |
| 89 | PX106525 | 4.7 | 2.8 | | 3.6 |
| 90 | PX106526 | 2.1 | | | |
| 91 | PX106527 | 1.0 | | | |
| 96 | PX116216 | 6.0 | | | |
| 98 | PX116220 | 3.7 | 9.5 | 2.4 | 4.5 |
| 100 | PX116226 | 4.1 | 5.1 | | 3.2 |
| 103 | PX116232 | 18.3 | 2.7 | 1.7 | 7.3 |
| 104 | PX116234 | 3.4 | 3.6 | | 2.7 |
| 105 | PX116235 | 1.0 | 2.6 | | 0.70 |
| 106 | PX116241 | 56.0 | | | |
| 107 | PX117224 | 26.0 | | | |
| 108 | PX117237 | 17.0 | | | |
| 109 | PX117239 | 10.0 | | | |
| 110 | PX117247 | 0.57 | | | |
| 111 | PX117249 | 11 | | | |
| 112 | PX117254 | 6.6 | | | |
| 113 | PX117255 | 18 | | | |
| 114 | PX117261 | 71 | | | |
| 115 | PX117406 | 6.9 | | | |
| 116 | PX117407 | 13 | | | |
| 117 | PX117408 | 11 | | | |
| 118 | PX117415 | 11 | | | |
| 119 | PX117416 | 7.4 | 8.5 | | 3.6 |
| 120 | PX117419 | 13 | >30 | | 3.5 |
| 121 | PX117420 | 15 | 23.5 | | 5.3 |
| 122 | PX117430 | 27 | 4.4 | | 4.6 |
| 123 | PX117436 | 8.5 | >30 | | 3.5 |
| 124 | PX117437 | 3.7 | 3.4 | | 1.4 |
| 125 | PX117441 | 17 | 4.9 | | 4.3 |
| 126 | PX117444 | 45 | | | |
| 127 | PX117451 | 22 | 12 | | |
| 128 | PX117454 | 15 | 13 | | 3.4 |
| 129 | PX117456 | 0.65 | 0.74 | 0.25 | 0.18 |
| 130 | PX117706 | 30 | 6.9 | | 1.8 |
| 131 | PX117707 | 43 | 7.7 | | 1.5 |
| 133 | PX117711 | 9.8 | 7.9 | | 0.92 |
| 134 | PX117717 | 5.9 | 2.34 | | 0.41 |
| 135 | PX117718 | 39 | 3.7 | | 4.4 |
| 136 | PX117719 | 6.8 | 0.94 | | 0.56 |
| 137 | PX117729 | 33 | 23 | | 2.8 |
| 138 | PX117737 | 32 | >30 | | 2.2 |
| 139 | PX117738 | 24 | 3.2 | | 1.7 |
| 140 | PX117767 | 15 | 6.2 | | 3.0 |
| 141 | PX117783 | 6 μM | 9.7 μM | | 1.6 μM |
| 142 | PX117785 | | Inactive | | Inactive |
| 143 | PX117797 | 21 | 21 | | 5.6 |

Comparative Data for Aryl Leader, $Q^1$

Comparative data for sets of compounds, where the only difference in chemical structure is the aryl leader, are shown below.

Compounds which employ, as $Q^1$, either: a covalent bond, or: an aryl leader having a backbone of at least 2 carbon atoms surprisingly and unexpectedly have superior activity as compared to their analogs which comprise, as $Q^1$, an aryl leader having a backbone of 1 carbon atom. The observation that, as $Q^1$, a 1 atom backbone gives substantially reduced activity as compared to a covalent bond, but that a 2 atom backbone give substantially improved activity as compared to a 1 atom backbone, is surprising and unexpected.

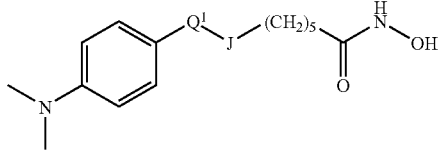

| Compound | $Q^1$ | J | HeLa IC50 |
|---|---|---|---|
| PX89274 | — | —CONH— | 110 nM |
| PX117458 | —CH$_2$— | —CONH— | 9% @ 500 nM |
| PX106527 | —CH=CHCH=CH— | —CONH— | 24 nM |

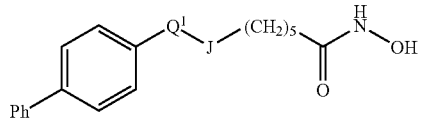

| Compound | $Q^1$ | J | HeLa IC50 |
|---|---|---|---|
| PX106488 | —CH$_2$— | —CONH— | 51% @ 500 nM |
| PX105848 | —CH=CHCH=CH— | —CONH— | 22 nM |

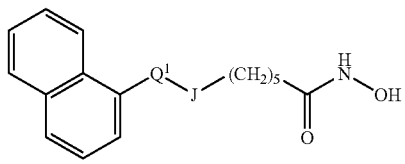

| Compound | $Q^1$ | J | HeLa IC50 |
|---|---|---|---|
| PX105828 | — | —CONH— | 333 nM |
| PX117441 | —CH=CH— | —CONH— | 48 nM |
| PX117237 | —CH=CHCH=CH— | —CONH— | 63 nM |

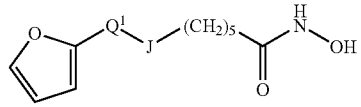

| Compound | $Q^1$ | J | HeLa IC50 |
|---|---|---|---|
| PX105826 | — | —CONH— | 400 nM |
| PX105827 | —CH$_2$CH$_2$— | —CONH— | 34% @ 500 nM |
| PX106491 | —CH=CH— | —CONH— | 83 nM |

Comparative Data for Acid Leader, $Q^2$

Comparative data for sets of compounds, where the only difference in chemical structure is the acid leader, are shown below.

Compounds which employ, as $Q^2$, an alkylene group (e.g., having a backbone of at least 3, 4, 5 carbon atoms) surprisingly and unexpectedly have superior activity as compared to their analogs which comprise, as $Q^1$, an aryl leader comprising an arylene group (e.g., arylene-alkylene).

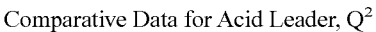

| Compound | J | $Q^2$ | HeLa IC50 |
|---|---|---|---|
| PX117231 | —CONH— | —PhCH=CH— | 72% @ 1 μM |
| PX117232 | —CONH— | —PhCH$_2$CH$_2$— | 43% @ 1 μM |
| PX83449 | —CONH— | —CH$_2$CH$_2$CH$_2$CH$_2$CH$_2$— | 238 nM |

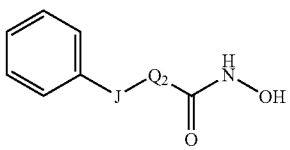

| Compound | J | $Q^2$ | HeLa IC50 |
|---|---|---|---|
| PX106513 | —CONH— | —PhCH=CH— | 43% @ 1 μM |
| PX106517 | —CONH— | —CH$_2$CH$_2$CH$_2$CH$_2$CH$_2$— | 83 nM |

Compounds which employ, as $Q^2$, an alkylene group having a backbone of at least 4 carbon atoms, or at least 5 carbon atoms) surprisingly and unexpectedly have superior activity as compared to their analogs which comprise, as $Q^1$, shorter backbone lengths.

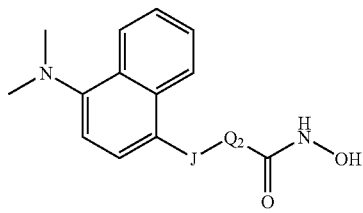

| Compound | J | $Q^2$ | HeLa IC50 |
|---|---|---|---|
| PX082530 | —CONH— | —CH$_2$CH$_2$— | 13% @ 1 μM |
| PX082533 | —CONH— | —CH$_2$CH$_2$CH$_2$— | 2% @ 1 μM |
| PX082534 | —CONH— | —CH$_2$CH$_2$CH$_2$CH$_2$— | 1500 nM |
| PX089275 | —CONH— | —CH$_2$CH$_2$CH$_2$CH$_2$CH$_2$— | 466 |

-continued

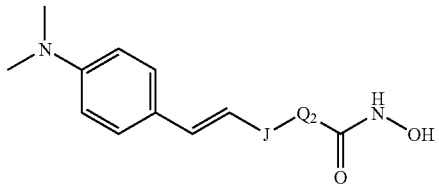

| Compound | J | $Q^2$ | HeLa IC50 |
|---|---|---|---|
| PX083448 | —CONH— | —CH$_2$CH$_2$— | >1000 |
| PX083808 | —CONH— | —CH$_2$CH$_2$CH$_2$— | >20000 |
| PX105832 | —CONH— | —CH$_2$CH$_2$CH$_2$CH$_2$— | 438 |
| PX105533 | —CONH— | —CH$_2$CH$_2$CH$_2$CH$_2$CH$_2$— | 18 |
| PX106518 | —CONH— | —CH$_2$CH$_2$CH$_2$CH$_2$CH$_2$CH$_2$— | 62 |
| PX105851 | —CONH— | —CH$_2$CH$_2$CH$_2$CH$_2$CH$_2$CH$_2$CH$_2$— | 18 |

REFERENCES

A number of patents and publications are cited herein in order to more fully describe and disclose the invention and the state of the art to which the invention pertains. Full citations for these references are provided herein. Each of these references is incorporated herein by reference in its entirety into the present disclosure.

Andrews et al., 2000, *Int. J. Parasitol.*, Vol. 30, No. 6, pp. 761-768.

Anghelova, Y. et al, 1973, *Chem. Ber., Vol.* 106, p. 2643.

Backer, H. J., et al., 1940, *Recl. Trav. Chim. Pays-Bas*, Vol. 59, p. 423.

Banerji, A., et al., 1984, *Indian J. Chem.*, Vol. 23B, pp. 546-549.

Bellamy, F. D., et al., 1984, *Tetrahedron Letters*, Vol. 25, No. 8, p. 839.

Bernhard, D. et al., 1999, "Apoptosis induced by the histone deacetylase inhibitor sodium butyrate in human leukemic lymphoblasts," *FASEB J.*, Vol. 13, No. 14, pp. 1991-2001.

Bernstein et al., 2000, *Proc. Natl. Acad. Sci. USA*, Vol. 97, No. 25, pp. 13708-13713.

Bistrzycki, 1912, *Chem. Ber.*, Vol. 45, p. 3483.

Brehm, A., et al., 1998, "Retinoblastoma protein recruits histone deacetylase to repress transcription," *Nature*, 1998, Vol. 391, pp. 597-601.

Breslow et al., 1994, "Potent inducers of terminal differentiation and methods of use thereof," U.S. Pat. No. 5,369,108 issued Nov. 29, 1994.

Breslow et al., 1995, "Novel potent inducers of terminal differentiation and methods of use thereof," published international (PCT) patent application number WO 95/31977 published Nov. 30, 1995.

Breslow et al., 1997, "Potent inducers of terminal differentiation and methods of use thereof," U.S. Pat. No. 5,700,811 issued Dec. 23, 1997.

Carbonnier, J., et al., 1981, *Physiol. Plant.*, 1981, Vol. 51, p. 1.

Chang et al., 2000, *Nucleic Acids Res.*, Vol. 28, No. 20, pp. 3918-3925.

Chen, W.-S., et al., 1978, *Biochemistry*, Vol. 17, No. 23, p. 4916.

Copeland, R. A. B., et al., 1943, *J. Amer. Chem. Soc.*, Vol. 65, p. 1072.

Corneil et al., 1998, published Japanese patent application, publication number JP 10114681 A2.

Dangond et al., 1998, *Biochem. Biophys. Res. Commun.*, Vol. 242, No. 3, pp. 648-652.

David, G., et al., 1998, *Oncogene*, Vol. 16(19), pp. 2549-2556.

Davie, J. R., 1998, "Covalent modifications of histones: expression from chromatic templates," *Curr. Opin. Genet. Dev.*, Vol. 8, pp. 173-178.

Delorme et al., 2001, "Inhibitors of Histone Deacetylase," published international (PCT) patent application number WO 01/38322 published May 31, 2001.

Desai et al., 1999, *Proc. AACR*, Vol. 40, abstract #2396.

Emiliani, S., et al., 1998, "Characterization of a human RPD3 ortholog, HDAC3," *Proc. Natl. Acad. Sci. USA*, Vol. 95, p. 2795-2800.

Finnin et al., 1999, *Nature*, Vol. 401, pp. 188-193.

Furukawa et al., 1998, U.S. Pat. No. 5,834,249, "Process for production of protein," Nov. 10, 1998.

Geerts et al., 1998, European patent publication no. EP 0 827 742 A1, published Mar. 11, 1998.

Glick, R. D., et al., 1999, "Hybrid polar histone deacetylase inhibitor induces apoptosis and CD95/CD95 ligand expression in human neuroblastoma," *Cancer Research*, Vol. 59, No. 17, pp. 4392-4399.

Grozinger et al., 1999, *Proc. Natl. Acad. Sci. USA*, Vol. 96, pp. 4868-4873.

Hashimoto, N., et al., 1989, "Cell proliferation inhibitors," European Patent Publication No. EP 0 301 861 A1.

Hoshikawa, Y., et al., 1994, *Exp. Cell. Res.*, Vol. 214(1), pp. 189-197.

Howe, L., et al., 1999, *Crit. Rev. Eukaryot. Gene Expr.*, Vol. 9(3-4), pp. 231-243.

Iavarone et al., 1999, *Mol. Cell Biol.*, Vol. 19, No. 1, pp. 916-922.

Jung et al., 1997, *Bioorganic & Medicinal Chemistry Letters*, Vol. 7, No. 13, pp. 1655-1658.

Jung et al., 1999, *J. Med. Chem.*, Vol. 42, pp. 4669-4679.

Kao et al., 2000, *Genes & Dev.*, Vol. 14, p. 55-66.

Kato et al., 1998, U.S. Pat. No. 5,804,601, "Aromatic hydroxamic acid compounds, their production and use," Sep. 8, 1998.

Kijima et al., 1993, *J. Biol. Chem.*, Vol. 268, pp. 22429-22435.

Kim et al., 1999, *Oncogene*, Vol. 18(15), pp. 2461-2470.

Kim et al., 2001, *Nature Medicine*, Vol. 7, No. 4, pp. 437-443.

Kim, M. S., et al., 2001 "Histone deacetylases induce angiogenesis by negative regulation of tumour suppressor genes," *Nature Medicine*, Vol 7. No. 4 pp. 437-443.

Kimura et al., 1994, *Biol. Pharm. Bull.*, Vol. 17, No. 3, pp. 399-402.

Kitamura, K., et al., 2000, *Br. J. Haematol.*, Vol. 108(4), pp. 696-702.

Kouzarides, T., 1999, "Histone acetylases and deacetylases in cell proliferation," *Curr. Opin. Genet. Dev.*, Vol. 9, No. 1, pp. 40-48.

Kuusisto et al., 2001, *Biochem. Biophys. Res. Commun.*, Vol. 280, No. 1, pp. 223-228.

Kwon et al., 1998, *Proc. Natl. Acad. Sci. USA*, Vol. 95, pp. 3356-3361.

Laherty, C. D., et al., 1997, *Cell*, Vol. 89(3), pp. 349-356.

Lea and Tulsyan, 1995, *Anticancer Res.*, Vol. 15, pp. 879-883.

Lea et al., 1999, *Int. J. Oncol.*, Vol. 2, pp. 347-352.

Lin, R. J., et al., 1998, *Nature*, Vol. 391(6669), pp. 811-814.

Massa et al., May 26, 2001, Journal of Medicinal Chemistry, Vol. 44, No. 13, pp. 2069-2072.

McCaffrey et al., 1997, *Blood*, Vol. 90, No. 5, pp. 2075-2083.

Mielnicki, L. M., et al., 1999, *Exp. Cell. Res.*, Vol. 249(1), pp. 161-176.

Ng, H. H. and Bird, A., 2000, *Trends Biochem. Sci.*, Vol. 25(3), pp. 121-126.

Niki et al., 1999, *Hepatology*, Vol. 29, No. 3, pp. 858-867.

Nokajima et al., 1998, *Exp. Cell Res.*, Vol. 241, pp. 126-133.

Ohtani et al., 1993, "Hydroxamic acid derivatives based on aromatic sulfonamide," published international (PCT) patent application number WO 93/12075 published Jun. 24, 1993.

Ohtani et al., 1996, "(2E)-5-[3-[(Phenylsulfonyl)amino] phenyl]-pent-2-en-4-yno-hydroxamic acid and its derivatives as novel and potent inhibitors of ras transformation," *J. Medicinal Chemistry*, Vol. 39, No. 15, pp. 2871-2873.

Onishi et al., 1996, *Science*, Vol. 274, pp. 939-940.

Parsons et al., 1998, "Hydroxamic acid compounds having anticancer and anti-parasitic properties," published international (PCT) patent application number WO 98/55449 published Dec. 10, 1998.

Pazin, M. J., et al., 1997, "What's up and down with histone deacetylation and transcription?," *Cell*, Vol. 89, No. 3, pp. 325-328.

Richon et al, 1996, *Proc. Natl. Acad. Sci. USA*, Vol. 93, pp. 5705-5708.

Richon et al., 1998, "A class of hybrid poler inducers of transformed cell differentiation inhibits histone deacetylases," *Proc. Natl. Acad. Sci. USA*, Vol. 95, pp. 3003-3007.

Richon et al., 2001, "Novel class of cytodifferentiating agents and histone deacetylase inhibitors, and methods of use thereof," published international (PCT) patent application number WO 01/18171 published Mar. 15, 2001.

Saito et al., 1999, *Proc. Natl. Acad. Sci. USA*, Vol. 96, pp. 4592-4597.

Saunders, N. et al, 1999 "Histone deacetylase inhibitors as potential anti-skin cancer agents," *Cancer Res.*, Vol. 59, No. 2 pp. 399-404.

Sonoda, H. et al., 1996, *Oncogene*, Vol. 13, pp. 143-149.

Spencer, V. A. and Davie, J. R., 1999, *Gene*, Vol. 240(1), pp. 1-12.

Suzuki et al., 1998, Japanese patent publication number 10-182583 published Jul. 07, 1998.

Suzuki et al., 1999, "Synthesis and histone deactylase inhibitory activity of new benzamide derivatives," *J. Med. Chem.*, Vol. 42, pp. 3001-3003.

Takahashi et al., 1996, *J. Antibiot. (Tokyo)*, Vol. 49, No. 5, pp. 453-457.

Takahashi, I., et al, 1996, "Selective inhibition of IL-2 gene expression by trichostatin A, a potent inhibitor of mammalian histone deacetylase," *J. Antibiot. (Tokyo)*, Vol. 49, No. 5, pp. 453-457.

Tauton, J., et al., 1996, "A mammalian histone deacetylase related to the yeast transcriptional regulator Rpd3p, " *Science*, Vol. 272, pp. 408-411.

Tsuji et al., 1976, *J. Antibiot. (Tokyo)*, Vol. 29, No. 1, pp. 1-6.

Ueda, H., et al., 1994, *J. Antibiot. (Tokyo)*, Vol. 47(3), pp. 315-323.

Van den Wyngaert et al., 2000, *FEBS*, Vol. 478, pp. 77-83.

Vig, B., et al., 1977, *Indian J. Chem.*, Vol. 15B, pp. 1048-9.

Vigushin et al., 2001, *Clin. Cancer Res.*, Vol. 7, No. 4, pp. 971-976.

Villieras, J., et al., 1983, *Synthesis*, pp. 300-3.

Warrell et al., 1998, *J. Natl. Cancer Inst.*, Vol. 90, pp. 1621-1625.

Wong, J., et al., 1998, *EMBO J.*, Vol. 17(2), pp. 520-534.

Yang, W. M., et al., 1996, "Transcriptional repression of YY1 is mediated by interaction with a mammalian homolog of the yeast global regulator RPD3," *Proc. Natl. Acad. Sci. USA*, Vol. 93, pp. 12845-12850.

Yang, W. M., et al., 1997, "Isolation and characterization of cDNAs corresponding to an additional member of the human histone deacetylase gene family," *J. Biol. Chem.*, Vol 272, pp. 28001-28007.

Yoshida et al., 1995, *Bioessays*, Vol. 17, pp. 423-430.

Yoshida, M. and Horinouchi, S., 1999, *Ann. N.Y. Acad. Sci.*, Vol. 886, pp. 23-36.

Yoshida, M., Beppu, T., 1988, "Reversible arrest of proliferation of rat 3Y1 fibroblasts in both G1 and G2 phases by trichostatin A," *Exp. Cell. Res.*, Vol. 177, pp. 122-131.

Yoshida, M., et al., 1990a, *J. Biol. Chem.*, Vol. 265(28), pp. 17174-17179.

Yoshida, M., et al., 1990b, *J. Antibiot. (Tokyo)*, Vol. 43(9), pp. 1101-1106.

What is claimed is:

1. A compound selected from compounds of the following formula and pharmaceutically acceptable salts, amides, esters, ethers, and chemically protected forms thereof:

$$A-Q^1-J-Q^2-\overset{O}{\underset{}{C}}-\underset{H}{N}-OH$$

wherein:

A is phenyl or naphthyl, and is optionally substituted;

$Q^1$ is a partially unsaturated $C_{2-7}$alkylene group having a backbone of at least 2 carbon atoms and is optionally substituted;

J is:

$$-\underset{R^1}{N}-\overset{O}{\underset{}{C}}-\quad\text{or}\quad-\overset{O}{\underset{}{C}}-\underset{R^1}{N}-;$$

$R^1$ is hydrogen, $C_{1-7}$alkyl, phenyl, or benzyl;

$Q^2$ has a backbone of at least 3 carbon atoms and is selected from:

unsubstituted $C_{3-7}$alkyene;

optionally substituted phenylene;

optionally substituted naphthalene-di-yl;

optionally substituted phenylene-$C_{1-7}$alkylene;

optionally substituted (naphthalene-di-yl)-$C_{1-7}$alkylene;
optionally substituted $C_{1-7}$alkylene-phenylene;
and
optionally substituted $C_{1-7}$alkylene-(naphthalene-di-yl);
wherein:
if $Q^2$ is phenylene-$C_{1-7}$alkylene, or (naphthalene-di-yl)-$C_{1-7}$alkylene, then:
(i) the $C_{1-7}$alkylene moiety does not comprise a carbon-carbon triple bond; or
(ii) $Q^2$ has a backbone of less than 7 carbon atoms.

2. A compound according to claim 1, wherein J is —C(=O)NR$^1$—.

3. A compound according to claim 1, wherein J is —NR$^1$C(=O)—.

4. A compound according to claim 1, wherein $Q^1$ is a partially unsaturated aliphatic $C_{2-7}$alkylene group.

5. A compound according to claim 1, wherein $Q^1$ is a partially unsaturated linear $C_{2-7}$alkylene group.

6. A compound according to claim 1, wherein $Q^1$ is a partially unsaturated branched $C_{2-7}$alkylene group.

7. A compound according to claim 1, wherein $Q^1$ is a partially unsaturated alicyclic $C_{3-7}$alkylene group.

8. A compound according to claim 1, wherein $Q^1$ is not saturated at the carbon atom adjacent to J.

9. A compound according to claim 1, wherein $Q^1$ has a backbone of from 2 to 7 carbon atoms.

10. A compound according to claim 1, wherein $Q^1$ is unsubstituted.

11. A compound according to claim 1, wherein $Q^1$ is substituted.

12. A compound according to claim 1, wherein $Q^1$ is unsubstituted, or is substituted with one or more groups selected from: halo, hydroxy, ether, phenyl, pyridyl, acyl, amido, and oxo.

13. A compound according to claim 1, wherein $Q^1$ is unsubstituted, or is substituted with one or more groups selected from: —F, —Cl, —Br, —I, —OH, —OMe, —OEt, —OPr, -Ph, and =O.

14. A compound according to claim 1, wherein $Q^1$ is selected from:

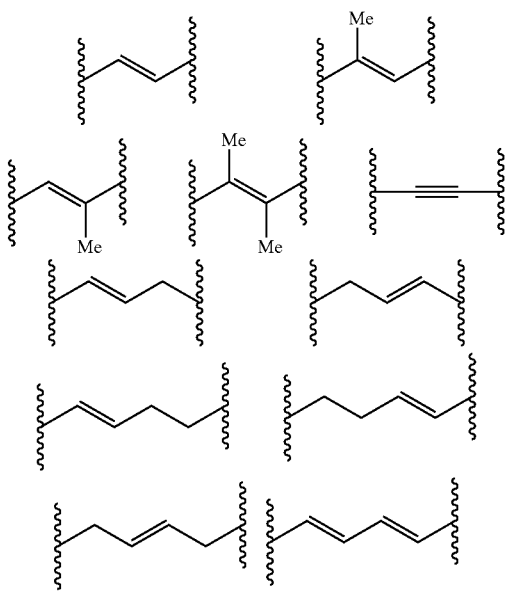

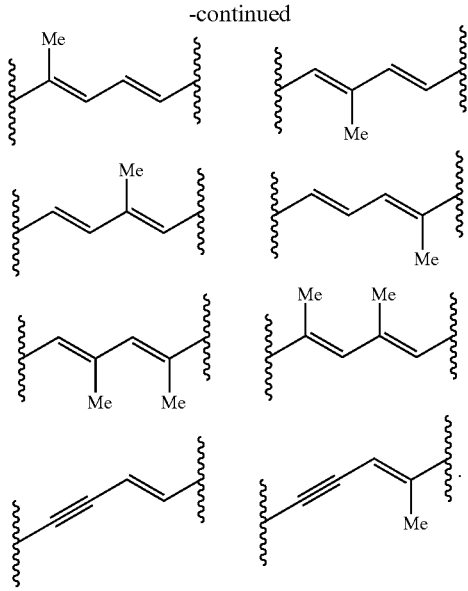

15. A compound according to claim 1, wherein $Q^1$ is selected from: —CH=CH— and —CH=CH—CH=CH—.

16. A compound according to claim 1, wherein $Q^2$ is a saturated $C_{3-10}$alkylene group.

17. A compound according to claim 1, wherein $Q^2$ is a partially unsaturated $C_{3-10}$alkylene group.

18. A compound according to claim 1, wherein $Q^2$ is an aliphatic $C_{3-10}$alkylene group.

19. A compound according to claim 1, wherein $Q^2$ is a linear $C_{3-10}$alkylene group.

20. A compound according to claim 1, wherein $Q^2$ is a branched $C_{4-10}$alkylene group.

21. A compound according to claim 1, wherein $Q^2$ is an alicyclic $C_{4-10}$alkylene group.

22. A compound according to claim 1, wherein $Q^2$ is a saturated aliphatic $C_{3-10}$alkylene group.

23. A compound according to claim 1, wherein $Q^2$ is a saturated linear $C_{3-10}$alkylene group.

24. A compound according to claim 1, wherein $Q^2$ is a saturated branched $C_{4-10}$alkylene group.

25. A compound according to claim 1, wherein $Q^2$ is a saturated alicyclic $C_{4-10}$alkylene group.

26. A compound according to claim 1, wherein $Q^2$ is a partially unsaturated aliphatic $C_{3-10}$alkylene group.

27. A compound according to claim 1, wherein $Q^2$ is a partially unsaturated linear $C_{3-10}$alkylene group.

28. A compound according to claim 1, wherein $Q^2$ is a partially unsaturated branched $C_{4-10}$alkylene group.

29. A compound according to claim 1, wherein $Q^2$ is a partially unsaturated alicyclic $C_{4-10}$alkylene group.

30. A compound according to claim 1, wherein $Q^2$ has a backbone of from 3 to 7 carbon atoms.

31. A compound according to claim 1, wherein $Q^2$ is unsubstituted.

32. A compound according to claim 1, wherein $Q^2$ is selected from: —(CH$_2$)$_3$—, —(CH$_2$)$_4$—, —(CH$_2$)$_5$—, —(CH$_2$)$_6$—, and —(CH$_2$)$_7$—.

33. A compound according to claim 1, wherein $Q^2$ is selected from: —(CH$_2$)$_4$—, —(CH$_2$)$_5$—, —(CH$_2$)$_6$—, and —(CH$_2$)$_7$—.

34. A compound according to claim 1, wherein $Q^2$ is selected from: —$(CH_2)_4$—, —$(CH_2)_5$—, and —$(CH_2)_6$—.

35. A compound according to claim 1, wherein $Q^2$ is selected from: —$(CH_2)_5$— and —$(CH_2)_6$—.

36. A compound according to claim 1, wherein $Q^2$ is phenylene, or naphthalene-di-yl, and is optionally substituted.

37. A compound according to claim 1, wherein $Q^2$ is phenylene, and is optionally substituted.

38. A compound according to claim 1, wherein $Q^2$ is phenylene-$C_{1-7}$alkylene, or (naphthalene-di-yl)-$C_{1-7}$alkylene, and is optionally substituted; and: (i) the $C_{1-7}$alkylene moiety does not comprise a carbon-carbon triple bond; or (ii) $Q^2$ has a backbone of less than 7 carbon atoms.

39. A compound according to claim 1, wherein $Q^2$ is phenylene-$C_{1-7}$alkylene, or (naphthalene-di-yl)-$C_{1-7}$alkylene, and is optionally substituted; and: (i) the $C_{1-7}$alkylene moiety does not comprise a carbon-carbon triple bond; or (ii) $Q^2$ has a backbone of less than 6 carbon atoms.

40. A compound according to claim 1, wherein $Q^2$ is phenylene-$C_{1-2}$alkylene, or (naphthalene-di-yl)-$C_{1-2}$alkylene, -and is optionally substituted.

41. A compound according to claim 1, wherein $Q^2$ is phenylene-$C_{1-2}$alkylene, and is optionally substituted.

42. A compound according to claim 1, wherein $Q^2$ is phenylene-$C_{1-7}$alkylene, and is optionally substituted; and: (i) the $C_{1-7}$alkylene moiety does not comprise a carbon-carbon triple bond; or (ii) $Q^2$ has a backbone of less than 7 carbon atoms.

43. A compound according to claim 1, wherein $Q^2$ is phenylene-meta-$C_{1-7}$alkylene or phenylene-para-$C_{1-7}$alkylene, and is optionally substituted; and: (i) the $C_{1-7}$alkylene moiety does not comprise a carbon-carbon triple bond; or (ii) $Q^2$ has a backbone of less than 7 carbon atoms.

44. A compound according to claim 1, wherein $Q^2$ is substituted.

45. A compound according to claim 1, wherein $Q^2$ is selected from:

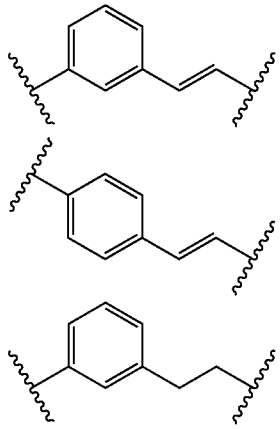

46. A compound according to claim 1, wherein $Q^2$ is:

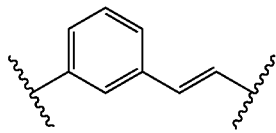

47. A compound according to claim 1, wherein A is an optionally substituted naphthyl group.

48. A compound according to claim 1, wherein A is an optionally substituted phenyl group.

49. A compound according to claim 1, wherein A is a phenyl group which is unsubstituted, or is substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

50. A compound according to claim 1, wherein A is a phenyl group which is unsubstituted, or is substituted with one or more of the following groups: fluoro, chloro, bromo, iodo, trifluoromethyl, and nitro.

51. A compound according to claim 1, wherein $R^1$ is hydrogen or $C_{1-7}$alkyl.

52. A compound according to claim 1, wherein $R^1$ is —H.

53. A compound according to claim 1, selected from the following compounds and pharmaceutically accepted salts thereof:

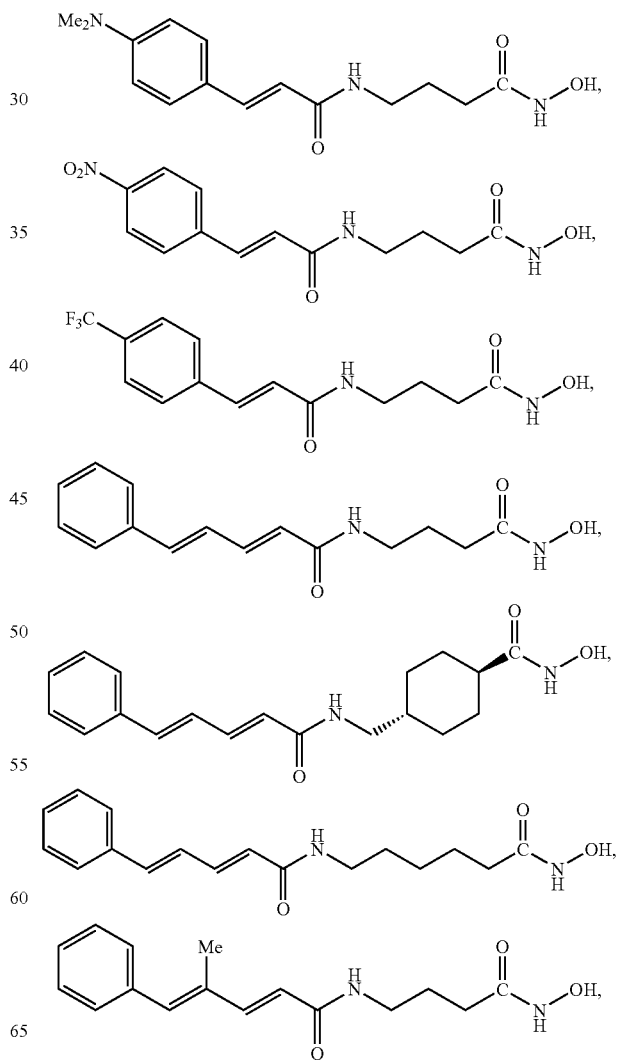

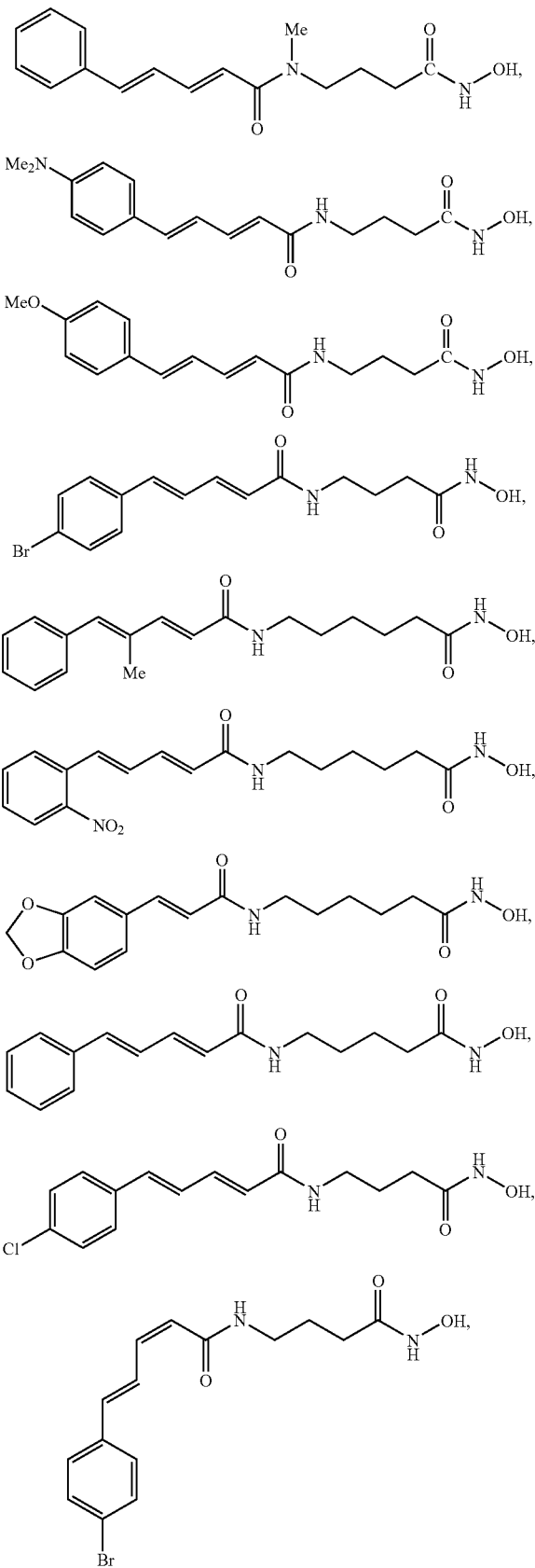
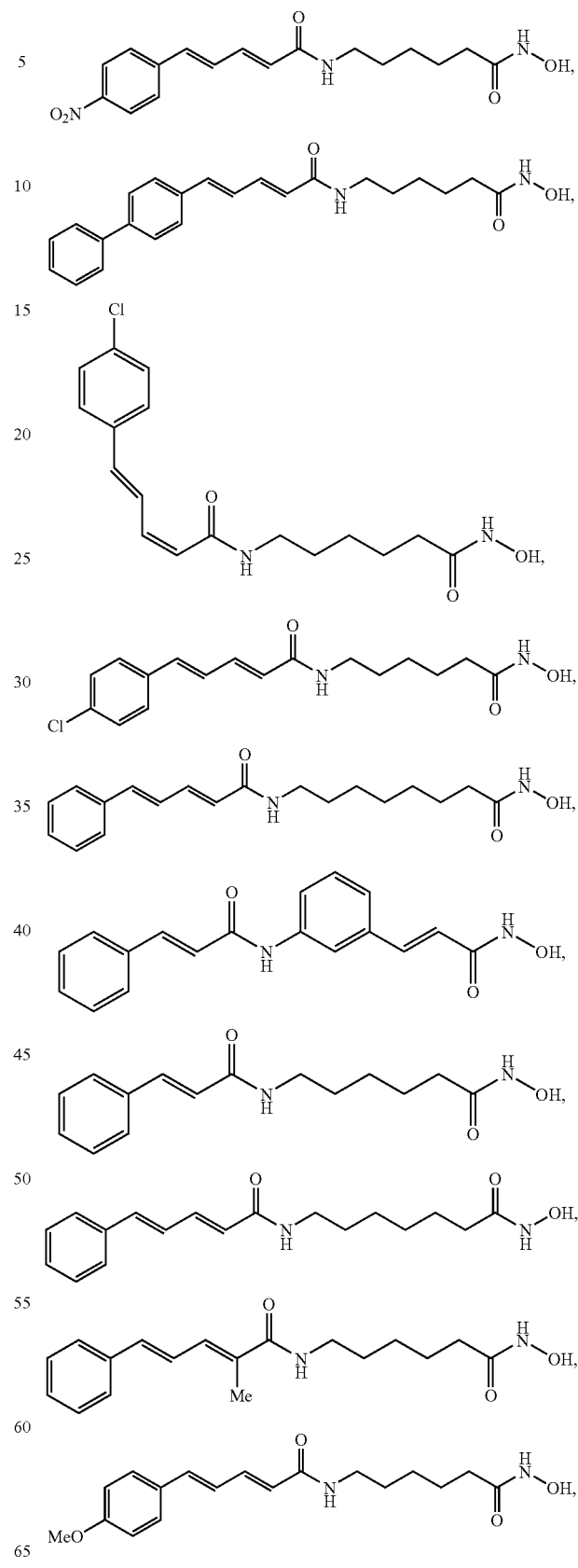

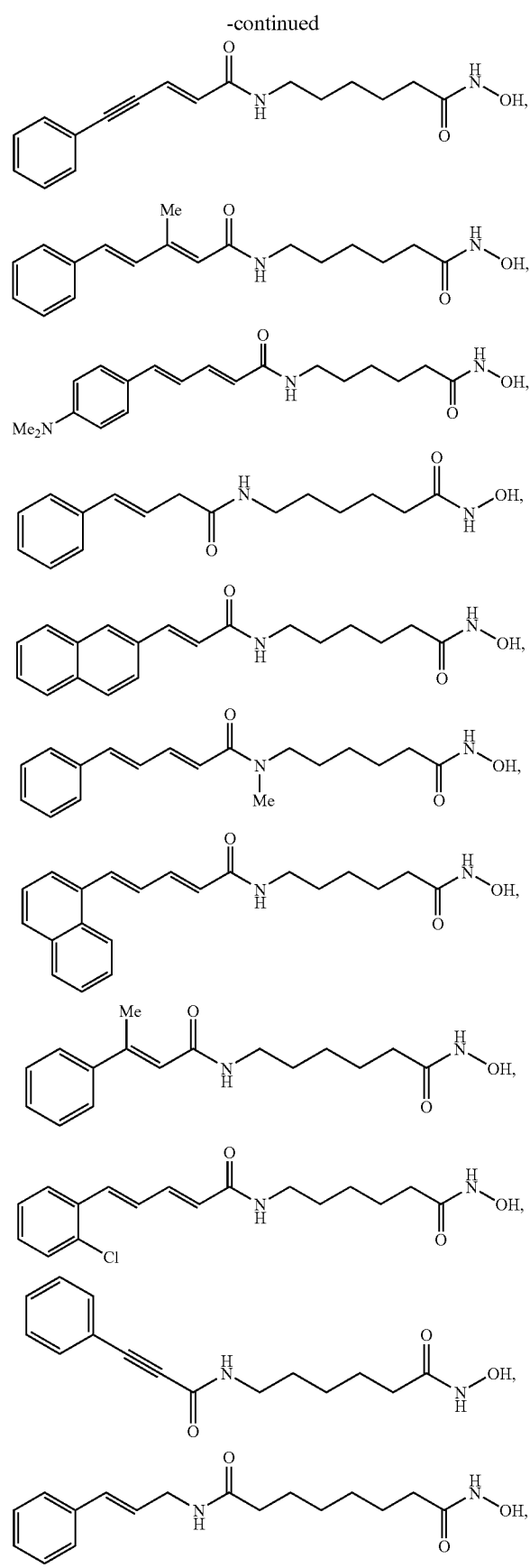
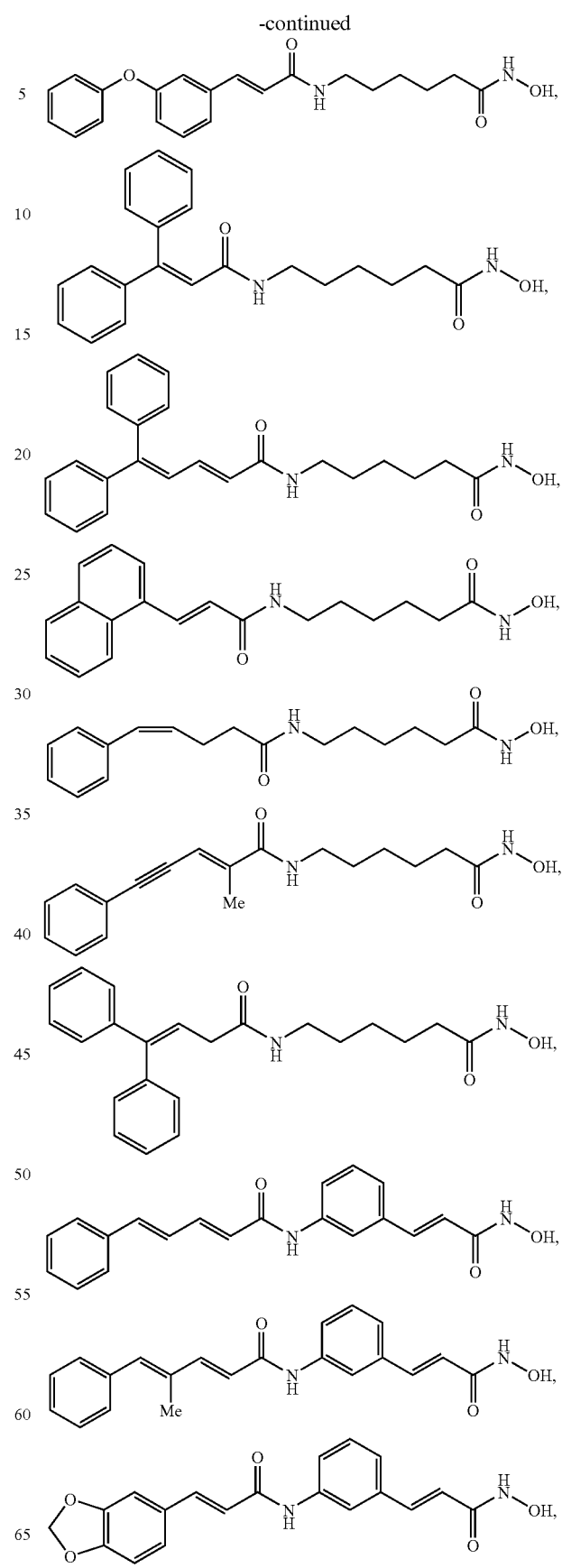

-continued

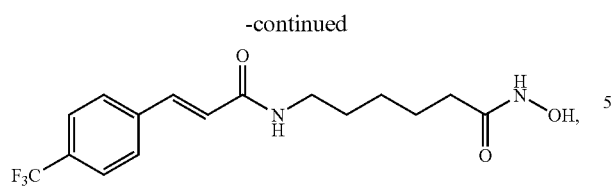

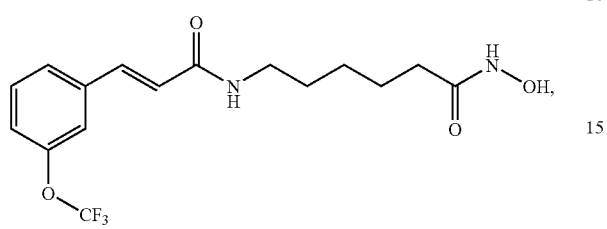

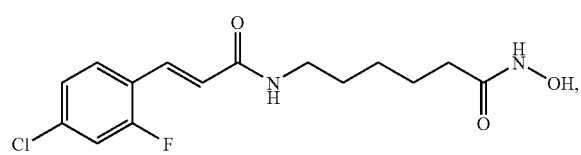

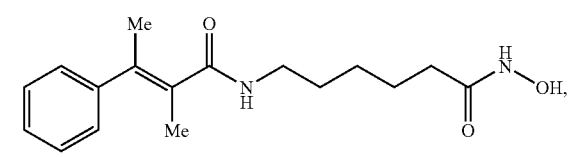

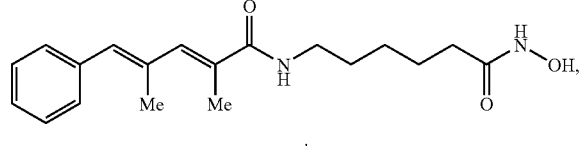

and

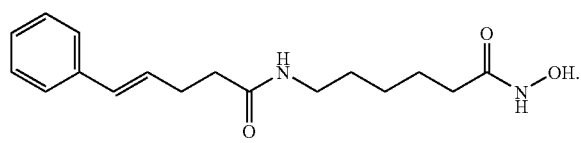

54. A pharmaceutical composition comprising a compound according to claim 1 and a pharmaceutically acceptable carrier or diluent.

55. A method of inhibiting HDAC in a cell comprising said cell with an effective amount of a compound according to claim 1.

56. A compound selected from compounds of the following formula and pharmaceutically acceptable salts thereof:

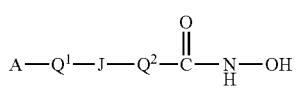

wherein:

the group A-$Q^1$- is:

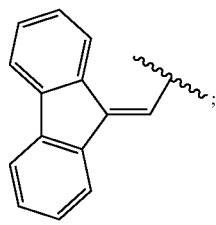

J is:

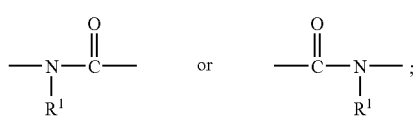

$R^1$ is hydrogen or $C_{1-7}$alkyl; and, $Q^2$ is —$(CH_2)_4$—, —$(CH_2)_5$—, —$(CH_2)_6$—, or —$(CH_2)_7$—.

57. A compound selected from compounds of the following formula and pharmaceutically acceptable salts thereof:

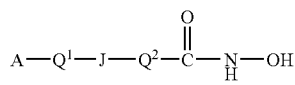

wherein:

A is phenyl or naphthyl, and is optionally substituted;

$Q^1$ is selected from:

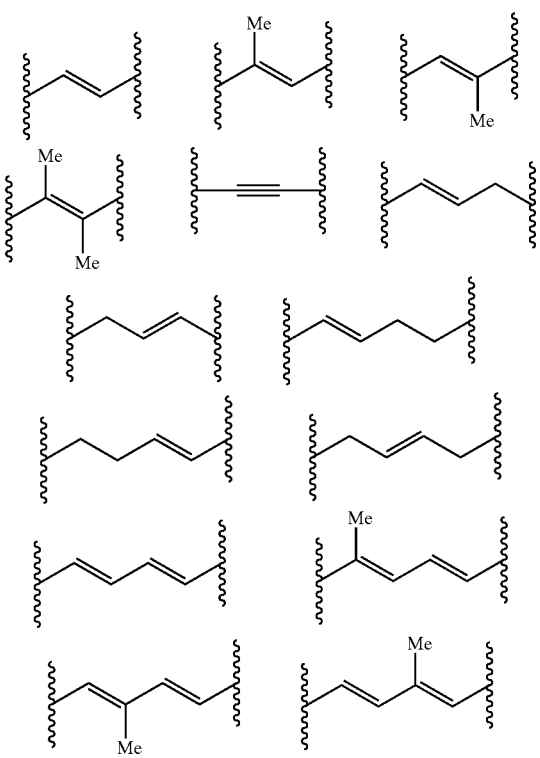

-continued

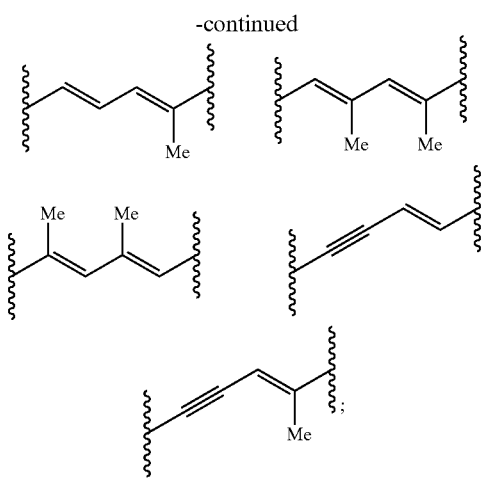

J is:

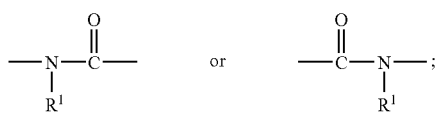

$R^1$ is hydrogen or $C_{1-7}$alkyl; and,
$Q^2$ is —$(CH_2)_4$—, —$(CH_2)_5$—, —$(CH_2)_6$—, or —$(CH_2)_7$—.

58. A compound according to claim 57, wherein J is:

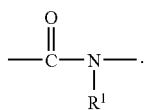

59. A compound according to claim 58, wherein A is phenyl, and is optionally substituted.

60. A compound according to claim 58, wherein A is phenyl, and is optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

61. A compound according to claim 58, wherein A is phenyl, and is optionally substituted with one or more of the following groups: fluoro, chloro, bromo, methyl, hydroxyl, methoxy, and trifluoromethyl.

62. A compound according to claim 58, wherein A is naphthyl, and is optionally substituted.

63. A compound according to claim 58, wherein A is naphthyl, and is optionally substituted with one or more of the following groups: fluoro, chloro, bromo, iodo, methyl, ethyl, isopropyl, t-butyl, cyano, trifluoromethyl, hydroxy, methoxy, ethoxy, isopropoxy, trifluoromethoxy, phenoxy, methylthio, trifluoromethylthio, hydroxymethyl, amino, dimethylamino, diethylamino, morpholino, amido, acetamido, acetyl, nitro, sulfonamido, and phenyl.

64. A compound according to claim 58, wherein $Q^2$ is —$(CH_2)_5$— or —$(CH_2)_6$—.

65. A compound according to claim 59, wherein $Q^2$ is —$(CH_2)_5$— or —$(CH_2)_6$—.

66. A compound according to claim 60, wherein $Q^2$ is —$(CH_2)_5$— or —$(CH_2)_6$—.

67. A compound according to claim 61, wherein $Q^2$ is —$(CH_2)_5$— or —$(CH_2)_6$—.

68. A compound according to claim 62, wherein $Q^2$ is —$(CH_2)_5$— or —$(CH_2)_6$—.

69. A compound according to claim 63, wherein $Q^2$ is —$(CH_2)_5$— or —$(CH_2)_6$—.

70. A compound according to claim 58, wherein $Q^1$ is selected from:

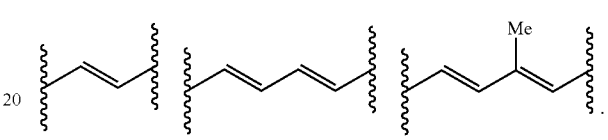

71. A compound according to claim 59, wherein $Q^1$ is selected from:

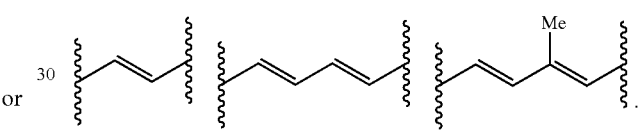

72. A compound according to claim 60, wherein $Q^1$ is selected from:

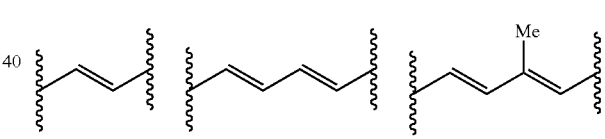

73. A compound according to claim 61, wherein $Q^1$ is selected from:

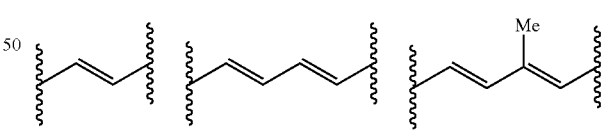

74. A compound according to claim 62, wherein $Q^1$ is selected from:

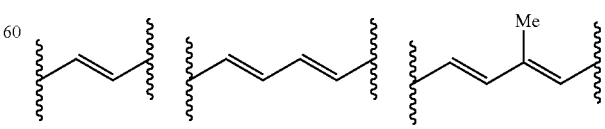

75. A compound according to claim 63, wherein $Q^1$ is selected from:

76. A compound according to claim 64, wherein $Q^1$ is selected from:

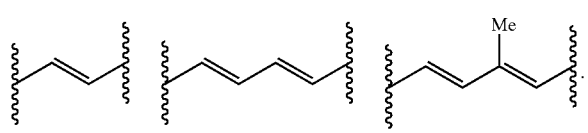

77. A compound according to claim 65, wherein $Q^1$ is selected from:

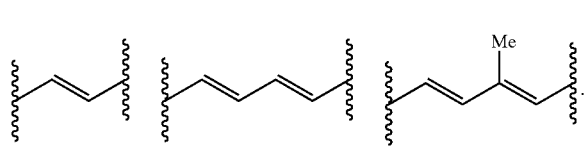

78. A compound according to claim 66, wherein $Q^1$ is selected from:

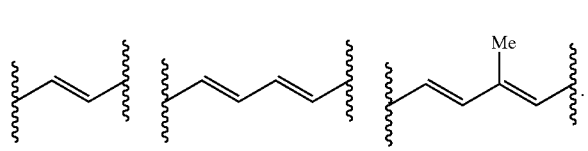

79. A compound according to claim 67, wherein $Q^1$ is selected from:

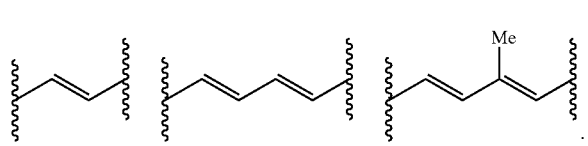

80. A compound according to claim 68, wherein $Q^1$ is selected from:

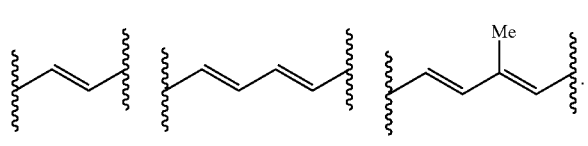

81. A compound according to claim 69, wherein $Q^1$ is selected from:

82. A compound according to claim 57, selected from the following compound, and pharmaceutically acceptable salts thereof:

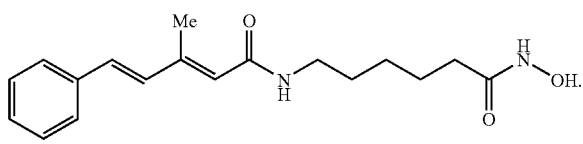

83. A compound according to claim 57, selected from the following compound, and pharmaceutically acceptable salts thereof:

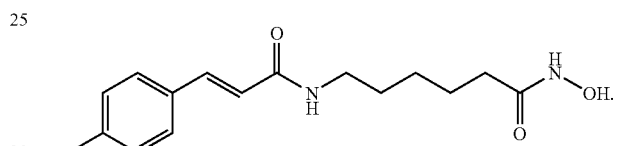

84. A compound according to claim 57, selected from the following compound, and pharmaceutically acceptable salts thereof:

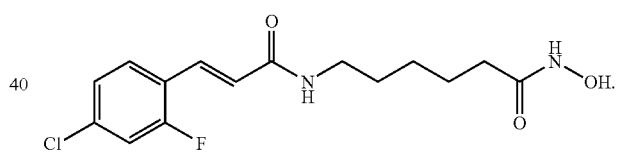

85. A compound according to claim 57, selected from the following compound, and pharmaceutically acceptable salts thereof:

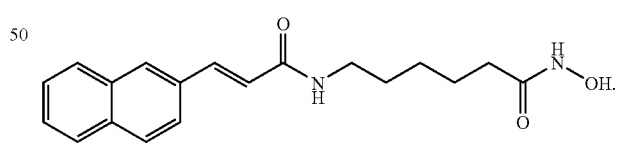

86. A compound according to claim 57, selected from the following compound, and pharmaceutically acceptable salts thereof:

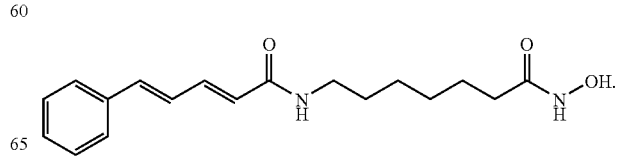

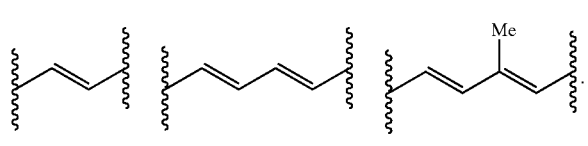

87. A pharmaceutical composition comprising a compound according to claim 57 and a pharmaceutically acceptable carrier or diluent.

88. A pharmaceutical composition comprising a compound according to claim 82 and a pharmaceutically acceptable carrier or diluent.

89. A pharmaceutical composition comprising a compound according to claim 83 and a pharmaceutically acceptable carrier or diluent.

90. A pharmaceutical composition comprising a compound according to claim 84 and a pharmaceutically acceptable carrier or diluent.

91. A pharmaceutical composition comprising a compound according to claim 85 and a pharmaceutically acceptable carrier or diluent.

92. A pharmaceutical composition comprising a compound according to claim 86 and a pharmaceutically acceptable carrier or diluent.

93. A compound according to claim 56, selected from the following compound, and pharmaceutically acceptable salts thereof:

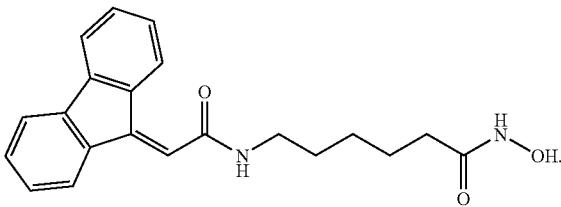

* * * * *